(12) United States Patent
Krieger et al.

(10) Patent No.: US 7,309,759 B2
(45) Date of Patent: *Dec. 18, 2007

(54) COMPOSITIONS AND METHODS FOR TREATING INFECTIONS USING CATIONIC PEPTIDES ALONE OR IN COMBINATION WITH ANTIBIOTICS

(75) Inventors: Timothy J Krieger, Monrovia, CA (US); Robert Taylor, White Rock (CA); Douglas Erfle, Vancouver (CA); Janet R Fraser, Vancouver (CA); Michael H P West, Caledon East (CA); Patricia J McNicol, Vancouver (CA)

(73) Assignee: Migenix Inc., Vancouver (CA)

( * ) Notice: Subject to any disclaimer, the term of this patent is extended or adjusted under 35 U.S.C. 154(b) by 477 days.

This patent is subject to a terminal disclaimer.

(21) Appl. No.: 10/277,233

(22) Filed: Oct. 18, 2002

(65) Prior Publication Data

US 2003/0232750 A1   Dec. 18, 2003

Related U.S. Application Data

(63) Continuation of application No. 09/030,619, filed on Feb. 25, 1998, now Pat. No. 6,503,881, and a continuation-in-part of application No. 08/915,314, filed on Aug. 20, 1997, now Pat. No. 6,180,604.

(60) Provisional application No. 60/060,099, filed on Sep. 26, 1997, provisional application No. 60/040,649, filed on Mar. 10, 1997, provisional application No. 60/034,949, filed on Jan. 13, 1997, provisional application No. 60/024,754, filed on Aug. 21, 1996.

(51) Int. Cl.
| | |
|---|---|
| A61K 38/00 | (2006.01) |
| A61K 49/00 | (2006.01) |
| A01N 37/18 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl. ............... 530/300; 530/324; 530/326; 530/327; 530/328; 514/2; 424/9.1

(58) Field of Classification Search ............... 530/300, 530/324, 326, 327, 328; 424/9.1; 514/2
See application file for complete search history.

(56) References Cited

U.S. PATENT DOCUMENTS

| | | | | |
|---|---|---|---|---|
| 4,510,132 A | | 4/1985 | Vaara | 514/11 |
| 5,324,716 A | * | 6/1994 | Selsted et al. | 514/14 |
| 5,359,030 A | | 10/1994 | Ekwuribe | 530/303 |
| 5,438,040 A | | 8/1995 | Ekwuribe | 514/3 |
| 5,523,288 A | | 6/1996 | Cohen et al. | 514/12 |
| 5,547,939 A | * | 8/1996 | Selsted | 514/14 |
| 5,574,017 A | * | 11/1996 | Gutheil | 514/19 |
| 5,578,572 A | | 11/1996 | Horwitz et al. | 514/12 |
| 5,593,866 A | | 1/1997 | Hancock et al. | 435/69.7 |
| 6,040,435 A | * | 3/2000 | Hancock et al. | 536/23.1 |
| 6,180,604 B1 | * | 1/2001 | Fraser et al. | 514/12 |
| 6,191,254 B1 | | 2/2001 | Falla et al. | 530/300 |
| 6,503,881 B2 | * | 1/2003 | Krieger et al. | 514/2 |
| 6,538,106 B1 | * | 3/2003 | Fraser et al. | 530/327 |
| 2004/0009910 A1 | * | 1/2004 | Fraser et al. | 514/12 |

FOREIGN PATENT DOCUMENTS

| | | |
|---|---|---|
| EP | 590 070 B1 | 2/1998 |
| WO | WO 91/12815 | 9/1991 |
| WO | WO 92/22308 | 12/1992 |
| WO | WO 95/22338 * | 8/1995 |
| WO | WO 96/38473 | 12/1996 |
| WO | WO 97/04796 | 2/1997 |
| WO | WO 97/08199 | 3/1997 |
| WO | WO 97/31942 | 9/1997 |
| WO | WO 98/07745 | 2/1998 |
| WO | WO 98/45319 | 10/1998 |
| WO | WO 99/43357 | 9/1999 |

OTHER PUBLICATIONS

Brewer NS, 1977, Antimicrobial agents—Part II. The aminoglycosides: streptomycin, kanamycin, gentamicin, tobramycin, amikacin, neomycin, Mayo Clin. Proc., 52(11): Abstract only.*

Sherris (Ryan ed.), 1994, Medical Microbiology: An Introduction to Infectious Diseases, Appleton & Lange Paramount Publishing Business and Professional Group, Third Edition, pp. 285, 295, 353, and 385.*

(Continued)

*Primary Examiner*—Mark L. Shibuya
*Assistant Examiner*—Amber D. Steele
(74) *Attorney, Agent, or Firm*—Darby & Darby PC; Bruce E. Black

(57) ABSTRACT

Compositions and methods for treating infections, especially bacterial infections, are provided. Indolicidin peptide analogues containing at least two basic amino acids are prepared. The analogues are administered as modified peptides, preferably containing photo-oxidized solubilizer.

41 Claims, 22 Drawing Sheets

OTHER PUBLICATIONS

Perez-Soler R, 1989, Liposomes as carriers of antitumor agents: toward a clinical reality, Cancer Treat. Rev., 16(2): Abstract only.*

Chalk et al., "Purification of An Insect Defensin from the Mosquito, *Aedes aegypti,*" *Insect Biochem. Molec. Biol.* 24(4):403-410, 1994.

Chalk et al., "Full Sequence and Characterization of Two Insect Defensins: Immune Peptides from the Mosquito *Aedes aegypti,*" *Proc. R. Soc. Land. B.* 261(1361):217-221, 1995.

Darveau et al., "β-Lactam Antibiotics Potentiate Magainin 2 Antimicrobial Activity In Vitro and In Vivo," *Antimicrobial Agents & Chemotherapy* 35(6):1153-1159, 1991.

Engström et al., "The Antibacterial Effect of Attacins from the Silk Moth *Hyalophora cecropia* is Directed Against the Outer Membrane of *Escherichia coli,*" *EMBO J.* 3(13):3347-3351, 1984.

Falla et al., "Mode of Action of the Antimicrobial Peptide Indolicidin," *The Journal of Biological Chemistry* 271(32): 19298-19303, Aug. 9, 1996.

Hancock, "The Role of Fundamental Research and Biotechnology in Finding Solutions to the Global Problem of Antibiotic Resistance," *Clin. Infectious Diseases* 24(Supp 1)S148-S150, 1997.

Ladokhin et al., "CD Spectra of Indolicidin Antimicrobial Peptides Suggest Turns, Not Polyproline Helix," *Biochemistry* 38:12313-12319, 1999.

Lawyer et al., "Antimicrobial Activity of a 13 Amino Acid Tryptophan-Rich Peptide Derived From a Putative Porcine Precursor Protein of a Novel Family of Antibacterial Peptides," *FEBS Letters* 390:95-98, 1996.

Piers et al., "Improvement of Outer Membrane-Permeabilizing and Lipopolysaccharide-Binding Activities of an Antimicrobial Cationic Peptide by C-Terminal Modification," *Antimicrobial Agents & Chemotherapy* 38(10):2311-2316, 1994.

Robinson, Jr. et al., "Anti-HIV-1 Activity of Indolicidin, an Antimicrobial Peptide from Neutrophils," *Journal of Leukocyte Biology* 63:94-100, 1998.

Selsted et al., "Purification, Characterization, Synthesis and cDNA Cloning of Indolicidin: A Tryptophan-Rich Microbicidal Tridecapeptide from Neutrophils," *Proceedings of the 12th American Peptide Symposium*, Jun. 16-21, 1991, Cambridge, MA, pp. 905-907.

Subbalakshmi et al., "Interaction of Indolicidin, a 13-Residue Peptide Rich in Tryptophan and Proline and its Analogues with Model Membranes," *J. Biosci.* 23(1):9-13, 1998.

Tanchak et al., "Tryptophanins: Isolation and Molecular Characterization of Oat cDNA Clones Encoding Proteins Structurally Related to Puroindoline and Wheat Grain Softness Proteins," *Plant Science* 137:173-184, 1998.

Uchida et al., "Structure-Activity of Antibacterial Peptide Indolicidin and Analogs," *Peptide Science*, pp. 221-224, 1998.

Van Abel et al., "Synthesis and Characterization of Indolicidin, a Tryptophan-Rich Antimicrobial Peptide from Bovine Neutrophils," *Int. J. Peptide Protein Res.* 45:401-409, 1995.

Vaara, "The Outer Membrane as the Penetration Barrier Against Mupirocin in Gram-Negative Enteric Bacteria," *J. Antimicrob. Chemother.* 29(2):221-222, 1992.

Vaara, "Agents That Increase the Permeability of the Outer Membrane," *Microbiological Reviews* 56(3):395-411, 1992.

Vaara and Porro, "Group of Peptides That Act Synergistically with Hydrophobic Antibiotics Against Gram-Negative Enteric Bacteria," *Antimicrobial Agents & Chemotherapy* 40(8):1801-1805, 1996.

Vaara and Vaara, "Polycations Sensitize Enteric Bacteria to Antibiotics," *Antimicrobial Agents & Chemotherapy* 24(1):107-113, 1983.

Vaara and Vaara, "Sensitization of Gram-Negative Bacteria to Antibiotics and Complement by a Nontoxic Oligopeptide," *Nature* 303:526-528, 1983.

Vaara and Vaara, "Ability of Cecropin B to Penetrate the Enterobacterial Outer Membrane," *Antimicrobail Agents & Chemotherapy* 38(10):2498-2501, 1994.

Wakabayashi et al., "N-Acylated and D Enantiomer Derivatives of a Nonamer Core Peptide of Lactoferricin B Showing Improved Antimicrobial Activity," *Antimicrobial Agents And Chemotherapy* 43(5):1267-1269, May 1999.

Bundgaard, H., "Design of prodrugs: Bioreversible derivatives for various functional groups and chemical entities," Chapter 1, pp. 1-92 in *Design of Prodrugs*, Bundgaard, H.(Ed.), Elsevier Science Publishers B.V. (Biomedical Division), 1985.

Falla and Hancock, "Improved Activity of a Synthetic Indolicidin Analog," *Antimicrobioal Agents and Chemotherapy* 41(4): 771-775, Apr. 1997.

Selsted et al., "Indolicidin, a Novel Bactericidal Tridecapeptide Amide from Neutrophils," *The Journal of Biological Chemistry* 267(7): 4292-4295, Mar. 5, 1992.

Subbalakshmi and Sitaram, "Mechanism of antimicrobial action of Indolicidin," *FEMS Microbiology Letters* 160: 91-96, 1998.

Subbalakshmi et al., "Requirements for antibacterial and hemolytic activities in the bovine neutrophil derived 13-residue peptide Indolicidin," *FEBS Letters* 395: 48-52, 1996.

Uchida et al., "Antibacterial Activity of the Mammalian Host Defense Peptide, Indolicidin, and Its Fragments," in *Peptide Chemistry*, N. Nishi (Ed.), Protien Research Foundation, Osaka, 1996, pp. 229-232.

* cited by examiner

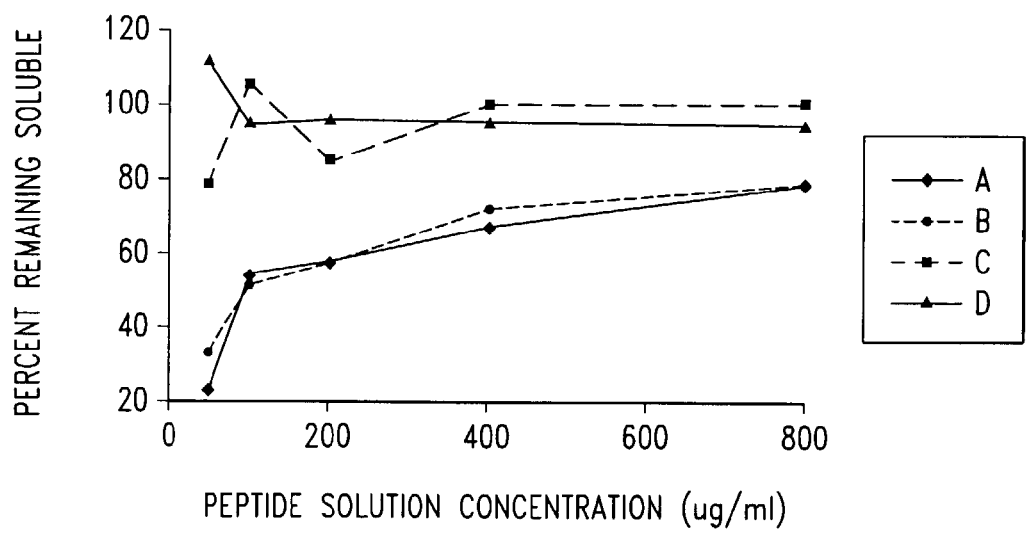
*Fig. 4*
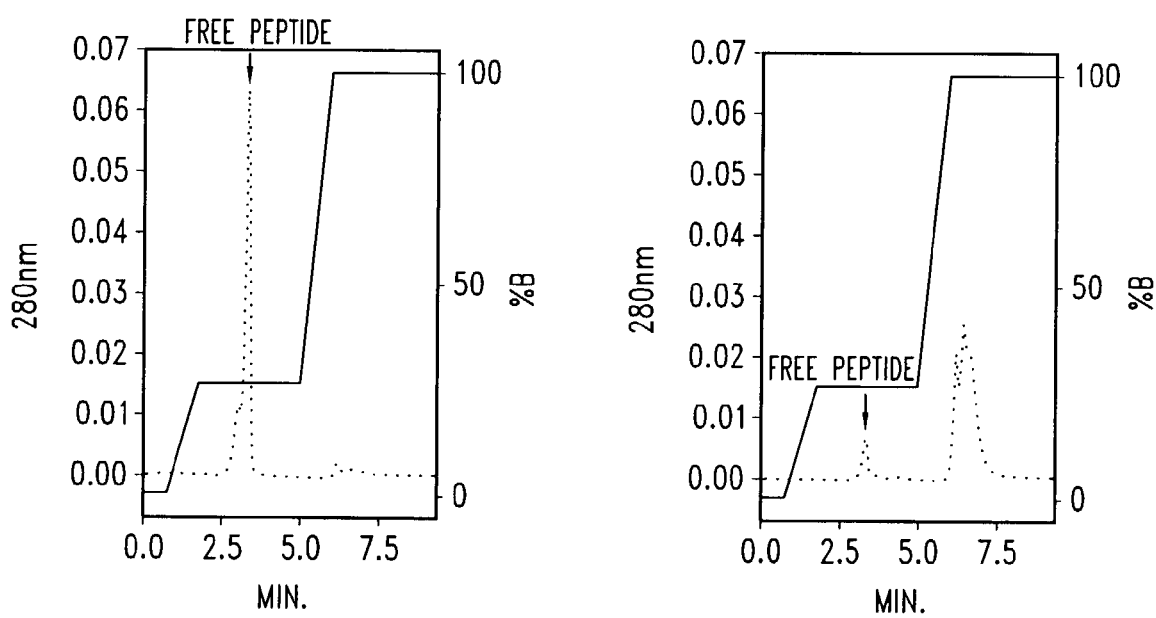
*Fig. 5A*  *Fig. 5B*

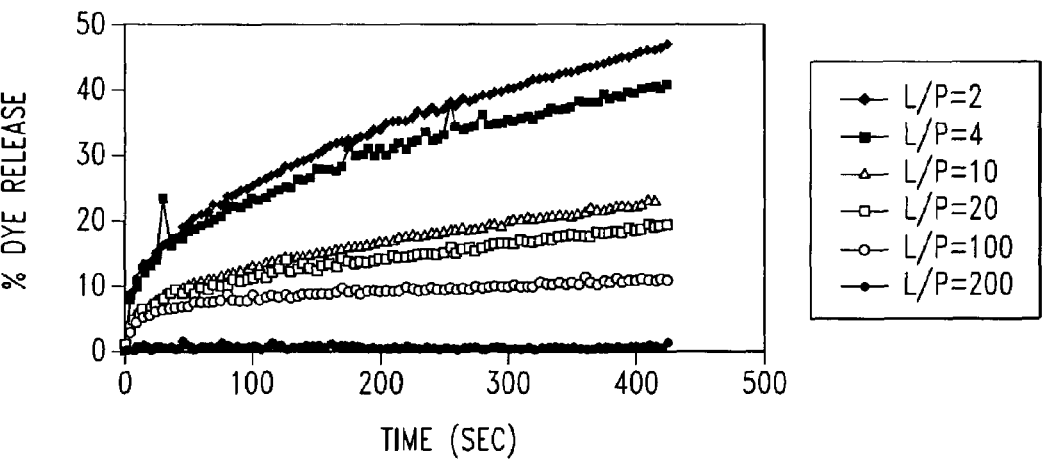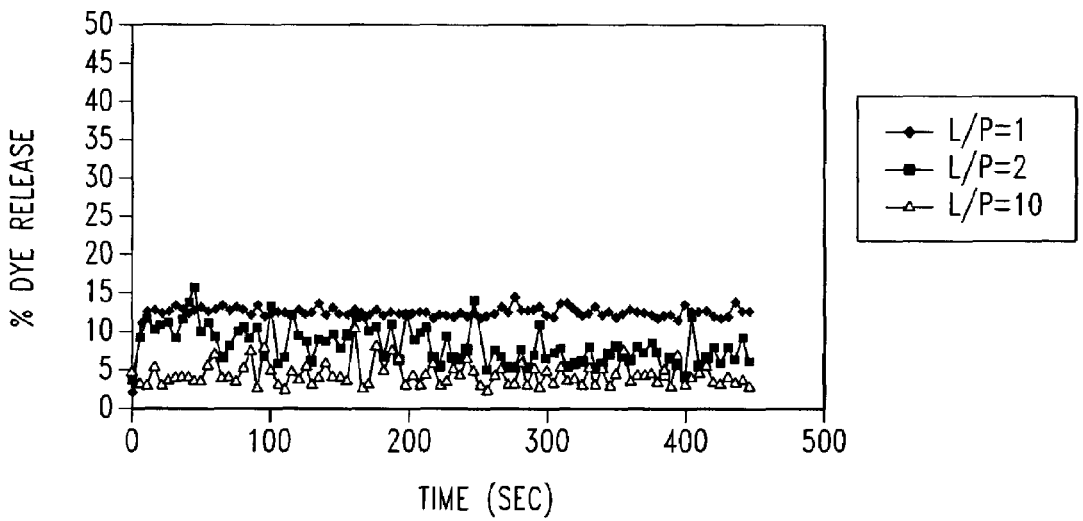
Fig. 7

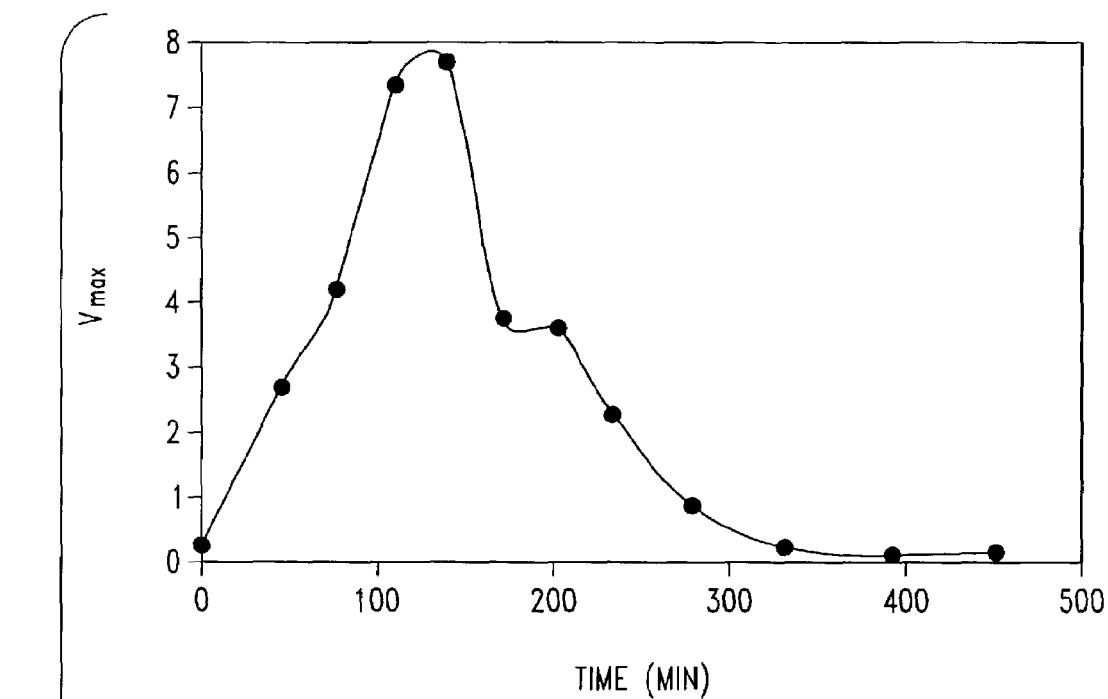
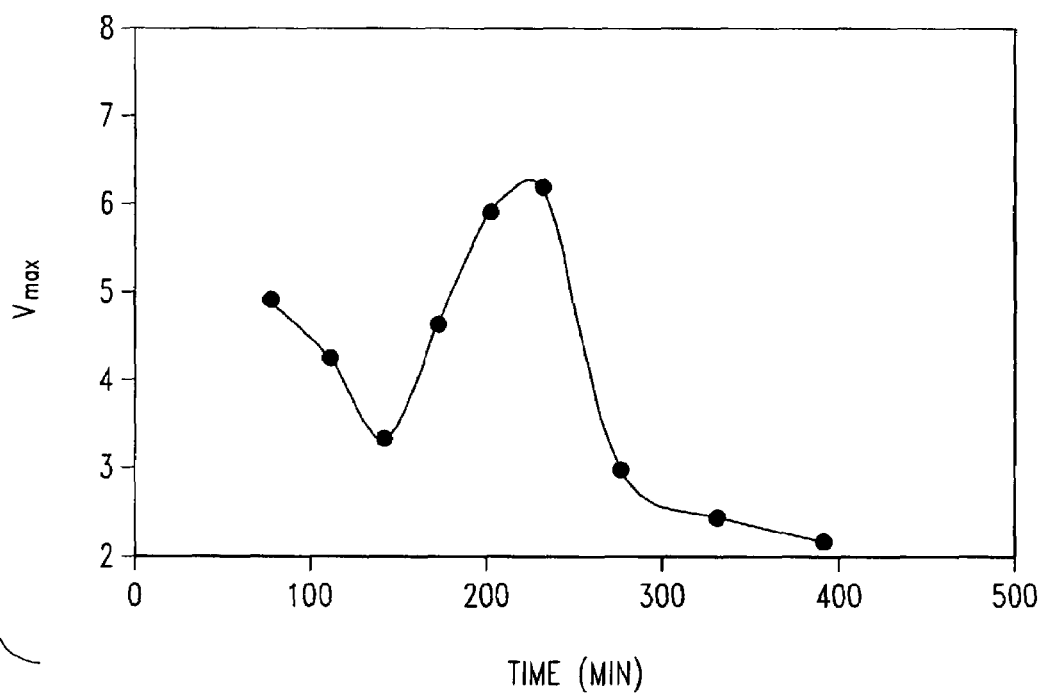
Fig. 8

Stability of MBI-11B7CN-Cl in Heat-inactivated Rabbit Serum

| Time | Area |
|---|---|
| 0 | 31027612 |
| 2 | 12767092 |
| 6 | 2804593 |

*Fig. 12*

COMPOSITIONS AND METHODS FOR TREATING INFECTIONS USING CATIONIC PEPTIDES ALONE OR IN COMBINATION WITH ANTIBIOTICS

CROSS-REFERENCE TO RELATED APPLICATIONS

The present application is a continuation of U.S. application Ser. No. 09/030,619, filed Feb. 25, 1998, issued as U.S. Pat. No. 6,503,881 on Jan. 7, 2003 which claims priority from U.S. Provisional Application No. 60/040,649, filed Mar. 10, 1997, and U.S. Provisional Application No. 60/060,099, filed Sep. 26, 1997, and is a continuation-in-part of U.S. application Ser. No. 08/915,314, filed Aug. 20, 1997, issued as U.S. Pat. No. 6,180,604 on Jan. 30, 2001 which claims priority from U.S. Provisional Application No. 60/024,754, filed Aug. 21, 1996, and U.S. Provisional Application No. 60/034,949, filed Jan. 13, 1997.

BACKGROUND OF THE INVENTION

1. Field of the Invention

The present invention relates generally to methods of treating microorganism-caused infections using cationic peptides or a combination of cationic peptides and antibiotic agents, and more particularly to using these peptides and antibiotic agents to overcome acquired resistance, tolerance, and inherent resistance of an infective organism to the antibiotic agent.

2. Description of the Related Art

For most healthy individuals, infections are irritating, but not generally life-threatening. Many infections are successfully combated by the immune system of the individual. Treatment is an adjunct and is generally readily available in developed countries. However, infectious diseases are a serious concern in developing countries and in immunocompromised individuals.

In developing countries, the lack of adequate sanitation and consequent poor hygiene provide an environment that fosters bacterial, parasitic, fungal and viral infections. Poor hygiene and nutritional deficiencies may diminish the effectiveness of natural barriers, such as skin and mucous membranes, to invasion by infectious agents or the ability of the immune system to clear the agents. As well, a constant onslaught of pathogens may stress the immune system defenses of antibody production and phagocytic cells (e.g., polymorphic neutrophils) to subnormal levels. A breakdown of host defenses can also occur due to conditions such as circulatory disturbances, mechanical obstruction, fatigue, smoking, excessive drinking, genetic defects, AIDS, bone marrow transplant, cancer, and diabetes. An increasingly prevalent problem in the world is opportunistic infections in individuals who are HIV positive.

Although vaccines may be available to protect against some of these organisms, vaccinations are not always feasible, due to factors such as inadequate delivery mechanisms and economic poverty, or effective, due to factors such as delivery too late in the infection, inability of the patient to mount an immune response to the vaccine, or evolution of the pathogen. For other pathogenic agents, no vaccines are available. When protection against infection is not possible, treatment of infection is generally pursued. The major weapon in the arsenal of treatments is antibiotics. While antibiotics have proved effective against many bacteria and thus saved countless lives, they are not a panacea. The overuse of antibiotics in certain situations has promoted the spread of resistant bacterial strains. And of great importance, antibacterials are useless against viral infections.

A variety of organisms make cationic (positively charged) peptides, molecules used as part of a non-specific defense mechanism against microorganisms. When isolated, these peptides are toxic to a wide variety of microorganisms, including bacteria, fungi, and certain enveloped viruses. One cationic peptide found in neutrophils is indolicidin. While indolicidin acts against many pathogens, notable exceptions and varying degrees of toxicity exist.

Although cationic peptides show efficacy in vitro against a variety of pathogenic cells including gram-positive bacteria, gram-negative bacteria, and fungi, these peptides are generally toxic to mammals when injected, and therapeutic indices are usually quite small. Approaches to reducing toxicity have included development of a derivative or delivery system that masks structural elements involved in the toxic response or that improves the efficacy at lower doses. Other approaches under evaluation include liposomes and micellular systems to improve the clinical effects of peptides, proteins, and hydrophobic drugs, and cyclodextrins to sequester hydrophobic surfaces during administration in aqueous media. For example, attachment of polyethylene glycol (PEG) polymers, most often by modification of amino groups, improves the medicinal value of some proteins such as asparaginase and adenosine deaminase, and increases circulatory half-lives of peptides such as interleukins.

None of these approaches are shown to improve administration of cationic peptides. For example, methods for the stepwise synthesis of polysorbate derivatives that can modify peptides by acylation reactions have been developed, but acylation alters the charge of a modified cationic peptide and frequently reduces or eliminates the antimicrobial activity of the compound. Thus, for delivery of cationic peptides, as well as other peptides and proteins, there is a need for a system combining the properties of increased circulatory half-lives with the ability to form a micellular structure.

The present invention discloses analogues of indolicidin, designed to broaden its range and effectiveness, and further provide other related advantages. The present invention also provides methods and compositions for modifying peptides, proteins, antibiotics and the like to reduce toxicity, as well as providing other advantages.

In addition neither antibiotic therapy alone of cationic peptide therapy alone can effectively combat all infections. By expanding the categories of microorganisms that respond to therapy, or by overcoming the resistance of a microorganism to antibiotic agents, health and welfare will be improved. Additionally quality of life will be improved, due to, for example, decreased duration-of therapy, reduced hospital stay including high-care facilities, with the concomitant reduced risk of serious nosocomial (hospital-acquired) infections.

The present invention discloses cationic peptides, including analogues of indolicidin, cecropin/melittin fusion peptides, in combination with antibiotics such that the combination either synergistic, able to overcome microorganismal tolerance, able to overcome resistance to antibiotic treatment, or further provides other related advantages.

BRIEF SUMMARY OF THE INVENTION

The present invention generally provides the co-administration of cationic peptides with an antibiotic agent and also provides indolicidin analogues.

In related aspects, an indolicidin analogue is provided, comprising up to 25 amino acids and containing the formula: RXZXXZXB (SEQ ID NO:1); BXZXXZXB (SEQ ID NO:2) wherein at least one Z is valine; BBBXZXXZXB (SEQ ID NO:3); BXZXXZXBBB$_n$(AA)$_n$MILBBAGS (SEQ ID NOs:5-8); BXZXXZXBB(AA)$_n$M (SEQ ID NOs:9-10); LBB$_n$XZ$_n$XXZ$_n$XRK (SEQ ID NOs:11-18); LK$_n$XZXXZXRRK (SEQ ID NOs:19-20); BBXZXXZX-BBB (SEQ ID NO:21), wherein at least two X residues are phenylalanine; BBXZXXZXBBB (SEQ ID NO:22), wherein at least two X residues are tyrosine; and wherein Z is proline or valine; X is a hydrophobic residue; B is a basic amino acid; AA is any amino acid, and n is 0 or 1. In preferred embodiments, Z is proline, X is tryptophan and B is arginine or lysine. In other aspects, indolicidin analogues having specific sequences are provided. In certain embodiments, the indolicidin analogues are coupled to form a branched peptide. In other embodiments, the analogue has one or more amino acids altered to a corresponding D-amino acid, and in certain preferred embodiments, the N-terminal and/or the C-terminal amino acid is a D-amino acid. Other preferred modifications include analogues that are acetylated at the N-terminal amino acid, amidated at the C-terminal amino acid, esterified at the C-terminal amino acid, modified by incorporation of homoserine/homoserine lactone at the C-terminal amino acid, and conjugated with polyethylene glycol or derivatives thereof.

In other aspects, the invention provides an isolated nucleic acid molecule whose sequence comprises one or more coding sequences of the indolicidin analogues, expression vectors, and host cells transfected or transformed with the expression vector.

Other aspects provide a pharmaceutical composition comprising at least one indolicidin analogue and a physiologically acceptable buffer, optionally comprising an antibiotic agent.

In other embodiments, the pharmaceutical composition further comprises an antiviral agent, an antiparasitic agent; and an antifungal agent. In yet other embodiments, the composition is incorporated in a liposome or a slow-release vehicle.

In yet another aspect, the invention provides a method of treating an infection, comprising administering to a patient a therapeutically effective amount of a pharmaceutical composition. The infection may be caused by, for example, a microorganism, such as a bacterium (e.g., Gram-negative or Gram-positive bacterium or anaerobe; parasite or virus.

In other aspects, a composition is provided, comprising an indolicidin analogue and an antibiotic. In addition, a device, which may be a medical device, is provided that is coated with the indolicidin analogue and may further comprise an antibiotic agent.

In other aspects, antibodies that react specifically with any one of the analogues described herein are provided. The antibody is preferably a monoclonal antibody or single chain antibody.

In a preferred aspect, the invention provides a composition comprising a compound modified by derivatization of an amino group with a conjugate comprising activated polyoxyalkylene and a lipophilic moiety. In preferred embodiments, the conjugate comprises sorbitan linking polyoxyalkylene glycol and fatty acid, and more preferably is polysorbate. In preferred embodiments, the fatty acid is from 12-18 carbons, and the polyoxyalkylene glycol is polyoxyethylene, such as with a chain length of from 2 to 100. In certain embodiments, the compound is a peptide or protein, such as a cationic peptide (e.g., indolicidin or an indolicidin analogue). In preferred embodiments, the polyoxyalkylene glycol is activated by irradiation with ultraviolet light or by treatment with ammonium persulfate.

The invention also provides a method of making a compound modified with a conjugate of an activated polyoxyalkylene and a lipophilic moiety, comprising: (a) freezing a mixture of the conjugate of an activated polyoxyalkylene and lipophilic moiety with the compound; and (b) lyophilizing the frozen mixture; wherein the compound has a free amino group. In preferred embodiments, the compound is a peptide or antibiotic. In other preferred embodiments, the mixture in step (a) is in an acetate buffer. In a related aspect, the method comprises mixing the conjugate of an activated polyoxyalkylene and lipophilic moiety with the compound; for a time sufficient to form modified compounds, wherein the mixture is in a carbonate buffer having a pH greater than 8.5 and the compound has a free amino group. The modified compound may be isolated by reversed-phase HPLC and/or precipitation from an organic solvent.

The invention also provides a pharmaceutical composition comprising at least one modified compound and a physiologically acceptable buffer, and in certain embodiments, further comprises an antibiotic agent, antiviral agent, an antiparasitic agent, and/or antifungal agent. The composition may be used to treat an infection, such as those caused by a microorganism (e.g., bacterium, fungus, parasite and virus).

This invention also generally provides methods for treating infections caused by a microorganism using a combination of cationic peptides and antibiotic agents. In one aspect, the method comprises administering to a patient a therapeutically effective dose of a combination of an antibiotic agent and a cationic peptide, wherein administration of an antibiotic agent alone is ineffective. Preferred peptides are provided.

In another aspect, a method of enhancing the activity of an antibiotic agent against an infection in a patient caused by a microorganism is provided, comprising administering to the patient a therapeutically effective dose of the antibiotic agent and a cationic peptide. In yet another aspect, a method is provided for enhancing the antibiotic activity of lysozyme or nisin, comprising administering lysozyme or nisin with a cationic peptide.

In other aspects, methods of treating an infection in a patient caused by a bacteria that is tolerant to an antibiotic agent, caused by a microorganism that is inherently resistant to an antibiotic agent; or caused by a microorganism that has acquired resistance to an antibiotic agent; comprises administering to the patient a therapeutically effective dose of the antibiotic agent and a cationic peptide, thereby overcoming tolerance, inherent or acquired resistance to the antibiotic agent.

In yet other related aspects, methods are provided for killing a microorganism that is tolerant, inherently resistant, or has acquired resistance to an antibiotic agent, comprising contacting the microorganism with the antibiotic agent and a cationic peptide, thereby overcoming tolerance, inherent resistance or acquired resistance to the antibiotic agent.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIG. 4 is a graph presenting the extent of solubility of MBI 11CN peptide in various buffers.

FIGS. 5A-B are a reversed phase HPLC profile of MBI 11CN in formulation C1 (5A) and formulation D (5B).

FIG. 7 presents results of ANTS/DPX dye release of egg PC liposomes at various ratios of lipid to protein.

FIG. 8 presents graphs showing the activity of MBI 11B7CN against mid-log cells grown in terrific broth (TB) or Luria-Bretani broth (LB).

FIG. 12 is a graph showing the stability of MBI-11B7CN-cl in heat-inactivated rabbit serum.

DETAILED DESCRIPTION OF THE INVENTION

Figure 1:
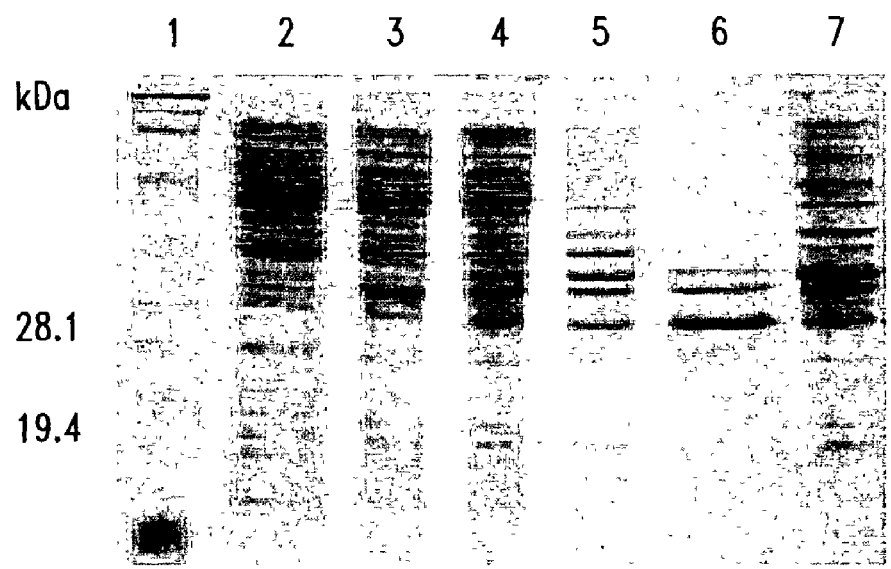
FIG. 1 is an SDS-PAGE showing the extraction profile of inclusion bodies (ib) from whole cells containing MBI-11 fusion protein. The fusion protein band is indicated by the arrow head. Lane 1, protein standards; lane 2, total lysate of XL1 Blue without plasmid; lane 3, total lysate of XL1 Blue (pR2h-11, pGP1-2), cultivated at 30° C.; lane 4, total lysate of XL1 Blue (pR2h-11, pGP1-2), induced at 42° C.; lane 5, insoluble fraction of inclusion bodies after Triton X100 wash; lane 6, organic extract of MBI-11 fusion protein; lane 7, concentrated material not soluble in organic extraction solvent.

Prior to setting forth the invention, it may be helpful to an understanding thereof to set forth definitions of certain terms that are used herein.

The amino acid designations herein are set forth as either the standard one-or three-letter code. A capital letter indicates an L-form amino acid; a small letter indicates a D-form amino acid.

As used herein, an "antibiotic agent" refers to a molecule that tends to prevent, inhibit, or destroy life. The term "antimicrobial agent" refers to an antibiotic agent specifically directed to a microorganism.

As used herein, "cationic peptide" refers to a peptide that has a net positive charge within the pH range of 4-10. A cationic peptide is at least 5 amino acids in length and has at least one basic amino acid (e.g., arginine, lysine, histidine). Preferably, the peptide has measurable anti-microbial activity when administered alone.

As used herein, "indolicidin" refers to an antimicrobial cationic peptide. Indolicidins may be isolated from a variety of organisms. One indolicidin is isolated from bovine neutrophils and is a 13 amino acid peptide amidated at the carboxy-terminus in its native form (Selsted et al., *J. Biol. Chem.* 267:4292, 1992). An amino acid sequence of indolicidin is presented in SEQ ID NO: 1.

As used herein, a "peptide analogue", "analogue", or "variant" of a cationic peptide, such as indolicidin, is at least 5 amino acids in length, has at least one basic amino acid (e.g., arginine and lysine) and has anti-microbial activity. Unless otherwise indicated, a named amino acid refers to the L-form. Basic amino acids include arginine, lysine, histidine and derivatives. Hydrophobic residues include tryptophan, phenylalanine, isoleucine, leucine, valine, and derivatives.

Also included within the scope of the present invention are amino acid derivatives that have been altered by chemical means, such as methylation (e.g., α methylvaline), amidation, especially of the C-terminal amino acid by an alkylamine (e.g., ethylamine, ethanolamine, and ethylene diamine) and alteration of an amino acid side chain, such as acylation of the ε-amino group of lysine. Other amino acids that may be incorporated in the analogue include any of the D-amino acids corresponding to the 20 L-amino acids commonly found in proteins, imino amino acids, rare amino acids, such as hydroxylysine, or non-protein amino acids, such as homoserine and ornithine. A peptide analogue may have none or one or more of these derivatives, and D-amino acids. In addition, a peptide may also be synthesized as a retro-, inverto- or retro-inverto-peptide.

As used herein "inherent resistance" of a microorganism to an antibiotic agent refers to a natural resistance to the action of the agent even in the absence of prior exposure to the agent. (R. C. Moellering Jr., *Principles of Anti-infective Therapy; In: Principles and Practice of Infectious Diseases*, 4th Edition, Eds.; G. L. Mandell, J. E. Bennett, R. Dolin. Churchill Livingstone, New York USA, 1995, page 200).

As used herein, "acquired resistance" of a microorganism to an antibiotic agent refers to a resistance that is not inhibited by the normal achievable serum concentrations of a recommended antibiotic agent based on the recommended dosage. (NCCLS guidelines).

As used herein, "tolerance" of a microorganism to an antibiotic agent refers to when there is microstatic, rather than microcidal effect of the agent. Tolerance is measured by an MBC:MIC ratio greater than or equal to 32. (*Textbook of Diagnostic Microbiology*, Eds., C. R. Mahon and G. Manuselis, W. B. Saunders Co., Toronto Canada, 1995, page 92).

As noted above, this invention provides methods of treating infections caused by a microorganism, methods of killing a microorganism, and methods of enhancing the activity of an antibiotic agent. In particular, these methods are especially applicable when a microorganism is resistant to an antibiotic agent, by a mechanism, such as tolerance, inherent resistance, or acquired resistance. In this invention, infections are treated by administering a therapeutically effective dose of a cationic peptide alone or in combination with an antibiotic agent to a patient with an infection. Similarly, the combination can be contacted with a microorganism to effect killing.

I. Cationic Peptides

As noted above, a cationic peptide is a peptide that has a net positive charge within the pH range 4-10. A peptide is at least 5 amino acids long and preferably not more than 25, 27, 30, 35, or 40 amino acids. Peptides from 12 to 30 residues are preferred. Examples of native cationic peptides include, but are not limited to, representative peptides presented in the following table.

TABLE 1

Cationic Peptides

| Group Name | Peptide | Origin | Sequence | Accession Number | Reference* |
|---|---|---|---|---|---|
| Abaecins | Abaecin | Honey bee (*Apis mellifera*) | YVPLPNVPQPGRRPFPTFPGQGPFNPKI KWPQGY (SEQ ID NO: 156) | P15450 | Casteels P. et al., (1990) |
| Andropins | Andropin | Fruit fly (*Drosophilia melanogaster*) | VFIDILDKVENAIHNAAQVGIGFAKPFEKLI NPK (SEQ ID NO: 157) | P21663 | Samakovlis, C. et al., (1991) |
| Apidaecins | Apidaecin IA | Lymph fluid of honey bee (*Apis mellifera*) | GNNRPVYIPQPRPPHPRI (SEQ ID NO: 158) | P11525 | Casteels, P. et al., (1989) |
|  | Apidaecin IB | Lymph fluid of honey bee (*Apis mellifera*) | GNNRPVYIPQPRPPHPRL (SEQ ID NO: 159) | P11526 | Casteels, P. et al., (1989) |
|  | Apidaecin II | Lymph fluid of honey bee (*Apis mellifera*) | GNNRPIYIPQPRPPHPRL (SEQ ID NO: 160) | P11527 | Casteels, P. et al., (1989) |
| AS | AS-48 | *Streptococcus faecalis* subsp. *Liquefacines* S-48 | 7.4 kDa |  | Galvez, A., et al., (1989) |
| Bactenecins | Bactenecin | Cytoplasmic granules of bovine neutrophils | RLCRIVVIRVCR (SEQ ID NO: 161) | A33799 | Romeo, D. et al., (1988) |
| Bac | Bac5 | Cytoplasmic granules of | RFRPPIRRPPIRPPFYPPFRPPIRPPIFPPI | B36589 | Frank, R. W. et al., |

TABLE 1-continued

Cationic Peptides

| Group Name | Peptide | Origin | Sequence | Accession Number | Reference* |
|---|---|---|---|---|---|
| | | bovine neutrophils | RPPFRPPLRFP (SEQ ID NO: 162) | | (1990) |
| | Bac7 | Cytoplasmic granules of bovine neutrophils | RRIRPRPPRLPRPRPRPLPFPRPGPRPIP RPLPFPRPGPRPIPRPLPFPRPGPRPIPR P (SEQ ID NO: 163) | A36589 | Frank, R. W. et al., (1990) |
| Bactericidins | Bactericidin B2 | Tobacco hornworm larvae hemolymph (*Manduca sexta*) | WNPFKELERAGQRVRDAVISAAPAVATV GQAAAIARG* (SEQ ID NO: 164) | P14662 | Dickinson, L. et al., (1988) |
| | Bactericidin B-3 | Tobacco hornworm larvae hemolymph (*Manduca sexta*) | WNPFKELERAGQRVRDAIISAGPAVATV GQAAAIARG (SEQ ID NO: 165) | P14663 | Dickinson, L. et al., (1988) |
| | Bactericidin B-4 | Tobacco hornworm larvae hemolymph (*Manduca sexta*) | WNPFKELERAGQRVRDAIISAAPAVATV GQAAAIARG* (SEQ ID NO: 166) | P14664 | Dickinson, L. et al., (1988) |
| | Bactericidin B-5P | Tobacco hornworm larvae hemolymph (*Manduca sexta*) | WNPFKELERAGQRVRDAVISAAAVATVG QAAAIARGG* (SEQ ID NO: 167) | P14665 | Dickinson, L., et al., (1988) |
| Bacteriocins | Bacteriocin C3603 | *Streptococcus* mutants | 4.8 kDa | | Takada, K., et al., (1984) |
| | Bacteriocin IY52 | *Staphylococcus aureus* | 5 kDa | | Nakamura, T., et al, (1983) |
| Bombinins | Bombinin | Yellow-bellied toad (*Bombina variegata*) | GIGALSAKGALKGLAKGLAZHFAN* (SEQ ID NO: 168) | P01505 | Csordas, A., and Michl, H. (1970) |
| | BLP-1 | Asian Toad (*Bombina orientalis*) | GIGASILSAGKSALKGLAKGLAEHFAN* (SEQ ID NO: 169) | M76483 | Gibson, B. W. et al., (1991) |
| | BLP-2 | Asian Toad (*Bombina orientalis*) | GIGSAILSAGKSALKGLAKGLAEHFAN* (SEQ ID NO: 170) | B41575 | Gibson, B. W. et al., (1991) |
| Bombolitins | Bombolitin BI | Bumblebee venom (*Megabombus pennsylvanicus*) | IKITTMLAKLGKVLAHV* (SEQ ID NO: 171) | P10521 | Argiolas, A. and Pisano, J. J. (1985) |
| | Bombolitin BII | Bumblebee venom (*Megabombus pennsylvanicus*) | SKITDILAKLGKVLAHV* (SEQ ID NO: 172) | P07493 | Argiolas, A. and Pisano, J. J. (1985) |
| BPTI | Bovine Pancreatic Trypsin Inhibitor (BPTI) | Bovine Pancreas | RPDFCLEPPYTGPCKARIIRYFYNAKAGL CQTFVYGGCRAKRNNFKSAEDCMRTCG GA (SEQ ID NO: 173) | P00974 | Creighton, T. and Charles, I. G. (1987) |
| Brevinins | Brevinin-1E | European frog (*Rana esculenta*) | FLPLLAGLAANFLPKIFCKITRKC (SEQ ID NO: 174) | S33729 | Simmaco, M. et al., (1993) |
| | Brevinin-2E | | GIMDTLKNLAKTAGKGALQSLLNKASCKL SGQC (SEQ ID NO: 175) | S33730 | Simmaco, M. et al., (1993) |
| Cecropins | Cecropin A | Silk moth (*Hyalophora cecropia*) | KWKLFKKIEKVGQNIRDGIIKAGPAVAVV GQATQIAK* (SEQ ID NO: 176) | M63845 | Gudmundsson, G. H. et al., (1991) |
| | Cecropin B | Silk moth (*Hyalophora cecropia*) | KWKVFKKIEKMGRNIRNGIVKAGPAIAVL GEAKAL* (SEQ ID NO: 177) | Z07404 | Xanthopoulos, G. et al. (1988) |
| | Cecropin C | Fruit fly (*Drosophila melanogaster*) | GWLKKLGKRIERIGQHTRDATIQGLGIAQ QAANVAATARG* (SEQ ID NO: 178) | Z11167 | Tryselius, Y. et al. (1992) |
| | Cecropin D | Silk moth pupae (*Hyalophora cecropia*) | WNPFKELEKVGQRVRDAVISAGPAVATV AQATALAK* (SEQ ID NO: 179) | P01510 | Hultmark, D. et al., (1982) |
| | Cecropin P$_1$ | Pig small intestine (*sus scrofa*) | SWLSKTAKKLENSAKKRISEGIAIAIQGGP R (SEQ ID NO: 180) | P14661 | Lee, J. -Y. et al., (1989) |
| Charybdtoxins | Charybdtoxin | Scorpion venom (*Leiurus quinquestriatus hebraeus*) | ZFTNVSCTTSKECWSVCQRLHNTSRGK CMNKKCRCYS (SEQ ID NO: 181) | P13487 | Schweitz, H. et al., (1989) |
| Coleoptericins | Coleoptericin | Beetle (*Zophobas atratus*) | 8.1 kDa | A41711 | Bulet, P. et al., (1991) |
| Crabolins | Crabolin | European hornet venom (*Vespa crabo*) | FLPLILRKIVTAL* (SEQ ID NO: 182) | A01781 | Argiolas, A. and Pisano, J. J. (1984) |
| Defensins-alpha | Cryptdin 1 | Mouse intestine (*Mus musculus*) | LRDLVCYCRSRGCKGRERMNGTCRKG HLLYTLCCR (SEQ ID NO: 183) | A43279 | Selsted, M. E. et al., (1992) |
| | Cryptdin 2 | Mouse intestine (*Mus musculus*) | LRDLVCYCRTRGCKRRERMNGTCRKGH LMYTLCCR (SEQ ID NO: 184) | C43279 | Selsted, M. E. et al., (1992) |
| | MCP1 | Rabbit alveolar macrophages (*Oryctolagus cuniculus*) | VVCACRRALCLPRERRAGFCRIRGRIHP LCCRR (SEQ ID NO: 185) | M28883 | Selsted, M. et al., (1983) |
| | MCP2 | Rabbit alveolar macrophages (*Oryctolagus cuniculus*) | VVCACRRALCLPLERRAGFCRIRGRIHPL CCRR (SEQ ID NO: 186) | M28073 | Ganz, T. et al., (1989) |
| | GNCP-1 | Guinea pig (*Cavia cutteri*) | RRCICTTRTCRFPYRRLGTCIFQNRVYTF CC (SEQ ID NO: 187) | S21169 | Yamashita, T. and Saito, K., (1989) |
| | GNCP-2 | Guinea pig (*Cavia cutteri*) | RRCICTTRTCRFPYRRLGTCLFQNRVYT FCC (SEQ ID NO: 188) | X63676 | Yamashita, T. and Saito, K., (1989) |
| | HNP-1 | Azurophil granules of human neutrophils | ACYCRIPACIAGERRYGTCIYQGRLWAF CC (SEQ ID NO: 189) | P11479 | Lehrer, R. et al., (1991) |

TABLE 1-continued

Cationic Peptides

| Group Name | Peptide | Origin | Sequence | Accession Number | Reference* |
|---|---|---|---|---|---|
| | HNP-2 | Azurophil granules of human neutrophils | CYCRIPACIAGERRYGTCIYQGRLWAFCC (SEQ ID NO: 190) | P11479 | Lehrer, R. et al., (1991) |
| | NP-1 | Rabbit neutrophils (*Oryctolagus cuniculus*) | VVCACRRALCLPRERRAGFCRIRGRIHPLCCRR (SEQ ID NO: 191) | P01376 | Ganz, T. et al., (1989) |
| | NP-2 | Rabbit neutrophils (*Oryctolagus cuniculus*) | VVCACRRALCLPLERRAGFCRIRGRIHPLCCRR (SEQ ID NO: 192) | P01377 | Ganz, T. et al., (1989) |
| | RatNP-1 | Rat neutrophils (*Rattus norvegicus*) | VTCYCRRTRCGFRERLSGACGYRGRIYRLCCR (SEQ ID NO: 193) | A60113 | Eisenhauer, P. B. et al., (1989) |
| | RatNP-2 | Rat neutrophils (*Rattus norvegicus*) | VTCYCRSTRCGFRERLSGACGYRGRIYRLCCR (SEQ ID NO: 194) | | Eisenhauer, P. B. et al., (1989) |
| Defensins-beta | BNBD-1 | Bovine neutrophils | DFASCHTNGGICLPNRCPGHMIQIGICFRPRVKCCRSW (SEQ ID NO: 195) | 127951 | Selsted, M.E. et at., (1993) |
| | BNBD-2 | Bovine neutrophils | VRNHVTCRINRGFCVPIRCPGRTRQIGTCFGPRIKCCRSW (SEQ ID NO: 196) | 127952 | Selsted, M. E., et al., (1993) |
| | TAP | Bovine tracheal mucosa (*Bos taurus*) | NPVSCVRNKGICVPIRCPGSMKQIGTCVGRAVKCCRKK (SEQ ID NO: 197) | P25068 | Diamond, G. et al., (1991) |
| Defensins-insect | Sapecin | Flesh fly (*Sacrophaga peregrina*) | ATCDLLSGTGINHSACAAHCLLRGNRGGYCNGKAVCVCRN (SEQ ID NO: 198) | J04053 | Hanzawa, H. et al., (1990) |
| | Insect defensin | Dragonfly larvae (*Aeschna cyanea*) | GFGCPLDQMQCHRHCQTITGRSGGYCSGPLKLTCTCYR (SEQ ID NO: 199) | P80154 | Bulet, P. et al., (1992) |
| Defensins-scorpion | Scorpion defensin | Scorpion (*Leiurus quinquestriatus*) | GFGCPLNQGACHRHCRSIRRRGGYCAGFFKQTCTCYRN (SEQ ID NO: 200) | | Cociancich, S. et al., (1993) |
| Dermaseptins | Dermaseptin | South American arboreal frog (*Phyllomedusa sauvagii*) | ALWKTMLKKLGTMALHAGKAALGAADTISQTQ (SEQ ID NO: 201) | P24302 | Mor, A., et al., (1991) |
| Diptericins | Diptericin | Nesting-suckling blowfly (*Phormia terranovae*) | 9 kDa | X15851 | Reichhardt, J. M. et al, (1989) |
| Drosocins | Drosocin | Fruit fly (*Drosophila melanogaster*) | GKPRPYSPRPTSHPRPIRV (SEQ ID NO: 202) | S35984 | Bulet, P. et al., (1993) |
| Esculentins | Esculentin | European frog (*Rana esculenta*) | GIFSKLGRKKIKNLLISGLKNVGKEVGMDVVRTGIDIAGCKIKGEC (SEQ ID NO: 203) | S33731 | Simmaco, M. et al., (1993) |
| Indolicidins | Indolicidin | Bovine neutrophils | ILPWKWPWWPWRR* (SEQ ID NO: 204) | A42387 | Selsted, M. et al., (1992) |
| Lactoferricins | Lactoferricin B | N terminal region of bovine lactoferrin | FKCRRWQWRMKKLGAPSITCVRRAF (SEQ ID NO: 205) | M63502 | Bellamy, W. et al., (1992b) |
| Lantibiotics | Nisin | *Lactococcus lactis* subsp. *Lactis* (bacterium) | ITSISLCTPGCKTGALMGCNMKTATCHCSIHVSK (SEQ ID NO: 206) | P13068 | Hurst, A. (1981) |
| | Pep 5 | *Staphylococcus epidermidis* | TAGPAIRASVKQCQKTLKATRLFTVSCKGKNGCK (SEQ ID NO: 207) | P19578 | Keletta, C. et al., (1989) |
| | Subtilin | *Bacillus subtilis* (bacterium) | MSKFDDFDLDVVKVSKQDSKITPQWKSESLCTPGCVTGALQTCFLQTLTCNCKISK (SEQ ID NO: 208) | P10946 | Banerjee, S. and Hansen, J. N. (1988) |
| Leukocins | Leukocin A-val 187 | *Leuconostoc gelidum* UAL 187 (bacterium) | KYYGNGVHCTKSGCSVNWGEAFSAGVHRLANGGNGFW (SEQ ID NO: 209) | S65611 | Hastings, J. W. et al., (1991) |
| Magainins | Magainin I | Amphibian skin (*Xenopus laevis*) | GIGKFLHSAGKFGKAFVGEIMKS* (SEQ ID NO: 210) | A29771 | Zasloff, M. (1987) |
| | Magainin II | Amphibian skin (*Xenopus laevis*) | GIGKFLHSAKKFGKAFVGEIMNS* (SEQ ID NO: 211) | A29771 | Zasloff, M. (1987) |
| | PGLa | Amphibian skin (*Xenopus laevis*) | GMASKAGAIAGKIAKVALKAL* (SEQ ID NO: 212) | X13388 | Kuchler, K. et al., (1989) |
| | PGQ | Amphibian stomach (*Xenopus laevis*) | GVLSNVIGYLKKLGTGALNAVLKQ (SEQ ID NO: 213) | | Moore, K.S. et al., (1989) |
| | XPF | Amphibian skin (*Xenopus laevis*) | GWASKIGQTLGKIAKVGLKELIQPK (SEQ ID NO: 214) | P07198 | Sures, I. And Crippa, M. (1984) |
| Mastoparans | Mastoparan | Wasp venom (*Vespula lewisii*) | INLKALAALAKKIL* (SEQ ID NO: 215) | P01514 | Bernheimer, A. and Rudy, B. (1986) |
| Melittins | Melittin | Bee venom (*Apis mellifera*) | GIGAVLKVLTTGLPALISWIKRKRQQ (SEQ ID NO: 216) | P01504 | Tosteson, M. T. and Tosteson, D. C.(1984) |
| Phormicins | Phormicin A | Nestling-suckling blowfly (*Phormia terranovae*) | ATCDLLSGTGINHSACAAHCLLRGNRGGYCNGKGVCVCRN (SEQ ID NO: 217) | P10891 | Lambert, J. et al., (1989) |
| | Phormicin B | Nestling-suckling blowfly (*Phormia terranovae*) | ATCDLLSGTGINHSACAAHCLLRGNRGGYCNRKGVCVRN (SEQ ID NO: 218) | P10891 | Lambert, J. et al., (1989) |
| Polyphemusins | Polyphemusin I | Atlantic horseshoe crab (*Limulus polyphemus*) | RRWCFRVCYRGFCYRKCR* (SEQ ID NO: 219) | P14215 | Miyata, T. et al., (1989) |
| | Polyphemusin II | Atlantic horseshoe crab (*Limulus polyphemus*) | RRWCFRVCYKGFCYRKCR* (SEQ ID NO: 220) | P14216 | Miyata, T. et al., (1989) |
| Protegrins | Protegrin I | Porcine leukocytes | RGGRLCYCRRRFCVCVGR (SEQ ID | S34585 | Kokryakov, V. N. et al., |

TABLE 1-continued

Cationic Peptides

| Group Name | Peptide | Origin | Sequence | Accession Number | Reference* |
|---|---|---|---|---|---|
| | | (sus scrofa) | NO: 221) | | (1993) |
| | Protegrin II | Porcine leukocytes (sus scrofa) | RGGRLCYCRRRFCICV (SEQ ID NO: 222) | S34586 | Kikryakov, V. N. et al., (1993) |
| | Protegrin III | Porcine leukocytes (sus scrofa) | RGGGLCYCRRRFCVCVGR (SEQ ID NO: 223) | S34587 | Kokryakov, V. N. et al., (1993) |
| Royalisins | Royalisin | Royal Jelly (Apis mellifera) | VTCDLLSFKGQVNDSACAANCLSLGKAG GHCEKGVCICRKTSFKDLWDKYF (SEQ ID NO: 224) | P17722 | Fujiwara, S. et al., (1990) |
| Sarcotoxins | Sarcotoxin IA | Flesh fly (Sacrophaga peregrina) | GWLKKIGKKIERVGQHTRDATIQGLGIAQ QAANVAATAR* (SEQ ID NO: 225) | P08375 | Okada, M. and Natori S., (1985b) |
| | Sarcotoxin IB | Flesh fly (Sacrophaga peregrina) | GWLKKIGKKIERVGQHTRDATIQVIGVAQ QAANVAATAR* (SEQ ID NO: 226) | P08376 | Okada, M. and Natori S., (1985b) |
| Seminal plasmins | Seminalplasmin | Bovine seminal plasma (Bos taurus) | SDEKASPDKHHRFSLSRYAKLANRLANP KLLETFLSKWIGDRGNRSV (SEQ ID NO: 227) | S08184 | Reddy, E. S. P. and Bhargava, P. M. (1979) |
| Tachyplesins | Tachyplesin 1 | Horseshoe crab (Tachypleus tridentatus) | KWCFRVCYRGICYRRCR* (SEQ ID NO: 228) | P23684 | Nakamura, T. et al., (1988) |
| | Tachyplesin II | Horseshoe crab (Tachypleus tridentatus) | RWCFRVCYRGICYRKCR* (SEQ ID NO: 229) | P14214 | Muta, T. et al., (1990) |
| Thionins | Thionin BTH6 | Barley leaf (Hordeum vulgare) | KSCCKDTLARNCYNTCRFAGGSRPVCA GACRCKIISGPKCPSDYPK (SEQ ID NO: 230) | S00825 | Bohlmann, H. et al., (1988) |
| Toxins | Toxin 1 | Waglers pit viper venom (Trimeresurus wagleri) | GGKPDLRPCIIPPCHYIPRPKPR (SEQ ID NO: 231) | P24335 | Schmidt, J J. et al., (1992) |
| | Toxin 2 | Sahara scorpion (Androctonus australis Hector) | VKDGYIVDDVNCTYFCGRNAYCNEECTK LKGESGYCQWASPYGNACYCKLPDHVR TKGPGRCH (SEQ ID NO: 232) | P01484 | Bontems, F., et al., (1991) |

Argiolas and Pisano, (1984). JBC 259, 10106; Argiolas and Pisano, (1985) JBC 260, 1437; Banerjee and Hansen, (1988). JBC 263, 9508; Bellamy et al, (1992). J. Appl. Bacter, 73, 472, Bernheimer and Rudy, (1986). BBA 864, 123; Bohlmann et al., (1988) EMBO J 7, 1559, Bontems et al, (1991) Science 254, 1521, Bulet et al., (1991). JBC 266, 24520; Bulet et al (1992). Eur J Biochem. 209, 977, Bulet et al., (1993). JBC 268, 14893; Casteels et al., (1989) EMBO J 8, 2387; Casteels et al, (1990). Eur. J. Biochem. 187, 381; Cociancich et al, (1993) BBRC 194, 17; Creighton and Charles, (1987). J. Mol Biol 194, 11; Csordas and Michl, (1970) Monatsh Chemistry 101, 182; Diamond et al., (1991) PNAS 88, 3952; Dickinson et al., (1988) JBC 263, 19424; Eisenhauer et al., (1989) Infect and Imm. 57, 2021; Frank et al., (1990). JBC 265, 18871; Fujiwara et al, (1990) JBC 265, 11333, Gálvez et al, (1989) Antimicrobial Agents and Chemotherapy 33, 437, Ganz et al, (1989). J. Immunol. 143, 1358; Gibson et al., (1991) JBC 266, 23103, Gudmundsson et al, (1991) JBC 266, 11510; Hanzawa et al., (1990). FEBS Letters 269, 413, Hastings et al., (1991). J of Bacteriology 173, 7491; Hultmark et al., (1982). Eur J Biochem. 127, 207; Hurst, A. (1981) Adv. Appl. Micro. 27, 85; Kaletta et al., (1989). Archives of Microbiology 152, 16; Kokryakov et al., (1993) FEBS Letters 327, 231; Kuchler et al, (1989) Eur J Biochem. 179, 281; Lambert et al, (1989). PNAS 86, 262; Lee et al, (1989). PNAS 86, 9159; Lehrer et al., (1991) Cell 64, 229, Miyata et al, (1989) J of Biochem 106, 663, Moore et al., (1991) JBC 266, 19851; Mor et al., (1991) Biochemistry 30, 8824, Muta et al., (1990) J. Biochem. 108, 261; Nakamura et al, (1988). JBC 263, 16709; Nakamura et al., (1983) Infection and Immunity 39, 609, Okada and Natori (1985) Biochem J 229, 453, Reddy and Bhargava, (1979) Nature 279, 725; Reichhart et al., (1989) Eur J Biochem 182, 423; Romeo et al, (1988). JBC 263, 9573; Samakovlis et al., (1991) EMBO J 10, 163, Schmidt et al, (1992). Toxicon 30, 1027, Schweitz et al., (1989). Biochem. 28, 9708, Selsted et al, (1983) JBC 258, 14485; Selsted et al., (1992) JBC 267, 4292; Simmaco et al, (1993). FEBS Letters 324, 159, Sures and Crippa (1984). PNAS 81, 380, Takada et al, (1984). Infect and Imm 44, 370; Tosteson and Tosteson, (1984) Biophysical J 45, 112, Tryselius et al, (1992). Eur J Biochem 204, 395, Xanthopoulos et al, (1988). Eur. J. Biochem. 172, 371; Yamashita and Saito, (1989). Infect and Imm. 57, 2405, Zasloff, M (1987). PNAS 84, 5449

In addition to the peptides listed above, chimeras and analogues of these peptides are useful within the context of the present invention. For this invention, analogues of native cationic peptides must retain a net positive charge, but may contain D-amino acids, amino acid derivatives, insertions, deletions, and the like, some of which are discussed below. Chimeras include fusions of cationic peptide, such as the peptides of fragments thereof listed above, and fusions of cationic peptides with non-cationic peptides.

As described herein, modification of any of the residues including the N- or C-terminus is within the scope of the invention. A preferred modification of the C-terminus is amidation. Other modifications of the C-terminus include esterification and lactone formation. N-terminal modifications include acetylation, acylation, alkylation, PEGylation, myristylation, and the like. Additionally, the peptide may be modified to form an polymer-modified peptide as described below. The peptides may also be labeled, such as with a radioactive label, a fluorescent label, a mass spectrometry tag, biotin and the like.

Unless otherwise indicated, a named amino acid refers to the L-form. Basic amino acids include arginine, lysine, histidine, and derivatives. Hydrophobic residues include tryptophan, phenylalanine, isoleucine, leucine, valine, and derivatives. The peptide may contain derivatives of amino acids that have been altered by chemical means, such as methylation (e.g., α-methylvaline), amidation, especially of the C-terminal amino acid by an alkylamine (e.g., ethylamine, ethanolamine, and ethylene diamine) and alteration of an amino acid side chain, such as acylation of the ε-amino group of lysine. Other amino acids that may be incorporated include any of the D-amino acids corresponding to the 20 L-amino acids commonly found in proteins, rare amino acids, such as hydroxylysine, or non-protein amino acids, such as homoserine and ornithine. A peptide may have none or one or more of these derivatives, and may contain D-amino acids (specified as a lower case letter when using the 1-letter code). Furthermore, modification of the N- or C-terminus is within the scope of the invention. A preferred modification of the C-terminus is amidation. Other modifications of the C-terminus include ester additions. N-terminal modifications include acetylation, myristlyation, and the like.

A. Indolicidin and Analogues

As noted above, the present invention provides cationic peptides, including indolicidin and indolicidin analogues. Analogues include peptides that have one or more insertions, deletions, modified amino acids, D-amino acids and the like. These analogues may be synthesized by chemical methods, especially using an automated peptide synthesizer, or produced by recombinant methods. The choice of an amino acid sequence is guided by a general formula presented herein.

The indolicidin analogues of the present invention are at least 5 or 7 amino acids in length and preferably not more than 15, 20, 25, 27, 30, or 35 amino acids. Analogues from 9 to 14 residues are preferred. General formulas for peptide analogues in the scope of the present invention may be set forth as:

| | | |
|---|---|---|
| RXZXXZXB | (1) | (SEQ ID NO:1) |
| BXZXXZXB | (2) | (SEQ ID NO:2) |
| BBBXZXXZXB | (3) | (SEQ ID NO:3) |
| BXZXXZXBBB$_n$(AA)$_n$MILBBAGS | (4) | (SEQ ID NOs:5-8) |
| BXZXXZXBB(AA)$_n$M | (5) | (SEQ ID NOs:9-10) |
| LBB$_n$XZ$_n$XXZ$_n$XRK | (6) | (SEQ ID NOs:11-18) |
| LK$_n$XZXXZXRRK | (7) | (SEQ ID NOs:19-20) |
| BBXZXXZXBBB | (8) | (SEQ ID NO:21) |
| BBXZXXZXBBB | (9) | (SEQ ID NO:22) |
| BXXBZBXBXZB | (10) | (SEQ ID NO:4) | wherein standard single letter amino abbreviations are used and; Z is proline, glycine or a hydrophobic residue, and preferably Z is proline or valine; X is a hydrophobic residue, such as tryptophan, phenylalanine, isoleucine, leucine and valine, and preferably tryptophan; B is a basic amino acid, preferably arginine or lysine; AA is any amino acid, and n is 0 or 1. In formula (2), at least one Z is valine; in formula (8), at least two Xs are phenylalanine; and in formula (9), at least two Xs are tyrosine. Additional residues may be present at the N-terminus, C-terminus, or both.

B. Cecropin Peptides

Cecropins are cationic peptides that have antimicrobial activity against both Gram-positive and Gram-negative bacteria. Cecropins have been isolated from both invertebrates (e.g., insect hemolymph) as well as vertebrates (e.g. pig intestines). Generally, these peptides are 35 to 39 residues. An exemplary cecropin has the sequence KWKLFK-KIEKVGQNIRDGIIKAGPAVAVVGQATQIAK (SEQ ID NO:176). Some additional cecropin sequences are presented in Table 1. Within the context of this invention, cecropins include analogues that have one or more insertions, deletions, modified amino acids, D-amino acids and the like.

C. Melittin Peptides

Melittin is a cationic peptide found in bee venom. An amino acid sequence of an exemplary melittin peptide is GIGAVLKVLTTGLPALISWIKRKKRQQ (SEQ ID NO:216). Like the cecropins, melittin exhibits antimicrobial activity against both Gram-positive and Gram-negative bacteria. Within the context of this invention, melittin includes analogues that have one or more insertions, deletions, modified amino acids, D-amino acids and the like.

D. Cecropin-Melittin Chimeric Peptides

As noted herein, cationic peptides include fusion peptides of native cationic peptides and analogues of fusion peptides. In particular, fusions of cecropin and melittin are provided. An exemplary fusion has the sequence: cecropin A (residues 1-8)/melittin (residues 1-18). Other fusion peptides useful within the context of this invention are described by the general formulas below.

| | |
|---|---|
| K W K R$_2$ R$_1$ R$_1$ R$_2$ R$_2$ R$_1$ R$_2$ R$_2$ R$_1$ R$_1$ R$_2$ R$_2$ V L T T G L P A L I S | (SEQ ID NO:128) |
| K W K R$_2$ R$_1$ R$_1$ R$_2$ R$_2$ R$_1$ R$_2$ R$_2$ R$_1$ R$_1$ R$_2$ R$_2$ V V T T A K P L I S S | (SEQ ID NO:129) |
| K W K R$_2$ R$_1$ R$_1$ R$_2$ R$_2$ R$_1$ R$_2$ R$_2$ R$_1$ R$_1$ R$_2$ R$_2$ I L T T G L P A L I S | (SEQ ID NO:130) |
| K W K R$_2$ R$_1$ R$_1$ R$_2$ R$_2$ R$_1$ R$_2$ R$_2$ R$_1$ R$_1$ R$_2$ R$_2$ G G L L S N I V T S L | (SEQ ID NO:131) |
| K W K R$_2$ R$_1$ R$_1$ R$_2$ R$_2$ R$_1$ R$_2$ R$_2$ R$_1$ R$_1$ R$_2$ R$_2$ G P I L A N L V S I V | (SEQ ID NO:132) |
| K K W W R R R$_1$ R$_1$ R$_2$ R$_1$ R$_1$ R$_2$ R$_2$ G P A L S N V | (SEQ ID NO:133) |
| K K W W R R X | (SEQ ID NO:134-144) |
| K K W W K X | (SEQ ID NO:145-155) | wherein $R_1$ is a hydrophobic amino acid residue, $R_2$ is a hydrophilic amino acid residue, and X is from about 14 to 24 amino acid residues.

E. Drosocin and Analogues

As noted herein, cationic peptides include drosocin and drosocin analogues. Drosocins are isolated from *Drosophila melanogaster*. An exemplary drosocin is a 19 amino acid peptide having the sequence: GKPRPYSPRPTSHPRPIRV (SEQ ID NO:202); GenBank Accession No. S35984). Analogues of drosocin include peptides that have insertions, deletions, modified amino acids, D-amino acids and the like.

F. Peptide Synthesis

Peptides may be synthesized by standard chemical methods, including synthesis by automated procedure. In general, peptide analogues are synthesized based on the standard solid-phase Fmoc protection strategy with HATU as the coupling agent. The peptide is cleaved from the solid-phase resin with trifluoroacetic acid containing appropriate scavengers, which also deprotects side chain functional groups.

Crude peptide is further purified using preparative reversed-phase chromatography. Other purification methods, such as partition chromatography, gel filtration, gel electrophoresis, or ion-exchange chromatography may be used.

Other synthesis techniques, known in the art, such as the tBoc protection strategy, or use of different coupling reagents or the like can be employed to produce equivalent peptides.

Peptides may be synthesized as a linear molecule or as branched molecules. Branched peptides typically contain a core peptide that provides a number of attachment points for additional peptides. Lysine is most commonly used for the core peptide because it has one carboxyl functional group and two (alpha and epsilon) amine functional groups. Other diamino acids can also be used. Preferably, either two or three levels of geometrically branched lysines are used; these cores form a tetrameric and octameric core structure, respectively (Tam, *Proc. Natl. Acad. Sci.* USA 85:5409, 1988). Schematically, examples of these cores are represented as shown (SEQ ID NO:92):

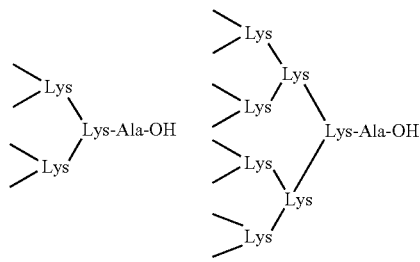

The attachment points for the peptides are typically at their carboxyl functional group to either the alpha or epsilon amine groups of the lysines. To synthesize these multimeric peptides, the solid phase resin is derivatized with the core matrix, and subsequent synthesis and cleavage from the resin follows standard procedures. The multimeric peptides may be used within the context of this invention as for any of the linear peptides and are preferred for use in generating antibodies to the peptides.

G. Recombinant Production of Peptides

Peptides may alternatively be synthesized by recombinant production (see e.g., U.S. Pat. No. 5,593,866). A variety of host systems are suitable for production of the peptide analogues, including bacteria (e.g., *E. coli*), east (e.g., *Saccharomyces cerevisiae*), insect (e.g., Sf9), and mammalian cells e.g., CHO, COS-7). Many expression vectors have been developed and are vailable for each of these hosts. Generally, bacteria cells and vectors that are functional in bacteria are used in this invention. However, at times, it may be preferable to have vectors that are functional in other hosts. Vectors and procedures for cloning and expression in *E. coli* are discussed herein and, for example, in Sambrook et al. (*Molecular Cloning: A Laboratory Manual*, Cold Spring Harbor Laboratory Press, Cold Spring Harbor, N.Y., 1987) and in Ausubel et al. (*Current Protocols in Molecular Biology*, Greene Publishing Co., 1995).

A DNA sequence encoding a cationic peptide is introduced into an expression vector appropriate for the host. In preferred embodiments, the gene is cloned into a vector to create a fusion protein. The fusion partner is chosen to contain an anionic region, such that a bacterial host is protected from the toxic effect of the peptide. This protective region effectively neutralizes the antimicrobial effects of the peptide and also may prevent peptide degradation by host proteases. The fusion partner (carrier protein) of the invention may further function to transport the fusion peptide to inclusion bodies, the periplasm, the outer membrane, or the extracellular environment. Carrier proteins suitable in the context of this invention specifically include, but are not limited to, glutathione-S-transferase (GST), protein A from *Staphylococcus aureus*, two synthetic IgG-binding domains (ZZ) of protein A, outer membrane protein F, β-galactosidase (lacZ), and various products of bacteriophage λ and bacteriophage T7. From the teachings provided herein, it is apparent that other proteins may be used as carriers. Furthermore, the entire carrier protein need not be used, as long as the protective anionic region is present. To facilitate isolation of the peptide sequence, amino acids susceptible to chemical cleavage (e.g., CNBr) or enzymatic cleavage (e.g., V8 protease, trypsin) are used to bridge the peptide and fusion partner. For expression in *E. coli*, the fusion partner is preferably a normal intracellular protein that directs expression toward inclusion body formation. In such a case, following cleavage to release the final product, there is no requirement for renaturation of the peptide. In the present invention, the DNA cassette, comprising fusion partner and peptide gene, may be inserted into an expression vector, which can be a plasmid, virus or other vehicle known in the art. Preferably, the expression vector is a plasmid that contains an inducible or constitutive promoter to facilitate the efficient transcription of the inserted DNA sequence in the host. Transformation of the host cell with the recombinant DNA may be carried out by $Ca^{++}$-mediated techniques, by electroporation, or other methods well known to those skilled in the art.

Briefly, a DNA fragment encoding a peptide is derived from an existing cDNA or genomic clone or synthesized. A convenient method is amplification of the gene from a single-stranded template. The template is generally the product of an automated oligonucleotide synthesis. Amplification primers are derived from the 5' and 3' ends of the template and typically incorporate restriction sites chosen with regard to the cloning site of the vector. If necessary, translational initiation and termination codons can be engineered into the primer sequences. The sequence encoding the protein may be codon-optimized for expression in the particular host. Thus, for example, if the analogue fusion protein is expressed in bacteria, codons are optimized for bacterial usage. Codon optimization is accomplished by automated synthesis of the entire gene or gene region, ligation of multiple oligonucleotides, mutagenesis of the native sequence, or other techniques known to those in the art.

At minimum, the expression vector should contain a promoter sequence. However, other regulatory sequences may also be included. Such sequences include an enhancer, ribosome binding site, transcription termination signal sequence, secretion signal sequence, origin of replication, selectable marker, and the like. The regulatory sequences are operationally associated with one another to allow transcription and subsequent translation. In preferred aspects, the plasmids used herein for expression include a promoter designed for expression of the proteins in bacteria. Suitable promoters, including both constitutive and inducible promoters, are widely available and are well known in the art. Commonly used promoters for expression in bacteria include promoters from T7, T3, T5, and SP6 phages, and the trp, lpp, and lac operons. Hybrid promoters (see, U.S. Pat. No. 4,551,433), such as tac and trc, may also be used.

Within a preferred embodiment, the vector is capable of replication in bacterial cells. Thus, the vector may contain a bacterial origin of replication. Preferred bacterial origins of replication include f1-ori and col E1 ori, especially the ori derived from pUC plasmids. Low copy number vectors (e.g., pPD100) may also be used, especially when the product is deleterious to the host.

The plasmids also preferably include at least one selectable marker that is functional in the host. A selectable marker gene confers a phenotype on the host that allows transformed cells to be identified and/or selectively grown. Suitable selectable marker genes for bacterial hosts include the chloroamphenicol resistance gene ($Cm^r$), ampicillin resistance gene ($Amp^r$), tetracycline resistance gene ($Tc^r$) kanamycin resistance gene ($Kan^r$), and others known in the art. To function in selection, some markers may require a complementary deficiency in the host.

In some aspects, the sequence of nucleotides encoding the peptide also encodes a secretion signal, such that the resulting peptide is synthesized as a precursor protein, which is subsequently processed and secreted. The resulting secreted protein may be recovered from the periplasmic space or the fermentation medium. Sequences of secretion signals suitable for use are widely available and are well known (von Heijne, *J. Mol. Biol.* 184:99-105, 1985).

The vector may also contain a gene coding for a repressor protein, which is capable of repressing the transcription of a promoter that contains a repressor binding site. Altering the physiological conditions of the cell can depress the promoter. For example, a molecule may be added that competitively binds the repressor, or the temperature of the growth media may be altered. Repressor proteins include, but are not limited to the *E. coli* lad repressor (responsive to induction by IPTG), the temperature sensitive $\lambda$cI857 repressor, and the like.

Examples of plasmids for expression in bacteria include the pET expression vectors pET3a, pET 11a, pET 12a-c, and pET 15b (see U.S. Pat. No. 4,952,496; available from Novagen, Madison, Wis.). Low copy number vectors (e.g., pPD100) can be used for efficient overproduction of peptides deleterious to the *E. coli* host (Dersch et al., FEMS Microbiol. Lett. 123: 19, 1994).

Bacterial hosts for the T7 expression vectors may contain chromosomal copies of DNA encoding T7 RNA polymerase operably linked to an inducible promoter (e.g., lacUV promoter; see, U.S. Pat. No. 4,952,496), such as found in the *E. coli* strains HMS174(DE3)pLysS, BL21(DE3)pLysS, HMS174(DE3) and BL21(DE3). T7 RNA polymerase can also be present on plasmids compatible with the T7 expression vector. The polymerase may be under control of a lambda promoter and repressor (e.g., pGP1-2; Tabor and Richardson, *Proc. Natl. Acad. Sci.* USA 82: 1074, 1985).

The peptide product is isolated by standard techniques, such as affinity, size exclusion, or ionic exchange chromatography, HPLC and the like. An isolated peptide should preferably show a major band by Coomassie blue stain of SDS-PAGE that is at least 90% of the material.

H. Generation of Analogues by Amplification-Based Semi-Random Mutagenesis

Cationic peptide analogues can be generated using an amplification (e.g., PCR)-based procedure in which primers are designed to target sequences at the 5' and 3' ends of an encoded parent peptide, for example indolicidin. Amplification conditions are chosen to facilitate misincorporation of nucleotides by the thermostable polymerase during synthesis. Thus, random mutations are introduced in the original sequence, some of which result in amino acid alteration(s). Amplification products may be cloned into a coat protein of a phage vector, such as a phagemid vector, packaged and amplified in an acceptable host to produce a display library.

These libraries can then be assayed for antibiotic activity of the peptides. Briefly, bacteria infected with the library are plated, grown, and overlaid with agarose containing a bacterial strain that the phage are unable to infect. Zones of growth inhibition in the agarose overlay are observed in the area of phage expressing an analogue with anti-bacterial activity. These inhibiting phage are isolated and the cloned peptide sequence determined by DNA sequence analysis. The peptide can then be independently synthesized and its antibiotic activity further investigated.

5. Antibodies to Cationic Peptides

Antibodies may be generated to a specific peptide analogue using multiple antigenic peptides (MAPs) that contain approximately eight copies of the peptide linked to a small non-immunogenic peptidyl core to form an immunogen. (See, in general, Harlow and Lane, supra.) Alternatively, the target peptide can be conjugated to bovine serum albumin (BSA), ovalbumin or another suitable conjugate. The MAP or peptide conjugate is injected subcutaneously into rabbits or into mice or other rodents, where they may have sufficiently long half-lives to facilitate antibody production. After twelve weeks blood samples are taken, serum is separated and tested in an ELISA assay against the original peptide, with a positive result indicating the presence of antibodies specific to the target peptide. This serum can then be stored and used in ELISA assays to specifically measure the amount of the specific analogue. Alternatively, other standard methods of antibody production may be employed, for example generation of monoclonal antibodies.

Within the context of the present invention, antibodies are understood to include monoclonal antibodies, polyclonal antibodies, anti-idiotypic antibodies, antibody fragments (e.g., Fab, and F(ab')$_2$, F$_v$ variable regions, or complementarity determining regions). Antibodies are generally accepted as specific against indolicidin analogues if they bind with a $K_d$ of greater than or equal to $10^{-7}$ M, preferably greater than of equal to $10^{-8}$ M. The affinity of a monoclonal antibody or binding partner can be readily determined by one of ordinary skill in the art (see Scatchard, *Ann. N.Y. Acad. Sci.* 51:660-672, 1949). Once suitable antibodies have been obtained, they may be isolated or purified by many techniques well known to those of ordinary skill in the art.

Monoclonal antibodies may also be readily generated from hybridoma cell lines using conventional techniques (see U.S. Pat. Nos. RE 32,011, 4,902,614, 4,543,439, and 4,411,993; see also *Antibodies: A Laboratory Manual*, Harlow and Lane (eds.), Cold Spring Harbor Laboratory Press, 1988). Briefly, within one embodiment, a subject animal such as a rat or mouse is injected with peptide, generally administered as an emulsion in an adjuvant such as Freund's complete or incomplete adjuvant in order to increase the immune response. The animal is generally boosted at least once prior to harvest of spleen and/or lymph nodes and immortalization of those cells. Various immortalization techniques, such as mediated by Epstein-Barr virus or fusion to produce a hybridoma, may be used. In a preferred embodiment, immortalization occurs by fusion with a suitable myeloma cell line to create a hybridoma that secretes monoclonal antibody. Suitable myeloma lines include, for example, NS-1 (ATCC No. TIB 18), and P3X63-Ag 8.653 (ATCC No. CRL 1580). The preferred fusion partners do not express endogenous antibody genes. After about seven days, the hybridomas may be screened for the presence of antibodies that are reactive against a telomerase protein. A wide variety of assays may be utilized (see *Antibodies: A Laboratory Manual*, Harlow and Lane (eds.), Cold Spring Harbor Laboratory Press, 1988).

Other techniques may also be utilized to construct monoclonal antibodies (see Huse et al., *Science* 246:1275-1281, 1989; Sastry et al., *Proc. Natl. Acad. Sci. USA* 86:5728-5732, 1989; Alting-Mees et al., *Strategies in Molecular Biology* 3:1-9, 1990; describing recombinant techniques). These techniques include cloning heavy and light chain immunoglobulin cDNA in suitable vectors, such as λImmunoZap(H) and λImmunoZap(L). These recombinants may be screened individually or co-expressed to form Fab fragments or antibodies (see Huse et al., supra; Sastry et al., supra). Positive plaques may subsequently be converted to a non-lytic plasmid that allows high level expression of monoclonal antibody fragments from *E. coli*.

Similarly, portions or fragments, such as Fab and Fv fragments, of antibodies may also be constructed utilizing conventional enzymatic digestion or recombinant DNA techniques to yield isolated variable regions of an antibody. Within one embodiment, the genes which encode the variable region from a hybridoma producing a monoclonal antibody of interest are amplified using nucleotide primers for the variable region. In addition, techniques may be utilized to change a "murine" antibody to a "human" antibody, without altering the binding specificity of the antibody.

II. Testing

Cationic peptides of the present invention are assessed either alone or in combination with an antibiotic agent or another analogue for their potential as antibiotic therapeutic agents using a series of assays. Preferably, all peptides are initially assessed in vitro, the most promising candidates are selected for further assessment in vivo, and then candidates are selected for pre-clinical studies. The in vitro assays include measurement of antibiotic activity, toxicity, solubility, pharmacology, secondary structure, liposome permeabilization and the like. In vivo assays include assessment of efficacy in animal models, antigenicity, toxicity, and the like. In general, in vitro assays are initially performed, followed by in vivo assays.

Generally, cationic peptides are initially tested for (1) anti-microbial activity in vitro; (2) in vitro toxicity to normal mammalian cells; and (3) in vivo toxicity in an animal model. Peptides that have some anti-microbial activity are preferred, although such activity may not be necessary for enhancing the activity of an antibiotic agent. Also, for in vivo use, peptides should preferably demonstrate acceptable toxicity profiles, as measured by standard procedures. Lower toxicity is preferred. Additional assays may be performed to demonstrate that the peptide is not immunogenic and to examine antimicrobial activity in vivo.

A. In vitro Assays

Cationic peptides, including indolicidin analogues, are assayed by, for example, an agarose dilution MIC assay, a broth dilution, time-kill assay, or equivalent methods. Antibiotic activity is measured as inhibition of growth or killing of a microorganism (e.g., bacteria, fungi).

Briefly, a candidate peptide in Mueller Hinton broth supplemented with calcium and magnesium is mixed with molten agarose. Other broths and agars may be used as long as the peptide can freely diffuse through the medium. The agarose is poured into petri dishes or wells, allowed to solidify, and a test strain is applied to the agarose plate. The test strain is chosen, in part, on the intended application of the peptide. Thus, by way of example, if an indolicidin analogue with activity against *S. aureus* is desired, an *S. aureus* strain is used. It may be desirable to assay the analogue on several strains and/or on clinical isolates of the test species. Plates are incubated overnight and inspected visually for bacterial growth. A minimum inhibitory concentration (MIC) of a cationic peptide is the lowest concentration of peptide that completely inhibits growth of the organism. Peptides that exhibit good activity against the test strain, or group of strains, typically having an MIC of less than or equal to 16 □g/ml are selected for further testing.

Alternatively, time kill curves can be used to determine the differences in colony counts over a set time period, typically 24 hours. Briefly, a suspension of organisms of known concentration is prepared and a candidate peptide is added. Aliquots of the suspension are removed at set times, diluted, plated on medium, incubated, and counted. MIC is measured as the lowest concentration of peptide that completely inhibits growth of the organism. In general, lower MIC values are preferred.

Candidate cationic peptides may be further tested for their toxicity to normal mammalian cells. An exemplary assay is a red blood cell (RBC) (erythrocyte) hemolysis assay. Briefly, in this assay, red blood cells are isolated from whole blood, typically by centrifugation, and washed free of plasma components. A 5% (v/v) suspension of erythrocytes in isotonic saline is incubated with different concentrations of peptide analogue. Generally, the peptide will be in a suitable formulation buffer. After incubation for approximately 1 hour at 37° C., the cells are centrifuged, and the absorbance of the supernatant at 540 nm is determined. A relative measure of lysis is determined by comparison to absorbance after complete lysis of erythrocytes using $NH_4Cl$ or equivalent (establishing a 100% value). A peptide with <10% lysis at 100 µg/ml is suitable. Preferably, there is <5% lysis at 100 µg/ml. Such peptides that are not lytic, or are only moderately lytic, are desirable and suitable for further screening. Other in vitro toxicity assays, for example measurement of toxicity towards cultured mammalian cells, may be used to assess in vitro toxicity.

Solubility of the peptide in formulation buffer is an additional parameter that may be examined. Several different assays may be used, such as appearance in buffer. Briefly, peptide is suspended in solution, such as broth or formulation buffer. The appearance is evaluated according to a scale that ranges from (a) clear, no precipitate, (b) light, diffuse precipitate, to (c) cloudy, heavy precipitate. Finer gradations may be used. In general, less precipitate is more desirable. However, some precipitate may be acceptable.

Additional in vitro assays may be carried out to assess the potential of the peptide as a therapeutic. Such assays include peptide solubility in formulations, pharmacology in blood or plasma, serum protein binding, analysis of secondary structure, for example by circular dichroism, liposome permeabilization, and bacterial inner membrane permeabilization. In general, it is desirable that analogues are soluble and perform better than the parent peptide (e.g., indolicidin).

B. In vivo Assays

Peptides, including peptide analogues, selected on the basis of the results from the in vitro assays can be tested in vivo for efficacy, toxicity and the like.

The antibiotic activity of selected peptides may be assessed in vivo for their ability to ameliorate microbial infections using animal models. A variety of methods and animal models are available. Within these assays, a peptide is useful as a therapeutic if inhibition of microorganismal growth compared to inhibition with vehicle alone is statistically significant. This measurement can be made directly from cultures isolated from body fluids or sites, or indirectly, by assessing survival rates of infected animals. For assessment of antibacterial activity several animal models are available, such as acute infection models including those in which (a) normal mice receive a lethal dose of microorganisms, (b) neutropenic mice receive a lethal dose of microorganisms or (c) rabbits receive an inoculum in the heart, and chronic infection models. The model selected will depend in part on the intended clinical indication of the analogue.

By way of example, in a normal mouse model, mice are inoculated ip or iv with a lethal dose of bacteria. Typically, the dose is such that 90-100% of animals die within 2 days. The choice of a microorganismal strain for this assay depends, in part, upon the intended application of the analogue, and in the accompanying examples, assays are carried out with three different *Staphylococcus* strains. Briefly, shortly before or after inoculation (generally within 60 minutes), analogue in a suitable formulation buffer is injected. Multiple injections of analogue may be administered. Animals are observed for up to 8 days post-infection and the survival of animals is recorded. Successful treatment either rescues animals from death or delays death to a statistically significant level, as compared with non-treatment control animals. Analogues that show better efficacy than indolicidin itself are preferred.

In vivo toxicity of a peptide is measured through administration of a range of doses to animals, typically mice, by a route defined in part by the intended clinical use. The survival of the animals is recorded and $LD_{50}$, $LD_{90-100}$, and maximum tolerated dose (MTD) can be calculated to enable comparison of analogues. Indolicidin analogues less toxic than indolicidin are preferred.

Furthermore, for in vivo use, low immunogenicity is preferred. To measure immunogenicity, peptides are injected into normal animals, generally rabbits. At various times after a single or multiple injections, serum is obtained and tested for antibody reactivity to the peptide analogue. Antibodies to peptides may be identified by ELISA, immunoprecipitation assays, Western blots, and other methods. (see, Harlow and Lane, *Antibodies: A Laboratory Manual*, Cold Spring Harbor Laboratory Press, Cold Spring Harbor, N.Y., 1988). No or minimal antibody reactivity is preferred. Additionally, pharmacokinetics of the analogues in animals and histopathology of animals treated with analogues may be determined.

Selection of cationic peptides as potential therapeutics is based on in vitro and in vivo assay results. In general, peptides that exhibit low toxicity at high dose levels and high efficacy at low dose levels are preferred candidates.

III. Antibiotic Agents

An antibiotic agent includes any molecule that tends to prevent, inhibit or destroy life and as such, includes antibacterial agents, anti-fungicides, anti-viral agents, and anti-parasitic agents. These agents may be isolated from an organism that produces the agent or procured from a commercial source (e.g., pharmaceutical company, such as Eli Lilly, Indianapolis, Ind.; Sigma, St. Louis, Mo.).

Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones (see Table below). Examples of antibiotic agents include, but are not limited to, Penicillin G (CAS Registry No. 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefmetazole (CAS Registry No.: 56796-20-4); Cefotetan (CAS Registry No.: 69712-56-7); Cefprozil (CAS Registry No.: 92665-29-7); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

A table presenting categories of antibiotics, their mode of action, and examples of antibiotics is shown below.

TABLE 2

| Class of Antibiotic | Antibiotic | Mode of Action |
|---|---|---|
| PENICILLINS | | Blocks the formation of new cell walls in bacteria |
| Natural | Penicillin G, Benzylpenicillin Penicillin V, Phenoxymethylpenicillin | |
| Penicillinase resistant | Methicillin, Nafcillin, Oxacillin Cloxacillin, Dicloxacillin | |
| Acylamino-penicillins | Ampicillin, Amoxicillin | |
| Carboxy-penicillins | Ticarcillin, Carbenicillin | |
| Ureido-penicillins | Mezlocillin, Azlocillin, Piperacillin | |
| CARBAPENEMS | Imipenem, Meropenem | Blocks the formation of new cell walls in bacteria |
| MONOBACTAMS | Aztreonam | Blocks the formation of new cell walls in bacteria |
| CEPHALOSPORINS | | Prevents formation of new cell walls in bacteria |
| 1st Generation | Cephalothin, Cefazolin | |
| 2nd Generation | Cefaclor, Cefamandole Cefuroxime, Cefonicid, Cefmetazole, Cefotetan, Cefprozil | |
| 3rd Generation | Cefetamet, Cefoperazone Cefotaxime, Ceftizoxime Ceftriaxone, Ceftazidime Cefixime, Cefpodoxime, Cefsulodin | |
| 4th Generation | Cefepime | |
| CARBACEPHEMS | Loracarbef | Prevents formation of new cell walls in bacteria |
| CEPHAMYCINS | Cefoxitin | Prevents formation of new cell walls in bacteria |
| QUINOLONES | Fleroxacin, Nalidixic Acid Norfloxacin, Ciprofloxacin Ofloxacin, Enoxacin Lomefloxacin, Cinoxacin | Inhibits bacterial DNA synthesis |
| TETRACYCLINES | Doxycycline, Minocycline, Tetracycline | Inhibits bacterial protein synthesis, binds to 30S ribosome subunit. |
| AMINOGLYCOSIDES | Amikacin, Gentamicin, Kanamycin, Netilmicin, Tobramycin, Streptomycin | Inhibits bacterial protein synthesis, binds to 30S ribosome subunit. |
| MACROLIDES | Azithromycin, Clarithromycin, Erythromycin | Inhibits bacterial protein synthesis, binds to 50S ribosome subunit |
| Derivatives of Erythromycin | Erythromycin estolate, Erythromycin stearate Erythromycin ethyl-succinate Erythromycin gluceptate Erythromycin lacto-bionate | |
| GLYCOPEPTIDES | Vancomycin, Teicoplanin | Inhibits cell wall synthesis, prevents peptidoglycan elongation. |
| MISCELLANEOUS | Chloramphenicol | Inhibits bacterial protein synthesis, binds to 50S ribosome subunit. |
| | Clindamycin | Inhibits bacterial protein synthesis, binds to 50S ribosome subunit. |

TABLE 2-continued

| Class of Antibiotic | Antibiotic | Mode of Action |
|---|---|---|
| | Trimethoprim | Inhibits the enzyme dihydrofolate reductase, which activates folic acid. |
| | Sulfamethoxazole | Acts as anti-metabolite of PABA & inhibits synthesis of folic acid |
| | Nitrofurantoin | Action unknown, but is concentrated in urine where it can act on urinary tract bacteria |
| | Rifampin | Inhibits bacterial RNA polymerase |
| | Mupirocin | Inhibits bacterial protein synthesis |

Anti-fungal agents include, but are not limited to, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

Anti-viral agents include, but are not limited to, amantadine hydrochloride, rimantadin, acyclovir, famciclovir, foscarnet, ganciclovir sodium, idoxuridine, ribavirin, sorivudine, trifluridine, valacyclovir, vidarabin, didanosine, stavudine, zalcitabine, zidovudine, interferon alpha, and edoxudine.

Anti-parasitic agents include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

IV. Enhanced Activity of Combinations of Cationic Peptides and Antibiotic Agents Enhanced activity occurs when a combination of peptide and antibiotic agent potentiates activity beyond the individual effects of the peptide or antibiotic agent alone or additive effects of peptide plus antibiotic agent. Enhanced activity is especially desirable in at least four scenarios: (1) the microorganism is sensitive to the antibiotic agent, but the dosage has associated problems; (2) the microorganism is tolerant to the antibiotic agent, and is inhibited from growing but is not killed; (3) the microorganism is inherently resistant to the antibiotic agent; and (4) the microorganism has acquired resistance to the antibiotic agent. Enhanced efficacy resulting from administration of the antibiotic agent in combination with a cationic peptide in the above scenarios: (1) allows for administration of lower dosages or antibiotic agent and cationic peptide; (2) restores a cytocidal effect; (3) overcomes inherent resistance; and (4) overcomes acquired resistance.

A. Enhancement of Antibiotic Agent or Cationic Peptide Activity

A synergistic combination of cationic peptide and antibiotic agent may permit a reduction in the dosage of one or both agents in order to achieve a similar therapeutic effect. This would allow smaller doses to be used, thus, decreasing the incidence of toxicity (e.g., from aminoglycosides) and lowering costs of expensive antibiotics (e.g., vancomycin). Concurrent or sequential administration of peptide and antibiotic agent is expected to provide more effective treatment of infections caused by micro-organisms (bacteria, viruses, fungi, and parasites). In particular, this could be achieved by using doses that the peptide or antibiotic agent alone would not achieve therapeutic success. Alternatively, the antibiotic agent and peptide can be administered at therapeutic doses for each, but wherein the combination of the two agents provides even more potent effects.

As used herein, "synergy" refers to the in vitro effect of administration of a combination of a cationic peptide and antibiotic agent such that (1) the fractional inhibitory concentration (FIC) is less than or equal to 0.5 in an FIC assay described herein; or (2) there is at least a 100-fold ($2\log_{10}$) increase in killing at 24 hours for the combination as compared with the antibiotic agent alone in a time kill curve assay as described herein.

Such synergy is conveniently measured in an in vitro assay, such as kinetic kill studies or a fractional inhibitory concentration (FIC) assay as determined by agarose or broth dilution assay. The agarose dilution assay is preferred.

Briefly, in the dilution assay, a checkerboard array of cationic peptides and antibiotic agents titrated in doubling dilutions are inoculated with a microbial (e.g., bacterial) isolate. The FIC is determined by observing the impact of one antibiotic agent on the MIC ("minimal inhibitory concentration") of the cationic peptide and vice versa. FIC is calculated by the following formula:

$$FIC = \frac{MIC(\text{peptide in combination})}{MIC(\text{peptide alone})} + \frac{MIC(\text{antibiotic in combination})}{MIC(\text{antibiotic alone})}$$

An FIC of $\leq 0.5$ is evidence of synergy. An additive response has an FIC value of $>0.5$ and less than or equal to 1, while an indifferent response has an FIC value of $>1$ and $\leq 2$. Although a synergistic effect is preferred, an additive effect may still indicate that the combination of antibiotic agent and cationic peptide are therapeutically useful.

B. Overcoming Tolerance

Tolerance is associated with a defect in bacterial cellular autolytic enzymes such that an antibacterial agent demonstrates bacteriostatic rather than bactericidal activity (Mahon and Manuselis, *Textbook of Diagnostic Microbiology*, W. B. Saunders Co., Toronto, Canada, p. 92, 1995). For antibiotic agents that have only bacteriostatic activity, the administration of cationic peptides in combination with antibiotic agents can restore bactericidal activity. Alternatively, the addition of a peptide to an antibiotic agent may increase the rate of a bactericidal effect of an antibiotic.

Bactericidal effects of antibiotics can be measured in vitro by a variety of assays. Typically, the assay is a measurement of MBC ("minimal bactericidal concentration"), which is an extension of the MIC determination. The agarose dilution assay is adapted to provide both MBC and MIC for an antimicrobial agent alone and the agent in combination with a cationic peptide. Alternatively, kinetic time-kill (or growth) curves can be used to determine MIC and MBC.

Briefly, following determination of MIC, MBC is determined from the assay plates by swabbing the inocula on plates containing antibiotic agent in concentrations at and above the MIC, resuspending the swab in saline or medium, and plating an aliquot on agarose plates. If the number of colonies on these agarose plates is less than 0.1% of the initial inoculum (as determined by a plate count immediately after inoculation of the MIC test plates), then $\geq 99.9\%$ killing has occurred. The MBC end point is defined as the lowest concentration of the antimicrobial agent that kills 99.9% of the test bacteria.

Thus, tolerance of a microorganism to an antimicrobial agent is indicated when the number of colonies growing on subculture plates exceeds the 0.1% cutoff for several successive concentrations above the observed MIC. A combination of antimicrobial agent and cationic peptide that breaks tolerance results in a decrease in the MBC:MIC ratio to <32.

C. Overcoming Inherent Resistance

The combination of a cationic peptide with an antibiotic agent, for which a microorganism is inherently resistant (i.e., the antibiotic has never been shown to be therapeutically effective against the organism in question), is used to overcome the resistance and confer susceptibility of the microorganism to the agent. Overcoming inherent resistance is especially useful for infections where the causative organism is becoming or has become resistant to most, if not all, of the currently prescribed antibiotics. Additionally, administering a combination therapy provides more options when toxicity of an antibiotic agent and/or price are a consideration.

Overcoming resistance can be conveniently measured in vitro. Resistance is overcome when the MIC for a particular antibiotic agent against a particular microorganism is decreased from the resistant range to the sensitive range (according to the National Committee for Clinical Laboratory Standards (NCCLS)) (see also, Moellering, in *Principles and Practice of Infectious Diseases*, 4th edition, Mandell et al., eds. Churchill Livingstone, NY, 1995). NCCLS standards are based on microbiological data in relation to pharmacokinetic data and clinical studies. Resistance is determined when the organism causing the infection is not inhibited by the normal achievable serum concentrations of the antibiotic agent based on recommended dosage. Susceptibility is determined when the organism responds to therapy with the antibiotic agent used at the recommended dosage for the type of infection and microorganism.

D. Overcoming Acquired Resistance

Acquired resistance in a microorganism that was previously sensitive to an antibiotic agent is generally due to mutational events in chromosomal DNA, acquisition of a resistance factor carried via plasmids or phage, or transposition of a resistance gene or genes from a plasmid or phage to chromosomal DNA.

When a microorganism acquires resistance to an antibiotic, the combination of a peptide and antibiotic agent can restore activity of the antibiotic agent by overcoming the resistance mechanism of the organism. This is particularly useful for organisms that are difficult to treat or where current therapy is costly or toxic. The ability to use a less expensive or less toxic antibiotic agent, which had been effective in the past, is an improvement for certain current therapies. The re-introduction of an antibiotic agent would enable previous clinical studies and prescription data to be used in its evaluation. Activity is measured in vitro by MICs or kinetic kill curves and in vivo using animal and human clinical trials.

E. Enhancement of Effect of Lysozyme and Nisin

The combination of cationic peptides and lysozyme or nisin may improve their antibacterial effectiveness and allow use in situations in which the single agent is inactive or inappropriate.

Lysozymes disrupt certain bacteria by cleaving the glycosidic bond between N-acetylglucosamine and N-acetylmuramic acid in the polysaccharide component of bacterial cell walls. However, lysozyme exhibits only weak antibacterial activity with a narrow spectrum of activity. The addition of cationic peptide may improve the effectiveness of this activity and broaden the spectrum of activity.

Nisins are 34-residue peptide lantibiotics with primarily anti-Gram-positive bacterial activity. Nisin is used in the food processing industry as a preservative, especially for cheese, canned fruits and vegetables. Nisin forms transient potential-dependent pores in the bacterial cytoplasmic membranes but also exhibits weak antibacterial activity with a narrow spectrum of activity. The addition of cationic peptide may improve the effectiveness of nisin and broaden the spectrum of activity.

F. In vivo Assays

In vivo testing involves the use of animal models of infection. Typically, but not exclusively, mice are used. The test organism is chosen according to the intended combination of cationic peptide and antibiotic to be evaluated. Generally, the test organism is injected intraperitoneally (IP) or intravenously (IV) at 10 to 100 times the fifty percent lethal dose ($LD_{50}$). The $LD_{50}$ is calculated using a method described by Reed and Muench (Reed L J and Muench H. *The American Journal of Hygiene*, 27:493-7.). The antibiotic agent and the cationic peptide are injected IP, IV, or subcutaneously (SC) individually as well as in combination to different groups of mice. The antimicrobial agents may be given in one or multiple doses. Animals are observed for 5 to 7 days. Other models of infection may also be used according to the clinical indication for the combination of antibiotic agents.

The number of mice in each group that survive the infectious insult is determined after 5 to 7 days. In addition, when bacteria are the test organisms, bacterial colony counts from blood, peritoneal lavage fluid, fluid from other body sites, and/or tissue from different body sites taken at various time intervals can be used to assess efficacy. Samples are serially diluted in isotonic saline and incubated for 20-24 hours, at 37° C., on a suitable growth medium for the bacterium.

Synergy between the cationic peptide and the antibiotic agent is assessed using a model of infection as described above. For a determination of synergy, one or more of the following should occur. The combination group should show greater survival rates compared to the groups treated with only one agent; the combination group and the antibiotic agent group have equivalent survival rates with the combination group receiving a lower concentration of antibiotic agent; the combination group has equivalent or better survival compared to an antibiotic agent group with a lower microorganismal load at various time points.

Overcoming tolerance can be demonstrated by lower bacterial colony counts at various time points in the combination group over the antibiotic agent group. This may also result in better survival rates for the combination group.

Similar animal models to those described above can be used to establish when inherent or acquired resistance is overcome. The microorganism strain used is, by definition, resistant to the antibiotic agent and so the survival rate in the antibiotic agent group will be close, if not equal, to zero percent. Thus, overcoming the inherent resistance of the microorganism to the antibiotic agent is demonstrated by increased survival of the combination group. Testing for reversing acquired resistance may be performed in a similar manner.

V. Combinations of Peptides and Antibiotic Agents

As discussed herein, cationic peptides are administered in combination with antibiotic agents. The combination enhances the activity of the antibiotic agents. Such combinations may be used to effect a synergistic result, overcome tolerance, overcome inherent resistance, or overcome acquired resistance of the microorganism to the antibiotic agent.

To achieve a synergistic effect, a combination of antibiotic agent and cationic peptide is administered to a patient or administered in such a manner as to contact the microorganism. Any combination of antibiotic agent and cationic peptide may result in a synergistic effect and, thus, is useful within the context of this invention.

In particular, certain microorganisms are preferred targets. In conjunction with these microorganisms, certain commonly used antibiotic agents are preferred to be enhanced. The table below sets out these microorganisms, antibiotic agents, and cationic peptide combinations that are preferred.

TABLE 3

| BACTERIAL SPECIES | ANTIMICROBIAL AGENTS | PEPTIDE |
|---|---|---|
| A. baumannii | Gentamicin | MBI 21A2 |
| B. cepacia | Ceftriaxone | MBI 11J02CN |
| E. cloacae | Ciprofloxacin | MBI 29A2 |
| E. faecalis | Amikacin | MBI 11B16CN |
| E. faecium | Vancomycin | MBI 29 |
| P. aeruginosa | Mupirocin | MBI 28 |
| P. aeruginosa | Tobramycin | MBI 11G13CN |
| S marcescens | Piperacillin | MBI 11G7CN |
| S. aureus | Piperacillin | MBI 11CN |
| S. maltophilia | Tobramycin | REWH 53A5CN |
| MYCOSES | ANTIFUNGAL AGENTS | PEPTIDE |
| *Candida* species | Fluconazole | MBI 28 |
| *Cryptococcus* | Fluconazole | MBI 29A3 |
| *Aspergillus* species | Itraconazole | MBI 26 |
| VIRUSES | ANTIVIRAL AGENTS | PEPTIDE |
| Herpes simplex virus | Acyclovir | MBI 11A2C N |
| Influenza A | virus Amantadine-rimantadine | MBI 21A1 |
| PARASITES | ANTIPARASITIC AGENTS | PEPTIDE |
| *Trichomonas vaginalis* | Metronidazole | MBI 29 |
| *Plasmodium falciparum* | Chloroquine | MBI 11D18CN |

To overcome tolerance, a combination of antibiotic agent and cationic peptide is administered to a patient or administered in such a manner as to contact the microorganism. Any combination of antibiotic agent and cationic peptide that overcomes tolerance is useful within the context of this invention. In particular, certain microorganisms, which exhibit tolerance to specific antibiotic agents are preferred targets. The table below sets out these microorganisms, antibiotic agents, and cationic peptide combinations that are preferred.

TABLE 4

| BACTERIAL SPECIES | ANTIMICROBIAL AGENTS | PEPTIDE |
|---|---|---|
| *Enterococcus* species | Ampicillin (Amino-penicillins) Piperacillin (Penicillins, antipseudomonal) | MBI 21A10 |
| *Enterococcus* species | Gentamicin (Aminoglycosides) | MBI 29 |
| *Enterococcus* species | Vancomycin, Teicoplanin (glycopeptides) | MBI 26 |
| *Streptococcus pneumoniae* | Penicillins | MBI 29A3 |
| *Salmonella typhi* | Chloramphenicol | MBI 11A1CN |
| *Campylobacter jejuni* | Erythromycin (Macrolides) | MBI 11B4CN |

To overcome inherent resistance, a combination of antibiotic agent and cationic peptide is administered to a patient or administered in such a manner as to contact the microorganism. Any combination of antibiotic agent and cationic peptide that overcomes resistance is useful within the context of this invention. In particular, certain microorganisms, which exhibit inherent resistance to specific antibiotic agents are preferred targets. The table below sets out these microorganisms, antibiotic agents, and cationic peptide combinations that are preferred.

TABLE 5

| BACTERIAL SPECIES | ANTIMICROBIAL AGENTS | PEPTIDE |
|---|---|---|
| Methicillin-resistant *S. aureus* | Amikacin | MBI 29F1 |
| *S. maltophilia* | Gentamicin | MBI 11D18CN |
| *S. maltophilia* | Gentamicin | MBI 26 |
| *S. maltophilia* | Tobramycin | MBI 29A3 |
| Methicillin-resistant *S. aureus* | Tobramycin | MBI 21A1 |
| *E. coli* | Mupirocin | MBI 21A1 |
| *S. maltophilia* | Amikacin | MBI 11B16CN |
| *S. maltophilia* | Amikacin | MBI 26 |
| *B. cepacia* | Amikacin | MBI 29A3 |
| Methicillin resistant *S. aureus* | Gentamicin | MBI 11D18CN |

| MYCOSES | ANTIFUNGAL AGENTS | PEPTIDE |
|---|---|---|
| Aspergillosis | Fluconazole | MBI 11D18CN |
| *Candida* species | Griseofulvin | MBI 29 |

To overcome acquired resistance, a combination of antibiotic agent and cationic peptide is administered to a patient or administered in such a manner as to contact the microorganism. Any combination of antibiotic agent and cationic peptide that overcomes resistance is useful within the context of this invention. In particular, certain microorganisms, which exhibit acquired resistance to specific antibiotic agents are preferred targets. The table below sets out these microorganisms, antibiotic agents, and cationic peptide combinations that are preferred.

TABLE 6

| BACTERIA | ANTIMICROBIAL AGENT | PEPTIDE |
|---|---|---|
| *Enterococcus* spp. | Vancomycin | MBI 26 |
| *P. aeruginosa* | Ceftriaxone | MBI 26 |
| *S. aureus* | Ciprofloxacin | MBI 29A2 |
| *E. cloacae* | Piperacillin | MBI 11F4CN |
| *P. aeruginosa* | Tobramycin | MBI 21A1 |
| *P. aeruginosa* | Ciprofloxacin | MBI 29A2 |
| *P. aeruginosa* | Gentamicin | MBI 11B16CN |
| *S. epidermidis* | Gentamicin | MBI 11D18CN |
| *Acinetobacter* spp. | Tobramycin | MBI 11F3CN |
| *Enterococcus* spp. | Vancomycin | MBI 11A1CN |

| MYCOSES | ANTIFUNGAL AGENTS | PEPTIDE |
|---|---|---|
| *Candida* species | Fluconazole | MBI 11CN |
| *Cryptococcus* | Fluconazole | MBI 11A1CN |

| VIRUSES | ANTIVIRAL AGENTS | PEPTIDE |
|---|---|---|
| *Herpes simplex* virus | Acyclovir | MBI 29 |
| Respiratory Syncytial Virus (RSV) | Ribavirin | MBI 26 |
| Influenza A virus | Amantadine-rimantadine | MBI 26 |

| PARASITES | ANTIPARASITIC AGENTS | PEPTIDE |
|---|---|---|
| *Trichomonas vaginalis* | Metronidazole | MBI 29 |
| *Pneumocystis carinii* | Cotrimoxazole | MBI 29A3 |
| *Plasmodium falciparum* | Chloroquine | MBI 26 |

Additional preferred combinations for indolicidin analogues are listed below:

| ANTIBIOTIC | PEPTIDE |
|---|---|
| Ciprofloxacin | MBI 11A1CN |
| Vancomycin | MBI 11A1CN |
| Piperacillin | MBI 11B9CN |
| Gentamicin | MBI 11B16CN |
| Piperacillin | MBI 11D18CN |
| Tobramycin | MBI 11D18CN |
| Vancomycin | MBI 11D18CN |
| Piperacillin | MBI 11E3CN |
| Tobramycin | MBI 11F3CN |
| Piperacillin | MBI 11F4CN |

VI. Polymer Modification of Peptides and Proteins

As noted herein, the present invention provides methods and compositions for modifying a compound with a free amine group. The amine group may be part of the native structure of the compound or added by a chemical method. Thus, peptides, proteins, and antibiotics and the like can be modified with an activated polyoxyalkylene and derivatives. When the compounds are peptides or proteins, the modified or derivatized forms are referred to herein as "APO-modified peptides" or "APO-modified proteins". Similarly, modified forms of antibiotics are referred to as "APO-modified antibiotics." APO-modified compounds (e.g., APO-cationic peptides) generally exhibit improved pharmacological properties.

A. Characteristics of an Activated Polyoxyalkylene Reagent

As discussed herein, a suitable reagent for formation of APO-modified compounds (e.g., peptides and proteins) comprises a hydrophobic region and a hydrophilic region, and optionally a linker. The hydrophobic region is a lipophilic compound with a suitable functional group for conjugation to the hydrophilic region or linker. The hydrophilic region is a polyoxyalkylene. As used herein, "polyoxyalkylene" refers to 2 or 3 carbon polyoxyalkylene polymers. The polymer chain is of a length 2 units or greater. Two carbon polyoxyalkylenes include polyoxyethylene and its derivatives, polyethylene glycol (PEG) of various molecular weights, and its derivatives, such as polysorbate. Three carbon polyoxyalkylenes include polyoxypropylene and derivatives and polypropylene glycol and its derivatives. Derivatives include alkyl- and aryl-polyoxyethylene compounds.

The hydrophobic region is a lipophilic moiety, generally a fatty acid, but may be a fatty alcohol, fatty thiol, hydrocarbons (such as 4-(1,1,3,3-tetramethylbutyl)-cyclohexyl), aryl compounds (such as 4-(1,1,3,3-tetramethylbutyl)-phenyl) and the like, which are also lipophilic compounds. The fatty acid may be saturated or unsaturated. The chain length does not appear to be important, although typically commercially available fatty acids are used and have chain lengths of $C_{12-18}$. The length may be limited however by solubility or solidity of the compound, that is longer lengths of fatty acids are solid at room temperature. Fatty acids of 12 carbons (lauryl), 14 carbons, 16 carbons (palmitate), and 18 carbons (monostearate or oleate) are preferred chain lengths.

The hydrophilic region is a polyoxyalkylene, such as polyethylene, polypropylene glycol monoether (for example Triton X114), and polysorbate. For polysorbate, the ether function is formed by the linkage between the polyoxyethylene chain, preferably having a chain length of from 2 to 100 monomeric units, and the sorbitan group. Polymethylene glycol is unsuitable for administration in animals due to formation of formaldehydes, and glycols with a chain length of $\geqq 4$ may be insoluble. Mixed polyoxyethylene-polyoxypropylene chains are also suitable.

A linker for bridging the hydrophilic and hydrophobic regions is not required, but if used, should be able to bridge both a polyoxyalkylene and the, hydrophobic region. Suitable linkers include sorbitan, sugar alcohols, ethanolamine, ethanolthiol, 2-mercaptoethanol, 1,6-diaminohexane, an amino acid (e.g., glutamine, lysine), other reduced sugars, and the like. For example, sorbitan forms an ester linkage with the fatty acid in a polysorbate.

Suitable compounds include polyoxyethylenesorbitans, such as the monolaurate, monooleate, monopalmitate, monostearate, trioleate, and tristearate esters. These and other suitable compounds may be synthesized by standard chemical methods or obtained commercially (e.g., Sigma Chemical Co., Mo.; Aldrich Chemical Co., Wis.; J. B. Baker, N. J.).

B. Activation of Reagent

The reagent is activated by exposure to UV light with free exchange of air or by chemical treatment with ammonium persulfate, or a combination of these methods.

Photoactivation is achieved using a lamp that irradiates at 254 nm or 302 nm. Preferably, the output is centered at 254 nm. Longer wave lengths may require longer activation time. While some evidence exists that fluorescent room light can activate the polysorbates, experiments have shown that use of UV light at 254 nm yields maximal activation before room light yields a detectable level of activation.

Air plays an important role in the activation of the polysorbates. Access to air doubles the rate of activation relative to activations performed in sealed containers. A shallow reaction chamber with a large surface area would facilitate oxygen exchange. It is not yet known which gas is responsible; an oxygen derivative is likely, although peroxides are not involved. UV exposure of compounds with ether linkages is known to generate peroxides, which can be detected and quantified using peroxide test strips. In a reaction, hydrogen peroxide at 1 to 10 fold higher level than found in UV-activated material was added to a polysorbate solution in the absence of light. No activation was obtained.

The reagent is placed in a suitable vessel for irradiation. Studies with 2% polysorbate 80 indicate that 254 nm light at 1800 $\mu W/cm^2$ is completely absorbed by the solution at a depth of 3-4 cm. Thus, the activation rate can be maximized by irradiating a relatively thin layer.

As such, a consideration for the vessel is the ability to achieve uniform irradiation. As noted above, a large shallow reaction chamber is desirable, however, it may be difficult to achieve on a large scale. To compensate, simple stirring that facilitates the replenishment of air in the solution achieves an equivalent result. Thus, if the pathlength is long or the reaction chamber is not shallow, the reagent may be mixed or agitated. The reagent can be activated in any aqueous solution and buffering is not required.

An exemplary activation takes place in a cuvette with a 1 cm liquid thickness. The reagent is irradiated at a distance of less than 9 cm at 1500 $\mu W/cm^2$ (initial source output) for approximately 24 hours. Under these conditions, the activated reagent converts a minimum of 85% of the peptide to APO-peptide.

As noted above, the polyoxyalkylenes can be activated via chemical oxidation with ammonium persulfate. The activation is rapid and the extent of activation increases with the concentration of ammonium persulfate. Ammonium persulfate can be used in a range from about 0.01%-0.5%, and most preferably from 0.025 to 0.1%. If the levels of ammonium persulfate are too high, the peroxide byproducts can have an adverse effect on the compounds being modified. This adverse effect can be diminished by treatment of activated polyoxyalkylenes with mercaptoethanol, or another mild reducing agent, which does not inhibit the formation of APO-therapeutics. Peroxides generated from UV treatment can also be reduced by treatment with mercaptoethanol. Furthermore, as noted above, the UV procedure can be performed in conjunction with chemical activation.

C. Modification of Peptides or Proteins with Activated Reagent

The therapeutics are reacted with the APO reagent in either a liquid or solid phase and become modified by the attachment of the APO derivative. The methods described herein for attachment offer the advantage of maintaining the charge on the therapeutic, such as a peptide or protein. When the charge of the peptide is critical to its function, such as the antibiotic activity of cationic peptides described herein, these attachment methods offer additional advantages. Methods that attach groups via acylation result in the loss of positive charge via conversion of amino to amido groups. In addition, no bulky or potentially antigenic linker, such as a triazine group, is known to be introduced by the methods described herein.

As noted above, APO-therapeutic formation occurs in solid phase or in aqueous solution. By way of example, briefly, in the solid phase method, a peptide or other therapeutic is suspended in a suitable buffer, such as an acetate buffer. Other suitable buffers that support APO-therapeutic formation may also be used. The acetate buffer may be sodium, potassium, lithium, and the like. Other acetate solutions, such as HAc or HAc-NaOH, are also suitable. A preferred pH range for the buffer is from 2 to 8.3, although a wider range may be used. When the starting pH of the acetic acid-NaOH buffer is varied, subsequent lyophilization from 200 mM acetic acid buffer yields only the Type I modified peptide (see Example 14). The presence of an alkaline buffer component results in the formation of Type II modified peptides. A typical peptide concentration is 1 mg/ml, which results in 85-95% modified peptide, however other concentrations are suitable. The major consideration for determining concentration appears to be economic. The activated polymer (APO) is added in molar excess to the therapeutic. Generally, a starting ratio of approximately 2.5:1 (APO:therapeutic) to 5:1 (APO:therapeutic) generates APO-modified therapeutic in good yield.

The reaction mix is then frozen (e.g., −80° C.) and lyophilized. Sodium acetate disproportionates into acetic acid and NaOH during lyophilization; removal of the volatile acetic acid by the vacuum leaves NaOH dispersed throughout the result solid matrix. This loss of acetic acid is confirmed by a pH increase detected upon dissolution of the lyophilizate. No APO-modified therapeutic is formed in acetate buffer if the samples are only frozen then thawed.

The modification reaction can also take place in aqueous solution. However, APO modifications do not occur at ambient temperature in any acetate buffer system tested regardless of pH. APO modifications also are not formed in phosphate buffers as high as pH 11.5. APO modification does occur in a sodium carbonate buffer at a pH greater than about 8.5. Other buffers may also be used if they support derivatization. A pH range of 9-11 is also suitable, and pH 10 is most commonly used. The reaction occurs in two phases: Type I modified peptides form first, followed by formation of Type II modified peptides.

In the present invention, linkage occurs at an amino or a nucleophilic group. The amino group may be a primary amine, a secondary amine, or an aryl amine. Nucleophilic groups that may be APO-modified include, but are not limited to, hydrazine derivatives, hydroxylamine derivatives, and sulfhydryl compounds. Preferably, the modification occurs at an amino group, more preferably at a primary or secondary amino group, and most preferably at a primary amino group.

For a peptide, linkage can occur at the α-NH$_2$ of the N-terminal amino acid or ε-NH$_2$ group of lysine. Other primary and secondary amines may also be modified. Complete blocking of all amino groups by acylation (MBI 11CNY1) inhibits APO-peptide formation. Thus, modification of arginine or tryptophan residues does not occur. If the only amino group available is the α-amino group (e.g., MBI 11B9CN and MBI 11G14CN), the Type I form is observed. The inclusion of a single lysine (e.g., MBI 11B1CN, MBI 11B7CN, MBI 11B8CN), providing an ε-amino group, results in Type II forms as well. The amount of Type II formed increases for peptides with more lysine residues.

Many antibiotics have free amine groups. Such antibiotics include but are not limited to ampicillin, amoxicillin, amikacin, ciprofloxacin, gentamicin, teicoplanin, tobramycin, and vancomycin. Using the methods described herein, several peptides, including indolicidin, indolicidin analogues, gramicidin and bacitracin-2 have been polymer modified.

Examples of compounds that have modified by the solid phase method are listed in the table below.

TABLE 7

| Compound | Action | Modification |
|---|---|---|
| Amoxicillin | penicillin antibiotic | Yes |
| Amphotericin B | anti-fungal | No |
| Ampicillin | penicillin antibiotic | Yes |
| Bacitracin | peptide antibiotic | Yes |
| Cephalosporin C | aminoglycoside antibiotic | No |
| Ciprofloxacin | quinolone antibiotic | Uncertain* |
| 4,4'-Diaminodiphenyl Sulfone | anti-leprotic | Yes |
| Gentamicin | aminoglycoside antibiotic | Yes |
| Gramicidin S | peptide antibiotic | Yes |
| Sulfadiazine | sulfonamide antibiotic | No |
| Vancomycin | glycopeptide antibiotic | Yes |

*Ciprofloxacin was partially destroyed by the process.

D. Purification and Physical Properties of APO-Modified Therapeutics

The APO-modified therapeutics may be purified. In circumstances in which the free therapeutic, such as a peptide is toxic, purification may be necessary to remove unmodified therapeutic and/or unreacted polyoxyalkylenes. Any of a variety of purification methods may be used. Such methods include reversed phase HPLC, precipitation by organic solvent to remove polysorbate, size exclusion chromatography, ion exchange chromatography, filtration and the like. RP-HPLC is preferred. Procedures for these separation methods are well known.

APO-therapeutic formation can result in the generation of products that are more hydrophobic than the parent compound. This property can be exploited to effect separation of the conjugate from free compound by RP-HPLC. As shown herein, peptide-conjugates are resolved into two populations based on their hydrophobicity as determined by RP-HPLC; the Type I population elutes slightly earlier than the Type II population.

The MBI 11 series of peptides have molecular weights between 1600 and 2500. When run on a Superose 12 column, a size exclusion column, these peptides adsorb to the resin, giving long retention times. In contrast, the APO-modified peptides do not adsorb and elute at 50 kDa (MBI11CN-Tw80) and at 69 kDa (MBI 11A3CN-Tw80), thus demonstrating a large increase in apparent molecular mass (Stokes radius).

An increase in apparent molecular mass could enhance the pharmacokinetics of peptides in particular because increased molecular mass reduces the rate at which peptides and proteins are removed from blood. Micelle formation may offer additional benefits by delivering "packets" of peptide molecules to microorganisms rather than relying on the multiple binding of single peptide molecules. In addition, APO-modified peptides are soluble in methylene chloride or chloroform (e.g., to at least 10 mg/mL), whereas the parent peptide is essentially insoluble. This increased organic solubility may significantly enhance the ability to penetrate tissue barriers and may be exploited for a simplified purification of the APO-peptide. The increased solubility in organic media may also allow the formulation of peptides in oil or lipid based delivery systems which target specific sites, such as solid tumors.

In addition, by circular dichroism (CD) studies, APO-modified peptides are observed to have an altered 3-dimensional conformation. As shown in the Examples, MBI 11CN and MBI 11B7CN have unordered structures in phosphate buffer or 40% aqueous trifluoroethanol (TFE) and form a β-turn conformation only upon insertion into liposomes. In contrast, CD spectra for APO-modified MBI 11CN and APO-modified MBI 11B7CN indicate β-turn structure in phosphate buffer.

Cationic peptides appear to maintain their original charge after modification with an APO, thereby preventing loss of activity sometimes caused by acylation reactions. Moreover, the present methods are not known to introduce antigenic linkers.

E. Biological Properties of APO-Modified Therapeutics

The biological properties of APO-modified therapeutics appear to be improved compared to unmodified therapeutics. For example, modified and unmodified peptides are compared. Because the product consists of a peptide of known composition coupled to one or more polyoxyalkylene components derived from a polymeric mixture, defining an exact molecular weight for concentration calculations is not readily achieved. It is possible, however, to determine the concentration by spectrophotometric assay. Such a measurement is used to normalize APO-peptide concentrations for biological assays. For example, a 1 mg/mL MBI 11CN-Tw80 solution contains the same amount of cationic peptide as a 1 mg/mL solution of the parent peptide, thus allowing direct comparison of toxicity and efficacy data. The modified peptides have an equivalent MIC to unmodified peptides. In vivo, however, the modified peptides demonstrate a lower $LC_{50}$ than the unmodified peptides against a panel of tumor cell lines. Thus, formation of APO-peptides increases the potency of cationic peptides against cancer cells in culture.

In general, the efficacy of a modified therapeutic is determined by in vitro and in vivo assays used for the unmodified therapeutic. Thus, the assays employed depend upon the therapeutic. Assays for the therapeutics disclosed herein are well known. Assays include those for biological activity, pharmacokinetics, toxicity, adverse reactions, immunogenicity, and the like. Such assays are available to those skilled in the art.

VII. Formulations and Administration

As noted above, the present invention provides methods for treating and preventing infections by administering to a patient a therapeutically effective amount of a peptide analogue of indolicidin as described herein. Patients suitable for such treatment may be identified by well-established hallmarks of an infection, such as fever, pus, culture of organisms, and the like. Infections that may be treated with peptide analogues include those caused by or due to microorganisms. Examples of microorganisms include bacteria (e.g., Gram-positive, Gram-negative), fungi, (e.g., yeast and molds), parasites (e.g., protozoans, nematodes, cestodes and trematodes), viruses, and prions. Specific organisms in these classes are well known (see for example, Davis et al., *Microbiology*, 3rd edition, Harper & Row, 1980). Infections include, but are not limited to, toxic shock syndrome, diphtheria, cholera, typhus, meningitis, whooping cough, botulism, tetanus, pyogenic infections, dysentery, gastroenteritis, anthrax, Lyme disease, syphilis, rubella, septicemia and plague.

More specifically, clinical indications include, but are not limited to: 1/ infections following insertion of intravascular devices or peritoneal dialysis catheters; 2/ infection associated with medical devices or prostheses; 3/ infection during hemodialysis; 4/ *S. aureus* nasal and extra-nasal carriage; 5/ burn wound infections; 6/ surgical wounds, 7/ acne, including severe acne vulgaris; 8/ nosocomial pneumonia; 9/ meningitis; 10/ cystic fibrosis; 11/ infective endocarditis; 12/ osteomyelitis; and 13/ sepsis in an immunocompromised host.

1/Infections following insertion of contaminated intravascular devices, such as central venous catheters, or peritoneal dialysis catheters. These catheters are cuffed or non-cuffed, although the infection rate is higher for non-cuffed catheters. Both local and systemic infection may result from contaminated intravascular devices, more than 25,000 patients develop device related bacteremia in the United States each year. The main organisms responsible are coagulase-negative staphylococci (CoNS), *Staphylococcus aureus, Enterococcus* spp, *E. coli* and *Candida* spp.

The peptide and/or antibiotic, preferably as an ointment or cream, can be applied to the catheter site prior to insertion of the catheter and then again at each dressing change. The peptide may be incorporated into the ointment or cream at a concentration preferably of about 0.5 to about 2% (w/v).

2/ Infection associated with medical devices or prostheses, e.g. catheter, grafts, prosthetic heart valves, artificial joints, etc. One to five percent of indwelling prostheses become infected which usually requires removal or replacement of the prostheses. The main organisms responsible for these infections are CoNS and *S. aureus.*

Preferably, the peptide and/or antibiotic can be coated, either covalently bonded or by any other means, onto the medical device either at manufacture of the device or after manufacture but prior to insertion of the device. In such an application, the peptide antibiotic is preferably applied as a 0.5 to 2% solution.

3/ Infection during hemodialysis. Infection is the second leading cause of death in patients on chronic hemodialysis. Approximately 23% of bacteremias are due to access site infections. The majority of graft infections are caused by coagulate-positive (*S. aureus*) and coagulate-negative staphylococci. To combat infection, the peptide alone or in combination with an antibiotic can be applied as an ointment or cream to the dialysis site prior to each hemodialysis procedure.

4/ *S. aureus* nasal and extra-nasal carriage. Infection by this organism may result in impetigenous lesions or infected wounds. It is also associated with increased infection rates following cardiac surgery, hemodialysis, orthopedic surgery and neutropenia, both disease induced and iatrogenic. Nasal and extra-nasal carriage of staphylococci can result in hospital outbreaks of the same staphylococci strain that is colonizing a patient's or hospital worker's nasal passage or extra-nasal site. Much attention has been paid to the eradication of nasal colonization, but the results of treatment have been generally unsatisfactory. The use of topical antimicrobial substances, such as Bacitracin, Tetracycline, or Chlorhexidine, results in the suppression of nasal colonization, as opposed to its eradication.

The peptide alone or in combination with an antibiotic are preferably applied intra-nasally, formulated for nasal application, as a 0.5 to 2% ointment, cream or solution. Application may occur once or multiple times until the colonization of staphylococci is reduced or eliminated.

5/ Burn wound infections. Although the occurrence of invasive burn wound infections has been significantly reduced, infection remains the most common cause of morbidity and mortality in extensively burned patients. Infection is the predominant determinant of wound healing, incidence of complications, and outcome of burn patients. The main organisms responsible are *Pseudomonas aeruginosa, S. aureus, Streptococcus pyogenes*, and various gram-negative organisms. Frequent debridements and establishment of an epidermis, or a surrogate such as a graft or a skin substitute, is essential for prevention of infection.

The peptide alone or in combination with antibiotics can be applied to burn wounds as an ointment or cream and/or administered systemically. Topical application may prevent systemic infection following superficial colonization or eradicate a superficial infection. The peptide is preferably administered as a 0.5 to 2% cream or ointment. Application to the skin could be done once a day or as often as dressings are changed. The systemic administration could be by intravenous, intramuscular or subcutaneous injections or infusions. Other routes of administration could also be used.

6/ Surgical wounds, especially those associated with foreign material, e.g. sutures. As many as 71% of all nosocomial infections occur in surgical patients, 40% of which are infections at the operative site. Despite efforts to prevent infection, it is estimated that between 500,000 and 920,000 surgical wound infections complicate the approximately 23 million surgical procedures performed annually in the United States. The infecting organisms are varied but staphylococci are important organisms in these infections.

The peptide alone or with an antibiotic may be applied as an ointment, cream or liquid to the wound site or as a liquid in the wound prior to and during closure of the wound. Following closure the peptide antibiotic could be applied at dressing changes. For wounds that are infected, the peptide antibiotic could be applied topically and/or systemically.

7/ Acne, including severe acne vulgaris. This condition is due to colonization and infection of hair follicles and sebaceous cysts by *Propionibacterium acne*. Most cases remain mild and do not lead to scarring although a subset of patients develop large inflammatory cysts and nodules, which may drain and result in significant scarring.

The peptide alone or with an antibiotic can be incorporated into soap or applied topically as a cream, lotion or gel to the affected areas either once a day or multiple times during the day. The length of treatment may be for as long as the lesions are present or used to prevent recurrent lesions. The peptide antibiotic could also be administered orally or systemically to treat or prevent acne lesions.

8/ Nosocomial pneumonia. Nosocomial pneumonias account for nearly 20% of all nosocomial infections. Patients most at risk for developing nosocomial pneumonia are those in an intensive care units, patients with altered levels of consciousness, elderly patients, patients with chronic lung disease, ventilated patients, smokers and post-operative patients. In a severely compromised patient, multiantibiotic-resistant nosocomial pathogens are likely to be the cause of the pneumonia.

The main organisms responsible are *P. aeruginosa, S. aureus, Klebsiella pneumoniae* and *Enterobacter* spp. The peptide alone or in combination with other antibiotics could be administered orally or systemically to treat pneumonia. Administration could be once a day or multiple administrations per day. Peptide antibiotics could be administered directly into the lung via inhalation or via installation of an endotracheal tube.

9/ Meningitis. Bacterial meningitis remains a common disease worldwide. Approximately 25,000 cases occur annually, of which 70% occur in children under 5 years of age. Despite an apparent recent decline in the incidence of severe neurologic sequelae among children surviving bacterial meningitis, the public health problems as a result of this disease are significant worldwide. The main responsible organisms are *H. influenzae, Streptococcus pneumoniae* and *Neisseria meningitidis*. Community acquired drug resistant *S. pneumoniae* are emerging as a widespread problem in the United States. The peptide alone or in combination with known antibiotics could be administered orally or systemically to treat meningitis. The preferred route would be intravenously either once a day or multiple administration per day. Treatment would preferably last for up to 14 days.

10/ Cystic fibrosis. Cystic fibrosis (CF) is the most common genetic disorder of the Caucasian population. Pulmonary disease is the most common cause of premature death in cystic fibrosis patients. Optimum antimicrobial therapy for CF is not known, and it is generally believed that the introduction of better anti-pseudomonal antibiotics has been the major factor contributing to the increase in life expectancy for CF patients. The most common organisms associated with lung disease in CF are *S. aureus, P. aeruginosa* and *H. influenzae*.

The peptide alone or in combination with other antibiotics could be administrated orally or systemically or via aerosol to treat cystic fibrosis. Preferably, treatment is effected for up to 3 weeks during acute pulmonary disease and/or for up to 2 weeks every 2-6 months to prevent acute exacerbations.

11/ Infective endocarditis. Infective endocarditis results from infection of the heart valve cusps, although any part of the endocardium or any prosthetic material inserted into the heart may be involved. It is usually fatal if untreated. Most infections are nosocomial in origin, caused by pathogens increasingly resistant to available drugs. The main organisms responsible are *Viridans streptococci, Enterococcus* spp, *S. aureus* and CoNS.

The peptide alone or in combination with other antibiotics could be administered orally or systemically to treat endocarditis, although systemic administration would be preferred. Treatment is preferably for 2-6 weeks in duration and may be given as a continuous infusion or multiple administration during the day.

12/ Osteomyelitis. In early acute disease the vascular supply to the bone is compromised by infection extending into surrounding tissue. Within this necrotic and ischemic tissue, the bacteria may be difficult to eradicate even after an intense host response, surgery, and/or antibiotic therapy. The main organisms responsible are *S. aureus, E. coli*, and *P. aeruginosa*.

The peptide antibiotic could be administered systemically alone or in combination with other antibiotics. Treatment would be 2-6 weeks in duration. The peptide antibiotic could be given as a continuous infusion or multiple administration during the day. Peptide antibiotic could be used as an antibiotic-impregnated cement or as antibiotic coated beads for joint replacement procedures.

13/ Sepsis in immunocompromised host. Treatment of infections in patients who are immunocompromised by virtue of chemotherapy-induced granulocytopenia and immunosuppression related to organ or bone marrow transplantation is always a big challenge. The neutropenic patient is especially susceptible to bacterial infection, so antibiotic therapy should be initiated promptly to cover likely pathogens, if infection is suspected. Organisms likely to cause infections in granulocytopenic patients are: *S. epidermidis, S. aureus, S. viridans, Enterococcus* spp, *E. coli, Klebsiella* spp, *P. aeruginosa* and *Candida* spp.

The peptide alone or with an antibiotic is preferably administered orally or systemically for 2-6 weeks in duration. The peptide antibiotic could be given as a continuous infusion or multiple administration during the day.

Effective treatment of infection may be examined in several different ways. The patient may exhibit reduced fever, reduced number of organisms, lower level of inflammatory molecules (e.g., IFN-γ, IL-12, IL-1, TNF), and the like.

The in vivo therapeutic efficacy from administering a cationic peptide and antibiotic agent in combination is based on a successful clinical outcome and does not require 100% elimination of the organisms involved in the infection. Achieving a level of antimicrobial activity at the site of infection that allows the host to survive or eradicate the microorganism is sufficient. When host defenses are maximally effective, such as in an otherwise healthy individual, only a minimal antimicrobial effect may suffice. Thus, reducing the organism load by even one log (a factor of 10) may permit the defenses of the host to control the infection. In addition, clinical therapeutic success may depend more on augmenting an early bactericidal effect than on the long-term effect. These early events are a significant and critical part of therapeutic success, because they allow time for the host defense mechanisms to activate. This is especially true for life-threatening infections (e.g. meningitis) and other serious chronic infections (e.g. infective endocarditis).

Peptides and antibiotic agents of the present invention are preferably administered as a pharmaceutical composition. Briefly, pharmaceutical compositions of the present invention may comprise one or more of the peptide analogues described herein, in combination with one or more physiologically acceptable carriers, diluents, or excipients. As noted herein, the formulation buffer used may affect the efficacy or activity of the peptide analogue. A suitable formulation buffer contains buffer and solubilizer. The formulation buffer may comprise buffers such as sodium acetate, sodium citrate, neutral buffered saline, phosphate-buffered saline, and the like or salts, such as NaCl. Sodium acetate is preferred. In general, an acetate buffer from 5 to 500 mM is used, and preferably from 100 to 200 mM. The pH of the final formulation may range from 3 to 10, and is preferably approximately neutral (about pH 7-8). Solubilizers, such as polyoxyethylenesorbitans (e.g., Tween 80, Tween 20) and polyoxyethylene ethers (e.g., Brij 56) may also be added if the compound is not already polymer-modified.

Although the formulation buffer is exemplified herein with peptide analogues of the present invention, this buffer is generally useful and desirable for delivery of other peptides. Peptides that may be delivered in this formulation buffer include indolicidin, other indolicidin analogues (see, PCT WO 95/22338), bacteriocins, gramicidin, bactenecin, drosocin, polyphemusins, defensins, cecropins, melittins, cecropin/melittin hybrids, magainins, sapecins, apidaecins, protegrins, tachyplesins, thionins; IL-1 through 15; corticotropin-releasing hormone; human growth hormone; insulin; erythropoietin; thrombopoietin; myelin basic protein peptides; various colony stimulating factors such as M-CSF, GM-CSF, kit ligand; and peptides and analogues of these and similar proteins.

Additional compounds may be included in the compositions. These include, for example, carbohydrates such as glucose, mannose, sucrose or dextrose, mannitol, other proteins, polypeptides or amino acids, chelating agents such as EDTA or glutathione, adjuvants and preservatives. As noted herein, pharmaceutical compositions of the present invention may also contain one or more additional active ingredients, such as an antibiotic (see discussion herein on synergy) or cytokine.

The compositions may be administered in a delivery vehicle. For example, the composition can be encapsulated in a liposome (see, e.g., WO 96/10585; WO 95/35094), complexed with lipids, encapsulated in slow-release or sustained release vehicles, such as poly-galactide, and the like.

Within other embodiments, compositions may be prepared as a lyophilizate, utilizing appropriate excipients to provide stability.

Pharmaceutical compositions of the present invention may be administered in various manners. For example, cationic peptides with or without antibiotic agents may be administered by intravenous injection, intraperitoneal injection or implantation, subcutaneous injection or implantation, intradermal injection, lavage, inhalation, implantation, intramuscular injection or implantation, intrathecal injection, bladder wash-out, suppositories, pessaries, topical (e.g., creams, ointments, skin patches, eye drops, ear drops, shampoos) application, enteric, oral, or nasal route. The combination is preferably administered intravenously. Systemic routes include intravenous, intramuscular or subcutaneous injection (including a depot for long-term release), intraocular or retrobulbar, intrathecal, intraperitoneal (e.g. by intraperitoneal lavage), transpulmonary using aerosolized or nebulized drug or transdermal. Topical routes include administration in the form of salves, ophthalmic drops, ear drops, or irrigation fluids (for, e.g. irrigation of wounds). The compositions may be applied locally as an injection, drops, spray, tablets, cream, ointment, gel, and the like. They may be administered as a bolus or as multiple doses over a period of time.

The level of peptide in serum and other tissues after administration can be monitored by various well-established techniques such as bacterial, chromatographic or antibody based, such as ELISA, assays.

Pharmaceutical compositions of the present invention are administered in a manner appropriate to the infection or disease to be treated. The amount and frequency of administration will be determined by factors such as the condition of the patient, the cause of the infection, and the severity of the infection. Appropriate dosages may be determined by clinical trials, but will generally range from about 0.1 to 50 mg/kg. The general range of dosages for the antibiotic agents are presented below.

TABLE 8

| ANTIMICROBIAL AGENT | DOSE RANGE |
|---|---|
| Ciprofloxacin | 400-1500 mg/day |
| Gentamicin | 3 mg/kg/day |
| Tobramycin | 3 mg/kg/day |
| Imipenem | 1500 mg/kg every 12 h |
| Piperacillin | 24 g/day |
| Vancomycin, Teicoplanin | 6-30 mg/kg/day |
| Streptomycin | 500 mg-1 g/every 12 h |
| Methicillin | 100-300 mg/day |
| Ampicillin, Amoxicillin | 250-500 mg/every 8 h |
| Penicillin | 200,000 units/day |
| Ceftriaxone | 4 g/day |
| Cefotaxime | 12 g/day |
| Metronidazole | 4 g/day |
| Tetracycline | 500 mg/every 6 h |
| Rifampin | 600 mg/day |
| Fluconazole | 150-400 mg/day |
| Acyclovir | 200-400 mg/day |
| Ribavirin | 20 mg/ml (aerosol). |
| Amantadine-rimantadine | 200 mg/day |
| Metronidazole | 2 g/day |
| Cotrimoxazole | 15-20 mg/kg/day |
| Chloroquine | 800 mg/day |

In addition, the compositions of the present invention may be used in the manner of common disinfectants or in any situation in which microorganisms are undesirable. For example, these peptides may be used as surface disinfectants, coatings, including covalent bonding, for medical devices, coatings for clothing, such as to inhibit growth of bacteria or repel mosquitoes, in filters for air purification, such as on an airplane, in water purification, constituents of shampoos and soaps, food preservatives, cosmetic preservatives, media preservatives, herbicide or insecticides, constituents of building materials, such as in silicone sealant, and in animal product processing, such as curing of animal hides. As used herein, "medical device" refers to any device for use in a patient, such as an implant or prosthesis. Such devices include, stents, tubing, probes, cannulas, catheters, synthetic vascular grafts, blood monitoring devices, artificial heart valves, needles, and the like.

For these purposes, typically the peptides alone or in conjunction with an antibiotic are included in compositions commonly employed or in a suitable applicator, such as for applying to clothing. They may be incorporated or impregnated into the material during manufacture, such as for an air filter, or otherwise applied to devices. The peptides and antibiotics need only be suspended in a solution appropriate for the device or article. Polymers are one type of carrier that can be used.

The peptides, especially the labeled analogues, may be used in image analysis and diagnostic assays or for targeting sites in eukaryotic multicellular and single cell cellular organisms and in prokaryotes. As a targeting system, the analogues may be coupled with other peptides, proteins, nucleic acids, antibodies and the like.

The following examples are offered by way of illustration, and not by way of limitation.

EXAMPLES

Example 1

Synthesis Purification and Characterization of Cationic Peptides and Analogues

Peptide synthesis is based on the standard solid-phase Fmoc protection strategy. The instrument employed is a 9050 Plus PepSynthesiser (PerSeptive BioSystems Inc.). Polyethylene glycol polystyrene (PEG-PS) graft resins are employed as the solid phase, derivatized with an Fmoc-protected amino acid linker for C-terminal amide synthesis. HATU (O-(7-azabenzotriazole-1-yl)-1,1,3,3-tetramethyluronium hexafluorophosphate) is used as the coupling reagent. During synthesis, coupling steps are continuously monitored to ensure that each amino acid is incorporated in high yield. The peptide is cleaved from the solid-phase resin using trifluoroacetic acid and appropriate scavengers and the crude peptide is purified using preparative reversed-phase chromatography. Typically the peptide is prepared as the trifluoroacetate salt, but other salts, such as acetate, chloride and sulfate, can also be prepared by salt exchange.

All peptides are analyzed by mass spectrometry to ensure that the product has the expected molecular mass. The product should have a single peak accounting for >95% of the total peak area when subjected to analytical reversed-phase high performance liquid chromatography (RP-HPLC), a separation method that depends on the hydrophobicity of the peptide. In addition, the peptide should show a single band accounting for >90% of the total band intensity when subjected to acid-urea gel electrophoresis, a separation method based on the charge to mass ration of the peptide.

Peptide content, the amount of the product that is peptide rather than retained water, salt or solvent, is measured by quantitative amino acid analysis, free amine derivatization or spectrophotometric quantitation. Amino acid analysis also provides information on the ratio of amino acids present in the peptide, which assists in confirming the authenticity of the peptide.

Peptide analogues and their names are listed below. In this list, and elsewhere, the amino acids are denoted by the one-letter amino acid code and lower case letters represent the D-form of the amino acid.

```
Apidaecin IA    G N N R P V Y I P Q P R P P H P R I         (SEQ ID NO:96)

Deber A2KA2     K K A A A K A A A A K A A W A A K A A A K K K K   (SEQ ID NO:97)

10              I L P W K W P W W P W R R                   (SEQ ID NO:98)

10CN            I L P W K W P W W P W R R                   (SEQ ID NO:98)

11              I L K K W P W W P W R R K                   (SEQ ID NO:99)

11CN            I L K K W P W W P W R R K                   (SEQ ID NO:99)

11CNR           K R R W P W W P W K K L I                   (SEQ ID NO:25)

11A1CN          I L K K F P F F P F R R K                   (SEQ ID NO:100)

11A2CN          I L K K I P I I P I R R K                   (SEQ ID NO:33)

11A3CN          I L K K Y P Y Y P Y R R K                   (SEQ ID NO:34)

11A4CN          I L K K W P W P W R R K                     (SEQ ID NO:65)

11A5CN          I L K K Y P W Y P W R R K                   (SEQ ID NO:35)

11A6CN          I L K K F P W F P W R R K                   (SEQ ID NO:36)

11A7CN          I L K K F P F W P W R R K                   (SEQ ID NO:37)

11A8CN          I L R Y V Y Y V Y R R K                     (SEQ ID NO:38)

11A9CN          I L R W P W W P W W P W R R K               (SEQ ID NO:39)

11A10CN         W W R W P W W P W R R K                     (SEQ ID NO:40)
```

-continued

| | | |
|---|---|---|
| 11B1CN | I L R R W P W W P W R R K | (SEQ ID NO:41) |
| 11B2CN | I L R R W P W W P W R K | (SEQ ID NO:42) |
| 11B3CN | I L K W P W W P W R R K | (SEQ ID NO:43) |
| 11B4CN | I L K K W P W W P W R K | (SEQ ID NO:44) |
| 11B5CN | I L K W P W W P W R K | (SEQ ID NO:45) |
| 11B7CN | I L R W P W W P W R R K | (SEQ ID NO:101) |
| 11B7CNR | K R R W P W W P W R L I | (SEQ ID NO:46) |
| 11B8CN | I L W P W W P W R R K | (SEQ ID NO:66) |
| 11B9CN | I L R R W P W W P W R R R | (SEQ ID NO:102) |
| 11B10CN | I L K K W P W W P W K K K | (SEQ ID NO:103) |
| 11B16CN | I L R W P W W P W R R K I M I L K K A G S | (SEQ ID NO:47) |
| 11B17CN | I L R W P W W P W R R K M I L K K A G S | (SEQ ID NO:24) |
| 11B18CN | I L R W P W W P W R R K D M I L K K A G S | (SEQ ID NO:48) |
| 11B19CN | I L R W P W R R W P W R R K | (SEQ ID NO:49) |
| 11B20CN | I L R W P W W P W R R K I L M R W P W W P W R R K M A A | (SEQ ID NO:104) |
| 11C3CN | I L K K W A W W P W R R K | (SEQ ID NO:105) |
| 11C4CN | I L K K W P W W A W R R K | (SEQ ID NO:106) |
| 11C5CN | W W K K W P W W P W R R K | (SEQ ID NO:107) |
| 11D1CN | L K K W P W W P W R R K | (SEQ ID NO:67) |
| 11D3CN | P W W P W R R K | (SEQ ID NO:68) |
| 11D4CN | I L K K W P W W P W R R K M I L K K A G S | (SEQ ID NO:69) |
| 11D5CN | I L K K W P W W P W R R M I L K K A G S | (SEQ ID NO:51) |
| 11D6CN | I L K K W P W W P W R R I M I L K K A G S | (SEQ ID NO:52) |
| 11D9M8 | W W P W R R K | (SEQ ID NO:70) |
| 11D10M8 | I L K K W P W | (SEQ ID NO:71) |
| 11D11H | I L K K W P W W P W R R K M | (SEQ ID NO:108) |
| 11D12H | I L K K W P W W P W R R M | (SEQ ID NO:109) |
| 11D13H | I L K K W P W W P W R R I M | (SEQ ID NO:110) |
| 11D14CN | I L K K W W W P W R K | (SEQ ID NO:55) |
| 11D15CN | I L K K W P W W W R K | (SEQ ID NO:56) |
| 11D18CN | W R I W K P K W R L P K W | (SEQ ID NO:26) |
| 11D19CN | C L R W P W W P W R R K | (SEQ ID NO:111) |
| 11E1CN | i L K K W P W W P W R R K | (SEQ ID NO:99) |
| 11E2CN | I L K K W P W W P W R R k | (SEQ ID NO:99) |
| 11E3CN | i L K K W P W W P W R R k | (SEQ ID NO:99) |
| 11F1CN | I L K K W V W W V W R R K | (SEQ ID NO:57) |
| 11F2CN | I L K K W P W W V W R R K | (SEQ ID NO:58) |
| 11F3CN | I L K K W V W W P W R R K | (SEQ ID NO:59) |
| 11F4CN | I L R W V W W V W R R K | (SEQ ID NO:27) |
| 11F4CNR | K R R W V W W V W R L I | (SEQ ID NO:66) |

-continued

| | | |
|---|---|---|
| 11F5CN | I L R R W V W W V W R R K | (SEQ ID NO:28) |
| 11F6CN | I L R W W V W W V W W R R K | (SEQ ID NO:61) |
| 11G2CN | I K K W P W W P W R R K | (SEQ ID NO:73) |
| 11G3CN | I L K K P W W P W R R K | (SEQ ID NO:74) |
| 11G4CN | I L K K W W W P W R R K | (SEQ ID NO:75) |
| 11G5CN | I L K K W P W W W R R K | (SEQ ID NO:76) |
| 11G6CN | I L K K W P W W P R R K | (SEQ ID NO:77) |
| 11G7CN | I L K K W P W W P W R R | (SEQ ID NO:112) |
| 11G13CN | I L K K W P W W P W K | (SEQ ID NO:113) |
| 11G14CN | I L K K W P W W P W R | (SEQ ID NO:114) |
| 11G24CN | L W P W W P W R R K | (SEQ ID NO:81) |
| 11G25CN | L R W W W P W R R K | (SEQ ID NO:29) |
| 11G26CN | L R W P W W P W | (SEQ ID NO:62) |
| 11G27CN | W P W W P W R R K | (SEQ ID NO:80) |
| 11G28CN | R W W W P W R R K | (SEQ ID NO:63) |
| 11H1CN | A L R W P W W P W R R K | (SEQ ID NO:30) |
| 11H2CN | I A R W P W W P W R R K | (SEQ ID NO:82) |
| 11H3CN | I L A W P W W P W R R K | (SEQ ID NO:83) |
| 11H4CN | I L R A P W W P W R R K | (SEQ ID NO:84) |
| 11H5CN | I L R W A W W P W R R K | (SEQ ID NO:31) |
| 11H6CN | I L R W P A W P W R R K | (SEQ ID NO:85) |
| 11H7CN | I L R W P W A P W R R K | (SEQ ID NO:86) |
| 11H8CN | I L R W P W W A W R R K | (SEQ ID NO:87) |
| 11H9CN | I L R W P W W P A R R K | (SEQ ID NO:88) |
| 11H10CN | I L R W P W W P W A R K | (SEQ ID NO:89) |
| 11H11CN | I L R W P W W P W R A K | (SEQ ID NO:90) |
| 11H12CN | I L R W P W W P W R R A | (SEQ ID NO:91) |
| 11J01CN | R R I W K P K W R L P K R | (SEQ ID NO:64) |
| 11J02CN | W R W W K P K W R W P K W | (SEQ ID NO:32) |
| 21A1 | K K W W R R V L S G L K T A G P A I Q S V L N K | (SEQ ID NO:115) |
| 21A2 | K K W W R R A L Q G L K T A G P A I Q S V L N K | (SEQ ID NO:116) |
| 21A10 | K K W W R R V L K G L S S G P A L S N V | (SEQ ID NO:117) |
| 22A1 | K K W W R R A L Q A L K N G L P A L I S | (SEQ ID NO:118) |
| 26 | K W K S F I K K L T S A A K K V V T T A K P L I S S | (SEQ ID NO:119) |
| 27 | K W K L F K K I G I G A V L K V L T T G L P A L I S | (SEQ ID NO:120) |
| 28 | K W K L F K K I G I G A V L K V L T T G L P A L K L T K | (SEQ ID NO:121) |
| 29 | K W K S F I K K L T T A V K K V L T T G L P A L I S | (SEQ ID NO:122) |
| 29A2 | K W K S F I K N L T K V L K K V V T T A L P A L I S | (SEQ ID NO:123) |
| 29A3 | K W K S F I K K L T S A A K K V L T T G L P A L I S | (SEQ ID NO:124) |
| 29F1 | K W K L F I K K L T P A V K K V L L T G L P A L I S | (SEQ ID NO:125) |

-continued

| | | | |
|---|---|---|---|
| 31 | G K P R P Y S P I P T S P R P I R Y | | (SEQ ID NO:126) |
| REWH 53A5 | R L A R I V V I R V A R | | (SEQ ID NO:127) |

CN suffix = amidated C-terminus
H suffix = homoserine at C-terminus
M suffix = MAP branched peptide
R suffix = retro-synthesized peptide Example 2

Synthesis of Modified Peptides

Cationic peptides, such as indolicidin analogues, are modified to alter the physical properties of the original peptide, either by use of modified amino acids in synthesis or by post-synthetic modification. Such modifications include: acetylation at the N-terminus, Fmoc-derivatized N-terminus, polymethylation, peracetylation, and branched derivatives.

α-N-terminal acetylation. Prior to cleaving the peptide from the resin and deprotecting it, the fully protected peptide is treated with N-acetylimidazole in DMF for 1 hour at room temperature, which results in selective reaction at the α-N-terminus. The peptide is then deprotected/cleaved and purified as for an unmodified peptide.

Fmoc-derivatized α-N-terminus. If the final Fmoc deprotection step is not carried out, the α-N-terminus Fmoc group remains on the peptide. The peptide is then side-chain deprotected/cleaved and purified as for an unmodified peptide.

Polymethylation. The purified peptide in a methanol solution is treated with excess sodium bicarbonate, followed by excess methyl iodide. The reaction mixture is stirred overnight at room temperature, extracted with organic solvent, neutralized and purified as for an unmodified peptide. Using this procedure, a peptide is not fully methylated; methylation of MBI 11CN yielded an average of 6 methyl groups. Thus, the modified peptide is a mixture of methylated products.

Peracetylation. A purified peptide in DMF solution is treated with N-acetylimidazole for 1 hour at room temperature. The crude product is concentrated, dissolved in water, lyophilized, re-dissolved in water and purified as for an unmodified peptide. Complete acetylation of primary amine groups is observed.

Four/eight branch derivatives. The branched peptides are synthesized on a four or eight branched core bound to the resin. Synthesis and deprotection/cleavage proceed as for an unmodified peptide. These peptides are purified by dialysis against 4 M guanidine hydrochloride then water, and analyzed by mass spectrometry.

Peptides modified using the above procedures are listed in Table 9.

TABLE 9

| Peptide modified | Peptide name | Sequence | Modification |
|---|---|---|---|
| 10 | 10A (SEQ ID NO: 98) | I L P W K W P W W P W R R | Acetylated α-N-terminus |
| 11 | 11A (SEQ ID NO: 99) | I L K K W P W W P W R R K | Acetylated α-N-terminus |
| 11CN | 11ACN (SEQ ID NO: 99) | I L K K W P W W P W R R K | Acetylated α-N-terminus |
| 11CN | 11CNW1 (SEQ ID NO: 99) | I L K K W P W W P W R R K | Fmoc-derivatized N-terminus |
| 11CN | 11CNX1 (SEQ ID NO: 99) | I L K K W P W W P W R R K | Polymethylated derivative |
| 11CN | 11CNY1 (SEQ ID NO: 99) | I L K K W P W W P W R R K | Peracetylated derivative |
| 11 | 11M4 (SEQ ID NO: 98) | I L K K W P W W P W R R K | Four branch derivative |
| 11 | 11M8 (SEQ ID NO: 98) | I L K K W P W W P W R R K | Eight branch derivative |
| 11B1CN | 11B1CNW1 (SEQ ID NO: 41) | I L R R W P W W P W R R K | Fmoc-derivatized N-terminus |
| 11B4CN | 11B4ACN (SEQ ID NO: 44) | I L K K W P W W P W R K | Acetylated N-terminus |
| 11B7CN | 11B7ACN (SEQ ID NO: 101) | I L R W P W W P W R R K | Acetylated N-terminus |
| 11B7CN | 11B7CNF12 (SEQ ID NO: 101) | I L R W P W W P W R R K | Formylated Lys[12] |
| 11B9CN | 11B9ACN (SEQ ID NO: 102) | I L R R W P W W P W R R R | Acetylated N-terminus |
| 11D9 | 11D9M8 (SEQ ID NO: 70) | W W P W R R K | Eight branch derivative |
| 11D10 | 11D10M8 (SEQ ID NO: 71) | I L K K W P W | Eight branch derivative |
| 11G6CN | 11G6ACN (SEQ ID NO: 77) | I L K K W P W W P R R K | Acetylated α-N-terminus |
| 11G7CN | 11G7ACN (SEQ ID NO: 112) | I L K K W P W W P W R R | Acetylated α-N-terminus |

Example 3

Recombinant Production of Peptide Analogues

Peptide analogues are alternatively produced by recombinant DNA technique in bacterial host cells. The peptide is produced as a fusion protein, chosen to assist in transporting the fusion peptide to inclusion bodies, periplasm, outer membrane or extracellular environment.

Construction of Plasmids Encoding MBI-11 Peptide Fusion Protein

Amplification by polymerase chain reaction is used to synthesize double-stranded DNA encoding the MBI peptide genes from single-stranded templates. For MBI-11, 100 μl of reaction mix is prepared containing 50 to 100 ng of template, 25 pmole of each primer, 1.5 mM $MgCl_2$, 200 μM of each dNTP, 2U of Taq polymerase in buffer supplied by the manufacturer. Amplification conditions are 25 cycles of 94° C. for 30 sec., 55° C. for 30 sec., 74° C. for 30 sec., followed by 74° C. for 1 min. Amplified product is digested with BamHI and HindIII and cloned into a plasmid expression vector encoding the fusion partner and a suitable selection marker.

Production of MBI-11 Peptide Fusion in E. coli

The plasmid pR2h-11, employing a T7 promoter, high copy origin of replication, $Ap^r$ marker and containing the gene of the fusion protein, is co-electroporated with pGP1-2 into E. coli strain XL1-Blue. Plasmid pGP1-2 contains a T7 RNA polymerase gene under control of a lambda promoter and c1857 repressor gene. Fusion protein expression is induced by a temperature shift from 30° C. to 42° C. Inclusion bodies are washed with solution containing solubilizer and extracted with organic extraction solvent. Profiles of the samples are analyzed by SDS-PAGE. FIG. 1 shows the SDS-PAGE analysis and an extraction profile of inclusion body from whole cell. The major contaminant in the organic solvent extracted material is β-lactamase (FIG. 1). The expression level in these cells is presented in Table 10.

TABLE 10

| Fusion protein | Mol. mass (kDa) | % protein in whole cell lysate | % in inclusion body extract | % which is MBI-11 peptide |
|---|---|---|---|---|
| MBI-11 | 20.1 | 15 | 42 | 7.2 |

Figure 2:
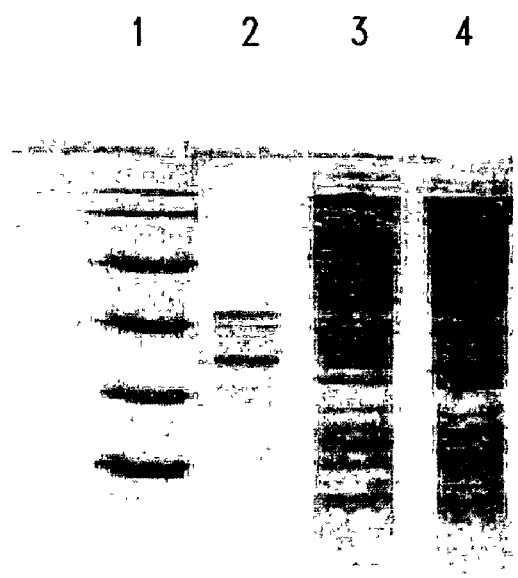
FIG. 2 is an SDS-PAGE showing the expression profile of the MBI-11 fusion protein using plasmid pPDR2h-11. Lane 1, protein standards; lane 2, organic solvent extracted MBI-11; lane 3, total lysate of XL1 Blue (pPDR2h-11, pGP1-2), cultured at 30° C.; lane 4, total lysate of XL1 Blue (pPDR2h-11, pGP1-2), induced at 42° C.

In addition, a low-copy-number vector, pPD100, which has a chloramphenicol resistance gene, is used to express MBI-11 in order to eliminate the need for using ampicillin, thereby reducing the appearance of β-lactamase in extracted material. This plasmid allows selective gene expression and high-level protein overproduction in E. coli using the bacteriophage T7 RNA polymerase/T7 promoter system (Dersch et al., FEMS Microbiol. Lett. 123: 19-26, 1994). pPD100 contains a chloramphenicol resistance gene (CAT) as a selective marker, a multiple cloning site, and an ori sequence derived from the low-copy-number vector pSC101. There are only about 4 to 6 copies of these plasmids per host cell. The resulting construct containing MBI-11 is called pPDR2h-11. FIG. 2 presents a gel electrophoresis analysis of the MBI-11 fusion protein expressed in this vector. Expression level of MBI-11 fusion protein is comparable with that obtained from plasmid pR2h-11. The CAT gene product is not apparent, presumably due to the low-copy-number nature of this plasmid, CAT protein is not expressed at high levels in pPDR2h-11.

Example 4

In vitro Assays to Measure Cationic Peptide Activity

A cationic peptide may be tested for antimicrobial activity alone before assessing its enhancing activity with antibiotic agents. Preferably, the peptide has measurable antimicrobial activity.

Agarose Dilution Assay

The agarose dilution assay measures antimicrobial activity of peptides and peptide analogues, which is expressed as the minimum inhibitory concentration (MIC) of the peptides.

In order to mimic in vivo conditions, calcium and magnesium supplemented Mueller Hinton broth is used in combination with a low EEO agarose as the bacterial growth medium. Agarose, rather than agar, is used as the charged groups in agar prevent peptide diffusion through the media. The media is autoclaved and then cooled to 50-55° C. in a water bath before aseptic addition of antimicrobial solutions. The same volume of different concentrations of peptide solution are added to the cooled molten agarose that is then poured to a depth of 3-4 mm.

The bacterial inoculum is adjusted to a 0.5 McFarland turbidity standard (PML Microbiological) and then diluted 1:10 before application on to the agarose plate. The final inoculum applied to the agarose is approximately $10^4$ CFU in a 5-8 mm diameter spot. The agarose plates are incubated at 35-37° C. for 16 to 20 hours.

The MIC is recorded as the lowest concentration of peptide that completely inhibits growth of the organism as determined by visual inspection. Representative MICs for various indolicidin analogues against bacteria are shown in Table 11 and representative MICs against Candida are shown in Table 12 below.

TABLE 11

| Organism | Organism # | MIC (μg/ml) |
|---|---|---|
| 1. MBI 10 | | |
| A. calcoaceticus | AC001 | 128 |
| E. coli | ECO002 | 128 |
| E. faecalis | EFS004 | 8 |
| K. pneumoniae | KP001 | 128 |
| P. aeruginosa | PA003 | >128 |
| S. aureus | SA007 | 2 |
| S. maltophilia | SMA001 | 128 |
| S. marcescens | SMS003 | >128 |
| 2. MBI 10A | | |
| E. faecalis | EFS004 | 16 |
| E. faecium | EFM003 | 8 |
| S. aureus | SA010 | 8 |
| 3. MBI 10CN | | |
| A. calcoaceticus | AC001 | 64 |
| E. cloacae | ECL007 | >128 |
| E. coli | ECO001 | 32 |
| E. coli | SBECO2 | 16 |
| E. faecalis | EFS004 | 8 |
| E. faecium | EFM003 | 2 |
| K. pneumoniae | KP002 | 64 |
| P. aeruginosa | PA002 | >128 |
| S. aureus | SA003 | 2 |
| S. epidermidis | SE010 | 4 |
| S. maltophilia | SMA002 | 64 |
| S. marcescens | SMS004 | >128 |
| 4. MBI 11 | | |
| A. calcoaceticus | AC002 | 8 |
| E. cloacae | ECL007 | >128 |
| E. coli | ECO002 | 64 |
| E. faecium | EFM003 | 4 |
| E. faecalis | EFS002 | 64 |
| K. pneumoniae | KP001 | 128 |
| P. aeruginosa | PA004 | >128 |
| S. aureus | SA004 | 4 |
| S. maltophilia | SMA002 | 128 |
| S. marcescens | SMS004 | >128 |
| 5. MBI 11A | | |
| A. calcoaceticus | AC001 | >64 |
| E. cloacae | ECL007 | >64 |
| E. coli | ECO005 | >64 |
| E. faecalis | EFS004 | 32 |
| K. pneumoniae | KP001 | 64 |
| P. aeruginosa | PA024 | >64 |
| S. aureus | SA002 | 4 |
| S. maltophilia | SMA002 | >64 |
| S. marcescens | SMS003 | >64 |

TABLE 11-continued

6. MBI 11ACN

| | | |
|---|---|---|
| A. calcoaceticus | AC002 | 2 |
| E. cloacae | ECL007 | >128 |
| E. coli | ECO005 | 16 |
| E. faecalis | EFS004 | 8 |
| E. faecalis | EFS008 | 64 |
| K. pneumoniae | KP001 | 16 |
| P. aeruginosa | PA004 | >128 |
| S. aureus | SA014 | 8 |
| S. epidermidis | SE010 | 4 |
| S. maltophilia | SMA002 | 64 |
| S. marcescens | SMS003 | >128 |

7. MBI 11CN

| | | |
|---|---|---|
| A. calcoaceticus | AC001 | 128 |
| E. cloacae | ECL007 | >64 |
| E. coli | ECO002 | 8 |
| E. faecium | EFM001 | 8 |
| E. faecalis | EFS001 | 32 |
| H. influenzae | HIN001 | >128 |
| K. pneumoniae | KP002 | 128 |
| P. aeruginosa | PA003 | >128 |
| P. mirabilis | PM002 | >128 |
| S. aureus | SA003 | 2 |
| S. marcescens | SBSM1 | >128 |
| S. pneumoniae | SBSPN2 | >128 |
| S. epidermidis | SE001 | 2 |
| S. maltophilia | SMA001 | 64 |
| S. marcescens | SMS003 | >128 |
| S. pyogenes | SPY003 | 8 |

8. MBI 11CNR

| | | |
|---|---|---|
| A. calcoaceticus | AC002 | 4 |
| E. cloacae | ECL007 | >128 |
| E. coli | ECO005 | 8 |
| E. faecalis | EFS001 | 4 |
| K. pneumoniae | KP001 | 4 |
| P. aeruginosa | PA004 | 32 |
| S. aureus | SA093 | 4 |
| S. epidermidis | SE010 | 4 |
| S. maltophilia | SMA002 | 32 |
| S. marcescens | SMS003 | 128 |

9. MBI 11CNW1

| | | |
|---|---|---|
| A. calcoaceticus | AC002 | 8 |
| E. cloacae | ECL007 | 64 |
| E. coli | ECO005 | 32 |
| E. faecalis | EFS001 | 8 |
| K. pneumoniae | KP001 | 32 |
| P. aeruginosa | PA004 | 64 |
| S. aureus | SA010 | 4 |
| S. maltophilia | SMA002 | 32 |
| S. marcescens | SMS003 | >128 |

10. MBI 11CNX1

| | | |
|---|---|---|
| A. calcoaceticus | AC001 | >64 |
| E. cloacae | ECL007 | >64 |
| E. coli | ECO005 | 64 |
| E. faecalis | EFS004 | 16 |
| K. pneumoniae | KP001 | >64 |
| P. aeruginosa | PA024 | >64 |
| S. aureus | SA006 | 2 |
| S. maltophilia | SMA002 | >64 |
| S. marcescens | SMS003 | >64 |

11. MBI 11CNY1

| | | |
|---|---|---|
| A. calcoaceticus | AC001 | >64 |
| E. cloacae | ECL007 | >64 |
| E. coli | ECO005 | >64 |
| E. faecalis | EFS004 | >64 |
| K. pneumoniae | KP001 | >64 |
| P. aeruginosa | PA004 | >64 |
| S. aureus | SA006 | 16 |
| S. epidermidis | SE010 | 128 |
| S. maltophilia | SMA002 | >64 |
| S. marcescens | SMS003 | >64 |

12. MBI 11M4

| | | |
|---|---|---|
| E. faecium | EFM001 | 32 |
| E. faecalis | EFS001 | 32 |
| S. aureus | SA008 | 8 |

13. MBI 11M8

| | | |
|---|---|---|
| E. faecalis | EFS002 | 32 |
| E. faecium | EFM002 | 32 |
| S. aureus | SA008 | 32 |

14. MBI 11A1CN

| | | |
|---|---|---|
| A. calcoaceticus | AC002 | 16 |
| E. cloacae | ECL007 | >128 |
| E. coli | ECO002 | 32 |
| E. faecium | EFM002 | 1 |
| E. faecalis | EFS002 | 32 |
| H. influenzae | HIN002 | >128 |
| K. pneumoniae | KP002 | >128 |
| P. aeruginosa | PA004 | >128 |
| S. aureus | SA005 | 8 |
| P. vulgaris | SBPV1 | >128 |
| S. marcescens | SBSM2 | >128 |
| S. pneumoniae | SBSPN2 | >128 |
| S. epidermidis | SE002 | 16 |
| S. maltophilia | SMA002 | >128 |

15. MBI 11A2CN

| | | |
|---|---|---|
| A. calcoaceticus | AC001 | >128 |
| E. cloacae | ECL007 | >128 |
| E. coli | ECO003 | >128 |
| E. faecium | EFM003 | 16 |
| E. faecalis | EFS002 | >128 |
| K. pneumoniae | KP002 | >128 |
| P. aeruginosa | PA004 | >128 |
| S. aureus | SA004 | 8 |
| S. maltophilia | SMA001 | >128 |
| S. marcescens | SMS003 | >128 |

16. MBI 11A3CN

| | | |
|---|---|---|
| A. calcoaceticus | AC001 | >128 |
| E. cloacae | ECL007 | >128 |
| E. coli | ECO002 | >128 |
| E. faecium | EFM003 | 64 |
| E. faecalis | EFS002 | >128 |
| H. influenzae | HIN002 | >128 |
| K. pneumoniae | KP001 | >128 |
| P. aeruginosa | PA002 | >128 |
| S. aureus | SA004 | 32 |
| P. vulgaris | SBPV1 | >128 |
| S. marcescens | SBSM2 | >128 |
| S. pneumoniae | SBSPN3 | >128 |
| S. epidermidis | SE002 | 128 |
| S. maltophilia | SMA001 | >128 |

17. MBI 11A4CN

| | | |
|---|---|---|
| A. calcoaceticus | AC002 | 8 |
| E. cloacae | ECL007 | >128 |
| E. coli | ECO003 | 32 |
| E. faecalis | EFS002 | 64 |
| E. faecium | EFM001 | 32 |
| K. pneumoniae | KP001 | >128 |
| P. aeruginosa | PA004 | >128 |
| S. aureus | SA005 | 2 |
| S. epidermidis | SE002 | 8 |
| S. maltophilia | SMA002 | >128 |
| S. marcescens | SMS004 | >128 |

18. MBI 11A5CN

| | | |
|---|---|---|
| A. calcoaceticus | AC001 | >128 |
| E. cloacae | ECL007 | >128 |
| E. coli | ECO003 | 128 |
| E. faecium | EFM003 | 4 |
| E. faecalis | EFS002 | 32 |
| K. pneumoniae | KP001 | >128 |
| P. aeruginosa | PA003 | >128 |
| S. aureus | SA002 | 16 |
| S. maltophilia | SMA002 | >128 |
| S. marcescens | SMS003 | >128 |

TABLE 11-continued

| | | |
|---|---|---|
| 19. MBI 11A6CN | | |
| E. faecium | EFM003 | 2 |
| E. faecalis | EFS004 | 64 |
| S. aureus | SA016 | 2 |
| 20. MBI 11A7CN | | |
| E. faecium | EFM003 | 2 |
| E. faecalis | EFS002 | 16 |
| S. aureus | SA009 | 2 |
| 21. MBI 11A8CN | | |
| A. calcoaceticus | AC002 | 8 |
| E. cloacae | ECL007 | >128 |
| E. coli | ECO005 | 32 |
| E. faecalis | EFS001 | 4 |
| K. pneumoniae | KP001 | 128 |
| P. aeruginosa | PA004 | >128 |
| S. aureus | SA093 | 1 |
| S. epidermidis | SE010 | 16 |
| S. maltophilia | SMA002 | 32 |
| S. marcescens | SMS003 | >128 |
| 22. MBI 11B1CN | | |
| A. calcoaceticus | AC001 | 32 |
| E. cloacae | ECL007 | >128 |
| E. coli | ECO003 | 8 |
| E. faecium | EFM002 | 2 |
| E. faecalis | EFS004 | 8 |
| K. pneumoniae | KP002 | 64 |
| P. aeruginosa | PA005 | >128 |
| S. aureus | SA005 | 2 |
| S. epidermidis | SE001 | 2 |
| S. maltophilia | SMA001 | 64 |
| S. marcescens | SMS004 | >128 |
| 23. MBI 11B1CNW1 | | |
| A. calcoaceticus | AC002 | 16 |
| E. cloacae | ECL007 | 64 |
| E. coli | ECO005 | 32 |
| E. faecalis | EFS004 | 8 |
| K. pneumoniae | KP001 | 32 |
| P. aeruginosa | PA004 | 64 |
| S. aureus | SA014 | 16 |
| S. epidermidis | SE010 | 8 |
| S. maltophilia | SMA002 | 32 |
| S. marcescens | SMS003 | >128 |
| 24. MBI 11B2CN | | |
| A. calcoaceticus | AC001 | 64 |
| E. cloacae | ECL007 | >128 |
| E. coli | ECO003 | 16 |
| E. faecium | EFM001 | 8 |
| E. faecalis | EFS004 | 8 |
| K. pneumoniae | KP002 | 64 |
| P. aeruginosa | PA003 | >128 |
| S. aureus | SA005 | 2 |
| S. maltophilia | SMA002 | 64 |
| S. marcescens | SMS004 | >128 |
| 25. MBI 11B3CN | | |
| A. calcoaceticus | AC001 | 64 |
| E. cloacae | ECL007 | >128 |
| E. coli | ECO002 | 16 |
| E. faecium | EFM001 | 8 |
| E. faecalis | EFS001 | 16 |
| K. pneumoniae | KP002 | 64 |
| P. aeruginosa | PA003 | >128 |
| S. aureus | SA010 | 4 |
| S. maltophilia | SMA002 | 32 |
| S. marcescens | SMS004 | >128 |
| 26. MBI 11B4CN | | |
| A. calcoaceticus | AC001 | >128 |
| E. cloacae | ECL007 | >128 |
| E. coli | ECO003 | 16 |
| E. faecalis | EFS002 | 16 |
| H. influenzae | HIN002 | >128 |
| K. pneumoniae | KP002 | 128 |
| P. aeruginosa | PA006 | >128 |
| S. aureus | SA004 | 2 |
| S. marcescens | SBSM2 | >128 |
| S. pneumoniae | SBSPN3 | 128 |
| S. epidermidis | SE010 | 4 |
| S. maltophilia | SMA002 | 64 |
| S. marcescens | SMS004 | >128 |
| 27. MBI 11B4ACN | | |
| A. calcoaceticus | AC002 | 4 |
| E. cloacae | ECL007 | >128 |
| E. coli | ECO005 | 32 |
| E. faecalis | EFS008 | 64 |
| K. pneumoniae | KP001 | 32 |
| P. aeruginosa | PA004 | >128 |
| S. aureus | SA008 | 1 |
| S. epidermidis | SE010 | 8 |
| S. maltophilia | SMA002 | 64 |
| S. marcescens | SMS003 | >128 |
| 28. MBI 11B5CN | | |
| E. faecium | EFM002 | 1 |
| E. faecalis | EFS002 | 16 |
| S. aureus | SA005 | 2 |
| 29. MBI 11B7 | | |
| A. calcoaceticus | AC002 | 4 |
| E. cloacae | ECL007 | >128 |
| E. coli | ECO005 | 16 |
| E. faecalis | EFS008 | 8 |
| K. pneumoniae | KP001 | 16 |
| P. aeruginosa | PA004 | >128 |
| S. aureus | SA093 | 1 |
| S. epidermidis | SE010 | 4 |
| S. maltophilia | SMA002 | 64 |
| S. marcescens | SMS003 | >128 |
| 30. MBI 11B7CN | | |
| A. calcoaceticus | AC003 | 32 |
| E. cloacae | ECL009 | 32 |
| E. coli | ECO002 | 8 |
| E. faecium | EFM001 | 4 |
| E. faecalis | EFS004 | 4 |
| H. influenzae | HIN002 | >128 |
| K. pneumoniae | KP001 | 32 |
| P. aeruginosa | PA004 | 128 |
| P. mirabilis | PM002 | >128 |
| S. aureus | SA009 | 2 |
| S. marcescens | SBSM1 | >128 |
| S. pneumoniae | SBSPN3 | >128 |
| S. epidermidis | SE003 | 2 |
| S. maltophilia | SMA004 | 128 |
| S. pyogenes | SPY006 | 16 |
| 31. MBI 11B7CNR | | |
| A. calcoaceticus | AC002 | 4 |
| E. cloacae | ECL007 | 64 |
| E. coli | ECO005 | 8 |
| E. faecalis | EFS001 | 4 |
| K. pneumoniae | KP001 | 8 |
| P. aeruginosa | PA004 | 64 |
| S. aureus | SA093 | 2 |
| S. epidermidis | SE010 | 4 |
| S. maltophilia | SMA002 | 32 |
| S. marcescens | SMS003 | >128 |
| 32. MBI 11B8CN | | |
| A. calcoaceticus | AC001 | >128 |
| E. cloacae | ECL007 | >128 |
| E. coli | ECO002 | 16 |
| E. faecium | EFM001 | 16 |
| E. faecalis | EFS002 | 32 |
| K. pneumoniae | KP001 | >128 |
| P. aeruginosa | PA005 | >128 |
| S. aureus | SA009 | 4 |
| S. epidermidis | SE002 | 4 |
| S. maltophilia | SMA002 | 128 |
| S. marcescens | SMS003 | >128 |

TABLE 11-continued

33. MBI 11B9CN

| | | |
|---|---|---|
| A. calcoaceticus | AC002 | 4 |
| E. cloacae | ECL007 | >128 |
| E. coli | ECO005 | 8 |
| E. faecium | EFM002 | 4 |
| E. faecalis | EFS002 | 8 |
| H. influenzae | HIN002 | >128 |
| K. pneumoniae | KP001 | 32 |
| P. aeruginosa | PA004 | 128 |
| P. mirabilis | PM002 | >128 |
| S. aureus | SA010 | 4 |
| S. pneumoniae | SBSPN2 | >128 |
| S. epidermidis | SE010 | 2 |
| S. maltophilia | SMA002 | 32 |
| S. marcescens | SMS003 | >128 |
| S. pneumoniae | SPN044 | >128 |
| S. pyogenes | SPY005 | 16 |

34. MBI 11B9ACN

| | | |
|---|---|---|
| A. calcoaceticus | AC001 | 32 |
| E. cloacae | ECL007 | >128 |
| E. coli | ECO003 | 8 |
| E. faecium | EFM001 | 4 |
| E. faecalis | EFS004 | 8 |
| K. pneumoniae | KP002 | 32 |
| P. aeruginosa | PA005 | >128 |
| S. aureus | SA019 | 2 |
| S. epidermidis | SE002 | 2 |
| S. maltophilia | SMA001 | 16 |
| S. marcescens | SMS004 | >128 |

35. MBI 11B10CN

| | | |
|---|---|---|
| E. faecium | EFM003 | 4 |
| E. faecalis | EFS002 | 64 |
| S. aureus | SA008 | 2 |

36. MBI 11B16CN

| | | |
|---|---|---|
| A. calcoaceticus | AC002 | 4 |
| E. cloacae | ECL007 | >128 |
| E. coli | ECO005 | 16 |
| E. faecalis | EFS001 | 2 |
| K. pneumoniae | KP001 | 16 |
| P. aeruginosa | PA004 | >128 |
| S. aureus | SA093 | 2 |
| S. epidermidis | SE010 | 4 |
| S. maltophilia | SMA002 | 32 |
| S. marcescens | SMS003 | >128 |

37. MBI 11B17CN

| | | |
|---|---|---|
| A. calcoaceticus | AC002 | 2 |
| E. cloacae | ECL007 | >128 |
| E. coli | ECO005 | 8 |
| E. faecalis | EFS008 | 4 |
| K. pneumoniae | KP001 | 16 |
| P. aeruginosa | PA004 | >128 |
| S. aureus | SA093 | 2 |
| S. epidermidis | SE010 | 4 |
| S. maltophilia | SMA002 | 32 |
| S. marcescens | SMS003 | >128 |

38. MBI 11B18CN

| | | |
|---|---|---|
| A. calcoaceticus | AC002 | 2 |
| E. cloacae | ECL007 | >128 |
| E. coli | ECO005 | 32 |
| E. faecalis | EFS008 | 4 |
| K. pneumoniae | KP001 | 32 |
| P. aeruginosa | PA004 | >128 |
| S. aureus | SA093 | 2 |
| S. epidermidis | SE010 | 4 |
| S. maltophilia | SMA002 | 64 |
| S. marcescens | SMS003 | >128 |

39. MBI 11C3CN

| | | |
|---|---|---|
| A. calcoaceticus | AC002 | 4 |
| E. cloacae | ECL007 | >128 |
| E. coli | ECO002 | 16 |
| E. faecium | EFM002 | 1 |
| E. faecalis | EFS002 | 32 |
| K. pneumoniae | KP001 | 128 |
| P. aeruginosa | PA005 | >128 |
| S. aureus | SA005 | 2 |
| S. epidermidis | SE002 | 2 |
| S. maltophilia | SMA002 | 64 |
| S. marcescens | SMS004 | >128 |

40. MBI 11C4CN

| | | |
|---|---|---|
| A. calcoaceticus | AC002 | 4 |
| E. cloacae | ECL007 | >128 |
| E. coli | ECO005 | 32 |
| E. faecium | EFM003 | 2 |
| E. faecalis | EFS002 | 32 |
| K. pneumoniae | KP001 | >128 |
| P. aeruginosa | PA005 | >128 |
| S. aureus | SA009 | 4 |
| S. epidermidis | SE002 | 4 |
| S. maltophilia | SMA002 | 64 |
| S. marcescens | SMS004 | >128 |

41. MBI 11C5CN

| | | |
|---|---|---|
| A. calcoaceticus | AC001 | 32 |
| E. cloacae | ECL007 | >128 |
| E. coli | ECO001 | 8 |
| E. faecium | EFM003 | 2 |
| E. faecalis | EFS002 | 16 |
| K. pneumoniae | KP002 | 16 |
| P. aeruginosa | PA003 | 64 |
| S. aureus | SA009 | 2 |
| S. epidermidis | SE002 | 2 |
| S. maltophilia | SMA002 | 16 |
| S. marcescens | SMS004 | >128 |

42. MBI 11D1CN

| | | |
|---|---|---|
| A. calcoaceticus | AC001 | >128 |
| E. cloacae | ECL007 | >128 |
| E. coli | ECO002 | 16 |
| E. faecium | EFM001 | 16 |
| E. faecalis | EFS002 | 32 |
| K. pneumoniae | KP002 | 64 |
| P. aeruginosa | PA003 | >128 |
| S. aureus | SA004 | 2 |
| S. epidermidis | SE010 | 8 |
| S. maltophilia | SMA001 | 64 |
| S. marcescens | SMS003 | >128 |

43. MBI 11D3CN

| | | |
|---|---|---|
| A. calcoaceticus | AC001 | >128 |
| E. cloacae | ECL007 | >128 |
| E. coli | ECO002 | 64 |
| E. faecium | EFM003 | 8 |
| E. faecalis | EFS002 | 32 |
| K. pneumoniae | KP002 | >128 |
| P. aeruginosa | PA024 | >128 |
| S. aureus | SA009 | 8 |
| S. maltophilia | SMA001 | 64 |
| S. marcescens | SMS004 | >128 |

44. MBI 11D4CN

| | | |
|---|---|---|
| A. calcoaceticus | AC001 | >64 |
| E. cloacae | ECL007 | >64 |
| E. coli | ECO003 | 64 |
| E. faecium | EFM002 | 1 |
| E. faecalis | EFS002 | 16 |
| K. pneumoniae | KP002 | >64 |
| P. aeruginosa | PA004 | >64 |
| S. aureus | SA009 | 4 |
| S. maltophilia | SMA001 | >64 |
| S. marcescens | SMS004 | >64 |

45. MBI 11D5CN

| | | |
|---|---|---|
| A. calcoaceticus | AC001 | >64 |
| E. cloacae | ECL007 | >64 |
| E. coli | ECO003 | 64 |
| E. faecium | EFM003 | 1 |
| E. faecalis | EFS002 | 16 |
| K. pneumoniae | KP001 | >64 |
| P. aeruginosa | PA003 | >64 |
| S. aureus | SA005 | 8 |

TABLE 11-continued

| | | |
|---|---|---|
| S. maltophilia | SMA001 | 64 |
| S. marcescens | SMS004 | >64 |
| 46. MBI 11D6CN | | |
| A. calcoaceticus | AC002 | 4 |
| E. cloacae | ECL007 | >32 |
| E. coli | ECO002 | 32 |
| E. faecium | EFM003 | 1 |
| E. faecalis | EFS002 | 4 |
| K. pneumoniae | KP002 | >64 |
| P. aeruginosa | PA024 | >64 |
| S. aureus | SA009 | 8 |
| S. epidermidis | SE010 | 4 |
| S. maltophilia | SMA001 | >64 |
| S. marcescens | SMS004 | >64 |
| 47. MBI 11D9M8 | | |
| E. faecium | EFM002 | 32 |
| S. aureus | SA007 | 32 |
| E. faecalis | EFS002 | 128 |
| S. aureus | SA016 | 128 |
| 48. MBI 11D10M8 | | |
| E. faecium | EFM003 | 32 |
| E. faecalis | EFS002 | 32 |
| S. aureus | SA008 | 32 |
| 49. MBI 11D11H | | |
| A. calcoaceticus | AC001 | >64 |
| E. cloacae | ECL007 | >64 |
| E. coli | ECO002 | 32 |
| K. pneumoniae | KP001 | >64 |
| P. aeruginosa | PA001 | >64 |
| S. aureus | SA008 | 4 |
| S. maltophilia | SMA002 | >64 |
| S. marcescens | SMS004 | >64 |
| 50. MBI 11D12H | | |
| A. calcoaceticus | AC001 | >64 |
| E. cloacae | ECL007 | >64 |
| E. coli | ECO003 | 64 |
| E. faecalis | EFS004 | 16 |
| K. pneumoniae | KP002 | >64 |
| P. aeruginosa | PA004 | >64 |
| S. aureus | SA014 | 16 |
| S. maltophilia | SMA002 | >64 |
| S. marcescens | SMS004 | >64 |
| 51. MBI 11D13H | | |
| A. calcoaceticus | AC001 | 64 |
| E. cloacae | ECL007 | >64 |
| E. coli | ECO002 | 32 |
| E. faecalis | EFS004 | 16 |
| K. pneumoniae | KP002 | >64 |
| P. aeruginosa | PA004 | >64 |
| S. aureus | SA025 | 4 |
| S. maltophilia | SMA002 | >64 |
| S. marcescens | SMS004 | >64 |
| 52. MBI 11D14CN | | |
| E. faecium | EFM003 | 1 |
| E. faecalis | EFS002 | 32 |
| S. aureus | SA009 | 4 |
| 53. MBI 11D15CN | | |
| E. faecium | EFM003 | 4 |
| E. faecalis | EFS002 | 32 |
| S. aureus | SA009 | 8 |
| 54. MBI 11D18CN | | |
| A. calcoaceticus | AC003 | 32 |
| E. cloacae | ECL009 | 64 |
| E. coli | ECO002 | 4 |
| E. faecium | EFM003 | 2 |
| E. faecalis | EFS002 | 32 |
| H. influenzae | HIN002 | >128 |
| K. pneumoniae | KP002 | 64 |
| P. aeruginosa | PA006 | >128 |
| P. mirabilis | PM003 | >128 |
| S. aureus | SA010 | 4 |
| P. vulgaris | SBPV1 | 32 |
| S. marcescens | SBSM2 | >128 |
| S. pneumoniae | SBSPN3 | 64 |
| S. epidermidis | SE010 | 2 |
| S. maltophilia | SMA003 | 16 |
| S. pyogenes | SPY003 | 32 |
| 55. MBI 11E1CN | | |
| A. calcoaceticus | AC001 | 32 |
| E. cloacae | ECL007 | >128 |
| E. coli | ECO003 | 8 |
| E. faecium | EFM001 | 8 |
| E. faecalis | EFS002 | 8 |
| K. pneumoniae | KP002 | 32 |
| P. aeruginosa | PA003 | 128 |
| S. aureus | SA006 | 1 |
| S. maltophilia | SMA001 | 64 |
| S. marcescens | SMS003 | >128 |
| 56. MBI 11E2CN | | |
| A. calcoaceticus | AC002 | 4 |
| E. cloacae | ECL007 | >128 |
| E. coli | ECO002 | 8 |
| E. faecium | EFM001 | 16 |
| E. faecalis | EFS002 | 32 |
| K. pneumoniae | KP002 | 64 |
| P. aeruginosa | PA001 | >128 |
| S. aureus | SA016 | 2 |
| S. epidermidis | SE010 | 4 |
| S. maltophilia | SMA001 | 64 |
| S. marcescens | SMS004 | >128 |
| 57. MBI 11E3CN | | |
| A. calcoaceticus | AC001 | 16 |
| E. cloacae | ECL007 | >128 |
| E. coli | ECO001 | 4 |
| E. faecium | EFM003 | 2 |
| E. faecalis | EFS004 | 8 |
| H. influenzae | HIN002 | >128 |
| K. pneumoniae | KP002 | 32 |
| P. aeruginosa | PA041 | 64 |
| P. mirabilis | PM001 | >128 |
| S. aureus | SA010 | 2 |
| S. pneumoniae | SBSPN2 | >128 |
| S. epidermidis | SE002 | 1 |
| S. maltophilia | SMA001 | 32 |
| S. marcescens | SMS004 | >128 |
| S. pneumoniae | SPN044 | >128 |
| S. pyogenes | SPY002 | 16 |
| 58. MBI 11F1CN | | |
| E. cloacae | ECL007 | >128 |
| E. coli | ECO003 | 8 |
| E. faecium | EFM003 | 2 |
| E. faecalis | EFS004 | 16 |
| K. pneumoniae | KP002 | 32 |
| P. aeruginosa | PA004 | 64 |
| S. aureus | SA009 | 2 |
| S. marcescens | SBSM1 | >128 |
| S. marcescens | SMS003 | >128 |
| 59. MBI 11F2CN | | |
| A. calcoaceticus | AC002 | 4 |
| E. coli | ECO002 | 8 |
| E. faecium | EFM002 | 4 |
| E. faecalis | EFS002 | 32 |
| K. pneumoniae | KP002 | 128 |
| P. aeruginosa | PA005 | >128 |
| S. aureus | SA012 | 4 |
| S. epidermidis | SE002 | 4 |
| S. maltophilia | SMA002 | 64 |
| S. marcescens | SMS004 | >128 |
| 60. MBI 11F3CN | | |
| A. calcoaceticus | AC002 | 4 |
| E. cloacae | ECL007 | >128 |
| E. coli | ECO002 | 8 |
| E. faecium | EFM003 | 4 |

TABLE 11-continued

| | | |
|---|---|---|
| E. faecalis | EFS002 | 8 |
| H. influenzae | HIN002 | >128 |
| K. pneumoniae | KP002 | 64 |
| P. aeruginosa | PA041 | 128 |
| S. aureus | SA005 | 2 |
| S. pneumoniae | SBSPN3 | >128 |
| S. epidermidis | SE003 | 2 |
| S. maltophilia | SMA002 | 64 |
| S. marcescens | SMS004 | >128 |
| S. pneumoniae | SPN044 | >128 |
| S. pyogenes | SPY006 | 8 |
| 61. MBI 11F4CN | | |
| A. calcoaceticus | AC003 | 16 |
| E. cloacae | ECL006 | 16 |
| E. coli | ECO001 | 8 |
| E. faecalis | EFS004 | 8 |
| H. influenzae | HIN003 | >128 |
| K. pneumoniae | KP001 | 8 |
| P. aeruginosa | PA020 | 32 |
| S. aureus | SA007 | 1 |
| S. marcescens | SBSM1 | >128 |
| S. pneumoniae | SBSPN3 | >128 |
| S. epidermidis | SE010 | 2 |
| S. maltophilia | SMA006 | 16 |
| S. pyogenes | SPY005 | 32 |
| 62. MBI 11F4CNR | | |
| A. calcoaceticus | AC002 | 16 |
| E. cloacae | ECL007 | 32 |
| E. coli | ECO005 | 32 |
| E. faecalis | EFS008 | 32 |
| K. pneumoniae | KP001 | 32 |
| P. aeruginosa | PA004 | 64 |
| S. aureus | SA093 | 8 |
| S. epidermidis | SE010 | 8 |
| S. maltophilia | SMA002 | 32 |
| S. marcescens | SMS003 | >128 |
| 63. MBI 11G2CN | | |
| E. cloacae | ECL007 | >128 |
| E. coli | ECO003 | 16 |
| E. faecium | EFM002 | 4 |
| E. faecalis | EFS004 | 16 |
| K. pneumoniae | KP002 | 128 |
| P. aeruginosa | PA004 | >128 |
| S. aureus | SA009 | 2 |
| S. maltophilia | SMA001 | >128 |
| S. marcescens | SMS004 | >128 |
| 64. MBI 11G3CN | | |
| E. cloacae | ECL007 | >128 |
| E. coli | ECO003 | 64 |
| E. faecium | EFM002 | 32 |
| E. faecalis | EFS002 | 64 |
| K. pneumoniae | KP001 | >128 |
| P. aeruginosa | PA003 | >128 |
| S. aureus | SA009 | 8 |
| S. maltophilia | SMA001 | >128 |
| S. marcescens | SMS004 | >128 |
| 65. MBI 11G4CN | | |
| A. calcoaceticus | AC002 | 4 |
| E. cloacae | ECL007 | >128 |
| E. coli | ECO005 | 32 |
| E. faecium | EFM003 | 1 |
| E. faecalis | EFS002 | 32 |
| K. pneumoniae | KP001 | >128 |
| P. aeruginosa | PA004 | >128 |
| S. aureus | SA004 | 1 |
| S. epidermidis | SE010 | 2 |
| S. maltophilia | SMA002 | 64 |
| S. marcescens | SMS003 | >128 |
| 66. MBI 11G5CN | | |
| A. calcoaceticus | AC002 | 4 |
| E. cloacae | ECL007 | >128 |
| E. coli | ECO003 | 16 |
| E. faecium | EFM002 | 8 |

TABLE 11-continued

| | | |
|---|---|---|
| E. faecalis | EFS002 | 16 |
| K. pneumoniae | KP001 | >128 |
| P. aeruginosa | PA003 | >128 |
| S. aureus | SA012 | 4 |
| S. epidermidis | SE002 | 2 |
| S. maltophilia | SMA002 | 64 |
| S. marcescens | SMS004 | >128 |
| 67. MBI 11G6CN | | |
| A. calcoaceticus | AC001 | >128 |
| E. cloacae | ECL007 | >128 |
| E. coli | ECO002 | 32 |
| E. faecium | EFM003 | 4 |
| E. faecalis | EFS002 | 128 |
| K. pneumoniae | KP001 | >128 |
| P. aeruginosa | PA004 | >128 |
| S. aureus | SA006 | 2 |
| S. epidermidis | SE002 | 8 |
| S. maltophilia | SMA001 | >128 |
| S. marcescens | SMS003 | >128 |
| 68. MBI 11G6ACN | | |
| A. calcoaceticus | AC002 | 4 |
| E. cloacae | ECL007 | >128 |
| E. coli | ECO005 | 64 |
| E. faecalis | EFS008 | >128 |
| K. pneumoniae | KP001 | >128 |
| P. aeruginosa | PA004 | >128 |
| S. aureus | SA014 | 64 |
| S. epidermidis | SE010 | 32 |
| S. maltophilia | SMA002 | >128 |
| S. marcescens | SMS003 | >128 |
| 69. MBI 11G7CN | | |
| A. calcoaceticus | AC001 | 128 |
| E. cloacae | ECL006 | 64 |
| E. coli | ECO005 | 8 |
| E. faecium | EFM001 | 8 |
| E. faecalis | EFS002 | 32 |
| H. influenzae | HIN002 | >128 |
| K. pneumoniae | KP001 | 16 |
| P. aeruginosa | PA006 | >128 |
| S. aureus | SA012 | 2 |
| H. influenzae | SBHIN2 | >128 |
| S. marcescens | SBSM1 | >128 |
| S. pneumoniae | SBSPN2 | >128 |
| S. epidermidis | SE002 | 2 |
| S. maltophilia | SMA001 | 32 |
| S. marcescens | SMS003 | >128 |
| S. pneumoniae | SPN044 | >128 |
| S. pyogenes | SPY006 | 16 |
| 70. MBI 11G7ACN | | |
| A. calcoaceticus | AC002 | 4 |
| E. cloacae | ECL007 | >32 |
| E. coli | ECO002 | 16 |
| E. faecium | EFM001 | 8 |
| E. faecalis | EFS008 | 32 |
| K. pneumoniae | KP002 | >32 |
| P. aeruginosa | PA006 | >32 |
| S. aureus | SA010 | 1 |
| S. epidermidis | SE002 | 4 |
| S. maltophilia | SMA001 | 32 |
| S. marcescens | SMS004 | >32 |
| 71. MBI 11G13CN | | |
| E. coli | ECO002 | 32 |
| E. faecium | EFM002 | 16 |
| E. faecalis | EFS002 | 64 |
| H. influenzae | HIN002 | >128 |
| P. aeruginosa | PA004 | >128 |
| S. aureus | SA004 | 4 |
| E. coli | SBECO3 | 32 |
| S. marcescens | SBSM1 | >128 |
| S. pneumoniae | SBSPN3 | 128 |
| 72. MBI 11G14CN | | |
| A. calcoaceticus | AC002 | 8 |
| E. cloacae | ECL007 | >128 |

TABLE 11-continued

| Organism | Organism # | MIC (μg/ml) |
|---|---|---|
| E. coli | ECO003 | 32 |
| E. faecium | EFM001 | 16 |
| E. faecalis | EFS002 | 32 |
| K. pneumoniae | KP002 | 128 |
| P. aeruginosa | PA006 | >128 |
| S. aureus | SA013 | 0.5 |
| S. epidermidis | SE002 | 8 |
| S. maltophilia | SMA002 | 128 |
| S. marcescens | SMS004 | >128 |
| 73. MBI 11G16CN | | |
| A. calcoaceticus | AC002 | 8 |
| E. cloacae | ECL007 | >128 |
| E. coli | ECO005 | 16 |
| E. faecalis | EFS008 | 16 |
| K. pneumoniae | KP001 | 16 |
| P. aeruginosa | PA004 | 128 |
| S. aureus | SA093 | 2 |
| S. epidermidis | SE010 | 4 |
| S. maltophilia | SMA002 | 64 |
| S. marcescens | SMS003 | >128 |
| 74. MBI 11A6CN | | |
| A. calcoaceticus | AC002 | 2 |
| E. cloacae | ECL007 | >128 |
| E. coli | ECO005 | 16 |
| E. faecalis | EFS001 | 1 |
| E. faecalis | EFS008 | 8 |
| K. pneumoniae | KP001 | 32 |
| P. aeruginosa | PA004 | >128 |
| S. aureus | SA014 | 4 |
| S. aureus | SA093 | 0.5 |
| S. epidermidis | SE010 | 4 |
| S. maltophilia | SMA002 | 128 |
| S. marcescens | SMS003 | >128 |
| 75. MBI 11A7CN | | |
| A. calcoaceticus | AC002 | 4 |
| E. cloacae | ECL007 | >128 |
| E. coli | ECO005 | 8 |
| E. faecalis | EFS001 | 2 |
| E. faecalis | EFS008 | 4 |
| K. pneumoniae | KP001 | 8 |
| P. aeruginosa | PA004 | >128 |
| S. aureus | SA014 | 4 |
| S. aureus | SA093 | 1 |
| S. epidermidis | SE010 | 4 |
| S. maltophilia | SMA002 | 64 |
| S. marcescens | SMS003 | >128 |
| 76. MBI 11A9CN | | |
| A. calcoaceticus | AC002 | 8 |
| E. cloacae | ECL007 | 128 |
| E. coli | ECO005 | 32 |
| E. faecalis | EFS001 | 2 |
| E. faecalis | EFS008 | 8 |
| K. pneumoniae | KP001 | 32 |
| P. aeruginosa | PA004 | 128 |
| S. aureus | SA014 | 4 |
| S. aureus | SA093 | 2 |
| S. epidermidis | SE010 | 4 |
| S. maltophilia | SMA002 | 32 |
| S. marcescens | SMS003 | >128 |
| 77. MBI 11A10CN | | |
| A. calcoaceticus | AC002 | 4 |
| E. cloacae | ECL007 | 64 |
| E. coli | ECO005 | 16 |
| E. faecalis | EFS001 | 4 |
| E. faecalis | EFS008 | 16 |
| K. pneumoniae | KP001 | 16 |
| P. aeruginosa | PA004 | 64 |
| S. aureus | SA014 | 4 |
| S. aureus | SA093 | 2 |
| S. epidermidis | SE010 | 4 |
| S. maltophilia | SMA002 | 32 |
| S. marcescens | SMS003 | >128 |
| 78. MBI 11B5CN | | |
| A. calcoaceticus | AC002 | 4 |
| E. cloacae | ECL007 | >128 |
| E. coli | ECO005 | 16 |
| E. faecalis | EFS001 | 2 |
| E. faecalis | EFS008 | 8 |
| K. pneumoniae | KP001 | 16 |
| P. aeruginosa | PA004 | >128 |
| S. aureus | SA014 | 2 |
| S. aureus | SA093 | 1 |
| S. epidermidis | SE010 | 1 |
| S. maltophilia | SMA002 | 64 |
| S. marcescens | SMS003 | >128 |
| 79. MBI 11B7ACN | | |
| A. calcoaceticus | AC002 | 2 |
| E. cloacae | ECL007 | >128 |
| E. coli | ECO005 | 8 |
| E. faecalis | EFS001 | 1 |
| E. faecalis | EFS008 | 8 |
| K. pneumoniae | KP001 | 8 |
| P. aeruginosa | PA004 | 128 |
| S. aureus | SA014 | 2 |
| S. aureus | SA093 | 1 |
| S. epidermidis | SE010 | 4 |
| S. maltophilia | SMA002 | 32 |
| S. marcescens | SMS003 | >128 |
| 80. MBI 11B7CNF12 | | |
| A. calcoaceticus | AC002 | 4 |
| E. cloacae | ECL007 | >128 |
| E. coli | ECO005 | 16 |
| E. faecalis | EFS001 | 2 |
| E. faecalis | EFS008 | 8 |
| K. pneumoniae | KP001 | 16 |
| P. aeruginosa | PA004 | >128 |
| S. aureus | SA014 | 2 |
| S. aureus | SA093 | 1 |
| S. epidermidis | SE010 | 4 |
| S. maltophilia | SMA002 | 64 |
| S. marcescens | SMS003 | >128 |
| 81. MBI 11B10CN | | |
| A. calcoaceticus | AC002 | 2 |
| E. cloacae | ECL007 | >128 |
| E. coli | ECO005 | 16 |
| E. faecalis | EFS001 | 8 |
| E. faecalis | EFS008 | 64 |
| K. pneumoniae | KP001 | 32 |
| P. aeruginosa | PA004 | >128 |
| S. aureus | SA014 | 4 |
| S. aureus | SA093 | 1 |
| S. epidermidis | SE010 | 4 |
| S. maltophilia | SMA002 | 128 |
| S. marcescens | SMS003 | >128 |
| 82. MBI 11B19CN | | |
| A. calcoaceticus | AC002 | 4 |
| E. cloacae | ECL007 | >128 |
| E. coli | ECO005 | 8 |
| E. faecalis | EFS001 | 2 |
| E. faecalis | EFS008 | 32 |
| K. pneumoniae | KP001 | 64 |
| P. aeruginosa | PA004 | 128 |
| S. aureus | SA014 | 4 |
| S. aureus | SA093 | 2 |
| S. epidermidis | SE010 | 4 |
| S. maltophilia | SMA002 | 32 |
| S. marcescens | SMS003 | >128 |
| 83. MBI 11B20 | | |
| A. calcoaceticus | AC002 | 32 |
| E. cloacae | ECL007 | 128 |
| E. coli | ECO005 | 32 |
| E. faecalis | EFS001 | 8 |
| E. faecalis | EFS008 | 32 |
| K. pneumoniae | KP001 | 64 |

TABLE 11-continued

| | | |
|---|---|---|
| P. aeruginosa | PA004 | 128 |
| S. aureus | SA014 | 32 |
| S. aureus | SA093 | 4 |
| S. epidermidis | SE010 | 32 |
| S. maltophilia | SMA002 | 64 |
| S. marcescens | SMS003 | >128 |
| 84. MBI 11D9M8 | | |
| A. calcoaceticus | AC002 | 128 |
| E. cloacae | ECL007 | >128 |
| E. coli | ECO005 | >128 |
| E. faecalis | EFS001 | 8 |
| E. faecalis | EFS008 | 128 |
| K. pneumoniae | KP001 | >128 |
| P. aeruginosa | PA004 | >128 |
| S. aureus | SA014 | 128 |
| S. aureus | SA093 | 8 |
| S. epidermidis | SE010 | 128 |
| S. maltophilia | SMA002 | >128 |
| S. marcescens | SMS003 | >128 |
| 85. MBI 11D19CN | | |
| A. calcoaceticus | AC002 | 8 |
| E. cloacae | ECL007 | >128 |
| E. coli | ECO005 | 32 |
| E. faecalis | EFS001 | 4 |
| E. faecalis | EFS008 | 64 |
| K. pneumoniae | KP001 | 32 |
| P. aeruginosa | PA004 | 128 |
| S. aureus | SA014 | 4 |
| S. aureus | SA093 | 2 |
| S. epidermidis | SE010 | 8 |
| S. maltophilia | SMA002 | 64 |
| S. marcescens | SMS003 | >128 |
| 86. MBI 11F4 | | |
| A. calcoaceticus | AC002 | 4 |
| E. cloacae | ECL007 | 128 |
| E. coli | ECO005 | 8 |
| E. faecalis | EFS001 | 2 |
| E. faecalis | EFS008 | 8 |
| K. pneumoniae | KP001 | 8 |
| P. aeruginosa | PA004 | 128 |
| S. aureus | SA014 | 2 |
| S. aureus | SA093 | 1 |
| S. epidermidis | SE010 | 4 |
| S. maltophilia | SMA002 | 16 |
| S. marcescens | SMS003 | >128 |
| 87. MBI 11F5CN | | |
| A. calcoaceticus | AC002 | 4 |
| E. cloacae | ECL007 | 128 |
| E. coli | ECO005 | 8 |
| E. faecalis | EFS001 | 2 |
| E. faecalis | EFS008 | 8 |
| K. pneumoniae | KP001 | 8 |
| P. aeruginosa | PA004 | 32 |
| S. aureus | SA014 | 4 |
| S. aureus | SA093 | 2 |
| S. epidermidis | SE010 | 4 |
| S. maltophilia | SMA002 | 16 |
| S. marcescens | SMS003 | >128 |
| 88. MBI 11F6CN | | |
| A. calcoaceticus | AC002 | 16 |
| E. cloacae | ECL007 | 64 |
| E. coli | ECO005 | 32 |
| E. faecalis | EFS001 | 16 |
| E. faecalis | EFS008 | 16 |
| K. pneumoniae | KP001 | 32 |
| P. aeruginosa | PA004 | 128 |
| S. aureus | SA014 | 16 |
| S. aureus | SA093 | 8 |
| S. epidermidis | SE010 | 8 |
| S. maltophilia | SMA002 | 64 |
| S. marcescens | SMS003 | >128 |
| 89. MBI 11G24CN | | |
| A. calcoaceticus | AC002 | 4 |
| E. cloacae | ECL007 | >128 |
| E. coli | ECO005 | 16 |
| E. faecalis | EFS001 | 2 |
| E. faecalis | EFS008 | 8 |
| K. pneumoniae | KP001 | 16 |
| P. aeruginosa | PA004 | 128 |
| S. aureus | SA014 | 2 |
| S. aureus | SA093 | 1 |
| S. epidermidis | SE010 | 4 |
| S. maltophilia | SMA002 | 32 |
| S. marcescens | SMS003 | >128 |
| 90. MBI 11G25CN | | |
| A. calcoaceticus | AC002 | 2 |
| E. cloacae | ECL007 | >128 |
| E. coli | ECO005 | 8 |
| E. faecalis | EFS001 | 2 |
| E. faecalis | EFS008 | 16 |
| K. pneumoniae | KP001 | 16 |
| P. aeruginosa | PA004 | 64 |
| S. aureus | SA014 | 2 |
| S. aureus | SA093 | 1 |
| S. epidermidis | SE010 | 2 |
| S. maltophilia | SMA002 | 32 |
| S. marcescens | SMS003 | >128 |
| 91. MBI 11G26CN | | |
| A. calcoaceticus | AC002 | 2 |
| E. cloacae | ECL007 | >128 |
| E. coli | ECO005 | 32 |
| E. faecalis | EFS001 | 2 |
| E. faecalis | EFS008 | 4 |
| K. pneumoniae | KP001 | 32 |
| P. aeruginosa | PA004 | >128 |
| S. aureus | SA014 | 4 |
| S. aureus | SA093 | 0.5 |
| S. epidermidis | SE010 | 4 |
| S. maltophilia | SMA002 | 128 |
| S. marcescens | SMS003 | >128 |
| 92. MBI 11G27CN | | |
| A. calcoaceticus | AC002 | 2 |
| E. cloacae | ECL007 | >128 |
| E. coli | ECO005 | 16 |
| E. faecalis | EFS001 | 8 |
| E. faecalis | EFS008 | 32 |
| K. pneumoniae | KP001 | 32 |
| P. aeruginosa | PA004 | 128 |
| S. aureus | SA014 | 4 |
| S. aureus | SA093 | 1 |
| S. epidermidis | SE010 | 8 |
| S. maltophilia | SMA002 | 32 |
| S. marcescens | SMS003 | >128 |
| 93. MBI 11G28CN | | |
| A. calcoaceticus | AC002 | 2 |
| E. cloacae | ECL007 | >128 |
| E. coli | ECO005 | 8 |
| E. faecalis | EFS001 | 4 |
| E. faecalis | EFS008 | 32 |
| K. pneumoniae | KP001 | 64 |
| P. aeruginosa | PA004 | 128 |
| S. aureus | SA014 | 4 |
| S. aureus | SA093 | 1 |
| S. epidermidis | SE010 | 4 |
| S. maltophilia | SMA002 | 32 |
| S. marcescens | SMS003 | >128 |
| 94. MBI 11H01CN | | |
| A. calcoaceticus | AC002 | 2 |
| E. cloacae | ECL007 | >128 |
| E. coli | ECO005 | 8 |
| E. faecalis | EFS001 | 2 |
| E. faecalis | EFS008 | 8 |
| K. pneumoniae | KP001 | 8 |
| P. aeruginosa | PA004 | 128 |
| S. aureus | SA014 | 2 |
| S. aureus | SA093 | 1 |
| S. epidermidis | SE010 | 2 |

TABLE 11-continued

| | | |
|---|---|---|
| S. maltophilia | SMA002 | 32 |
| S. marcescens | SMS003 | >128 |
| 95. MBI 11H02CN | | |
| A. calcoaceticus | AC002 | 4 |
| E. cloacae | ECL007 | >128 |
| E. coli | ECO005 | 16 |
| E. faecalis | EFS001 | 2 |
| E. faecalis | EFS008 | 16 |
| K. pneumoniae | KP001 | 32 |
| P. aeruginosa | PA004 | >128 |
| S. aureus | SA014 | 2 |
| S. aureus | SA093 | 1 |
| S. epidermidis | SE010 | 4 |
| S. maltophilia | SMA002 | 64 |
| S. marcescens | SMS003 | >128 |
| 96. MBI 11H03CN | | |
| A. calcoaceticus | AC002 | 8 |
| E. cloacae | ECL007 | >128 |
| E. coli | ECO005 | 16 |
| E. faecalis | EFS001 | 2 |
| E. faecalis | EFS008 | 8 |
| K. pneumoniae | KP001 | 16 |
| P. aeruginosa | PA004 | >128 |
| S. aureus | SA014 | 2 |
| S. aureus | SA093 | 2 |
| S. epidermidis | SE010 | 4 |
| S. maltophilia | SMA002 | 64 |
| S. marcescens | SMS003 | >128 |
| 97. MBI 11H04CN | | |
| A. calcoaceticus | AC002 | 8 |
| E. cloacae | ECL007 | >128 |
| E. coli | ECO005 | 32 |
| E. faecalis | EFS001 | 2 |
| E. faecalis | EFS008 | 8 |
| K. pneumoniae | KP001 | 64 |
| P. aeruginosa | PA004 | >128 |
| S. aureus | SA014 | 4 |
| S. aureus | SA093 | 2 |
| S. epidermidis | SE010 | 16 |
| S. maltophilia | SMA002 | >128 |
| S. marcescens | SMS003 | >128 |
| 98. MBI 11H05CN | | |
| A. calcoaceticus | AC002 | 4 |
| E. cloacae | ECL007 | >128 |
| E. coli | ECO005 | 8 |
| E. faecalis | EFS001 | 2 |
| E. faecalis | EFS008 | 8 |
| K. pneumoniae | KP001 | 8 |
| P. aeruginosa | PA004 | 128 |
| S. aureus | SA014 | 2 |
| S. aureus | SA093 | 1 |
| S. epidermidis | SE010 | 4 |
| S. maltophilia | SMA002 | 16 |
| S. marcescens | SMS003 | >128 |
| 99. MBI 11H06CN | | |
| A. calcoaceticus | AC002 | 8 |
| E. cloacae | ECL007 | >128 |
| E. coli | ECO005 | 16 |
| E. faecalis | EFS001 | 2 |
| E. faecalis | EFS008 | 16 |
| K. pneumoniae | KP001 | 64 |
| P. aeruginosa | PA004 | >128 |
| S. aureus | SA014 | 8 |
| S. aureus | SA093 | 1 |
| S. epidermidis | SE010 | 8 |
| S. maltophilia | SMA002 | 64 |
| S. marcescens | SMS003 | >128 |
| 100. MBI 11H07CN | | |
| A. calcoaceticus | AC002 | 8 |
| E. cloacae | ECL007 | >128 |
| E. coli | ECO005 | 32 |
| E. faecalis | EFS001 | 4 |
| E. faecalis | EFS008 | 16 |
| K. pneumoniae | KP001 | 128 |
| P. aeruginosa | PA004 | >128 |
| S. aureus | SA014 | 8 |
| S. aureus | SA093 | 2 |
| S. epidermidis | SE010 | 16 |
| S. maltophilia | SMA002 | 128 |
| S. marcescens | SMS003 | >128 |
| 101. MBI 11H08CN | | |
| A. calcoaceticus | AC002 | 4 |
| E. cloacae | ECL007 | >128 |
| E. coli | ECO005 | 8 |
| E. faecalis | EFS001 | 2 |
| E. faecalis | EFS008 | 8 |
| K. pneumoniae | KP001 | 32 |
| P. aeruginosa | PA004 | >128 |
| S. aureus | SA014 | 4 |
| S. aureus | SA093 | 1 |
| S. epidermidis | SE010 | 4 |
| S. maltophilia | SMA002 | 32 |
| S. marcescens | SMS003 | >128 |
| 102. MBI 11H09CN | | |
| A. calcoaceticus | AC002 | 4 |
| E. cloacae | ECL007 | >128 |
| E. coli | ECO005 | 32 |
| E. faecalis | EFS001 | 4 |
| E. faecalis | EFS008 | 64 |
| K. pneumoniae | KP001 | 64 |
| P. aeruginosa | PA004 | >128 |
| S. aureus | SA014 | 8 |
| S. aureus | SA093 | 2 |
| S. epidermidis | SE010 | 16 |
| S. maltophilia | SMA002 | 64 |
| S. marcescens | SMS003 | >128 |
| 103. MBI 11H10CN | | |
| A. calcoaceticus | AC002 | 4 |
| E. cloacae | ECL007 | >128 |
| E. coli | ECO005 | 16 |
| E. faecalis | EFS001 | 2 |
| E. faecalis | EFS008 | 8 |
| K. pneumoniae | KP001 | 16 |
| P. aeruginosa | PA004 | >128 |
| S. aureus | SA014 | 4 |
| S. aureus | SA093 | 1 |
| S. epidermidis | SE010 | 4 |
| S. maltophilia | SMA002 | 64 |
| S. marcescens | SMS003 | >128 |
| 104. MBI 11H11CN | | |
| A. calcoaceticus | AC002 | 4 |
| E. cloacae | ECL007 | >128 |
| E. coli | ECO005 | 16 |
| E. faecalis | EFS001 | 2 |
| E. faecalis | EFS008 | 8 |
| K. pneumoniae | KP001 | 16 |
| P. aeruginosa | PA004 | >128 |
| S. aureus | SA014 | 4 |
| S. aureus | SA093 | 1 |
| S. epidermidis | SE010 | 4 |
| S. maltophilia | SMA002 | 64 |
| S. marcescens | SMS003 | >128 |
| 105. MBI 11H12CN | | |
| A. calcoaceticus | AC002 | 4 |
| E. cloacae | ECL007 | >128 |
| E. coli | ECO005 | 16 |
| E. faecalis | EFS001 | 2 |
| E. faecalis | EFS008 | 8 |
| K. pneumoniae | KP001 | 16 |
| P. aeruginosa | PA004 | >128 |
| S. aureus | SA014 | 2 |
| S. aureus | SA093 | 1 |
| S. epidermidis | SE010 | 4 |
| S. maltophilia | SMA002 | 64 |
| S. marcescens | SMS003 | >128 |

TABLE 11-continued

106. MBI 11J01CN

| | | |
|---|---|---|
| A. calcoaceticus | AC002 | 4 |
| E. cloacae | ECL007 | >128 |
| E. coli | ECO005 | 64 |
| E. faecalis | EFS001 | 128 |
| E. faecalis | EFS008 | >128 |
| K. pneumoniae | KP001 | >128 |
| P. aeruginosa | PA004 | >128 |
| S. aureus | SA014 | 16 |
| S. aureus | SA093 | 2 |
| S. epidermidis | SE010 | 32 |
| S. maltophilia | SMA002 | >128 |
| S. marcescens | SMS003 | >128 |

107. MBI 11J02CN

| | | |
|---|---|---|
| A. calcoaceticus | AC002 | 4 |
| E. cloacae | ECL007 | 64 |
| E. coli | ECO005 | 4 |
| E. faecalis | EFS001 | 4 |
| E. faecalis | EFS008 | 16 |
| K. pneumoniae | KP001 | 4 |
| P. aeruginosa | PA004 | 32 |
| S. aureus | SA014 | 2 |
| S. aureus | SA093 | 1 |
| S. epidermidis | SE010 | 2 |
| S. maltophilia | SMA002 | 8 |
| S. marcescens | SMS003 | >128 |

TABLE 12

| Organism | MBI 11CN MIC (µg/ml) | MBI 11B7CN MIC (µg/ml) |
|---|---|---|
| C. albicans CA001 | 128 | 64 |
| C. albicans CA002 | 64 | 32 |
| C. albicans CA003 | 128 | 64 |
| C. albicans CA004 | 64 | 32 |
| C. albicans CA005 | 128 | 32 |
| C. albicans CA006 | 128 | 64 |
| C. albicans CA007 | 128 | 64 |
| C. albicans CA008 | 64 | 32 |
| C. albicans CA009 | 64 | 32 |
| C. albicans CA010 | 128 | 64 |
| C. albicans CA011 | 64 | 64 |
| C. albicans CA012 | 128 | 64 |
| C. albicans CA013 | 128 | 64 |
| C. albicans CA014 | 64 | 32 |
| C. albicans CA015 | 128 | 64 |
| C. albicans CA016 | 128 | 64 |
| C. albicans CA017 | 128 | 64 |
| C. albicans CA018 | 128 | 64 |
| C. albicans CA019 | 128 | 64 |
| C. albicans CA020 | 128 | 32 |
| C. albicans CA021 | 128 | 32 |
| C. albicans CA022 | 32 | 32 |
| C. albicans CA023 | 128 | 64 |
| C. albicans CA024 | 16 | 8 |
| C. glabrata CGL001 | >128 | 128 |
| C. glabrata CGL002 | >128 | 128 |
| C. glabrata CGL003 | >128 | 128 |
| C. glabrata CGL004 | >128 | 128 |
| C. glabrata CGL005 | >128 | 128 |
| C. glabrata CGL009 | >128 | 128 |
| C. glabrata CGL010 | >128 | 128 |
| C. krusei CKR001 | 0.5 | 1 |
| C. tropicalis CTR001 | 4 | 4 |
| C. tropicalis CTR002 | 4 | 8 |
| C. tropicalis CTR003 | 8 | 8 |
| C. tropicalis CTR004 | 4 | 8 |
| C. tropicalis CTR005 | 4 | 4 |
| C. tropicalis CTR006 | 16 | 8 |
| C. tropicalis CTR007 | 16 | 8 |
| C. tropicalis CTR008 | 8 | 4 |
| C. tropicalis CTR009 | 8 | 4 |

Broth Dilution Assay

Typically 100 µl of calcium and magnesium supplemented Mueller Hinton broth is dispensed into each well of a 96-well microtitre plate and 100 µl volumes of two-fold serial dilutions of the peptide are prepared across the plate. One row of wells receives no peptide and is used as a growth control. Each well is inoculated with approximately $5 \times 10^5$ CFU of bacteria and the plate is incubated at 35-37° C. for 16-20 hours. The MIC is recorded at the lowest concentration of peptide that completely inhibits growth of the organism as determined by visual inspection.

For example, MIC values in µg/ml are established by broth dilution assay (Table 13) or by agarose dilution assay (Table 14) for a series of cationic peptides against various bacterial strains.

TABLE 13

| Organism | MBI 11CN | MBI 11A1CN |
|---|---|---|
| A. calcoaceticus 8191 | 256 | >256 |
| E. cloacae 13047 | >128 | >256 |
| E. coli KL4 | 64 | 256 |
| E. coli DH1 | 64 | 128 |
| E. coli ECO003 | 64 | >256 |
| E. coli 25922 | 128 | 512 |
| E. faecalis 29212 | 64 | >256 |
| K. pneumoniae 13883 | >128 | >256 |
| K. pneumoniae B44 | 64 | >256 |
| P. aeruginosa H650 | 256 | >256 |
| P. aeruginosa H652 | 256 | >256 |
| P. aeruginosa 27853 | >128 | >256 |
| P. aeruginosa 9503024 | >256 | >256 |
| P. aeruginosa 8509041 | 256 | >256 |
| P. aeruginosa 9308077 | 128 | >256 |
| S. aureus 25923 | 32 | 512 |
| S. aureus 27217 | 64 | >256 |
| S. aureus 33593 | 64 | >256 |
| S. aureus 29213 | 32 | 512 |
| S. aureus 8809014 | 32 | >256 |
| S. aureus 8809025 | 64 | >256 |
| S. aureus 8402093 | 32 | >256 |
| S. maltophilia 13637 | 128 | 256 |
| S. epidermidis 14990 | 8 | 512 |
| S. maltophilia H361 | 64 | 256 |
| S. marcescens 13880 | >128 | >256 |
| S. marcescens B21 | >256 | >256 |

TABLE 14

| | Peptide MIC values in ug/ml | | | | | | | | |
|---|---|---|---|---|---|---|---|---|---|
| Organism | MBI 10CN | MBI 11CN | MBI 11A1CN | MBI 11A3CN | MBI 11B4CN | MBI 11B8CN | MBI 11D18CN | MBI 11F1CN | MBI 11G13CN |
| E. coli ATCC 25922 | 16 | 16 | 128 | >128 | 32 | 32 | 16 | 8 | 64 |
| E. coli ESS | ND | ND | 16 | >128 | 8 | ND | 2 | ND | 32 |
| E. coli NCTC 10418 | 8 | 4 | 16 | 64 | 8 | 4 | 2 | 2 | 16 |
| E. faecium ATCC 29212 | 4 | 8 | 128 | >128 | 8 | 8 | 8 | 8 | 32 |
| P. aeruginosa ATCC 27853 | >128 | >128 | >128 | >128 | >128 | >128 | 128 | 64 | >128 |
| P. aeruginosa NCTC 10662 | >128 | >128 | >128 | >128 | >128 | >128 | 128 | 64 | >128 |
| P. vulgaris ATCC 13315 | ND | ND | >128 | >128 | >128 | ND | 32 | ND | >128 |
| S. aureus ATCC 29213 | ND | ND | 2 | 16 | 1 | ND | 0.5 | ND | 1 |
| S. aureus MRSA13 | 4 | 16 | >128 | >128 | 32 | 32 | 8 | 16 | 64 |
| S. aureus MRSA17 | 2 | 4 | 32 | >128 | 8 | 4 | 2 | 2 | 16 |
| S. aureus MRSA9 | 1 | 2 | 8 | 128 | 4 | 2 | 2 | 2 | 8 |
| S. aureus SA206 | ND | ND | 128 | >128 | 16 | ND | 4 | ND | 32 |
| S. marcescens SM76 | ND | ND | >128 | >128 | >128 | ND | >128 | ND | >128 |
| S. marcescens SM82 | >128 | >128 | >128 | >128 | >128 | >128 | >128 | >128 | >128 |
| S. pneumoniae 406LE8 | >128 | >128 | >128 | >128 | 128 | >128 | 64 | 128 | 128 |
| S. pneumoniae 60120 | 64 | >128 | >128 | >128 | >128 | >128 | 128 | 128 | >128 |
| S. pneumoniae ATCC 49619 | 32 | 64 | >128 | >128 | 64 | 128 | 64 | 64 | 128 |

ND = Not determined

Time Kill Assay

Time kill curves are used to determine the antimicrobial activity of cationic peptides over a time interval. Briefly, in this assay, a suspension of microorganisms equivalent to a 0.5 McFarland Standard is prepared in 0.9% saline. This suspension is then diluted such that when added to a total volume of 9 ml of cation-adjusted Mueller Hinton broth, the inoculum size is 1×10$^6$ CFU/ml. An aliquot of 0.1 ml is removed from each tube at pre-determined intervals up to 24 hours, diluted in 0.9% saline and plated in triplicate to determine viable colony counts. The number of bacteria remaining in each sample is plotted over time to determine the rate of cationic peptide killing. Generally a three or more log$_{10}$ reduction in bacterial counts in the antimicrobial suspension compared to the growth controls indicate an adequate bactericidal response.

As shown in FIGS. 3A-E, most of the peptides demonstrate a three or more log$_{10}$ reduction in bacterial counts in the antimicrobial suspension compared to the growth controls, indicating that these peptides have met the criteria for a bactericidal response.

Example 5

Assays to Measure Enhanced Activity of Antibiotic Agent and Cationic Peptide Combinations Killing Curves Time kill curves resulting from combination of cationic peptide and antibiotic agent are compared to that resulting from agent alone.

Figure 3A:
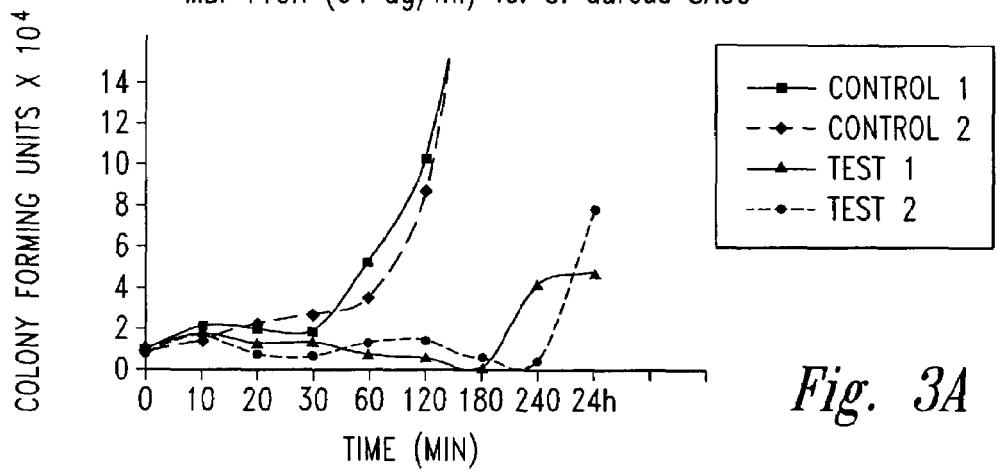
FIGS. 3A-E presents time kill assay results for MBI 11CN, MBI 11F4CN, MBI 11B7CN, MBI 11F4CN, and MBI 26 plus vancomycin. The number of colony forming units $\times 10^4$ is plotted versus time.
Figure 3B:
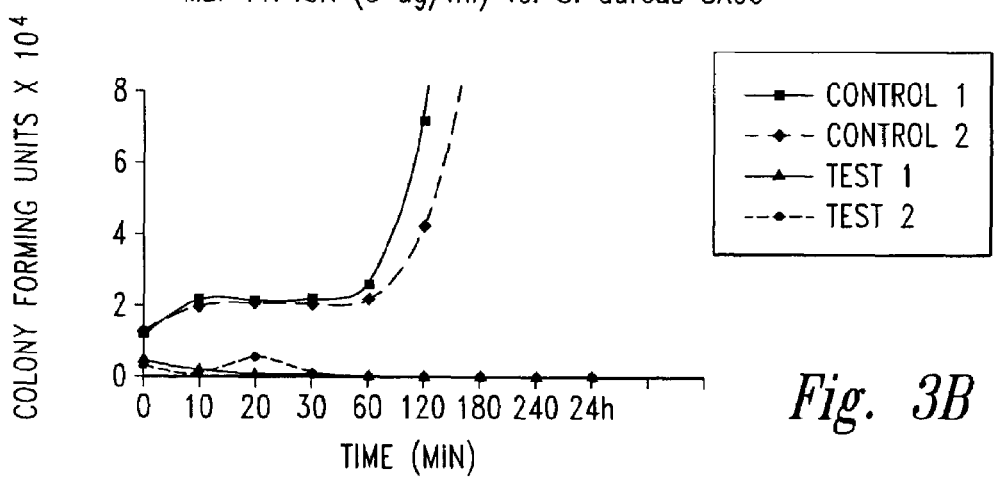
Figure 3C:
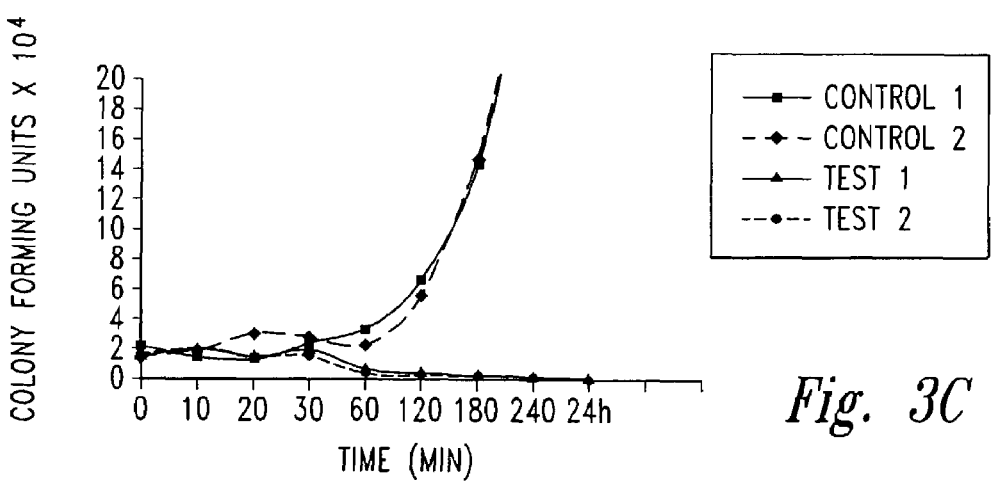
Figure 3D:
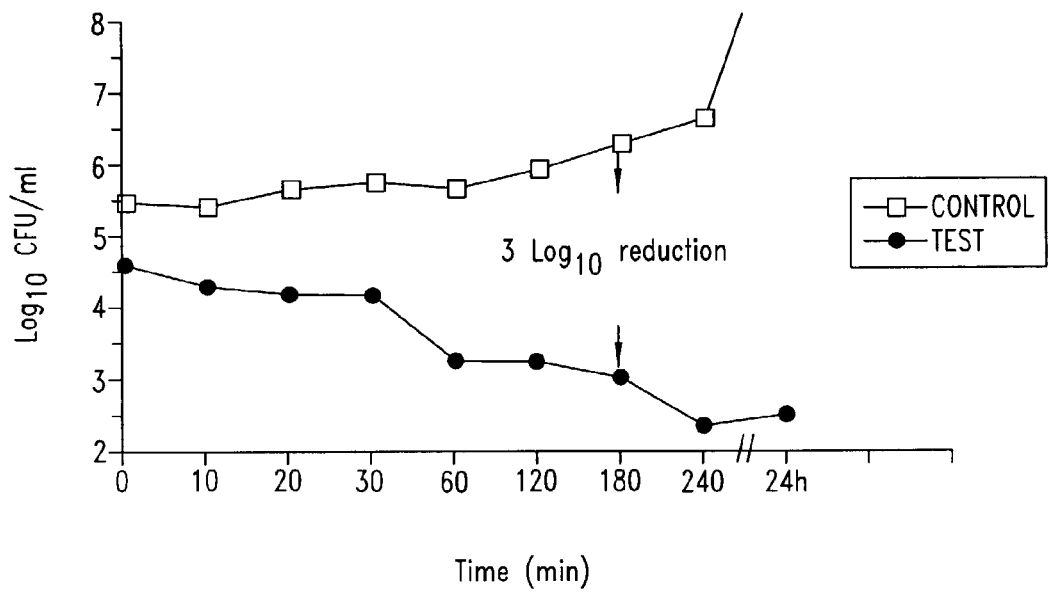
Figure 3E:
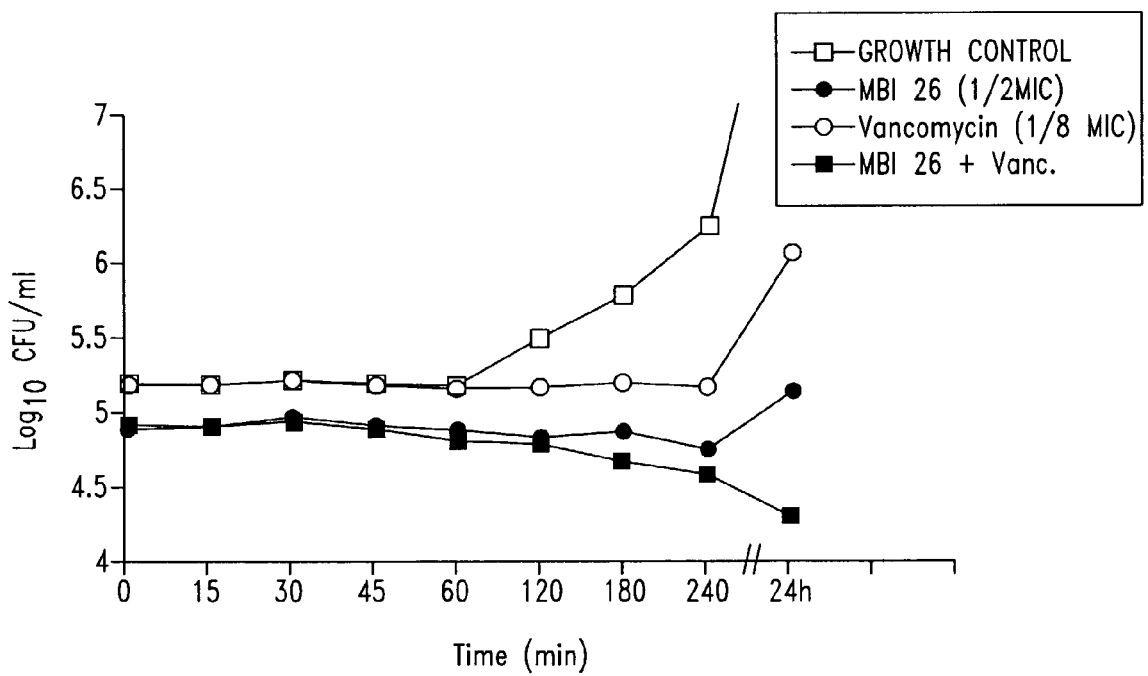

The assay is performed as described above except that duplicate tubes are set up for each concentration of the antibiotic agent alone and of the combination of antibiotic agent and cationic peptide. Synergy is demonstrated by at least a 100-fold (2 log$_{10}$) increase in killing at 24 hours by the antibiotic agent and cationic peptide combination compared to the antibiotic agent alone. A time kill assay is shown in FIG. 3E for MBI 26 in combination with vancomycin against a bacterial strain. The combination of peptide and antibiotic agent gave greater killing than either peptide or antibiotic agent alone.

FIC Measurements

In this method, synergy is determined using the agarose dilution technique. An array of plates or tubes, each containing a combination of peptide and antibiotic in a unique concentration mix, is inoculated with bacterial isolates. When performing solid phase assays, calcium and magnesium supplemented Mueller Hinton broth is used in combination with a low EEO agarose as the bacterial growth medium. Broth dilution assays can also be used to determine synergy. Synergy is determined for cationic peptides in combination with a number of conventional antibiotic agents, for example, penicillins, cephalosporins, carbapenems, monobactams, aminoglycosides, macrolides, fluoroquinolones, nisin and lysozyme.

Synergy is expressed as a fractional inhibitory concentration (FIC), which is calculated according to the equation below. An FIC$\leq$0.5 is evidence of synergy. An additive response has an FIC value >0.5 and $\leq$1, while an indifferent response has an FIC value >1 and $\leq$2.

$$FIC = \frac{MIC(\text{peptide in combination})}{MIC(\text{peptide alone})} + \frac{MIC(\text{antibiotic in combination})}{MIC(\text{antibiotic alone})}$$

Tables 15, 16 and 17 present combinations of cationic peptides and antibiotic agents that display an FIC value of less than or equal to 1. Although FIC is measured in vitro and synergy defined as an FIC of less than or equal to 0.5, an additive effect may be therapeutically useful. As shown below, although all the microorganisms are susceptible (NCCLS breakpoint definitions) to the tested antibiotic agents, the addition of the cationic peptide improves the efficacy of the antibiotic agent.

TABLE 15

| Microorganism | Strain | Antibiotic | FIC | Peptide |
|---|---|---|---|---|
| S. aureus | SA014 | Ciprofloxacin | 0.63 | MBI 26 |
| S. aureus | SA014 | Ciprofloxacin | 0.75 | MBI 28 |
| S. aureus | SA014 | Ciprofloxacin | 1.00 | MBI 11A2CN |
| S. aureus | SA093 | Ciprofloxacin | 0.75 | MBI 11A2CN |
| S. aureus | SA7609 | Clindamycin | 0.25 | MBI 26 |
| S. aureus | SA7609 | Methicillin | 0.56 | MBI 26 |
| S. aureus | SA7610 | Clindamycin | 0.63 | MBI 26 |
| S. aureus | SA7610 | Methicillin | 0.31 | MBI 26 |
| S. aureus | SA7795 | Ampicillin | 0.52 | MBI 26 |
| S. aureus | SA7795 | Clindamycin | 0.53 | MBI 26 |
| S. aureus | SA7796 | Ampicillin | 1.00 | MBI 26 |
| S. aureus | SA7796 | Clindamycin | 0.51 | MBI 26 |
| S. aureus | SA7817 | Ampicillin | 0.50 | MBI 26 |
| S. aureus | SA7818 | Ampicillin | 1.00 | MBI 26 |
| S. aureus | SA7818 | Erythromycin | 0.15 | MBI 26 |
| S. aureus | SA7818 | Erythromycin | 0.15 | MBI 26 |
| S. aureus | SA7821 | Erythromycin | 0.50 | MBI 26 |
| S. aureus | SA7821 | Erythromycin | 0.50 | MBI 26 |
| S. aureus | SA7822 | Ampicillin | 0.25 | MBI 26 |
| S. aureus | SA7823 | Ampicillin | 0.25 | MBI 26 |
| S. aureus | SA7824 | Ampicillin | 1.00 | MBI 26 |
| S. aureus | SA7825 | Ampicillin | 1.00 | MBI 26 |
| S. aureus | SA7825 | Erythromycin | 1.00 | MBI 26 |
| S. aureus | SA7825 | Erythromycin | 1.00 | MBI 26 |
| S. aureus | SA7834 | Ampicillin | 0.53 | MBI 26 |
| S. aureus | SA7834 | Clindamycin | 0.56 | MBI 26 |
| S. aureus | SA7835 | Ampicillin | 0.53 | MBI 26 |
| S. aureus | SA7836 | Ampicillin | 0.75 | MBI 26 |
| S. aureus | SA7837 | Ampicillin | 1.00 | MBI 26 |
| S. aureus | SAATCC25293 | Methicillin | 0.50 | MBI 26 |
| S. aureus | SAATCC29213 | Methicillin | 0.31 | MBI 26 |
| S. aureus | SAW1133 | Methicillin | 0.75 | MBI 26 |
| S. epidermidis | SE8406 | Clindamycin | 0.50 | MBI 26 |
| S. epidermidis | SE8416 | Ampicillin | 0.52 | MBI 31 |
| S. epidermidis | SE8416 | Clindamycin | 0.56 | MBI 26 |
| S. epidermidis | SE8505 | Ampicillin | 1.00 | MBI 26 |
| S. epidermidis | SE8565 | Ampicillin | 1.00 | MBI 26 |
| S. epidermidis | SH8575 | Ampicillin | 0.27 | MBI 31 |
| S. haemolyticus | SA7797 | Ampicillin | 0.50 | MBI 31 |
| S. haemolyticus | SA7817 | Ampicillin | 0.26 | MBI 31 |
| S. haemolyticus | SA7818 | Ampicillin | 0.52 | MBI 31 |
| S. haemolyticus | SA7834 | Ampicillin | 0.52 | MBI 31 |
| S. haemolyticus | SA7835 | Ampicillin | 0.50 | MBI 31 |
| S. haemolyticus | SH8459 | Ampicillin | 0.52 | MBI 26 |
| S. haemolyticus | SH8472 | Ampicillin | 0.56 | MBI 26 |
| S. haemolyticus | SH8563 | Ampicillin | 0.75 | MBI 26 |
| S. haemolyticus | SH8564 | Ampicillin | 0.62 | MBI 26 |
| S. haemolyticus | SH8575 | Ampicillin | 0.75 | MBI 26 |
| S. haemolyticus | SH8576 | Ampicillin | 0.62 | MBI 26 |
| S. haemolyticus | SH8578 | Ampicillin | 1.00 | MBI 26 |
| S. haemolyticus | SH8597 | Ampicillin | 1.00 | MBI 31 |

TABLE 16

| Microorganism | Strain | Teicoplanin (µg/ml) Alone | Teicoplanin (µg/ml) +MBI 26 | MBI 26 (µg/ml) Alone | MBI 26 (µg/ml) +Teicoplanin |
|---|---|---|---|---|---|
| E. faecium 97001 | VanB | 0.5 | 0.25 | 64 | 4 |
| E. faecium 97002 | VanB | 0.5 | 0.25 | 64 | 1 |
| E. faecium 97003 | VanB | 0.5 | 0.25 | 64 | 1 |
| E. faecium 97005 | VanB | 1 | 0.25 | 64 | 2 |
| E. faecium 97006 | VanB | 0.5 | 0.5 | 64 | 4 |
| E. faecium 97007 | VanB | 0.5 | 0.25 | 64 | 1 |
| E. faecium 97008 | VanB | 0.5 | 0.25 | 64 | 4 |
| E. faecium 97009 | VanB | 0.5 | 0.25 | 32 | 1 |
| E. faecium 97010 | VanB | 0.5 | 0.25 | 64 | 4 |
| E. faecium 97011 | VanB | 0.5 | 0.25 | 64 | 4 |
| E. faecium 97012 | VanB | 8 | 0.25 | 64 | 4 |
| E. faecium 97013 | VanB | 8 | 0.25 | 64 | 8 |
| E. faecium 97014 | VanB | 8 | 0.25 | 32 | 4 |
| E. faecium 97015 | VanB | 0.5 | 0.25 | 64 | 4 |
| E. faecium 97016 | VanB | 0.5 | 0.25 | 64 | 4 |
| E. faecalis 97040 | VanB | 0.5 | 0.25 | 64 | 8 |
| E. faecalis 97041 | VanB | 1 | 0.25 | 64 | 8 |
| E. faecalis 97042 | VanB | 1 | 0.25 | 64 | 8 |
| E. faecalis 97043 | VanB | 0.5 | 0.25 | 64 | 8 |

TABLE 17

1. Amikacin

| Peptide | Organism | FIC | Amikacin MIC (µg/ml) Alone | Amikacin MIC (µg/ml) +Peptide | Peptide MIC (µg/ml) Alone | Peptide MIC (µg/ml) +Amikacin |
|---|---|---|---|---|---|---|
| MBI 11B16CN | A. baumannii ABI001 | 0.50 | 32 | 0.125 | 32 | 16 |
| | A. baumannii ABI003 | 0.53 | 16 | 0.5 | 16 | 8 |
| | P. aeruginosa PA022 | 0.38 | 64 | 8 | 64 | 16 |
| | P. aeruginosa PA037 | 0.25 | 16 | 2 | >128 | 32 |
| | S. maltophilia SMA018 | 0.31 | 128 | 8 | 32 | 8 |
| | S. maltophilia SMA022 | 0.09 | >128 | 8 | >128 | 16 |
| | E. faecalis EFS008 | 0.28 | 32 | 8 | 8 | 0.25 |
| MBI 21A2 | A. baumannii ABI001 | 0.52 | 64 | 32 | 8 | 0.125 |
| | A. baumannii ABI003 | 0.52 | 16 | 8 | 8 | 4 |
| | P. aeruginosa PA022 | 0.50 | 64 | 16 | 8 | 2 |
| | S. maltophilia SMA018 | 0.50 | >128 | 64 | 16 | 4 |
| | S. maltophilia SMA022 | 0.25 | >128 | 32 | >128 | 32 |
| | E. faecium EFM004 | 0.56 | 128 | 64 | >128 | 16 |
| | E. faecalis EFS008 | 0.50 | 64 | 32 | >128 | 0.125 |
| | S. aureus SA025 MRSA | 0.56 | 32 | 2 | 2 | 1 |
| | S. epidermidis SE003 | 0.38 | 32 | 4 | >128 | 64 |

TABLE 17-continued

| | | | | | | |
|---|---|---|---|---|---|---|
| 26 | A. baumannii ABI001 | 0.50 | 32 | 8 | 8 | 2 |
| | A. baumannii ABI003 | 0.38 | 16 | 2 | 8 | 2 |
| | S. maltophilia SMA021 | 0.13 | 128 | 8 | 32 | 2 |
| | S. maltophilia SMA037 | 0.19 | 128 | 16 | >128 | 16 |
| 27 | A. baumannii ABI003 | 0.52 | 16 | 0.25 | 8 | 4 |
| | B. cepacia BC005 | 0.50 | 64 | 16 | >128 | 64 |
| | S. maltophilia SMA037 | 0.31 | 64 | 4 | 64 | 16 |
| | S. maltophilia SMA060 | 0.50 | >128 | 0.125 | 16 | 8 |
| | E. faecalis EFS008 | 0.53 | 32 | 1 | 4 | 2 |
| MBI 29A3 | B. cepacia BC003 | 0.50 | 32 | 8 | >128 | 64 |
| | B. cepacia BC005 | 0.38 | 128 | 32 | >128 | 32 |
| | S. maltophilia SMA036 | 0.38 | >128 | 32 | 64 | 16 |
| | S. maltophilia SMA063 | 0.56 | >128 | 16 | 8 | 4 |
| | S. maltophilia SMA064 | 0.56 | >128 | 16 | 8 | 4 |
| | E. faecium EFM004 | 0.56 | 128 | 8 | 8 | 4 |
| MBI 29F1 | A. baumannii ABI001 | 0.51 | 32 | 0.25 | 8 | 4 |
| | A. baumannii ABI003 | 0.63 | 16 | 2 | 4 | 2 |
| | E. coli ECO022 | 0.51 | 16 | 0.125 | 4 | 2 |
| | P. aeruginosa PA022 | 0.53 | 128 | 64 | 4 | 0.125 |
| | S. maltophilia SMA021 | 0.31 | 128 | 8 | 8 | 2 |
| | S. maltophilia SMA022 | 0.31 | >128 | 16 | 16 | 4 |
| | E. faecium EFM004 | 0.38 | >128 | 32 | 32 | 8 |
| | E. faecalis EFS008 | 0.28 | 64 | 16 | 4 | 0.125 |
| | S. aureus SA014 MRSA | 0.53 | 32 | 16 | 4 | 0.125 |
| | S. epidermidis SE002 | 0.38 | 64 | 16 | 32 | 4 |
| | S. epidermidis SE003 | 0.50 | 64 | 16 | 32 | 8 |

2. Ceftriaxone

| Peptide | Organism | FIC | Ceftriaxone MIC (µg/ml) Alone | +Peptide | Peptide MIC (µg/ml) Alone | +Ceftriaxone |
|---|---|---|---|---|---|---|
| MBI 11B7CN | A. baumannii ABI002 | 0.50 | 32 | 8 | 32 | 8 |
| | A. baumannii ABI006 | 0.25 | 128 | 16 | 32 | 4 |
| | B. cepacia BC003 | 0.52 | 32 | 16 | >128 | 4 |
| | P. aeruginosa PA008 | 0.25 | 128 | 16 | 128 | 16 |
| | P. aeruginosa PA024 | 0.50 | 64 | 32 | >128 | 0.125 |
| | S. maltophilia SMA020 | 0.75 | >128 | 64 | 16 | 8 |
| | S. maltophilia SMA021 | 0.50 | >128 | 64 | 32 | 8 |
| | S. maltophilia SMA023 | 0.38 | 128 | 32 | 128 | 16 |
| MBI 11J02CN | A. baumannii ABI005 | 0.56 | 16 | 8 | 8 | 0.5 |
| | B. cepacia BC003 | 0.50 | 16 | 4 | >128 | 64 |
| | E. cloacae ECL014 | 0.38 | 128 | 16 | 32 | 8 |
| | E. cloacae ECL015 | 0.50 | 64 | 16 | 32 | 8 |
| | P. aeruginosa PA008 | 0.50 | 64 | 0.125 | 64 | 32 |
| | P. aeruginosa PA039 | 0.50 | 64 | 16 | 64 | 16 |
| | S. aureus SA025 MRSA | 0.52 | 8 | 0.125 | 2 | 1 |
| | S. epidermidis SE012 | 0.50 | 64 | 16 | 4 | 1 |
| | S. epidermidis SE073 | 0.38 | 128 | 16 | 4 | 1 |
| 26 | A. baumannii ABI002 | 0.50 | 64 | 16 | 8 | 2 |
| | A. baumannii ABI005 | 0.56 | 16 | 8 | 2 | 0.125 |
| | B. cepacia BC003 | 0.50 | 16 | 8 | >128 | 0.125 |
| | E. cloacae ECL014 | 0.50 | 128 | 32 | 8 | 2 |
| | E. cloacae ECL015 | 0.19 | 64 | 4 | 32 | 4 |
| | K. pneumonia KP003 | 0.56 | 8 | 4 | 16 | 1 |
| | P. aeruginosa PA008 | 0.13 | 64 | 8 | 128 | 0.125 |
| | P. aeruginosa PA024 | 0.50 | 16 | 4 | 128 | 32 |
| | S. maltophilia SMA019 | 0.50 | >128 | 64 | 4 | 1 |
| | S. maltophilia SMA020 | 0.38 | >128 | 32 | 4 | 1 |
| | S. aureus SA025 MRSA | 0.52 | 8 | 0.125 | 1 | 0.5 |
| | S. epidermidis SE007 | 0.27 | 8 | 2 | 32 | 0.5 |
| | S. epidermidis SE012 | 0.27 | 64 | 16 | 64 | 1 |

3. Ciprofloxacin

| Peptide | Organism | FIC | Ciprofloxacin MIC (µg/ml) Alone | +Peptide | Peptide MIC (µg/ml) Alone | +Ciprofloxacin |
|---|---|---|---|---|---|---|
| MBI 11A1CN | S. aureus SA10 | 0.53 | 32 | 16 | 128 | 4 |
| | S. aureus SA11 | 0.50 | 64 | 32 | >128 | 1 |
| MBI 11D18CN | P. aeruginosa PA24 | 0.31 | 16 | 4 | >128 | 16 |
| | P. aeruginosa PA77 | 0.50 | 2 | 0.5 | 128 | 32 |
| MBI 21A1 | S. aureus SA25 | 0.16 | 4 | 0.125 | 32 | 4 |
| | S. aureus SA93 | 0.50 | 32 | 8 | 4 | 1 |
| | P. aeruginosa PA4 | 0.50 | 0.5 | 0.125 | 128 | 32 |

TABLE 17-continued

|  |  |  |  |  |  |  |
|---|---|---|---|---|---|---|
|  | P. aeruginosa PA41 | 0.50 | 4 | 1 | 16 | 4 |
| MBI 21A2 | S. aureus SA25 | 0.50 | 2 | 0.5 | 16 | 4 |
|  | S. aureus SA93 | 0.38 | 32 | 8 | 16 | 2 |
|  | P. aeruginosa PA4 | 0.50 | 0.5 | 0.125 | >128 | 64 |
|  | P. aeruginosa PA41 | 0.50 | 4 | 1 | 64 | 16 |
| MBI 26 | S. aureus SA11 | 0.50 | 64 | 32 | 128 | 0.125 |
|  | P. aeruginosa PA41 | 0.50 | 4 | 1 | 128 | 32 |
|  | P. aeruginosa PA77 | 0.56 | 2 | 0.125 | 128 | 64 |
|  | A. calcoaceticus 1 | 0.51 | 0.5 | 0.25 | >64 | 1 |
|  | A. calcoaceticus 6 | 0.50 | 1 | 0.25 | >32 | 16 |
|  | E. cloacae 13 | 0.27 | 1 | 0.25 | >128 | 4 |
|  | E. cloacae 15 | 0.38 | 1 | 0.25 | >32 | 8 |
|  | E. cloacae 16 | 0.38 | 2 | 0.25 | >32 | 16 |
|  | P. aeruginosa 23 | 0.53 | 1 | 0.5 | >32 | 2 |
|  | P. aeruginosa 24 | 0.53 | 1 | 0.5 | >32 | 2 |
|  | S. maltophilia 34 | 0.25 | 2 | 0.25 | >32 | 8 |
|  | S. maltophilia 35 | 0.50 | 2 | 0.5 | >32 | 16 |
| MBI 27 | S. aureus SA10 | 0.75 | 32 | 8 | 2 | 1 |
|  | S. aureus SA93 | 0.63 | 32 | 4 | 2 | 1 |
|  | P. aeruginosa PA4 | 0.75 | 0.5 | 0.25 | 32 | 8 |
| MBI 28 | S. aureus SA11 | 0.63 | 32 | 16 | 64 | 8 |
|  | S. aureus SA25 | 0.56 | 2 | 0.125 | 2 | 1 |
|  | P. aeruginosa PA24 | 0.75 | 32 | 8 | 64 | 32 |
| 29 | S. aureus SA10 | 0.38 | 32 | 4 | 4 | 1 |
|  | S. aureus SA93 | 0.50 | 32 | 8 | 2 | 0.5 |
|  | P. aeruginosa PA41 | 0.52 | 8 | 4 | 8 | 0.125 |
|  | P. aeruginosa PA77 | 0.50 | 2 | 0.5 | 64 | 16 |
|  | A. calcoaceticus 5 | 0.56 | 2 | 1 | 16 | 1 |
|  | A. calcoaceticus 9 | 0.56 | 2 | 1 | 16 | 1 |
|  | E. cloacae 14 | 0.50 | 1 | 0.25 | >16 | 8 |
|  | E. cloacae 15 | 0.50 | 1 | 0.25 | >16 | 8 |
|  | P. aeruginosa 30 | 0.56 | 4 | 0.25 | >16 | 16 |
|  | P. aeruginosa 31 | 0.53 | 16 | 0.5 | >16 | 16 |
|  | S. maltophilia 34 | 0.27 | 2 | 0.5 | >16 | 0.5 |
|  | S. maltophilia 35 | 0.63 | 2 | 0.25 | >16 | 16 |
|  | S. maltophilia 36 | 0.56 | 8 | 0.5 | >16 | 16 |
| MBI 29A2 | S. aureus SA10 | 0.52 | 32 | 0.5 | 4 | 2 |
|  | S. aureus SA93 | 0.50 | 32 | 8 | 2 | 0.5 |
|  | P. aeruginosa PA24 | 0.63 | 32 | 16 | 64 | 8 |
| MBI 29A3 | S. aureus SA10 | 0.75 | 32 | 16 | 2 | 0.5 |
|  | S. aureus SA25 | 0.63 | 4 | 2 | 1 | 0.125 |
|  | P. aeruginosa PA24 | 0.50 | 32 | 16 | 64 | 0.125 |
|  | P. aeruginosa PA41 | 0.63 | 4 | 0.5 | 8 | 4 |

4. Gentamicin

| Peptide | Organism | FIC | Gentamicin MIC (µg/ml) | | Peptide MIC (µg/ml) | |
|---|---|---|---|---|---|---|
|  |  |  | Alone | +Peptide | Alone | +Gentamicin |
| MBI 11A1CN | S. maltophilia SMA019 | 0.31 | 8 | 2 | >128 | 16 |
|  | S. maltophilia SMA020 | 0.31 | 8 | 2 | >128 | 16 |
|  | E. faecium EFM004 | 0.28 | >128 | 64 | 32 | 1 |
|  | S. aureus SA014 MRSA | 0.56 | 32 | 2 | 8 | 4 |
|  | S. epidermidis SE074 | 0.51 | 128 | 1 | 32 | 16 |
| MBI 11B16CN | A. baumannii ABI001 | 0.31 | 64 | 4 | 16 | 4 |
|  | A. baumannii ABI002 | 0.31 | 32 | 2 | 16 | 4 |
|  | A. calcoaceticus AC001 | 0.25 | 8 | 1 | 32 | 4 |
|  | P. aeruginosa PA022 | 0.38 | 32 | 8 | 64 | 8 |
|  | P. aeruginosa PA041 | 0.31 | 8 | 2 | >128 | 16 |
|  | S. maltophilia SMA016 | 0.31 | >128 | 64 | >128 | 16 |
|  | S. maltophilia SMA019 | 0.38 | 64 | 8 | 32 | 8 |
|  | E. faecalis EFS008 | 0.38 | >128 | 64 | 4 | 0.5 |
|  | S. aureus SA014 MRSA | 0.53 | 32 | 1 | 8 | 4 |
| MBI 11D18CN | A. baumannii ABI001 | 0.27 | 64 | 16 | 32 | 0.5 |
|  | A. baumannii ABI002 | 0.56 | 16 | 8 | 32 | 2 |
|  | E. coli ECO006 | 0.27 | 64 | 16 | 8 | 0.125 |
|  | K. pneumonia KP020 | 0.50 | 64 | 32 | 32 | 0.125 |
|  | P. aeruginosa PA022 | 0.52 | 16 | 8 | 8 | 0.125 |
|  | P. aeruginosa PA041 | 0.14 | 8 | 0.125 | 64 | 8 |
|  | S. maltophilia | 0.38 | 128 | 16 | 64 | 16 |

TABLE 17-continued

| | | | | | | |
|---|---|---|---|---|---|---|
| | SMA016 | | | | | |
| | S. maltophilia SMA019 | 0.19 | 32 | 4 | 8 | 0.5 |
| | E. faecium EFM004 | 0.05 | >128 | 8 | 8 | 0.125 |
| | E. faecalis EFS008 | 0.19 | 128 | 8 | 2 | 0.25 |
| | S. aureus SA014 MRSA | 0.13 | 32 | 2 | 2 | 0.125 |
| | S. aureus SA025 MRSA | 0.14 | 64 | 1 | 1 | 0.125 |
| | S. epidermidis SE071 | 0.27 | 16 | 4 | 8 | 0.125 |
| | S. epidermidis SE074 | 0.09 | 64 | 4 | 4 | 0.125 |
| MBI 21A2 | A. baumannii ABI002 | 0.56 | 32 | 16 | 8 | 0.5 |
| | P. aeruginosa PA022 | 0.50 | 32 | 8 | 8 | 2 |
| | S. maltophilia SMA019 | 0.50 | 64 | 16 | 16 | 4 |
| | S. maltophilia SMA020 | 0.50 | 64 | 16 | 16 | 4 |
| | S. maltophilia SMA021 | 0.50 | 64 | 16 | 16 | 4 |
| | S. aureus SA025 MRSA | 0.63 | 64 | 32 | 8 | 1 |
| MBI 26 | A. baumannii ABI001 | 0.50 | 64 | 16 | 8 | 2 |
| | A. baumannii ABI002 | 0.53 | 16 | 0.5 | 8 | 4 |
| | P. aeruginosa PA041 | 0.63 | 8 | 1 | 64 | 32 |
| | S. maltophilia SMA016 | 0.25 | >128 | 32 | >128 | 32 |
| | S. maltophilia SMA017 | 0.38 | 64 | 16 | 16 | 2 |
| MBI 27 | A. baumannii ABI002 | 0.52 | 32 | 0.5 | 8 | 4 |
| | P. aeruginosa PA022 | 0.52 | 32 | 16 | 8 | 0.125 |
| | S. maltophilia SMA016 | 0.50 | >128 | 64 | 64 | 16 |
| | S. maltophilia SMA017 | 0.52 | 128 | 64 | 8 | 0.125 |
| | E. faecalis EFS008 | 0.38 | >128 | 64 | 4 | 0.5 |
| | S. aureus SA014 MRSA | 0.50 | 32 | 0.125 | 2 | 1 |
| MBI 29 | S. maltophilia SMA019 | 0.53 | 32 | 16 | 4 | 0.125 |
| | S. maltophilia SMA020 | 0.53 | 32 | 16 | 4 | 0.125 |
| | E. faecalis EFS008 | 0.38 | 128 | 32 | 1 | 0.125 |
| | S. epidermidis SE074 | 0.50 | 128 | 0.5 | 4 | 2 |
| MBI 29A3 | S. maltophilia SMA019 | 0.31 | 64 | 16 | 2 | 0.125 |
| | S. maltophilia SMA021 | 0.31 | 64 | 16 | 2 | 0.125 |
| MBI 29F1 | P. aeruginosa PA023 | 0.52 | 8 | 0.125 | 128 | 64 |
| | S. maltophilia SMA016 | 0.56 | >128 | 16 | 32 | 16 |
| | S. maltophilia SMA017 | 0.53 | 64 | 32 | 4 | 0.125 |
| Deber A2KA2 | A. baumannii ABI001 | 0.53 | 64 | 32 | >128 | 8 |
| | A. baumannii ABI002 | 0.50 | 64 | 32 | >128 | 0.125 |
| | A. calcoaceticus AC001 | 0.56 | 8 | 4 | >128 | 16 |
| | P. aeruginosa PA022 | 0.52 | 32 | 16 | >128 | 4 |
| | P. aeruginosa PA041 | 0.50 | 16 | 8 | >128 | 0.125 |
| | S. maltophilia SMA017 | 0.50 | 128 | 64 | >128 | 0.125 |
| | S. maltophilia SMA020 | 0.50 | 128 | 64 | >128 | 0.125 |

5. Mupirocin

| | | | Mupirocin MIC (μg/ml) | | Peptide MIC (μg/ml) | |
|---|---|---|---|---|---|---|
| Peptide | Organism | FIC | Alone | +Peptide | Alone | +Mupirocin |
| MBI 11A1CN | E. coli SBECO2 | 0.05 | >100 | 30 | 128 | 2 |
| | E. coli ECO1 | 0.14 | >100 | 10 | 32 | 4 |
| MBI 11A3CN | E. coli SBECO1 | 0.43 | 100 | 30 | 64 | 8 |
| MBI 11B4CN | E. coli SBECO1 | 0.36 | 100 | 30 | 8 | 0.5 |
| | E. coli SBECO2 | 0.09 | >100 | 30 | 32 | 2 |
| MBI 11D18CN | E. coli SBECO1 | 0.36 | 100 | 30 | 2 | 0.125 |
| | E. coli SBECO2 | 0.06 | >100 | 30 | 16 | 0.5 |
| | P. aeruginosa SBPA1 | 0.35 | >100 | 100 | 128 | 32 |
| | P. aeruginosa PA4 | 0.53 | >100 | 30 | 128 | 64 |

TABLE 17-continued

|  |  |  |  |  |  |  |
|---|---|---|---|---|---|---|
|  | S. marcescens SBSM1 | 0.16 | >100 | 100 | >128 | 16 |
|  | S. marcescens SBSM2 | 0.35 | >100 | 100 | >128 | 64 |
| MBI 11G13CN | E. coli SBECO2 | 0.16 | >100 | 30 | 64 | 8 |
|  | E. coli ECO5 | 0.43 | 100 | 30 | 64 | 8 |
| MBI 21A1 | E. coli SBECO2 | 0.28 | >100 | 30 | 8 | 2 |
|  | E. coli ECO3 | 0.28 | 100 | 3 | 8 | 2 |
|  | P. aeruginosa SBPA1 | 0.53 | >100 | 30 | 64 | 32 |
| MBI 26 | E. coli SBECO2 | 0.16 | >100 | 30 | 8 | 1 |
|  | E. coli ECO5 | 0.43 | 100 | 30 | 8 | 1 |
|  | P. aeruginosa PA2 | 0.51 | >100 | 10 | 128 | 64 |
|  | P. aeruginosa PA4 | 0.23 | >100 | 100 | >128 | 32 |
|  | S. aureus SBSA4 | 0.28 | >100 | 30 | 32 | 8 |
| MBI 27 | E. coli SBECO2 | 0.51 | >100 | 10 | 4 | 2 |
|  | P. aeruginosa PA2 | 0.25 | >100 | 0.1 | 64 | 16 |
|  | P. aeruginosa PA4 | 0.50 | >100 | 0.3 | 32 | 16 |
|  | S. aureus SBSA3 | 0.23 | 100 | 10 | 16 | 2 |
|  | S. aureus SBSA4 | 0.50 | >100 | 0.3 | 4 | 2 |
| MBI 28 | E. coli SBECO1 | 0.50 | 100 | 0.1 | 4 | 2 |
|  | E. coli ECO2 | 0.33 | 100 | 30 | 4 | 0.125 |
|  | P. aeruginosa SBPA1 | 0.53 | >100 | 30 | 32 | 16 |
|  | P. aeruginosa PA4 | 0.50 | >100 | 3 | 32 | 16 |
|  | S. aureus SBSA4 | 0.51 | >100 | 10 | 4 | 2 |
| MBI 29 | S. marcescens SBSM1 | 0.23 | >100 | 100 | >128 | 32 |
|  | S. aureus SBSA3 | 0.35 | 100 | 10 | 16 | 4 |
|  | S. aureus SBSA4 | 0.51 | >100 | 10 | 4 | 2 |
| MBI 29A3 | P. aeruginosa PA2 | 0.50 | >100 | 0.1 | 32 | 16 |
|  | P. aeruginosa PA3 | 0.50 | >100 | 0.1 | 16 | 8 |
|  | S. marcescens SBSM1 | 0.16 | >100 | 100 | >128 | 16 |
|  | S. marcescens SBSM2 | 0.35 | >100 | 100 | >128 | 64 |

6. Piperacillin

| Peptide | Organism | FIC | Piperacillin MIC (μg/ml) | | Peptide MIC (μg/ml) | |
|---|---|---|---|---|---|---|
|  |  |  | Alone | +Peptide | Alone | +Piperacillin |
| MBI 11B7CN | E. cloacae 6 | 0.56 | >128 | 16 | 32 | 16 |
|  | E. cloacae 9 | 0.50 | >128 | 1 | 32 | 16 |
|  | E. cloacae 10 | 0.50 | >128 | 0.5 | 32 | 16 |
|  | S. maltophilia 5 | 0.50 | >128 | 64 | >128 | 64 |
|  | S. maltophilia 9 | 0.50 | >128 | 64 | >128 | 64 |
|  | S. maltophilia 11 | 0.38 | >128 | 64 | >128 | 32 |
|  | S. marcescens 1 | 0.27 | 32 | 8 | >128 | 4 |
|  | P. aeruginosa 23 | 0.56 | 32 | 2 | 128 | 64 |
|  | H. influenzae 1 | 0.50 | 64 | 32 | >128 | 0.125 |
|  | H. influenzae SB1 | 0.50 | 0.5 | 0.25 | >128 | 0.125 |
|  | S. aureus 19 MRSA | 0.50 | 128 | 32 | 4 | 1 |
| MBI 11B9CN | A. calcoaceticus 3 | 0.56 | 64 | 32 | 32 | 2 |
|  | S. maltophilia 5 | 0.50 | >128 | 64 | >128 | 64 |
|  | S. maltophilia 13 | 0.38 | >128 | 64 | >128 | 32 |
|  | S. marcescens SB1 | 0.26 | 64 | 16 | >128 | 2 |
|  | P. aeruginosa 15 | 0.50 | >128 | 64 | >128 | 64 |
|  | P. aeruginosa 23 | 0.13 | 128 | 16 | 64 | 0.5 |
|  | H. influenzae 3 | 0.50 | 0.5 | 0.25 | >128 | 0.125 |
|  | H. influenzae SB1 | 0.50 | 0.5 | 0.25 | >128 | 0.125 |
|  | S. aureus19 MRSA | 0.38 | 128 | 16 | 4 | 1 |
|  | S. aureus SB2MRSA | 0.56 | 128 | 8 | 2 | 1 |
| MBI 11CN | P. aeruginosa 22 | 0.52 | >128 | 4 | 64 | 32 |
|  | P. aeruginosa 23 | 0.53 | 128 | 64 | 128 | 4 |
|  | S. aureus 18 MRSA | 0.50 | >128 | 0.5 | 32 | 16 |
|  | S. aureus 19 MRSA | 0.38 | >128 | 64 | 8 | 1 |
| MBI 11D18CN | A. calcoaceticus 3 | 0.38 | 64 | 8 | 32 | 8 |
|  | E. cloacae 9 | 0.31 | >128 | 16 | 64 | 16 |
|  | E. cloacae 10 | 0.50 | >128 | 64 | 32 | 8 |
|  | S. maltophilia 2 | 0.50 | 64 | 16 | 32 | 8 |
|  | S. marcescens 1 | 0.14 | 64 | 8 | >128 | 4 |
|  | P. aeruginosa 23 | 0.38 | 128 | 32 | 64 | 8 |
|  | P. aeruginosa 41 | 0.56 | 64 | 32 | >128 | 16 |
|  | H. influenzae 3 | 0.53 | 0.5 | 0.25 | >128 | 8 |
|  | H. influenzae SB1 | 0.52 | 0.5 | 0.25 | >128 | 4 |
|  | S. aureus19 MRSA | 0.38 | 128 | 16 | 4 | 1 |

TABLE 17-continued

| Peptide | Organism | FIC | Alone | +Peptide | Alone | +Tobramycin |
|---|---|---|---|---|---|---|
| | S. aureus SB2MRSA | 0.50 | 128 | 32 | 2 | 0.5 |
| MBI 11E3CN | S. maltophilia 11 | 0.51 | >128 | 2 | 128 | 64 |
| | S. marcescens SB1 | 0.26 | 64 | 16 | >128 | 2 |
| | P. aeruginosa 23 | 0.27 | 128 | 32 | 64 | 1 |
| | P. aeruginosa 32 | 0.63 | 64 | 32 | 64 | 8 |
| | H. influenzae 1 | 0.52 | 64 | 32 | >128 | 4 |
| | H. influenzae 2 | 0.31 | 32 | 8 | >128 | 16 |
| | S. aureus 19 MRSA | 0.50 | >128 | 64 | 4 | 1 |
| MBI 11F3CN | P. aeruginosa 23 | 0.51 | 128 | 64 | 64 | 0.5 |
| | P. aeruginosa 41 | 0.63 | 32 | 4 | 128 | 64 |
| | S. aureus19 MRSA | 0.38 | >128 | 32 | 4 | 1 |
| | S. aureus SB3MRSA | 0.50 | >128 | 64 | 8 | 2 |
| MBI 11F4CN | E. cloacae 10 | 0.52 | >128 | 4 | 16 | 8 |
| | S. maltophilia 2 | 0.53 | 64 | 32 | 16 | 0.5 |
| | S. marcescens 1 | 0.25 | >128 | 64 | >128 | 0.5 |
| | P. aeruginosa 7 | 0.38 | >128 | 64 | 64 | 8 |
| | P. aeruginosa 23 | 0.31 | >128 | 64 | 64 | 4 |
| | H. influenzae SB1 | 0.50 | 0.5 | 0.25 | >128 | 0.125 |
| | S. aureus 19 MRSA | 0.53 | 128 | 4 | 4 | 2 |
| MBI 11G7CN | A. calcoaceticus 3 | 0.50 | 128 | 32 | 64 | 16 |
| | S. marcescens 1 | 0.25 | 64 | 16 | >128 | 1 |
| | P. aeruginosa 7 | 0.50 | >128 | 64 | >128 | 64 |
| | P. aeruginosa 23 | 0.50 | 128 | 64 | >128 | 1 |
| | H. influenzae SB1 | 0.52 | 0.5 | 0.25 | >128 | 4 |
| | S. aureus 18 MRSA | 0.50 | >128 | 64 | 32 | 8 |
| | S. aureus 19 MRSA | 0.56 | 128 | 64 | 8 | 0.5 |
| MBI 21A2 | E. coli 1 | 0.53 | >128 | 8 | 4 | 2 |
| | S. maltophilia 6 | 0.38 | >128 | 64 | 128 | 16 |
| | S. maltophilia 14 | 0.53 | 128 | 4 | 32 | 16 |
| | S. marcescens 1 | 0.27 | 64 | 16 | >128 | 4 |
| | P. aeruginosa 23 | 0.19 | 64 | 8 | >128 | 16 |
| | H. influenzae 1 | 0.31 | 64 | 4 | >128 | 64 |
| | H. influenzae 2 | 0.38 | 128 | 32 | >128 | 32 |
| | S. aureus 19 MRSA | 0.51 | 128 | 64 | >128 | 2 |
| | S. aureus SB2MRSA | 0.56 | 128 | 64 | 32 | 2 |
| MBI 26 | S. maltophilia 3 | 0.50 | 128 | 32 | 16 | 4 |
| | S. marcescens 1 | 0.50 | 64 | 32 | >128 | 0.5 |
| | P. aeruginosa 7 | 0.25 | >128 | 32 | >128 | 32 |
| | P. aeruginosa 41 | 0.53 | 64 | 32 | 128 | 4 |
| | H. influenzae 1 | 0.53 | 64 | 32 | >128 | 8 |
| | H. influenzae 2 | 0.51 | 128 | 64 | >128 | 2 |
| | S. aureus 19 MRSA | 0.16 | 128 | 16 | 32 | 1 |
| | S. aureus SB3MRSA | 0.31 | 128 | 64 | >128 | 16 |
| | A. calcoaceticus 7 | 0.25 | 32 | 4 | >32 | 8 |
| | A. calcoaceticus 8 | 0.19 | 64 | 4 | >32 | 8 |
| | E. cloacae 13 | 0.16 | 128 | 4 | >32 | 8 |
| | P. aeruginosa 23 | 0.27 | 256 | 4 | >64 | 32 |
| | P. aeruginosa 28 | 0.14 | >512 | 16 | >128 | 32 |
| | S. maltophilia 34 | 0.25 | >512 | 4 | >32 | 16 |
| | S. maltophilia 35 | 0.26 | >256 | 4 | >32 | 16 |
| MBI 29 | S. marcescens 1 | 0.14 | 64 | 32 | >128 | 4 |
| | P. aeruginosa 7 | 0.53 | 128 | 4 | 16 | 8 |
| | P. aeruginosa 23 | 0.50 | 128 | 32 | 16 | 4 |
| | P. aeruginosa 41 | 0.56 | 64 | 32 | 64 | 4 |
| | H. influenzae 1 | 0.51 | 32 | 16 | 16 | 0.125 |
| | S. aureus 11 MRSA | 0.50 | >128 | 0.5 | 16 | 8 |
| | A. calcoaceticus 2 | 0.50 | >512 | 4 | 16 | 8 |
| | A. calcoaceticus 7 | 0.25 | 32 | 4 | >16 | 4 |
| | E. cloacae 16 | 0.50 | >512 | 4 | >16 | 16 |
| | E. cloacae 17 | 0.50 | >512 | 4 | >16 | 16 |
| | P. aeruginosa 28 | 0.13 | >512 | 8 | >64 | 16 |
| | P. aeruginosa 29 | 0.27 | 512 | 8 | >32 | 16 |
| | S. maltophilia 34 | 0.25 | >512 | 4 | >16 | 8 |
| | S. maltophilia 38 | 0.28 | >512 | 32 | >32 | 16 |
| | S. maltophilia 40 | 0.25 | >512 | 4 | >32 | 16 |
| | S. maltophilia 42 | 0.25 | >512 | 4 | >16 | 8 |

7. Tobramycin

| Peptide | Organism | FIC | Tobramycin MIC (µg/ml) | | Peptide MIC (µg/ml) | |
|---|---|---|---|---|---|---|
| | | | Alone | +Peptide | Alone | +Tobramycin |
| MBI 11A1CN | P. aeruginosa PA026 | 0.50 | 8 | 4 | >128 | 0.125 |

TABLE 17-continued

|  |  |  |  |  |  |  |
|---|---|---|---|---|---|---|
|  | P. aeruginosa PA032 | 0.50 | 16 | 8 | >128 | 0.5 |
|  | S. maltophilia SMA029 | 0.16 | 128 | 4 | >128 | 32 |
|  | S. maltophilia SMA030 | 0.27 | 128 | 2 | >128 | 64 |
|  | S. aureus SA014 | 0.50 | >128 | 0.125 | 16 | 8 |
|  | S. aureus SA025 | 0.50 | >128 | 0.125 | 8 | 4 |
|  | S. haemolyticus SHA001 | 0.52 | 4 | 2 | 8 | 0.125 |
|  | S. haemolyticus SHA005 | 0.51 | 8 | 4 | 16 | 0.125 |
| MBI 11B9CN | A. baumannii ABI001 | 0.50 | 16 | 4 | 32 | 8 |
|  | B. cepacia BC002 | 0.38 | >128 | 64 | >128 | 32 |
|  | P. aeruginosa PA008 | 0.50 | 32 | 0.125 | 128 | 64 |
|  | P. aeruginosa PA025 | 0.56 | 32 | 2 | 128 | 64 |
|  | S. maltophilia SMA029 | 0.13 | 64 | 4 | >128 | 16 |
| MBI 11CN | A. baumannii ABI001 | 0.50 | 16 | 4 | 64 | 16 |
|  | E. coli ECO006 | 0.53 | 8 | 4 | 8 | 0.25 |
|  | P. aeruginosa PA032 | 0.52 | 16 | 8 | >128 | 4 |
|  | S. maltophilia SMA029 | 0.51 | 128 | 64 | >128 | 2 |
|  | S. maltophilia SMA035 | 0.38 | 32 | 4 | 128 | 32 |
| MBI 11D18CN | A. baumannii ABI001 | 0.31 | 16 | 4 | 64 | 4 |
|  | A. baumannii ABI002 | 0.53 | 8 | 4 | 16 | 0.5 |
|  | S. maltophilia SMA027 | 0.19 | 32 | 4 | >128 | 16 |
|  | S. maltophilia SMA029 | 0.16 | 128 | 4 | 32 | 4 |
|  | S. aureus SA018 MRSA | 0.56 | 64 | 4 | 32 | 16 |
|  | S. haemolyticus SHA001 | 0.53 | 4 | 0.125 | 2 | 1 |
| MBI 11F3CN | A. baumannii ABI001 | 0.53 | 16 | 0.5 | 32 | 16 |
|  | A. baumannii ABI002 | 1.00 | 4 | 2 | 16 | 8 |
|  | P. aeruginosa PA032 | 0.50 | 16 | 4 | >128 | 64 |
|  | S. maltophilia SMA029 | 0.28 | 128 | 32 | 128 | 4 |
|  | S. maltophilia SMA030 | 0.26 | 128 | 1 | 128 | 32 |
|  | S. aureus SA014 MRSA | 0.51 | >128 | 2 | 4 | 2 |
|  | S. haemolyticus SHA005 | 0.56 | 4 | 0.25 | 4 | 2 |
| MBI 11G13CN | A. baumannii ABI001 | 0.50 | 16 | 4 | 128 | 32 |
|  | P. aeruginosa PA022 | 0.56 | 8 | 4 | >128 | 16 |
|  | S. maltophilia SMA029 | 0.50 | 128 | 64 | >128 | 0.125 |
|  | S. maltophilia SMA030 | 0.50 | 128 | 64 | >128 | 0.125 |
|  | S. aureus SA025 MRSA | 0.50 | >128 | 0.125 | 4 | 2 |
| MBI 21A1 | B. cepacia BC001 | 0.25 | 128 | 32 | >128 | 0.25 |
|  | P. aeruginosa PA022 | 0.53 | 8 | 4 | 4 | 0.125 |
|  | P. aeruginosa PA026 | 0.51 | 8 | 4 | 16 | 0.125 |
|  | S. maltophilia SMA029 | 0.28 | 128 | 4 | 128 | 32 |
|  | S. maltophilia SMA030 | 0.16 | 128 | 4 | >128 | 32 |
|  | S. aureus SA014 MRSA | 0.50 | >128 | 0.125 | 32 | 16 |
|  | S. aureus SA025 MRSA | 0.50 | >128 | 0.125 | 2 | 1 |
|  | S. haemolyticus SHA001 | 0.50 | 2 | 0.5 | 16 | 4 |
|  | S. haemolyticus SHA005 | 0.38 | 4 | 1 | 32 | 4 |
| MBI 22A1 | S. maltophilia SMA030 | 0.26 | 128 | 1 | 32 | 8 |
|  | S. maltophilia SMA031 | 0.25 | 128 | 0.5 | 32 | 8 |
|  | S. aureus SA014 MRSA | 0.27 | >128 | 4 | 8 | 2 |
|  | S. epidermidis SE072 | 0.50 | >128 | 0.125 | 16 | 8 |
|  | S. epidermidis SE073 | 0.50 | >128 | 0.125 | 16 | 8 |
|  | S. epidermidis SE080 | 0.56 | 32 | 16 | 2 | 0.125 |
| MBI 26 | S. maltophilia SMA029 | 0.05 | 128 | 4 | >128 | 4 |
|  | S. maltophilia SMA030 | 0.05 | 128 | 4 | >128 | 4 |
|  | S. epidermidis SE067 | 0.38 | >128 | 64 | 2 | 0.25 |
|  | S. epidermidis SE068 | 0.27 | >128 | 4 | 2 | 0.5 |
| MBI 27 | E. coli ECO006 | 0.56 | 8 | 0.5 | 8 | 4 |
|  | S. maltophilia SMA029 | 0.50 | 64 | 16 | 16 | 4 |
|  | S. maltophilia SMA031 | 0.53 | 128 | 4 | 16 | 8 |
| MBI 29 | A. baumannii ABI001 | 0.53 | 16 | 8 | 4 | 0.125 |
|  | E. coli ECO004 | 0.53 | 2 | 1 | 4 | 0.125 |
|  | E. coli ECO006 | 0.53 | 8 | 4 | 4 | 0.125 |
|  | K. pneumonia KP008 | 0.52 | 0.5 | 0.25 | 8 | 0.125 |
|  | P. aeruginosa PA030 | 0.52 | 16 | 8 | 8 | 0.125 |
|  | S. maltophilia SMA031 | 0.50 | >128 | 0.25 | 16 | 8 |
|  | S. maltophilia SMA032 | 0.53 | 128 | 4 | 16 | 8 |
|  | S. epidermidis SE072 | 0.53 | >128 | 8 | 16 | 8 |
| MBI 29A3 | P. aeruginosa PA022 | 0.56 | 8 | 4 | 4 | 0.25 |
|  | P. aeruginosa PA028 | 0.50 | 32 | 16 | 32 | 0.125 |
|  | P. aeruginosa PA029 | 0.51 | 32 | 16 | 16 | 0.125 |
|  | S. maltophilia SMA029 | 0.28 | 128 | 4 | 16 | 4 |
|  | S. maltophilia SMA030 | 0.28 | 128 | 4 | 16 | 4 |

TABLE 17-continued

| | | | | | | |
|---|---|---|---|---|---|---|
| REWH 53A5CN | S. maltophilia SMA029 | 0.08 | 128 | 2 | >128 | 16 |
| | S. maltophilia SMA030 | 0.13 | 128 | 0.25 | >128 | 32 |
| | S. aureus SA014 MRSA | 0.50 | >128 | 0.125 | 16 | 8 |

8. Vancomycin

| Peptide | Organism | FIC | Vancomycin MIC (µg/ml) Alone | +Peptide | Peptide MIC (µg/ml) Alone | +Vancomycin |
|---|---|---|---|---|---|---|
| MBI 11A1CN | E. faecalis EFS001 | 0.53 | 1 | 0.5 | 4 | 0.125 |
| | E. faecalis EFS006 | 0.50 | 8 | 4 | 128 | 0.25 |
| | E. faecalis EFS007 | 0.50 | 4 | 2 | 128 | 0.5 |
| | E. faecalis EFS010 | 0.27 | 16 | 4 | 128 | 2 |
| | E. faecalis EFS012 | 0.25 | >128 | 32 | 64 | 8 |
| | E. faecalis EFS014 | 0.51 | 128 | 1 | 4 | 2 |
| | E. faecium EFM004 | 0.50 | >128 | 0.5 | 32 | 16 |
| | E. faecium EFM007 | 0.28 | 128 | 4 | 64 | 16 |
| | E. faecium EFM009 | 0.25 | 32 | 4 | 64 | 8 |
| MBI 11D18CN | E. faecalis EFS001 | 0.38 | 1 | 0.125 | 8 | 2 |
| | E. faecalis EFS004 | 0.50 | 2 | 0.5 | 8 | 2 |
| | E. faecalis EFS011 | 0.50 | 64 | 32 | 64 | 0.125 |
| | E. faecalis EFS012 | 0.38 | >128 | 64 | 16 | 2 |
| | E. faecalis EFS014 | 0.16 | 128 | 4 | 4 | 0.5 |
| | E. faecium EFM004 | 0.50 | >128 | 64 | 8 | 2 |
| | E. faecium EFM009 | 0.52 | 64 | 32 | 8 | 0.125 |
| | E. faecium EFM010 | 0.28 | >128 | 64 | 8 | 0.25 |
| | E. faecium EFM011 | 0.50 | >128 | 64 | 8 | 2 |
| MBI 21A1 | E. faecalis EFS007 | 0.56 | 2 | 1 | 16 | 1 |
| | E. faecalis EFS012 | 0.16 | 128 | 16 | 32 | 1 |
| | E. faecalis EFS013 | 0.28 | 128 | 32 | 32 | 1 |
| | E. faecium EFM010 | 0.56 | 64 | 32 | 32 | 2 |
| MBI 26 | E. faecalis EFS005 | 0.31 | 16 | 4 | >128 | 16 |
| | E. faecalis EFS012 | 0.07 | >128 | 2 | 16 | 1 |
| | E. faecalis EFS013 | 0.07 | >128 | 2 | 16 | 1 |
| | E. faecium EFM010 | 0.31 | 32 | 2 | 32 | 8 |
| | E. faecium EFM011 | 0.31 | 32 | 2 | 32 | 8 |
| | E. faecium EFM012 | 0.31 | 32 | 2 | 64 | 16 |
| | E. faecium EFM014 | 0.27 | >128 | 4 | 32 | 8 |
| | E. faecium EFM016 | 0.51 | 128 | 1 | 8 | 4 |
| MBI 29 | E. faecalis EFS005 | 0.38 | 16 | 4 | 32 | 4 |
| | E. faecalis EFS010 | 0.38 | 64 | 16 | 2 | 0.25 |
| | E. faecalis EFS012 | 0.50 | >128 | 64 | 2 | 0.5 |
| | E. faecium EFM005 | 0.53 | 128 | 4 | | 4 |
| | E. faecium EFM016 | 0.51 | 128 | 1 | 4 | 2 |
| MBI 29A3 | E. faecalis EFS003 | 0.56 | 4 | 2 | 32 | 2 |
| | E. faecalis EFS005 | 0.28 | 16 | 4 | 32 | 1 |
| | E. faecalis EFS011 | 0.50 | 16 | 4 | 32 | 8 |
| | E. faecalis EFS014 | 0.52 | 64 | 1 | 1 | 0.5 |
| | E. faecium EFM006 | 0.52 | >128 | 4 | 4 | 2 |

Example 6

Overcoming Tolerance by Administering a Combination of Antibiotic Agent and Cationic Peptide Tolerance to an antibiotic agent is associated with a defect in bacterial cellular autolytic enzymes such that an antimicrobial agent is bacteriostatic rather than bactericidal. Tolerance is indicated when a ratio of minimum bactericidal concentration (MBC) to minimum inhibitory concentration (MIC) (MBC:MIC) is $\geq 32$.

The agarose dilution assay is adapted to provide both the MBC and MIC for an antimicrobial agent alone and an agent in combination with a peptide. Following determination of MIC, MBC is determined from the agarose dilution assay plates by swabbing the inocula on plates at and above the MIC and resuspending the swab in 1.0 ml of saline. A 0.01 ml aliquot is plated on agarose medium (subculture plates) and the resulting colonies are counted. If the number of colonies is less than 0.1% of the initial inoculum (as determined by a plate count immediately after inoculation of the MIC test plates), then $\geq 99.9\%$ killing has occurred. The MBC end point is defined as the lowest concentration of the antimicrobial agent that kills 99.9% of the test bacteria.

Thus, tolerance of a microorganism to an antimicrobial agent occurs when the number of colonies growing on subculture plates exceeds the 0.1% cutoff for several successive concentrations above the observed MIC. A combination of antimicrobial agent and cationic peptide that breaks tolerance results in a decrease in the MBC:MIC ratio to <32. Table 18 shows that the combination of Vancomycin and MBI 26 overcomes the tolerance of the organisms listed.

TABLE 18

| | Vancomycin | | | Vancomycin + MBI 26 | | |
|---|---|---|---|---|---|---|
| Organism | MIC (µg/ml) | MBC (µg/ml) | MBC/ MIC | MIC (µg/ml) | MBC (µg/ml) | MBC/ MIC |
| E. casseliflavus ECA001 | 2 | >128 | >64 | 0.5 | 2 | 4 |

TABLE 18-continued

|  | Vancomycin | | | Vancomycin + MBI 26 | | |
| --- | --- | --- | --- | --- | --- | --- |
| Organism | MIC (μg/ml) | MBC (μg/ml) | MBC/MIC | MIC (μg/ml) | MBC (μg/ml) | MBC/MIC |
| E. faecium EFM001 | 0.5 | >128 | >256 | 0.5 | 0.5 | 1 |
| E. faecium EFM020 | 1 | >128 | >128 | 0.5 | 4 | 8 |
| E. faecalis EFS001 | 1 | >128 | >128 | 0.5 | 4 | 8 |
| E. faecalis EFS004 | 1 | >128 | >128 | 1 | 2 | 2 |
| E. faecalis EFS007 | 4 | 128 | 32 | 2 | 2 | 1 |
| E. faecalis EFS009 | 4 | >128 | >32 | 4 | 4 | 1 |
| E. faecalis EFS015 | 1 | >128 | >128 | 0.5 | 0.5 | 1 |

Example 7

Overcoming Inherent Resistance by Administering a Combination of Antibiotic Agent and Cationic Peptide Peptides are tested for their ability to overcome the inherent antimicrobial resistance of microorganisms, including those encountered in hospital settings, to specific antimicrobials. Overcoming resistance is demonstrated when the antibiotic agent alone exhibits minimal or no activity against the microorganism, but when used in combination with a cationic peptide, results in susceptibility of the microorganism.

The agarose dilution assay described above is used to determine the minimum inhibitory concentration (MIC) of antimicrobial agents and cationic peptides, alone and in combination. Alternatively, the broth dilution assay or time kill curves can be used to determine MICs. Tables 19, 20, 21 and 22 present MIC values for antibiotic agents alone and in combination with peptide at the concentration shown. In all cases, the microorganism is inherently resistant to its mode of action, thus, the antibiotic agent is not effective against the test microorganism. In addition, the antibiotic agent is not clinically prescribed against the test microorganism.

In the data presented below, the MIC values for the antibiotic agents when administered in combination with peptide are decreased, from equal to or above the resistant breakpoint to below it.

TABLE 19

|  | Erythromycin MIC (μg/ml) | | MBI 26 MIC (μg/ml) | |
| --- | --- | --- | --- | --- |
| Microorganism | Alone | + MBI 26 | Alone | + Erythro. |
| A. calcoaceticus AC001 | 32 | 1 | 16 | 8 |
| K. pneumoniae KP001 | 32 | 0.25 | 16 | 8 |
| K. pneumoniae KP002 | 256 | 0.5 | 64 | 32 |
| P. aeruginosa PA041 | 128 | 4 | 64 | 32 |

TABLE 20

|  | Vancomycin MIC (μg/ml) | | MBI 26 MIC (μg/ml) | |
| --- | --- | --- | --- | --- |
| Microorganism | Alone | + MBI 26 | Alone | + Vancomycin |
| E. gallinarum 97044 VanC | 8 | 2 | 8 | 0.5 |
| E. gallinarum 97046 VanC | 32 | 1 | 2 | 4 |
| E. gallinarum 97047 VanC | 128 | 16 | 64 | 8 |
| E. gallinarum 97048 VanC | 32 | 4 | 2 | 2 |
| E. gallinarum 97049 VanC | 128 | 4 | 64 | 16 |
| E. casseliflavus 97056 VanC | 8 | 2 | 8 | 1 |
| E. casseliflavus 97057 VanC | 4 | 2 | 2 | 0.5 |
| E. casseliflavus 97058 VanC | 2 | 1 | 4 | 0.25 |
| E. casseliflavus 97059 VanC | 4 | 2 | 32 | 0.5 |
| E. casseliflavus 97060 VanC | 2 | 2 | 0.5 | 0.25 |

TABLE 21

|  | Teicoplanin MIC (μg/ml) | | MBI 26 MIC (μg/ml) | |
| --- | --- | --- | --- | --- |
| Microorganism | Alone | + MBI 26 | Alone | + Vancomycin |
| E. gallinarum 97044 VanC | 0.5 | 0.25 | 64 | 1 |
| E. gallinarum 97046 VanC | 1 | 0.25 | 8 | 1 |
| E. gallinarum 97047 VanC | 8 | 0.25 | 64 | 32 |
| E. gallinarum 97048 VanC | 0.5 | 0.25 | 8 | 1 |
| E. gallinarum 97049 VanC | 2 | 0.25 | 64 | 32 |
| E. casseliflavus 97056 VanC | 0.5 | 0.25 | 64 | 2 |
| E. casseliflavus 97057 VanC | 0.5 | 0.25 | 64 | 0.5 |
| E. casseliflavus 97058 VanC | 0.5 | 0.25 | 32 | 0.5 |
| E. casseliflavus 97059 VanC | 0.5 | 0.25 | 64 | 1 |
| E. casseliflavus 97060 VanC | 0.5 | 0.25 | 64 | 1 |

TABLE 22

1. Amikacin

|  |  |  | Amikacin MIC (μg/ml) | | Peptide MIC (μg/ml) | |
| --- | --- | --- | --- | --- | --- | --- |
| Peptide | Organism | FIC | Alone | +Peptide | Alone | +Amikacin |
| MBI 11B16CN | A. baumannii ABI001 | 0.25 | 32 | 4 | 32 | 4 |
|  | S. maltophilia SMA018 | 0.31 | 128 | 8 | 32 | 8 |
|  | S. maltophilia SMA022 | 0.14 | >128 | 4 | >128 | 32 |
|  | S. aureus SA014 MRSA | 0.75 | 32 | 8 | 8 | 4 |
|  | S. aureus SA025 MRSA | 0.63 | 32 | 4 | 8 | 4 |
| MBI 21A2 | S. maltophilia SMA018 | 0.53 | >128 | 8 | 16 | 8 |
|  | S. maltophilia SMA060 | 0.31 | >128 | 16 | >128 | 64 |
|  | S. aureus SA025 MRSA | 0.56 | 32 | 2 | 2 | 1 |

TABLE 22-continued

| Peptide | Organism | | | | | |
|---|---|---|---|---|---|---|
| MBI 26 | S. maltophilia SMA022 | 0.19 | 128 | 8 | 64 | 8 |
| | S. maltophilia SMA037 | 0.19 | 128 | 16 | >128 | 16 |
| MBI 27 | A. baumannii ABI001 | 1.00 | 32 | 16 | 8 | 4 |
| | B. cepacia BC005 | 0.50 | 64 | 16 | >128 | 64 |
| | S. maltophilia SMA036 | 0.56 | >128 | 16 | 64 | 32 |
| | S. maltophilia SMA037 | 0.31 | 64 | 4 | 64 | 16 |
| | S. aureus SA025 MRSA | 0.75 | 32 | 16 | 2 | 0.5 |
| MBI 29A3 | B. cepacia BC003 | 0.63 | 32 | 16 | >128 | 32 |
| | B. cepacia BC005 | 0.38 | 128 | 32 | >128 | 32 |
| | S. maltophilia SMA036 | 0.53 | >128 | 8 | 64 | 32 |
| | S. maltophilia SMA063 | 0.56 | >128 | 16 | 8 | 4 |
| MBI 29F1 | A. baumannii ABI001 | 0.75 | 32 | 16 | 8 | 2 |
| | S. maltophilia SMA018 | 0.56 | 128 | 8 | 4 | 2 |
| | S. maltophilia SMA021 | 0.31 | 128 | 8 | 8 | 2 |
| | S. aureus SA014 MRSA | 0.53 | 32 | 16 | 4 | 0.125 |
| | S. aureus SA025 MRSA | 0.63 | 32 | 16 | 1 | 0.125 |
| Deber A2KA2 | A. baumannii ABI001 | 0.63 | 32 | 16 | >128 | 32 |
| | S. aureus SA025 MRSA | 0.50 | 32 | 0.125 | 16 | 8 |

2. Ceftriaxone

| | | | Ceftriaxone MIC (µg/ml) | | Peptide MIC (µg/ml) | |
|---|---|---|---|---|---|---|
| Peptide | Organism | FIC | Alone | +Peptide | Alone | +Ceftriaxone |
| MBI 11B7CN | P. aeruginosa PA008 | 0.50 | 128 | 0.125 | 128 | 64 |
| | S. maltophilia SMA021 | 0.50 | >128 | 1 | 32 | 16 |
| | S. maltophilia SMA023 | 0.56 | 128 | 8 | 128 | 64 |
| MBI 11J02CN | P. aeruginosa PA008 | 0.50 | 64 | 0.125 | 64 | 32 |
| | P. aeruginosa PA039 | 0.52 | 64 | 1 | 64 | 32 |
| MBI 26 | P. aeruginosa PA008 | 0.13 | 64 | 8 | 128 | 0.125 |
| | P. aeruginosa PA024 | 0.50 | 16 | 4 | 128 | 32 |
| | S. maltophilia SMA021 | 0.25 | >128 | 1 | 8 | 2 |

3. Gentamicin

| | | | Gentamicin MIC (µg/ml) | | Peptide MIC (µg/ml) | |
|---|---|---|---|---|---|---|
| Peptide | Organism | FIC | Alone | +Peptide | Alone | +Gentamicin |
| MBI 11B16CN | S. aureus SA014 MRSA | 0.53 | 32 | 1 | 8 | 4 |
| MBI 27 | S. aureus SA014 MRSA | 0.50 | 32 | 0.125 | 2 | 1 |

4. Mupirocin

| | | | Mupirocin MIC (µg/ml) | | Peptide MIC (µg/ml) | |
|---|---|---|---|---|---|---|
| Peptide | Organism | FIC | Alone | +Peptide | Alone | +Mupirocin |
| MBI 11B4CN | E. coli ECO3 | 0.53 | 100 | 3 | 16 | 8 |
| MBI 11D18CN | E. coli ECO3 | 0.26 | 100 | 1 | 4 | 1 |
| MBI 21A1 | E. coli ECO1 | 0.50 | >100 | 3 | 2 | 1 |
| | E. coli ECO2 | 0.53 | 100 | 3 | 2 | 1 |
| | E. coli ECO3 | 0.28 | 100 | 3 | 8 | 2 |
| MBI 26 | E. coli ECO1 | 0.50 | >100 | 3 | 2 | 1 |
| MBI 27 | P. aeruginosa PA2 | 0.25 | >100 | 0.1 | 64 | 16 |
| | P. aeruginosa PA4 | 0.50 | >100 | 0.3 | 32 | 16 |
| MBI 28 | E. coli SBECO1 | 0.50 | 100 | 0.1 | 4 | 2 |
| | P. aeruginosa PA4 | 0.50 | >100 | 3 | 32 | 16 |
| MBI 29A3 | P. aeruginosa SBPA2 | 0.50 | >100 | 0.1 | 16 | 8 |
| | P. aeruginosa PA2 | 0.50 | >100 | 0.1 | 32 | 16 |
| | P. aeruginosa PA3 | 0.50 | >100 | 0.1 | 16 | 8 |
| | P. aeruginosa PA4 | 0.50 | >100 | 0.1 | 16 | 8 |

5. Piperacillin

| | | | Piperacillin MIC (µg/ml) | | Peptide MIC (µg/ml) | |
|---|---|---|---|---|---|---|
| Peptide | Organism | FIC | Alone | +Peptide | Alone | +Piperacillin |
| MBI 11B7CN | S. aureus 19 MRSA | 0.50 | 128 | 0.5 | 4 | 2 |
| MBI 11D18CN | S. aureus 19 MRSA | 0.52 | 128 | 2 | 4 | 2 |
| MBI 11E3CN | S. aureus 19 MRSA | 0.51 | >128 | 2 | 4 | 2 |
| MBI 11F3CN | S. aureus 19 MRSA | 0.51 | >128 | 2 | 4 | 2 |
| | S. aureus SB3MRSA | 0.52 | >128 | 4 | 8 | 4 |
| MBI 11F4CN | S. aureus 19 MRSA | 0.53 | 128 | 4 | 4 | 2 |
| MBI 11G7CN | S. aureus 19 MRSA | 0.25 | 128 | 0.5 | 8 | 2 |
| MBI 21A2 | S. aureus 19 MRSA | 0.25 | 128 | 0.5 | >128 | 64 |
| MBI 26 | S. aureus 19 MRSA | 0.13 | 128 | 0.5 | 32 | 4 |

TABLE 22-continued

| MBI 29 | S. aureus 18 MRSA | 0.52 | >128 | 4 | 16 | 8 |

6. Tobramycin

| | | | Tobramycin MIC (µg/ml) | | Peptide MIC (µg/ml) | |
|---|---|---|---|---|---|---|
| Peptide | Organism | FIC | Alone | +Peptide | Alone | +Tobramycin |
| MBI 11A1CN | S. aureus SA014 | 0.50 | >128 | 0.125 | 16 | 8 |
| | S. aureus SA025 | 0.50 | >128 | 0.125 | 8 | 4 |
| | S. haemolyticus SHA005 | 0.51 | 8 | 4 | 16 | 0.125 |
| MBI 11D18CN | S. aureus SA018 MRSA | 0.56 | 64 | 4 | 32 | 16 |
| MBI 11F3CN | S. aureus SA014 MRSA | 0.51 | >128 | 2 | 4 | 2 |
| MBI 11G13CN | S. aureus SA025 MRSA | 0.50 | >128 | 0.125 | 4 | 2 |
| MBI 21A1 | S. aureus SA014 MRSA | 0.50 | >128 | 0.125 | 32 | 16 |
| | S. aureus SA025 MRSA | 0.50 | >128 | 0.125 | 2 | 1 |
| MBI 22A1 | S. aureus SA014 MRSA | 0.27 | >128 | 4 | 8 | 2 |

Example 8

Overcoming Acquired Resistance by Administering a Combination of Antibiotic Agent and Cationic Peptide An antibiotic agent can become ineffective against a previously susceptible microorganism if the microorganism acquires resistance to the agent. However, acquired resistance can be overcome when the agent is administered in combination with a cationic peptide. For example vancomycin resistant enterococci (VRE) become susceptible to vancomycin when it is used in combination with a cationic peptide such as MBI 26. This combination is likely to be effective against other organisms acquiring resistance to vancomycin including but not limited to strains of methicillin resistant S. aureus (MRSA).

Similarly teicoplanin resistant enterococci become susceptible to teicoplanin when teicoplanin is used in combination with cationic peptides such as MBI 26.

As described previously, the agarose dilution assay is used to determine the MIC for antibiotic agents administered alone and in combination with cationic peptide. Alternatively the broth dilution assay or time kill curves can be employed. Tables 23 and 25 presents results showing that administration of a cationic peptide in combination with an antibiotic agent overcomes acquired resistance. Table 24 presents results showing administration of MBI 26 in combination with teicoplanin against teicoplanin resistant enterococci.

TABLE 23

| Microorganism | Strain | Antibiotic agent | MIC alone (µg/ml) | MIC comb. (µg/ml) | Peptide | Peptide MIC |
|---|---|---|---|---|---|---|
| A. calcoaceticus | 002 | Tobramycin | 8 | 1 | MBI 29 | 4 |
| A. calcoaceticus | 003 | Ceftazidime | 32 | 2 | MBI 26 | 32 |
| A. calcoaceticus | 003 | Ceftazidime | 32 | 2 | MBI 29 | 8 |
| A. calcoaceticus | 003 | Ciprofloxacin | 8 | 1 | MBI 29 | 16 |
| A. calcoaceticus | 004 | Ciprofloxacin | 8 | 4 | MBI 26 | 4 |
| A. calcoaceticus | 010 | Ceftazidime | 32 | 2 | MBI 26 | 32 |
| E. faecium | ATCC 29212 | Mupirocin | 100 | 0.1 | MBI 11CN | 8 |
| E. faecium | ATCC 29212 | Mupirocin | 100 | 0.1 | MBI 11G13CN | 32 |
| P. aeruginosa | PA41 | Ciprofloxacin | 4 | 0.125 | MBI 21A1 | 16 |
| P. aeruginosa | PA41 | Ciprofloxacin | 4 | 1 | MBI 21A2 | 16 |
| P. aeruginosa | PA41 | Ciprofloxacin | 8 | 2 | MBI 28 | 8 |
| P. aeruginosa | 001 | Piperacillin | 128 | 64 | MBI 27 | 8 |
| P. aeruginosa | 023 | Piperacillin | 128 | 64 | MBI 29 | 8 |
| P. aeruginosa | 024 | Tobramycin | 64 | 1 | MBI 29 | 8 |
| P. aeruginosa | 025 | Ceftazidime | 64 | 16 | MBI 29 | 8 |
| P. aeruginosa | 027 | Imipenem | 16 | 8 | MBI 29 | 16 |
| P. aeruginosa | 028 | Imipenem | 16 | 8 | MBI 29 | 16 |
| S. haemolyticus | SH8578 | Erythromycin | 8 | 0.5 | MBI 31 | 1 |
| S. aureus | SA7338 | Ampicillin | 2 | 0.25 | MBI 26 | 0.25 |
| S. aureus | SA7609 | Erythromycin | 32 | 0.5 | MBI 26 | 1 |
| S. aureus | SA7835 | Erythromycin | 8 | 0.125 | MBI 26 | 2 |
| S. aureus | SA7795 | Erythromycin | 32 | 1 | MBI 26 | 8 |
| S. aureus | SA7796 | Erythromycin | 32 | 1 | MBI 26 | 2 |
| S. aureus | SA7795 | Erythromycin | 32 | 4 | MBI 31 | 0.125 |
| S. aureus | SA7818 | Erythromycin | 32 | 2 | MBI 31 | 0.125 |
| S. aureus | SA7796 | Erythromycin | 32 | 2 | MBI 31 | 0.125 |
| S. aureus | SA7834 | Methicillin | 32 | 8 | MBI 26 | 4 |
| S. aureus | SA7835 | Methicillin | 32 | 4 | MBI 26 | 16 |
| S. aureus | SA7796 | Methicillin | 16 | 2 | MBI 31 | 16 |
| S. aureus | SA7797 | Methicillin | 16 | 2 | MBI 31 | 16 |
| S. aureus | SA7823 | Methicillin | 16 | 2 | MBI 31 | 0.5 |
| S. aureus | SA7834 | Methicillin | 64 | 1 | MBI 31 | 32 |

TABLE 23-continued

| Microorganism | Strain | Antibiotic agent | MIC alone (μg/ml) | MIC comb. (μg/ml) | Peptide | Peptide MIC |
|---|---|---|---|---|---|---|
| S. aureus | SA7835 | Methicillin | 64 | 2 | MBI 31 | 16 |
| S. aureus | SA007 | Piperacillin | 128 | 64 | MBI 27 | 0.5 |
| S. aureus | MRSA 9 | Mupirocin | >100 | 0.1 | MBI 11D18CN | 2 |
| S. aureus | MRSA 9 | Mupirocin | >100 | 0.1 | MBI 11G13CN | 8 |
| S. aureus | MRSA 9 | Mupirocin | >100 | 0.1 | MBI 21A1 | 16 |
| S. aureus | MRSA 9 | Mupirocin | >100 | 0.3 | MBI 21A10 | 32 |
| S. aureus | MRSA 9 | Mupirocin | >100 | 0.1 | MBI 21A2 | 32 |
| S. aureus | MRSA 9 | Mupirocin | >100 | 0.1 | MBI 26 | 4 |
| S. aureus | MRSA 9 | Mupirocin | >100 | 0.1 | MBI 27 | 2 |
| S. aureus | MRSA 13 | Mupirocin | 100 | 3 | MBI 10CN | 4 |
| S. aureus | MRSA 13 | Mupirocin | 100 | 0.1 | MBI 11CN | 16 |
| S. aureus | MRSA 13 | Mupirocin | 100 | 3 | MBI 11F1CN | 8 |
| S. aureus | 014 | Ciprofloxacin | 8 | 0.125 | MBI 21A2 | 4 |
| S. aureus | MRSA 17 | Mupirocin | >100 | 1 | MBI 10CN | 1 |
| | | | | 0.3 | | 2 |
| S. aureus | MRSA 17 | Mupirocin | >100 | 1 | MBI 11A1CN | 32 |
| S. aureus | MRSA 17 | Mupirocin | >100 | 1 | MBI 11G13CN | 16 |
| S. aureus | MRSA 17 | Mupirocin | >100 | 0.3 | MBI 27 | 2 |
| S. aureus | MRSA 17 | Mupirocin | >100 | 0.1 | MBI 29A3 | 4 |
| S. aureus | 093 | Ciprofloxacin | 32 | 0.125 | MBI 21A1 | 2 |
| S. aureus | 093 | Ciprofloxacin | 32 | 1 | MBI 21A2 | 4 |
| S. aureus | SA 7818 | Methicillin | 16 | 4 | MBI 26 | 2 |
| S. epidermidis | SE8497 | Clindamycin | 32 | 0.125 | MBI 26 | 2 |
| S. epidermidis | SE8403 | Erythromycin | 8 | 0.125 | MBI 26 | 2 |
| S. epidermidis | SE8410 | Erythromycin | 32 | 0.5 | MBI 26 | 1 |
| S. epidermidis | SE8411 | Erythromycin | 32 | 0.5 | MBI 26 | 1 |
| S. epidermidis | SE8497 | Erythromycin | 32 | 0.125 | MBI 26 | 1 |
| S. epidermidis | SE8503 | Erythromycin | 32 | 0.5 | MBI 26 | 1 |
| S. epidermidis | SE8565 | Erythromycin | 32 | 0.5 | MBI 26 | 1 |
| S. epidermidis | SE8403 | Erythromycin | 8 | 0.125 | MBI 31 | 2 |
| S. epidermidis | SE8410 | Erythromycin | 32 | 0.5 | MBI 31 | 1 |
| S. epidermidis | SE8411 | Erythromycin | 32 | 0.5 | MBI 31 | 1 |
| S. epidermidis | SE8497 | Erythromycin | 32 | 0.125 | MBI 31 | 1 |
| S. epidermidis | SE8503 | Erythromycin | 32 | 0.5 | MBI 31 | 1 |
| S. epidermidis | SE8565 | Erythromycin | 32 | 0.5 | MBI 31 | 1 |
| S. haemolyticus | SH8459 | Ampicillin | 0.5 | 0.25 | MBI 26 | 0.25 |
| S. haemolyticus | SH8472 | Ampicillin | 2 | 0.25 | MBI 26 | 16 |
| S. haemolyticus | SH8564 | Ampicillin | 64 | 0.25 | MBI 26 | 32 |
| S. haemolyticus | SH8575 | Ampicillin | 0.5 | 0.25 | MBI 26 | 8 |
| S. haemolyticus | SH8578 | Ampicillin | 0.5 | 0.25 | MBI 26 | 4 |
| S. haemolyticus | SH8597 | Clindamycin | 16 | 0.125 | MBI 26 | 1 |
| S. haemolyticus | SH8463 | Erythromycin | 8 | 0.5 | MBI 26 | 0.5 |
| S. haemolyticus | SH8472 | Erythromycin | 8 | 0.5 | MBI 26 | 0.5 |
| S. haemolyticus | SH8575 | Erythromycin | 32 | 2 | MBI 26 | 0.5 |
| S. haemolyticus | SH8578 | Erythromycin | 8 | 0.5 | MBI 26 | 01 |
| S. haemolyticus | SH8597 | Erythromycin | 32 | 0.5 | MBI 26 | 0.5 |
| S. haemolyticus | SH8463 | Erythromycin | 8 | 0.5 | MBI 31 | 0.5 |
| S. haemolyticus | SH8472 | Erythromycin | 8 | 0.5 | MBI 31 | 0.5 |
| S. haemolyticus | SH8564 | Erythromycin | 32 | 2 | MBI 31 | 0.5 |
| S. haemolyticus | SH8575 | Erythromycin | 32 | 2 | MBI 31 | 0.5 |
| S. haemolyticus | SH8563 | Methicillin | 64 | 0.25 | MBI 26 | 2 |
| S. maltophilia | 034 | Tobramycin | 8 | 1 | MBI 29 | 4 |
| S. maltophilia | 037 | Tobramycin | 32 | 4 | MBI 29 | 16 |
| S. maltophilia | 039 | Ciprofloxacin | 4 | 2 | MBI 29 | 16 |
| S. maltophilia | 041 | Tobramycin | 16 | 1 | MBI 29 | 8 |
| S. maltophilia | 043 | Imipenem | >256 | 4 | MBI 29 | 16 |
| S. maltophilia | 044 | Piperacillin | >512 | 16 | MBI 26 | 32 |

TABLE 24

| Microorganism | Strain | Teicoplanin (μg/ml) | | MBI 26 (μg/ml) | |
|---|---|---|---|---|---|
| | | Alone | +MBI 26 | Alone | +Teicoplanin |
| E. faecium | 97017 VanA | 32 | 0.25 | 64 | 4 |
| E. faecium | 97018 VanA | 32 | 0.25 | 64 | 8 |
| E. faecium | 97019 VanA | 32 | 0.5 | 64 | 16 |
| E. faecium | 97020 VanA | 32 | 0.5 | 64 | 16 |
| E. faecium | 97021 VanA | 32 | 0.5 | 64 | 32 |
| E. faecium | 97022 VanA | 32 | 0.5 | 64 | 4 |
| E. faecium | 97023 VanA | 32 | 0.25 | 64 | 4 |
| E. faecium | 97024 VanA | 32 | 0.25 | 64 | 8 |
| E. faecium | 97025 VanA | 32 | 0.5 | 16 | 4 |
| E. faecium | 97026 VanA | 32 | 0.5 | 64 | 16 |

TABLE 24-continued

| Microorganism | Strain | Teicoplanin (µg/ml) Alone | +MBI 26 | MBI 26 (µg/ml) Alone | +Teicoplanin |
|---|---|---|---|---|---|
| E. faecium 97027 | VanA | 32 | 8 | 64 | 8 |
| E. faecium 97028 | VanA | 32 | 0.25 | 8 | 8 |
| E. faecium 97029 | VanA | 32 | 0.25 | 64 | 8 |
| E. faecium 97030 | VanA | 32 | 0.25 | 64 | 32 |
| E. faecium 97031 | VanA | 32 | 0.25 | 64 | 32 |
| E. faecium 97032 | VanA | 32 | 0.25 | 64 | 8 |
| E. faecium 97033 | VanA | 32 | 0.25 | 64 | 8 |
| E. faecium 97034 | VanA | 32 | 0.25 | 64 | 8 |
| E. faecium 97035 | VanA | 32 | 0.25 | 64 | 0.5 |
| E. faecium 97036 | VanA | 8 | 0.25 | 8 | 4 |
| E. faecalis 97050 | VanA | 32 | 0.25 | 64 | 8 |
| E. faecalis 97051 | VanA | 32 | 0.25 | 64 | 8 |
| E. faecalis 97052 | VanA | 32 | 0.25 | 64 | 8 |
| E. faecalis 97053 | VanA | 32 | 0.25 | 64 | 8 |
| E. faecalis 97054 | VanA | 32 | 0.25 | 64 | 8 |
| E. faecalis 97055 | VanA | 32 | 0.25 | 64 | 8 |

TABLE 25

1. Amikacin

| Peptide | Organism | FIC | Amikacin MIC (µg/ml) Alone | +Peptide | Peptide MIC (µg/ml) Alone | +Amikacin |
|---|---|---|---|---|---|---|
| MBI 11B16CN | P. aeruginosa PA022 | 0.38 | 64 | 8 | 64 | 16 |
| MBI 21A2 | P. aeruginosa PA022 | 0.50 | 64 | 16 | 8 | 2 |
|  | E. faecium EFM020 | 0.56 | 32 | 2 | 128 | 64 |
|  | E. faecalis EFS008 | 0.19 | 64 | 8 | >128 | 16 |
| MBI 26 | E. faecium EFM004 | 0.56 | 128 | 8 | 64 | 32 |
|  | E. faecium EFM020 | 0.75 | 32 | 8 | 64 | 32 |
| MBI 27 | E. faecium EFM004 | 0.75 | 64 | 16 | 16 | 8 |
|  | E. faecium EFM020 | 0.63 | 32 | 4 | 16 | 8 |
|  | E. faecalis EFS008 | 0.56 | 32 | 16 | 4 | 0.25 |
| MBI 29A3 | E. faecium EFM004 | 0.56 | 128 | 8 | 8 | 4 |
|  | E. faecium EFM020 | 1.00 | 32 | 16 | 4 | 2 |
| MBI 29F1 | E. faecium EFM004 | 0.53 | >128 | 8 | 32 | 16 |
|  | E. faecalis EFS008 | 0.19 | 64 | 4 | 4 | 0.5 |
| Deber A2KA2 | E. faecalis EFS008 | 0.19 | 64 | 8 | >128 | 16 |

2. Ceftriaxone

| Peptide | Organism | FIC | Ceftriaxone MIC (µg/ml) Alone | +Peptide | Peptide MIC (µg/ml) Alone | +Ceftriaxone |
|---|---|---|---|---|---|---|
| MBI 11B7CN | A. baumannii ABI002 | 0.50 | 32 | 8 | 32 | 8 |
|  | A. baumannii ABI005 | 0.56 | 16 | 8 | 16 | 1 |
| MBI 11J02CN | A. baumannii ABI005 | 0.56 | 16 | 8 | 8 | 0.5 |
|  | A. lwoffii ALW007 | 0.75 | 16 | 4 | 4 | 2 |
|  | B. cepacia BC003 | 0.63 | 16 | 8 | >128 | 32 |
|  | E. cloacae ECL014 | 0.50 | 128 | 0.25 | 32 | 16 |
|  | E. cloacae ECL015 | 0.52 | 64 | 1 | 32 | 16 |
| MBI 26 | A. baumannii ABI005 | 0.53 | 16 | 0.5 | 2 | 1 |
|  | A. baumannii ABI006 | 0.56 | 128 | 8 | 2 | 1 |
|  | B. cepacia BC003 | 0.50 | 16 | 8 | >128 | 0.125 |
|  | E. cloacae ECL015 | 0.19 | 64 | 4 | 32 | 4 |

3. Ciprofloxacin

| Peptide | Organism | FIC | Ciprofloxacin MIC (µg/ml) Alone | +Peptide | Peptide MIC (µg/ml) Alone | +Ciprofloxacin |
|---|---|---|---|---|---|---|
| MBI 11A1CN | S. aureus SA10 | 0.50 | 32 | 0.125 | 128 | 64 |
|  | S. aureus SA25 | 0.53 | 4 | 0.125 | 16 | 8 |
| MBI 11D18CN | P. aeruginosa PA77 | 0.50 | 2 | 0.5 | 128 | 32 |

TABLE 25-continued

| | | | | | | |
|---|---|---|---|---|---|---|
| MBI 21A1 | S. aureus SA25 | 0.16 | 4 | 0.125 | 32 | 4 |
| | P. aeruginosa PA41 | 0.50 | 4 | 1 | 16 | 4 |
| | P. aeruginosa PA77 | 1.00 | 2 | 1 | 32 | 16 |
| MBI 21A2 | S. aureus SA25 | 0.56 | 2 | 1 | 16 | 1 |
| | P. aeruginosa PA41 | 0.50 | 4 | 1 | 64 | 16 |
| | P. aeruginosa PA77 | 0.63 | 2 | 0.25 | 64 | 32 |
| MBI 26 | A. calcoaceticus 5 | 0.38 | 2 | 0.25 | >32 | 16 |
| | E. cloacae 16 | 0.38 | 2 | 0.25 | >32 | 16 |
| | E. cloacae 17 | 0.38 | 2 | 0.25 | >32 | 16 |
| | P. aeruginosa PA41 | 0.50 | 4 | 1 | 128 | 32 |
| | P. aeruginosa PA77 | 0.56 | 2 | 0.125 | 128 | 64 |
| | P. aeruginosa 30 | 0.09 | 4 | 0.25 | >32 | 2 |
| | P. aeruginosa 31 | 0.27 | 16 | 0.25 | >32 | 16 |
| | S. maltophilia 34 | 0.25 | 2 | 0.25 | >32 | 8 |
| | S. maltophilia 35 | 0.50 | 2 | 0.5 | >32 | 16 |
| MBI 27 | S. aureus SA25 | 0.75 | 4 | 1 | 2 | 1 |
| MBI 28 | S. aureus SA25 | 0.56 | 2 | 0.125 | 2 | 1 |
| MBI 29 | A. calcoaceticus 3 | 0.63 | 8 | 1 | >16 | 16 |
| | A. calcoaceticus 4 | 0.63 | 8 | 1 | >16 | 16 |
| | E. cloacae 16 | 0.63 | 2 | 0.25 | >16 | 16 |
| | E. cloacae 17 | 0.75 | 2 | 1 | 16 | 4 |
| | S. aureus SA10 | 0.50 | 32 | 0.125 | 4 | 2 |
| | S. aureus SA14 | 0.63 | 8 | 1 | 8 | 4 |
| | P. aeruginosa PA41 | 0.63 | 8 | 1 | 8 | 4 |
| | P. aeruginosa PA77 | 0.50 | 2 | 0.5 | 64 | 16 |
| | P. aeruginosa 30 | 0.56 | 4 | 0.25 | >16 | 16 |
| | P. aeruginosa 31 | 0.53 | 16 | 0.5 | >16 | 16 |
| | S. maltophilia 34 | 0.63 | 2 | 0.25 | >16 | 16 |
| | S. maltophilia 35 | 0.63 | 2 | 0.25 | >16 | 16 |
| MBI 29A2 | S. aureus SA10 | 0.52 | 32 | 0.5 | 4 | 2 |
| | S. aureus SA25 | 0.63 | 4 | 0.5 | 2 | 1 |
| | P. aeruginosa PA41 | 1.00 | 4 | 2 | 8 | 4 |
| | P. aeruginosa PA77 | 1.00 | 2 | 1 | 16 | 8 |
| MBI 29A3 | S. aureus SA25 | 0.75 | 4 | 1 | 1 | 0.5 |
| | P. aeruginosa PA41 | 0.63 | 4 | 0.5 | 8 | 4 |

4. Gentamicin

| | | | Gentamicin MIC (μg/ml) | | Peptide MIC (μg/ml) | |
|---|---|---|---|---|---|---|
| Peptide | Organism | FIC | Alone | +Peptide | Alone | +Gentamicin |
| MBI 11B16CN | A. baumannii ABI001 | 0.31 | 64 | 4 | 16 | 4 |
| | A. baumannii ABI002 | 0.31 | 32 | 2 | 16 | 4 |
| | A. calcoaceticus AC001 | 0.25 | 8 | 1 | 32 | 4 |
| | P. aeruginosa PA023 | 0.56 | 8 | 4 | >128 | 16 |
| | P. aeruginosa PA041 | 0.31 | 8 | 2 | >128 | 16 |
| | S. maltophilia SMA017 | 0.16 | 64 | 2 | 128 | 16 |
| | S. maltophilia SMA019 | 0.51 | 64 | 0.5 | 32 | 16 |
| MBI 21A2 | A. calcoaceticus AC001 | 1.00 | 8 | 4 | 16 | 8 |
| | P. aeruginosa PA022 | 0.56 | 32 | 2 | 8 | 4 |
| | S. maltophilia SMA020 | 0.50 | 64 | 0.125 | 16 | 8 |
| | S. maltophilia SMA021 | 0.50 | 64 | 0.125 | 16 | 8 |
| MBI 26 | A. baumannii ABI001 | 0.56 | 64 | 4 | 8 | 4 |
| | A. baumannii ABI002 | 0.53 | 16 | 0.5 | 8 | 4 |
| | P. aeruginosa PA023 | 0.75 | 8 | 4 | >128 | 64 |
| | P. aeruginosa PA041 | 0.75 | 8 | 4 | 64 | 16 |
| | S. maltophilia SMA017 | 0.52 | 64 | 1 | 16 | 8 |
| | S. maltophilia SMA019 | 0.53 | 64 | 2 | 4 | 2 |
| MBI 27 | A. baumannii ABI002 | 0.52 | 32 | 0.5 | 8 | 4 |
| | A. calcoaceticus AC001 | 0.63 | 8 | 1 | 8 | 4 |
| | P. aeruginosa PA023 | 0.50 | 16 | 4 | 32 | 8 |
| | P. aeruginosa PA041 | 1.00 | 8 | 4 | 16 | 8 |
| | S. maltophilia SMA019 | 0.50 | 64 | 0.125 | 8 | 4 |
| | S. maltophilia SMA020 | 0.50 | 64 | 0.125 | 8 | 4 |
| MBI 29A3 | A. baumannii ABI002 | 0.75 | 16 | 4 | 2 | 1 |
| | P. aeruginosa PA041 | 1.00 | 8 | 4 | 8 | 4 |
| MBI 29F1 | A. calcoaceticus AC001 | 0.75 | 8 | 2 | 8 | 4 |
| | P. aeruginosa PA023 | 0.52 | 8 | 0.125 | 128 | 64 |
| Deber A2KA2 | A. calcoaceticus AC001 | 0.56 | 8 | 4 | >128 | 16 |
| | P. aeruginosa PA041 | 0.50 | 16 | 4 | >128 | 64 |

TABLE 25-continued

5. Mupirocin

| Peptide | Organism | FIC | Mupirocin MIC (µg/ml) Alone | +Peptide | Peptide MIC (µg/ml) Alone | +Mupirocin |
|---|---|---|---|---|---|---|
| MBI 27 | S. aureus SBSA4 | 0.50 | >100 | 0.3 | 4 | 2 |

6. Piperacillin

| Peptide | Organism | FIC | Piperacillin MIC (µg/ml) Alone | +Peptide | Peptide MIC (µg/ml) Alone | +Piperacillin |
|---|---|---|---|---|---|---|
| MB1 11B7CN | S. maltophilia 2 | 1.00 | 32 | 16 | 128 | 8 |
| | S. marcescens 1 | 0.27 | 32 | 8 | >128 | 4 |
| | H. influenzas 1 | 0.13 | 64 | 8 | >128 | 1 |
| MBI 11B9CN | A. calcoaceticus 3 | 0.75 | 64 | 16 | 32 | 16 |
| | S. maltophilia 2 | 0.75 | 64 | 16 | 32 | 16 |
| | S. marcescens SB1 | 0.26 | 64 | 16 | >128 | 2 |
| | P. aeruginosa 12 | 0.75 | >128 | 64 | 128 | 64 |
| | P. aeruginosa 15 | 0.50 | >128 | 64 | >128 | 64 |
| MBI 11CN | A. calcoaceticus 3 | 1.00 | 32 | 16 | 64 | 32 |
| | S. maltophilia 2 | 0.75 | 64 | 16 | 64 | 32 |
| | P. aeruginosa 22 | 0.52 | >128 | 4 | 64 | 32 |
| | P. aeruginosa 23 | 0.53 | 128 | 64 | 128 | 4 |
| MBI 11D18CN | A. calcoaceticus 3 | 0.38 | 64 | 8 | 32 | 8 |
| | E. cloacae 9 | 0.31 | >128 | 16 | 64 | 16 |
| | E. cloacae 10 | 0.56 | >128 | 16 | 32 | 16 |
| | S. maltophilia 2 | 0.50 | 64 | 16 | 32 | 8 |
| | S. maltophilia 14 | 0.63 | 128 | 16 | 16 | 8 |
| | S. marcescens 1 | 0.14 | 64 | 8 | >128 | 4 |
| | P. aeruginosa 23 | 0.56 | 128 | 64 | 64 | 4 |
| MBI 11E3CN | A. calcoaceticus 3 | 0.75 | 32 | 16 | 32 | 8 |
| | S. maltophilia 3 | 0.75 | 64 | 16 | 32 | 16 |
| | S. maltophilia 4 | 0.75 | 64 | 16 | 32 | 16 |
| | S. marcescens SB1 | 0.26 | 64 | 16 | >128 | 2 |
| | P. aeruginosa 7 | 1.00 | 128 | 64 | 64 | 32 |
| | P. aeruginosa 23 | 0.27 | 128 | 32 | 64 | 1 |
| | H. influenzae 1 | 0.38 | 64 | 8 | >128 | 64 |
| | H. influenzae 2 | 0.31 | 32 | 8 | >128 | 16 |
| MBI 11F3CN | A. calcoaceticus 3 | 0.63 | 32 | 16 | 32 | 4 |
| | S. maltophilia 2 | 0.75 | 64 | 16 | 32 | 16 |
| | P. aeruginosa 7 | 1.00 | 128 | 64 | 128 | 64 |
| | P. aeruginosa 23 | 0.51 | 128 | 64 | 64 | 0.5 |
| MBI 11F4CN | E. cloacae 10 | 0.52 | >128 | 4 | 16 | 8 |
| | S. maltophilia 2 | 0.50 | 64 | 16 | 16 | 4 |
| | S. marcescens 1 | 0.08 | >128 | 16 | >128 | 4 |
| | P. aeruginosa 7 | 0.38 | >128 | 64 | 64 | 8 |
| | P. aeruginosa 23 | 0.31 | >128 | 64 | 64 | 4 |
| | H. influenzae 1 | 0.75 | 32 | 16 | >128 | 64 |
| MBI 11G7CN | A. calcoaceticus 3 | 0.63 | 128 | 16 | 64 | 32 |
| | S. maltophilia 2 | 0.75 | 64 | 16 | 64 | 16 |
| | S. marcescens 1 | 0.25 | 64 | 16 | >128 | 1 |
| | P. aeruginosa 7 | 0.50 | >128 | 64 | >128 | 64 |
| | P. aeruginosa 23 | 0.50 | 128 | 64 | >128 | 1 |
| | H. influenzae 1 | 0.75 | 32 | 16 | >128 | 64 |
| MBI 21A2 | E. coli 1 | 0.53 | >128 | 8 | 4 | 2 |
| | S. maltophilia 3 | 0.75 | 64 | 16 | 32 | 16 |
| | S. maltophilia 11 | 0.75 | 32 | 8 | 128 | 64 |
| | S. marcescens 1 | 0.27 | 64 | 16 | >128 | 4 |
| | H. influenzae 1 | 0.31 | 64 | 4 | >128 | 64 |
| | H. influenzae 2 | 0.28 | 128 | 4 | >128 | 64 |
| MBI 26 | S. maltophilia 2 | 0.75 | 64 | 16 | 4 | 2 |
| | S. maltophilia 4 | 0.63 | 128 | 16 | 16 | 8 |
| | S. marcescens 1 | 0.09 | 64 | 2 | >128 | 16 |
| | P. aeruginosa 7 | 0.25 | >128 | 32 | >128 | 32 |
| | H. influenzae 1 | 0.19 | 64 | 4 | >128 | 32 |
| | H. influenzae 2 | 0.19 | 128 | 16 | >128 | 16 |
| | A. calcoaceticus 2 | 0.50 | >512 | 4 | 32 | 16 |
| | A. calcoaceticus 7 | 0.25 | 32 | 4 | >32 | 8 |
| | E. cloacae 13 | 0.16 | 128 | 4 | >32 | 8 |
| | E. cloacae 19 | 0.31 | 64 | 4 | >32 | 16 |
| | P. aeruginosa 23 | 0.27 | 256 | 4 | >64 | 32 |
| | P. aeruginosa 26 | 0.56 | 128 | 8 | >32 | 32 |
| | S. maltophilia 35 | 0.26 | >256 | 4 | >32 | 16 |
| | S. maltophilia 41 | 0.52 | >512 | 16 | >32 | 32 |

TABLE 25-continued

| | | | | | | |
|---|---|---|---|---|---|---|
| MBI 29 | S. marcescens 1 | 0.09 | 64 | 16 | >128 | 8 |
| | P. aeruginosa 23 | 0.63 | 128 | 64 | 16 | 2 |
| | H. influenzae 1 | 0.51 | 32 | 16 | 16 | 0.125 |
| | A. calcoaceticus 2 | 0.50 | >512 | 4 | 16 | 8 |
| | A. calcoaceticus 7 | 0.25 | 32 | 4 | >16 | 4 |
| | E. cloacae 16 | 0.50 | >512 | 4 | >16 | 16 |
| | E. cloacae 17 | 0.50 | >512 | 4 | >16 | 16 |
| | P. aeruginosa 23 | 0.63 | 128 | 64 | >32 | 8 |
| | P. aeruginosa 24 | 0.50 | >512 | 4 | >16 | 16 |
| | S. maltophilia 34 | 0.25 | >512 | 4 | >16 | 8 |
| | S. maltophilia 35 | 0.50 | >512 | 4 | >16 | 16 |

7. Tobramycin

| Peptide | Organism | FIC | Tobramycin MIC (µg/ml) Alone | +Peptide | Peptide MIC (µg/ml) Alone | +Tobramycin |
|---|---|---|---|---|---|---|
| MBI 11A1CN | P. aeruginosa PA026 | 0.50 | 8 | 4 | >128 | 0.125 |
| | S. maltophilia SMA029 | 0.16 | 128 | 4 | >128 | 32 |
| | S. maltophilia SMA030 | 0.27 | 128 | 2 | >128 | 64 |
| MBI 11B9CN | A. baumannii ABI001 | 0.50 | 16 | 4 | 32 | 8 |
| | E. coli ECO006 | 0.75 | 8 | 4 | 32 | 8 |
| | P. aeruginosa PA008 | 0.50 | 32 | 0.125 | 128 | 64 |
| | P. aeruginosa PA025 | 0.56 | 32 | 2 | 128 | 64 |
| | S. maltophilia SMA027 | 0.63 | 8 | 4 | >128 | 32 |
| | S. maltophilia SMA031 | 0.19 | 64 | 4 | >128 | 32 |
| MBI 11CN | A. baumannii ABI001 | 0.50 | 16 | 4 | 64 | 16 |
| | E. coli ECO006 | 0.53 | 8 | 4 | 8 | 0.25 |
| | P. aeruginosa PA032 | 0.50 | 16 | 4 | >128 | 64 |
| | S. maltophilia SMA029 | 0.27 | 128 | 2 | >128 | 64 |
| | S. maltophilia SMA030 | 0.27 | 128 | 2 | >128 | 64 |
| MBI 11D18CN | A. baumannii ABI001 | 0.31 | 16 | 4 | 64 | 4 |
| | A. baumannii ABI002 | 0.53 | 8 | 4 | 16 | 0.5 |
| | P. aeruginosa PA032 | 1.00 | 8 | 4 | 64 | 32 |
| | S. maltophilia SMA027 | 0.19 | 32 | 4 | >128 | 16 |
| | S. maltophilia SMA029 | 0.27 | 128 | 2 | 32 | 8 |
| | S. epidermidis SE080 | 0.75 | 16 | 4 | 2 | 1 |
| MBI 11F3CN | A. baumannii ABI001 | 0.53 | 16 | 0.5 | 32 | 16 |
| | P. aeruginosa PA032 | 0.50 | 16 | 4 | >128 | 64 |
| | S. maltophilia SMA029 | 0.26 | 128 | 1 | 128 | 32 |
| | S. maltophilia SMA030 | 0.26 | 128 | 1 | 128 | 32 |
| MBI 11G13CN | A. baumannii ABI001 | 0.50 | 16 | 4 | 128 | 32 |
| | P. aeruginosa PA022 | 0.56 | 8 | 4 | >128 | 16 |
| MBI 21A1 | P. aeruginosa PA022 | 0.53 | 8 | 4 | 4 | 0.125 |
| | P. aeruginosa PA026 | 0.51 | 8 | 4 | 16 | 0.125 |
| | P. aeruginosa PA030 | 0.52 | 16 | 0.25 | 16 | 8 |
| | P. aeruginosa PA032 | 0.63 | 8 | 1 | 64 | 32 |
| | S. maltophilia SMA029 | 0.28 | 128 | 4 | 128 | 32 |
| | S. maltophilia SMA030 | 0.16 | 128 | 4 | >128 | 32 |
| MBI 22A1 | A. baumannii ABI001 | 0.75 | 16 | 4 | 4 | 2 |
| | S. maltophilia SMA029 | 0.51 | 128 | 1 | 16 | 8 |
| | S. maltophilia SMA029 | 0.50 | 128 | 0.125 | 32 | 16 |
| | S. epidermidis SE072 | 0.50 | >128 | 0.125 | 16 | 8 |
| | S. epidermidis SE073 | 0.50 | >128 | 0.125 | 16 | 8 |
| MBI 26 | P. aeruginosa PA031 | 0.75 | 16 | 4 | 32 | 16 |
| | S. maltophilia SMA027 | 0.50 | 16 | 4 | >128 | 64 |
| | S. epidermidis SE068 | 0.27 | >128 | 4 | 2 | 0.5 |
| | S. epidermidis SE071 | 0.50 | >128 | 0.125 | 16 | 8 |
| MBI 27 | E. coli ECO006 | 0.56 | 8 | 0.5 | 8 | 4 |
| | S. maltophilia SMA027 | 1.00 | 8 | 4 | 32 | 16 |
| | S. maltophilia SMA031 | 0.53 | 128 | 4 | 16 | 8 |
| MBI 29 | E. coli ECO006 | 0.53 | 8 | 4 | 4 | 0.125 |
| | P. aeruginosa PA032 | 1.00 | 8 | 4 | 128 | 64 |
| | S. maltophilia SMA031 | 0.50 | >128 | 0.25 | 16 | 8 |
| | S. maltophilia SMA032 | 0.53 | 128 | 4 | 16 | 8 |
| MBI 29A3 | E. coli ECO006 | 0.75 | 8 | 2 | 4 | 2 |
| | P. aeruginosa PA022 | 0.56 | 8 | 4 | 4 | 0.25 |
| | S. maltophilia SMA027 | 0.75 | 16 | 4 | 32 | 16 |
| | S. maltophilia SMA029 | 0.28 | 128 | 4 | 16 | 4 |
| REWH 53A5CN | S. maltophilia SMA029 | 0.13 | 128 | 0.25 | >128 | 32 |
| | S. maltophilia SMA030 | 0.13 | 128 | 0.25 | >128 | 32 |

TABLE 25-continued

8. Vancomycin

| Peptide | Organism | FIC | Vancomycin MIC (µg/ml) Alone | +Peptide | Peptide MIC (µg/ml) Alone | + Vancomycin |
|---|---|---|---|---|---|---|
| MBI 11A1CN | E. faecalis EFS003 | 0.63 | 8 | 4 | >128 | 32 |
| | E. faecalis EFS006 | 0.50 | 8 | 4 | 128 | 0.25 |
| | E. faecalis EFS010 | 0.13 | 16 | 1 | 128 | 8 |
| | E. faecalis EFS014 | 0.51 | 128 | 1 | 4 | 2 |
| | E. faecium EFM004 | 0.50 | >128 | 0.5 | 32 | 16 |
| | E. faecium EFM007 | 0.28 | 128 | 4 | 64 | 16 |
| | E. faecium EFM009 | 0.25 | 32 | 4 | 64 | 8 |
| MBI 11D18CN | E. faecalis EFS003 | 0.75 | 8 | 2 | 64 | 32 |
| | E. faecalis EFS007 | 0.63 | 8 | 1 | 16 | 8 |
| | E. faecalis EFS009 | 0.75 | 8 | 2 | 8 | 4 |
| | E. faecium EFM004 | 0.50 | >128 | 0.5 | 8 | 4 |
| | E. faecium EFM007 | 0.50 | >128 | 0.5 | 8 | 4 |
| | E. faecium EFM009 | 0.52 | 64 | 1 | 8 | 4 |
| | E. faecium EFM010 | 0.50 | >128 | 1 | 8 | 4 |
| MBI 21A1 | E. faecalis EFS012 | 0.09 | 128 | 4 | 32 | 2 |
| | E. faecalis EFS013 | 0.09 | 128 | 4 | 32 | 2 |
| | E. faecium EFM010 | 0.56 | 64 | 4 | 32 | 16 |
| MBI 26 | E. faecalis EFS005 | 0.31 | 16 | 4 | >128 | 16 |
| | E. faecalis EFS010 | 0.27 | 64 | 1 | 4 | 1 |
| | E. faecalis EFS011 | 0.25 | 16 | 2 | >128 | 32 |
| | E. faecium EFM004 | 0.25 | >128 | 0.125 | 64 | 16 |
| | E. faecium EFM010 | 0.53 | 128 | 1 | 32 | 16 |
| | E. faecium EFM011 | 0.31 | 32 | 2 | 32 | 8 |
| MBI 29 | E. faecalis EFS012 | 0.50 | >128 | 1 | 2 | 1 |
| | E. faecalis EFS013 | 0.50 | >128 | 1 | 2 | 1 |
| | E. faecium EFM005 | 0.53 | 128 | 4 | 8 | 4 |
| | E. faecium EFM009 | 0.75 | 16 | 4 | 8 | 4 |
| | E. faecium EFM010 | 0.63 | 32 | 4 | 8 | 4 |
| | E. faecium EFM016 | 0.51 | 128 | 1 | 4 | 2 |
| MBI 29A3 | E. faecalis EFS005 | 0.19 | 16 | 1 | 32 | 4 |
| | E. faecalis EFS011 | 0.50 | 16 | 4 | 32 | 8 |
| | E. faecalis EFS014 | 0.52 | 64 | 1 | 1 | 0.5 |
| | E. faecium EFM006 | 0.52 | >128 | 4 | 4 | 2 |

These data show that acquired resistance can be overcome. For example, the acquired resistance of S. aureus, a Gram-positive organism, to piperacillin and ciprofloxacin is overcome when these antibiotic agents are combined with peptides MBI 27, MBI 21A1 or MBI 21A2 respectively. Similar results are obtained for peptides MBI 26 and MBI 31 in combination with methicillin, ampicillin and erythromycin, and for peptide MBI 26 in combination with vancomycin or teicoplanin against resistant enterococci.

Example 9

Synergy of Cationic Peptides and Lysozyme or Nisin

The effectiveness of the antibiotic activity of lysozyme or nisin is improved when either agent is administered in combination with a cationic peptide. The improvement is demonstrated by measurement of the MICs of lysozyme or nisin alone and in combination with the peptide, whereby the lysozyme or nisin MIC is lower in combination than alone. The MICs can be measured by the agarose dilution assay, the broth dilution assay or by time kill curves.

Example 10

Biochemical Characterization of Peptide Analogues

Solubility in Formulation Buffer

The primary factor affecting solubility of a peptide is its amino acid sequence. Polycationic peptides are preferably freely soluble in aqueous solutions, especially under low pH conditions. However, in certain formulations, polycationic peptides may form an aggregate that is removed in a filtration step. As peptide solutions for in vivo assays are filtered prior to administration, the accuracy and reproducibility of dosing levels following filtration are examined.

Peptides dissolved in formulations are filtered through a hydrophilic 0.2 µm filter membrane and then analyzed for total peptide content using reversed-phase HPLC. A 100% soluble standard for each concentration is prepared by dissolving the peptide in MilliQ water. Total peak area for each condition is measured and compared with the peak area of the standard in order to provide a relative recovery value for each concentration/formulation combination.

MBI 11CN was prepared in four different buffer systems (A, B, C, and C1) (Table 26, below) at 50, 100, 200 and 400 µg/ml peptide concentrations. With formulations A or B, both commonly used for solvation of peptides and proteins, peptide was lost through filtration in a concentration dependent manner (FIG. 4). Recovery only reached a maximum of 70% at a concentration of 400 µg/ml. In contrast, peptides dissolved in formulations C and C1 were fully recovered. Buffers containing polyanionic ions appear to encourage aggregation, and it is likely that the aggregate takes the form of a matrix which is trapped by the filter. Monoanionic counterions are more suitable for the maintenance of peptides in a non-aggregated, soluble form, while the addition of other solubilizing agents may further improve the formulation.

TABLE 26

| Code | Formulation Buffer |
|------|-------------------|
| A    | PBS 200 mM, pH 7.1 |
| B    | Sodium Citrate 100 mM, pH 5.2 |
| C    | Sodium Acetate 200 mM, pH 4.6 |
| C1   | Sodium Acetate 200 mM/0.5% Polysorbate 80, pH 4.6 |
| D    | Sodium Acetate 100 mM/0.5% Activated Polysorbate 80, pH 7.5: Lyophilized/Reconstituted |

Solubility in Broth

The solubility of peptide analogues is assessed in calcium and magnesium supplemented Mueller Hinton broth by visual inspection. The procedure employed is that used for the broth dilution assay except that bacteria are not added to the wells. The appearance of the solution in each well is evaluated according to the scale: (a) clear, no precipitate, (b) light diffuse precipitate and (c) cloudy, heavy precipitate. Results show that, for example, MBI 10CN is less soluble than MBI 11CN under these conditions and that MBI 11BCN analogues are less soluble than MBI 11ACN analogues.

Reversed Phase HPLC Analysis of Peptide Analogue Formulations

Reversed-phase HPLC, which provides an analytical method for peptide quantification, is used to examine peptides in two different formulations. A 400 µg/mL solution of MBI 11CN prepared in formulations C1 and D is analyzed by using a stepwise gradient to resolve free peptide from other species. Standard chromatographic conditions are used as follows:

Solvent A: 0.1% trifluoroacetic acid (TFA) in water
Solvent B: 0.1% TFA/95% acetonitrile in water
Media: POROS® R2-20 (polystyrene divinylbenzene)

As shown in FIG. 5, MBI 11CN could be separated in two forms, as free peptide in formulation C1, and as a principally formulation-complex peptide in formulation D. This complex survives the separation protocol in gradients containing acetonitrile, which might be expected to disrupt the stability of the complex. A peak corresponding to a small amount (<10%) of free peptide is also observed in formulation D. If the shape of the elution gradient is changed, the associated peptide elutes as a broad low peak, indicating that complexes of peptide in the formulation are heterogeneous.

Example 11

Structural Analysis of Indolicidin Variants Using Circular Dichroism Spectroscopy Circular dichroism (CD) is a spectroscopic technique that measures secondary structures of peptides and proteins in solution, see for example, R. W. Woody, (*Methods in Enzymology*, 246: 34, 1995). The CD spectra of □-helical peptides is most readily interpretable due to the characteristic double minima at 208 and 222 nm. For peptides with other secondary structures however, interpretation of CD spectra is more complicated and less reliable. The CD data for peptides is used to relate solution structure to in vitro activity.

CD measurements of indolicidin analogues are performed in three different aqueous environments, (1) 10 mM sodium phosphate buffer, pH 7.2, (2) phosphate buffer and 40% (v/v) trifluoroethanol (TFE) and (3) phosphate buffer and large (100 nm diameter) unilamellar phospholipid vesicles (liposomes) (Table 27). The organic solvent TFE and the liposomes provide a hydrophobic environment intended to mimic the bacterial membrane where the peptides are presumed to adopt an active conformation.

Figure 6:
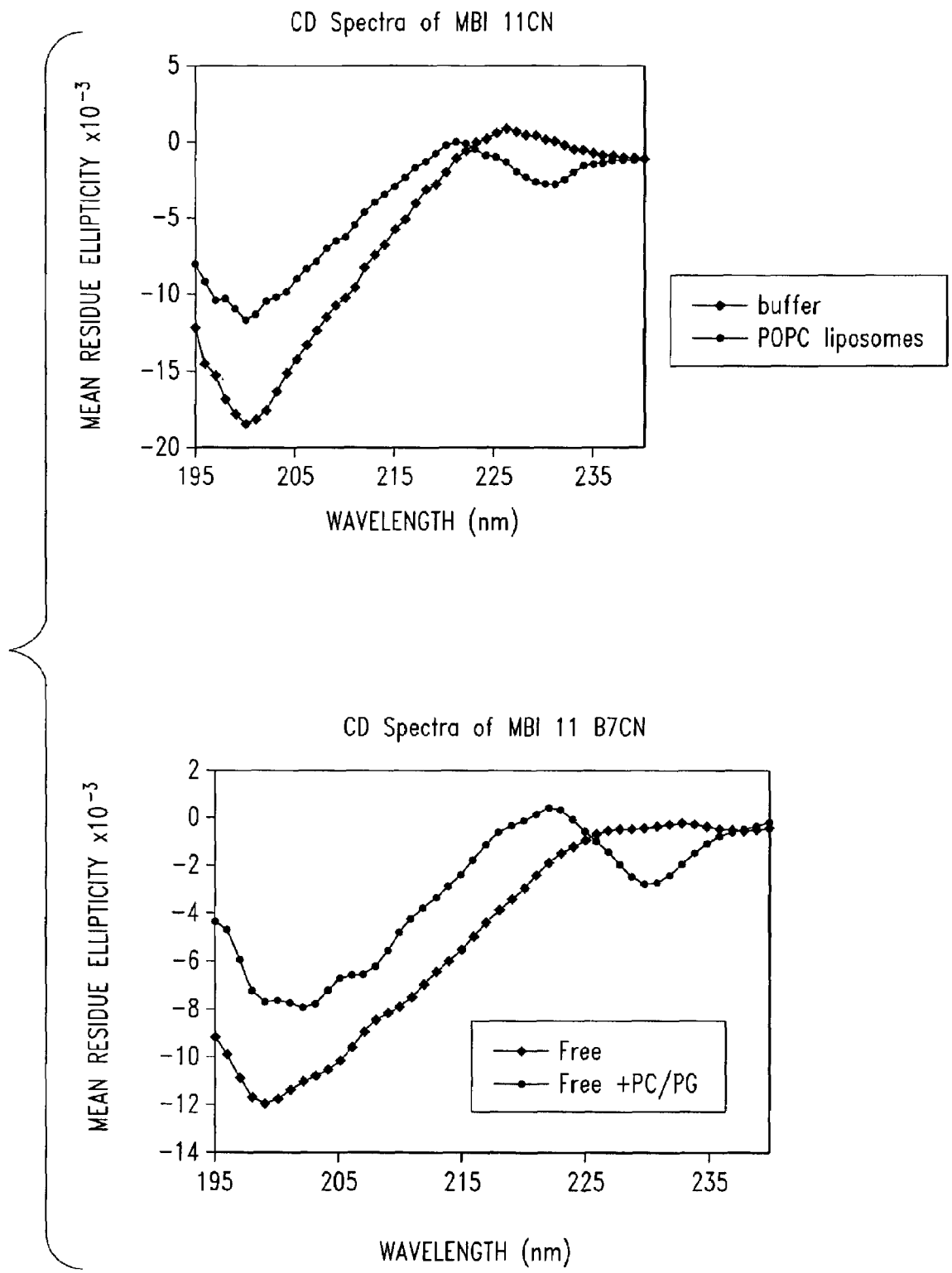
FIG. 6 presents CD spectra of MBI 11CN and MBI 11B7CN.

The results indicate that the peptides are primarily unordered in phosphate buffer (a negative minima at around 200 nm) with the exception of MBI 11F4CN, which displays an additional minima at 220 nm (see below). The presence of TFE induces □-turn structure in MBI 11 and MBI 11G4CN, and increases □-helicity in MBI 11F4CN, although most of the peptides remain unordered. In the presence of liposomes, peptides MBI 11CN and MBI 11B7CN, which are unordered in TFE, display □-turn structure (a negative minima at around 230 nm) (FIG. 6). Hence, liposomes appear to induce more ordered secondary structure than TFE.

A □-turn is the predominant secondary structure that appears in a hydrophobic environment, suggesting that it is the primary conformation in the active, membrane-associated form. In contrast, MBI 11F4CN displays increased □-helical conformation in the presence of TFE. Peptide MBI 11F4CN is also the most insoluble and hemolytic of the peptides tested, suggesting that □-helical secondary structure may introduce unwanted properties in these analogues.

Additionally CD spectra are recorded for APO-modified peptides (Table 28). The results show that these compounds have significant □-turn secondary structure in phosphate buffer, which is only slightly altered in TFE.

Again, the CD results suggest that a □-turn structure (i.e. membrane-associated) is the preferred active conformation among the indolicidin analogues tested.

TABLE 27

| Peptide | Phosphate buffer min □ | max □ | Conformation in buffer | TFE min □ | max □ | Conformation in TFE |
|---------|------|------|------|------|------|------|
| MBI 10CN | 201 | — | Unordered | 203 | ~219 | Unordered |
| MBI 11 | 199 | — | Unordered | 202, 227 | 220 | □-turn |
| MBI 11ACN | 199 | — | Unordered | 203 | 219 | Unordered |
| MBI 11CN | 200 | — | Unordered | 200 | — | Unordered |
| MBI 11CNY1 | 200 | — | Unordered | 200 | — | Unordered |
| MBI 11B1CNW1 | 201 | — | Unordered | 201 | — | Unordered |
| MBI 11B4ACN | 200 | — | Unordered | 200 | — | Unordered |
| MBI 11B7CN | 200 | — | Unordered | 204, ~219 | — | Unordered |
| MBI 11B9ACN | 200 | — | Unordered | 200 | — | Unordered |

TABLE 27-continued

| Peptide | Phosphate buffer min □ | max □ | Conformation in buffer | TFE min □ | max □ | Conformation in TFE |
|---|---|---|---|---|---|---|
| MBI 11B9CN | 200 | — | Unordered | 200 | — | Unordered |
| MBI 11D1CN | 200 | — | Unordered | 204 | — | Unordered |
| MBI 11E1CN | 201 | — | Unordered | 201 | — | Unordered |
| MBI 11E2CN | 200 | — | Unordered | 201 | — | Unordered |
| MBI 11E3CN | 202 | 226 | ppII helix | 200 | — | Unordered |
| MBI 11F3CN | 199 | 228 | ppII helix | 202 | — | Unordered |
| MBI 11F4CN | 202, 220 | — | Unordered | 206, 222 | — | slight □-helix |
| MBI 11G4CN | 199, 221 | — | Unordered | 201, 226 | 215 | □-turn |
| MBI 11G6ACN | 200 | — | Unordered | 199 | — | Unordered |
| MBI 11G7ACN | 200 | — | Unordered | 202 | 221 | Unordered |

TABLE 28

| APO-modified peptide | Phosphate buffer min □ | max □ | Conformation in buffer | TFE min □ | max □ | Conformation in TFE |
|---|---|---|---|---|---|---|
| MBI 11CN | 202, 229 | 220 | □-turn | 203 | 223 | □-turn |
| MBI 11BCN | 200, 229 | — | □-turn | 202 | 222 | □-turn |
| MBI 11B7CN | 202, 230 | 223 | □-turn | 199 | 230 | □-turn |
| MBI 11E3CN | 202, 229 | 220 | □-turn | 199 | — | □-turn |
| MBI 11F3CN | 205 | — | ppII helix | 203 | 230 | ppII helix |

Example 12

Membrane Permeabilization Assays

Liposome Dye Release

A method for measuring the ability of peptides to permeabilize phospholipid bilayers is described (Parente et al., Biochemistry, 29, 8720, 1990) Briefly, liposomes of a defined phospholipid composition are prepared in the presence of a fluorescent dye molecule. In this example, a dye pair consisting of the fluorescent molecule 8-aminonapthalene-1,3,6-trisulfonic acid (ANTS) and its quencher molecule p-xylene-bis-pyridinium bromide (DPX) are used. The mixture of free dye molecules, dye free liposomes, and liposomes containing encapsulated ANTS-DPX are separated by size exclusion chromatography. In the assay, the test peptide is incubated with the ANTS-DPX containing liposomes and the fluorescence due to ANTS release to the outside of the liposome is measured over time.

Using this assay, peptide activity, measured by dye release, is shown to be extremely sensitive to the composition of the liposomes at many liposome to peptide ratios (L/P) (FIG. 7). Specifically, addition of cholesterol to liposomes composed of egg phosphotidylcholine (PC) virtually abolishes membrane permeabilizing activity of MBI 11CN, even at very high lipid to peptide molar ratios (compare with egg PC liposomes containing no cholesterol). This in vitro selectivity may mimic that observed in vitro for bacterial cells in the presence of mammalian cells.

In addition, there is a size limitation to the membrane disruption induced by MBI 11CN. ANTS/DPX can be replaced with fluorescein isothiocyanate-labeled dextran (FD-4), molecular weight 4,400, in the egg PC liposomes. No increase in FD-4 fluorescence is detected upon incubation with MBI 11CN. These results indicate that MBI 11CN-mediated membrane disruption allows the release of the relatively smaller ANTS/DPX molecules (~400 Da), but not the bulkier FD-4 molecules.

*E. coli* ML-35 Inner Membrane Assay

An alternative method for measuring peptide-membrane interaction uses the *E. coli* strain ML-35 (Lehrer et al., *J. Clin. Invest.*, 84: 553, 1989), which contains a chromosomal copy of the lacZ gene encoding □-galactosidase and is permease deficient. This strain is used to measure the effect of peptide on the inner membrane through release of □-galactosidase into the periplasm. Release of □-galactosidase is measured by spectrophotometrically monitoring the hydrolysis of its substrate o-nitrophenol □-D-galactopyranoside (ONPG). The maximum rate of hydrolysis ($V_{max}$) is determined for aliquots of cells taken at various growth points.

A preliminary experiment to determine the concentration of peptide required for maximal activity against mid-log cells, diluted to $4 \times 10^7$ CFU/ml, yields a value of 50 μLg/ml, which is used in all subsequent experiments. Cells are grown in two different growth media, Terrific broth (TB) and Luria broth (LB) and equivalent amounts of cells are assayed during their growth cycles. The resulting activity profile of MBI 11B7CN is shown in FIG. 8. For cells grown in the enriched TB media, maximum activity occurs at early mid-log (140 min), whereas for cells grown in LB media, the maximum occurs at late mid-log (230 min). Additionally, only in LB, a dip in activity is observed at 140 min. This drop in activity may be related to a transition in metabolism, such as a requirement for utilization of a new energy source due to depletion of the original source, which does not occur in the more enriched TB media. A consequence of a metabolism switch would be changes in the membrane potential.

Figure 9:
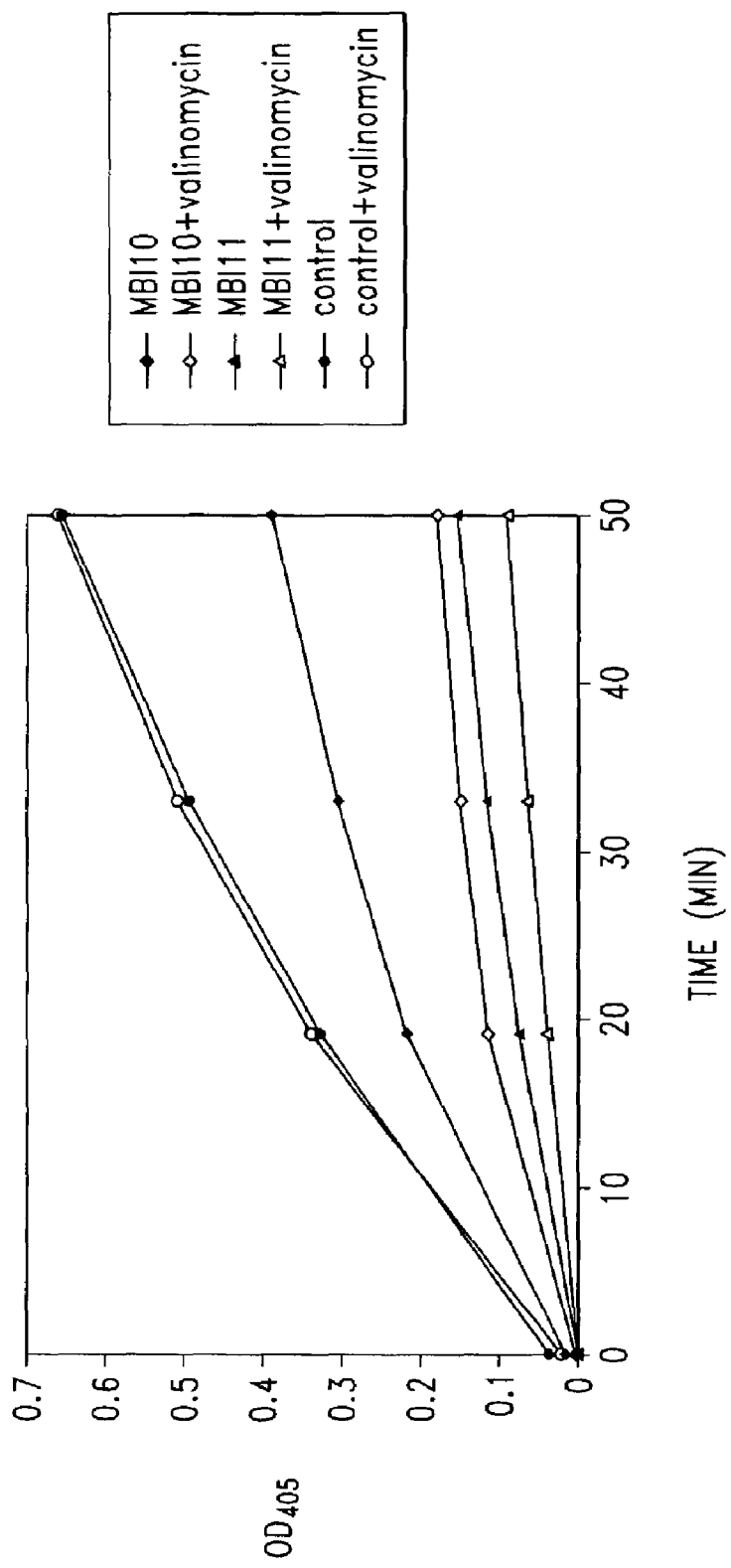
FIG. 9 shows results of treatment of bacteria with MBI 10CN, MBI 11CN, or a control peptide alone or in combination with valinomycin.

To test whether membrane potential has an effect on peptide activity, the effect of disrupting the electrochemical gradient using the potassium ionophore valinomycin is examined. Cells pre-incubated with valinomycin are treated with peptide and for MBI 10CN and MBI 11CN ONPG hydrolysis diminished by approximately 50% compared to no pre-incubation with valinomycin (FIG. 9). Another cationic peptide that is not sensitive to valinomycin is used as a positive control.

Figure 10:
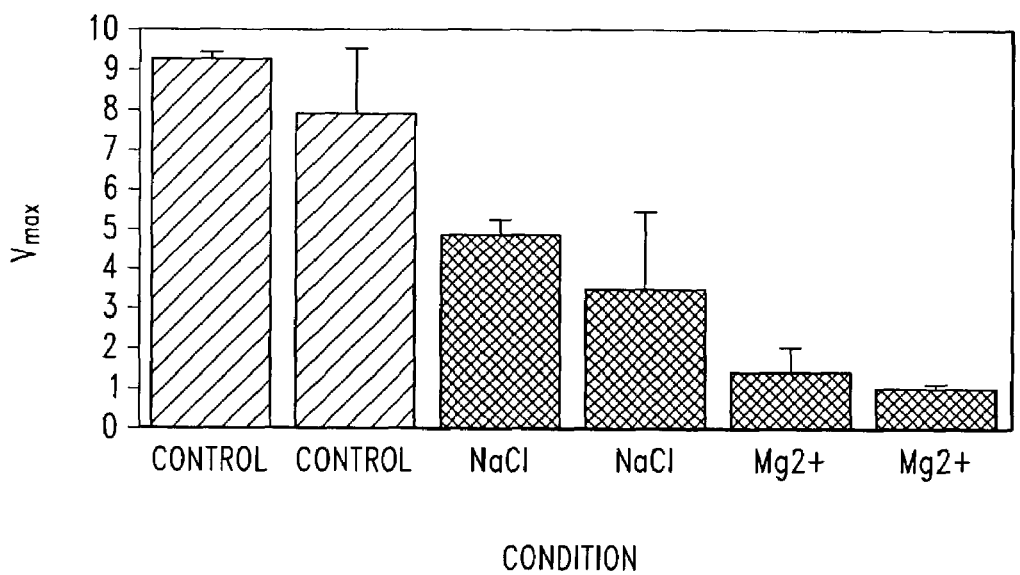
FIG. 10 is a graph showing treatment of bacteria with MBI 11B7CN in the presence of NaCl or $Mg^{2+}$.

Further delineation of the factors influencing membrane permeabilizing activity are tested. In an exemplary test, MBI 11B7CN is pre-incubated with isotonic HEPES/sucrose buffer containing either 150 mM sodium chloride (NaCl) or 5 mM magnesium ions ($Mg^{2+}$) and assayed as described earlier. In FIG. 10, a significant inhibition is observed with either solution, suggesting involvement of electrostatic interactions in the permeabilizing action of peptides.

Example 13

Erythrocyte Hemolysis by Cationic Peptides

Cationic peptides are tested for toxicity towards eukaryotic cells by measuring the extent of lysis of mammalian red blood cells (RBC). Briefly, in this assay, red blood cells are separated from whole blood by centrifugation and washed free of plasma components. A 5% (v/v) washed red blood cell suspension is prepared in isotonic saline. An aliquot of peptide in formulation is then added and mixed in. After incubation at 37° C. for 1 hour with constant agitation, the solution is centrifuged and the supernatant measured for absorbance at 540 nm to detect released hemoglobin. When compared with the absorbance for a 100% lysed standard, a relative measure of the amount of hemoglobin that has been released from inside the red blood cells is determined and hence the ability of the peptide/formulation to cause red blood cell lysis.

Three peptide analogues, MBI 10CN, MBI 11 and MBI 11CN, in formulation C1 at 800 µg/ml cause substantial lysis, which is due primarily to the pH of the buffer. In contrast, formulation D has a more neutral pH and causes significantly less lysis. Under these conditions, MBI 10CN, MBI 11, and MBI 11CN are essentially non-lytic, resulting in 3.9, 2.3, and 3.2% lysis, respectively.

Various cationic peptides are tested for the extent of erythrocyte lysis. As shown in the following table, very little toxicity is observed.

TABLE 29

| Peptide # | % Lysis |
| --- | --- |
| Apidaecin IA | 0.3 |
| MBI 10CN | 4.3 |
| MBI 11CN | 0.8 |
| MBI 11A1CN | 0.5 |
| MBI 11A2C N | 0.1 |
| MBI 11A3CN | 0.0 |
| MBI 11A4CN | 0.3 |
| MBI 11A5CN | 0.3 |
| MBI 11A6CN | 0.7 |
| MBI 11A7CN | 0.5 |
| MBI 11B1CN | 3.1 |
| MBI 11B2CN | 3.2 |
| MBI 11B3CN | 3.3 |
| MBI 11B4CN | 1.6 |
| MBI 11B5CN | 1.7 |
| MBI 11B7CN | 3.2 |
| MBI 11B8CN | 1.1 |
| MBI 11B9CN | 0.4 |
| MBI 11B10CN | 0.2 |
| MBI 11D3CN | 0.8 |
| MBI 11D4CN | 0.9 |
| MBI 11D5CN | 0.7 |
| MBI 11D6CN | 1.1 |
| MBI 11D11H | 0.7 |
| MBI 11D13H | 1.7 |
| MBI 11D14CN | 1.1 |
| MBI 11D15CN | 0.9 |
| MBI 11D18CN | 0.8 |
| MBI 11E1CN | 0.8 |
| MBI F11E2CN | 0.5 |
| MBI 11E3CN | 1.3 |
| MBI 11F1CN | 2.1 |
| MBI 11F2CN | 1.4 |
| MBI 11G3CN | 0.5 |
| MBI 11G5CN | 0.6 |
| MBI 11G6CN | 0.6 |
| MBI 11G7CN | 1.5 |
| MBI 11G13CN | 0.2 |
| MBI 11G14CN | 1.1 |
| MBI 21A2 | 0.5 |
| MBI 26 | 0.6 |
| MBI 27 | 2.7 |
| MBI 28 | 4.7 |
| MBI 29 | 1.9 |
| MBI 29A3 | 2.0 |
| MBI 31 | 0.3 |

A combination of cationic peptide and antibiotic agent is tested for toxicity towards eukaryotic cells by measuring the extent of lysis of mammalian red blood cells. Briefly, red blood cells are separated from whole blood by centrifugation, washed free of plasma components, and resuspended to a 5% (v/v) suspension in isotonic saline. The peptide and antibiotic agent are pre-mixed in isotonic saline, or other acceptable solution, and an aliquot of this solution is added to the red blood cell suspension. Following incubation with constant agitation at 37° C. for 1 hour, the solution is centrifuged, and the absorbance of the supernatant is measured at 540 nm, which detects released hemoglobin. Comparison to the $A_{540}$ for a 100% lysed standard provides a relative measure of hemoglobin release from red blood cells, indicating the lytic ability of the cationic peptide and antibiotic agent combination.

A red blood cell (RBC) lysis assay is used to group peptides according to their ability to lyse RBC under standardized conditions compared with MBI 11CN and Gramicidin-S. Peptide samples and washed sheep RBC are prepared in isotonic saline with the final pH adjusted to between 6 and 7. Peptide samples and RBC suspension are mixed together to yield solutions that are 1% (v/v) RBC and 5, 50 or 500 µg/ml peptide. The assay is performed as described above. Each set of assays also includes MBI 11CN (500 µg/ml) and Gramicidin-S (5 µg/ml) as "low lysis" and "high lysis" controls, respectively.

MBI11B7CN, MB 11F3CN and MB 11F4CN are tested using this procedure and the results are presented in Table 30 below.

TABLE 30

| Peptide | % lysis at 5 µg/ml | % lysis at 50 µg/ml | % lysis at 500 µg/ml |
| --- | --- | --- | --- |
| MBI 11B7CN | 4 | 13 | 46 |
| MBI 11F3CN | 1 | 6 | 17 |
| MBI 11F4CN | 4 | 32 | 38 |

TABLE 30-continued

| Peptide | % lysis at 5 µg/ml | % lysis at 50 µg/ml | % lysis at 500 µg/ml |
|---|---|---|---|
| MBI 11CN | N/D | N/D | 9 |
| Gramicidin-S | 30 | N/D | N/D |

N/D = not done

Peptides that at 5 µg/ml lyse RBC to an equal or greater extent than Gramicidin-S, the "high lysis" control, are considered to be highly lytic. Peptides that at 500 µg/ml lyse RBC to an equal to or lesser extent than MBI 11CN, the "low lysis" control, are considered to be non-lytic. The three analogues tested are all "moderately lytic" as they cause more lysis than MBI 11CN and less than Gramicidin S. In addition one of the analogues, MBI-11F3CN, is significantly less lytic than the other two variants at all three concentrations tested.

Example 14

Production of Antibodies to Peptide Analogues

Multiple antigenic peptides (MAPs), which contain four or eight copies of the target peptide linked to a small non-immunogenic peptidyl core, are prepared as immunogens. Alternatively, the target peptide is conjugated to bovine serum albumin (BSA) or ovalbumin. For example, MBI 11B7 conjugated to ovalbumin is used as an immunogen. The immunogens are injected subcutaneously into rabbits to raise IgG antibodies using standard protocols (see, Harlow and Lane, *Antibodies: A Laboratory Manual*, Cold Spring Harbor Laboratory Press, Cold Spring Harbor, N.Y., 1988). After repeated boosters (usually monthly), serum from a blood sample is tested in an ELISA against the target peptide. A positive result indicates the presence of antibodies and further tests determine the specificity of the antibody binding to the target peptide. Purified antibodies can then be isolated from this serum and used in ELISAs to selectively identify and measure the amount of the target peptide in research and clinical samples.

Example 15

Pharmacology of Cationic Peptides in Plasma and Blood

The in vitro lifetime of free peptides in plasma and in blood is determined by measuring the amount of peptide present after set incubation times. Blood is collected from sheep, treated with an anticoagulant (not heparin) and, for plasma preparation, centrifuged to remove cells. Formulated peptide is added to either the plasma fraction or to whole blood and incubated. Following incubation, peptide is identified and quantified directly by reversed phase HPLC or an antibody-based assay. The antibiotic agent is quantified by a suitable assay, selected on the basis of its structure. Chromatographic conditions are as described above. Extraction is not required as the free peptide peak does not overlie any peaks from blood or plasma.

Figure 11:
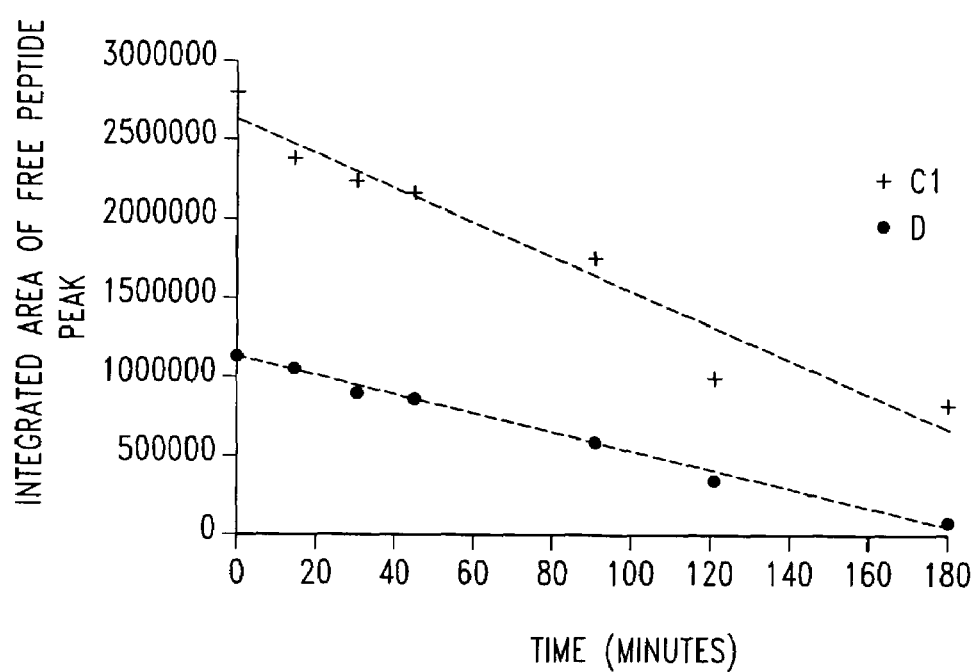
FIG. 11 is a graph presenting the in vitro amount of free MBI 11CN in plasma over time. Data is shown for peptide in formulation C1 and formulation D.

A 1 mg/mL solution of MBI 11CN in formulations C1 and D is added to freshly prepared sheep plasma at a final peptide concentration of 100 µg/mL and incubated at 37° C. At various times, aliquots of plasma are removed and analyzed for free peptide by reversed phase HPLC. From each chromatogram, the area of the peak corresponding to free peptide is integrated and plotted against time of incubation. As shown in FIG. 11, peptide levels diminish over time. Moreover, when administered in formulation D, up to 50% of the peptide is immediately released from formulation-peptide complex on addition to the blood. The decay curve for free peptide yields an apparent half-life in blood of 90 minutes for both formulation C1 and D. These results indicate that in sheep's blood MBI 11CN is relatively resistant to plasma peptidases and proteases. New peaks that appeared during incubation may be breakdown products of the peptide.

A 1 mg/mL solution of MBI 11B7CN in isotonic saline is added to freshly prepared heat-inactivated rabbit serum, to give a final peptide concentration of 100 µg/mL and is incubated at 32° C. The peptide levels detected are shown in FIG. 12.

Figure 13:
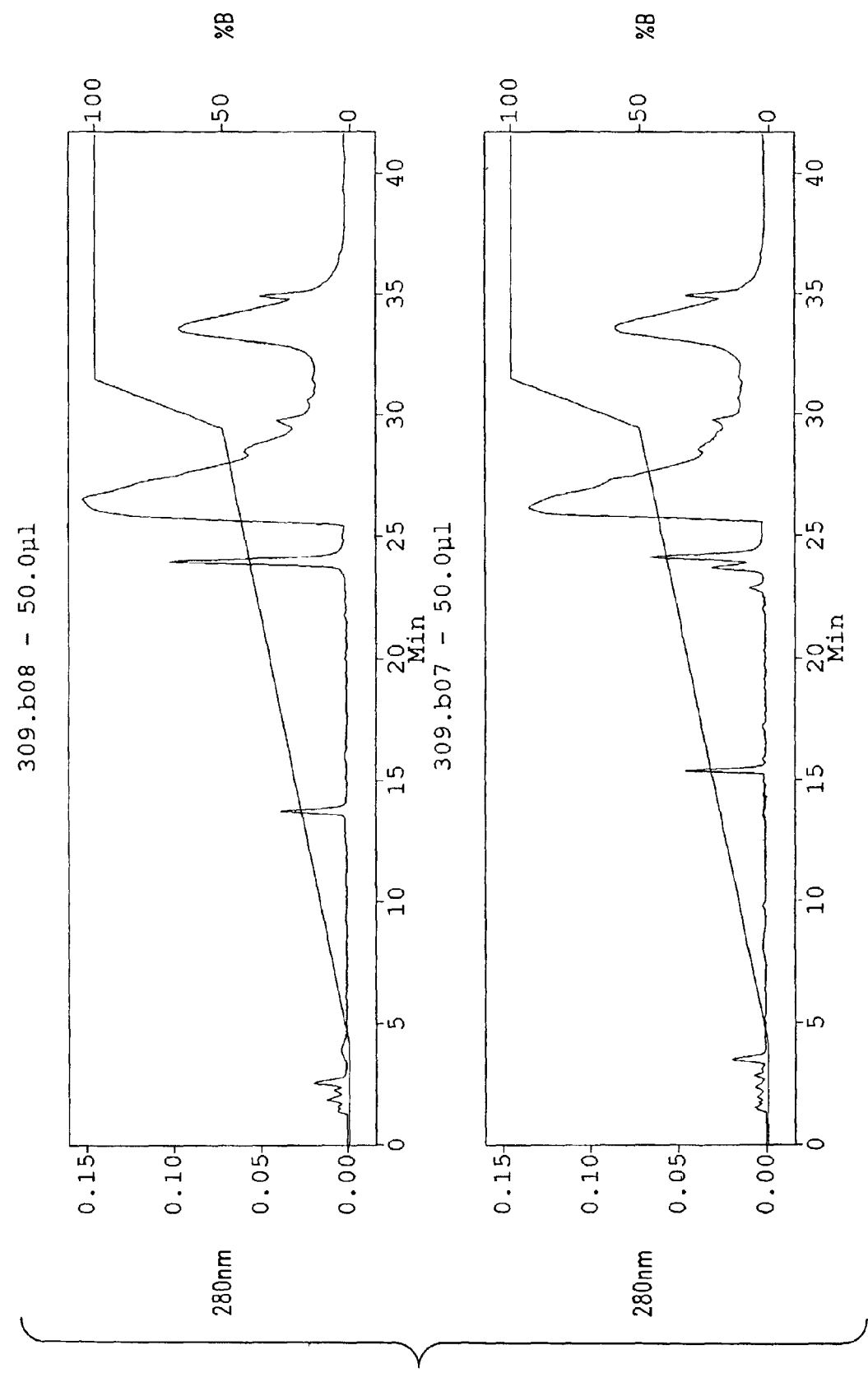
FIG. 13 presents HPLC tracings showing the effects of amastatin and bestatin on peptide degradation.

A series of peptide stability studies are performed to investigate the action of protease inhibitors on peptide degradation. Peptide is added to rabbit serum or plasma, either with or without protease inhibitors, then incubated at 22° C. for 3 hrs. Protease inhibitors tested include amastatin, bestatin, COMPLETE protease inhibitor cocktail, leupeptin, pepstatin A and EDTA. Amastatin and bestatin at 100 µM prevent the degradation of MBI 11B7CN in plasma over 3 hrs (FIG. 13). For this experiments 10 mM stock solutions of amastatin and bestatin are prepared in dimethylsulfoxide. These solutions are diluted 1:100 in heat-inactivated rabbit serum and incubated at 22° C. for 15 mins prior to addition of peptide. MBI 11B7CN is added to the serum at a final concentration of 100 µg/mL and incubated for 3 hrs at 22° C. After the incubation period, the serum samples are analyzed on an analytical $C_8$ column (Waters Nova Pak $C_8$ 3.9×170 mm) with detection at 280 nm. In FIG. 13, MBI 11B7CN elutes at 25 min.

Figure 14:
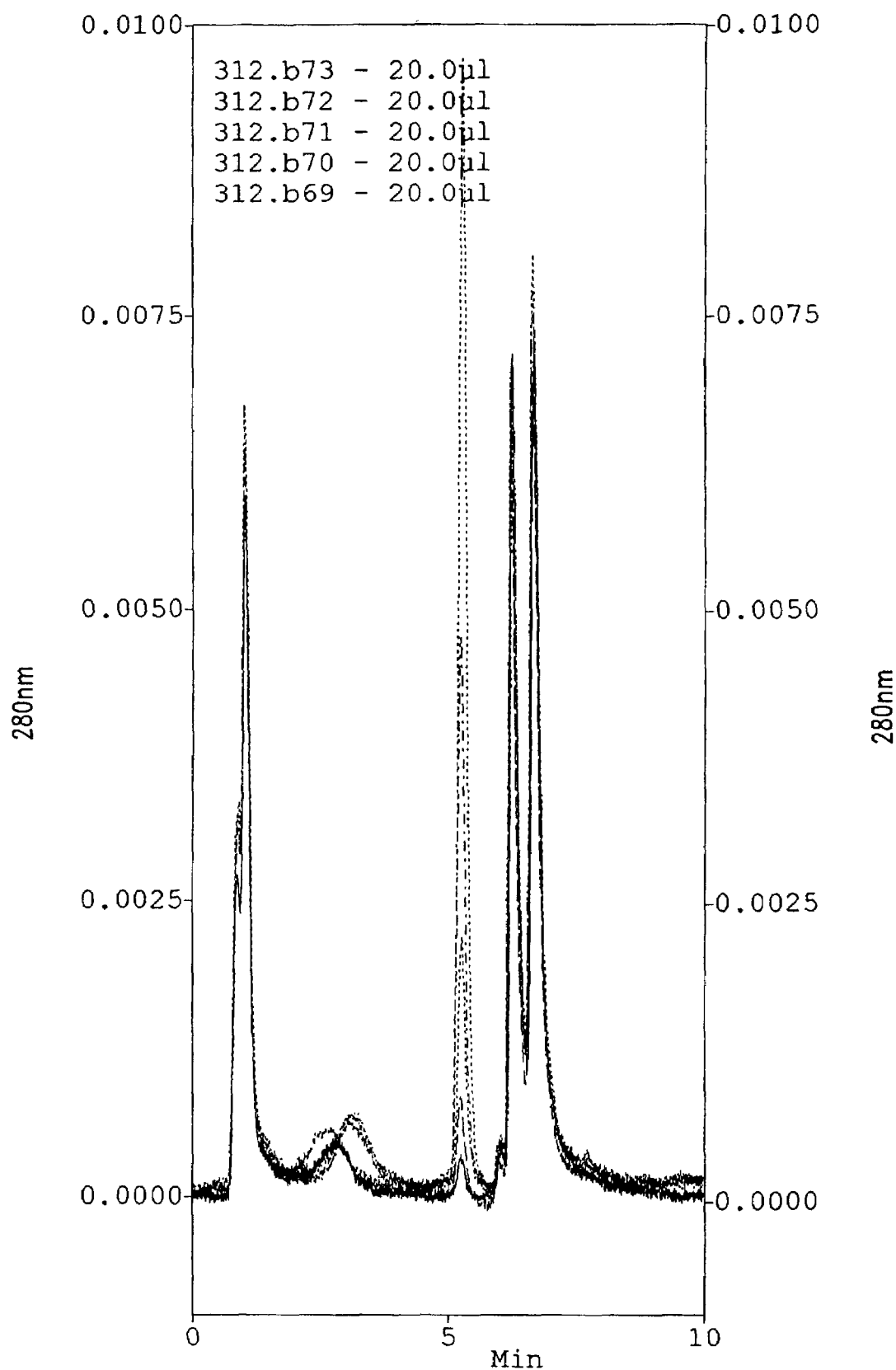
FIG. 14 is a chromatogram showing extraction of peptides in rabbit plasma.

Peptide is extracted from plasma using $C_8$ Sep Pak cartridges at peptide concentrations between 0 and 50 µg/mL. Each extraction also contains MBI 11CN at 10 µg/mL as an internal standard. Immediately after addition of the peptides to fresh rabbit plasma, the samples are mixed then diluted 1:10 with a 1% aqueous trifluoroacetic acid (TFA) solution, to give a final TFA concentration of 0.1%. Five hundred µL of this solution is immediately loaded onto a $C_8$ Sep Pak cartridge and eluted with 0.1% TFA in 40% acetonitrile/60% $H_2O$. Twenty µL of this eluant is loaded onto a 4.6×45 mm analytical $C_{18}$ column and is eluted with an acetonitrile gradient of 25% to 65% over 8 column volumes. The peptides are detected at 280 nm. A chromatogram showing the extraction MBI 11B7CN with MBI 11CN as an internal standard is shown in FIG. 14. MBI 11B7CN and MBI 11CN elute at 5 and 3 min respectively. MBI 11B7CN is detected over background at concentrations of 5 µg/mL and above.

Figure 15:
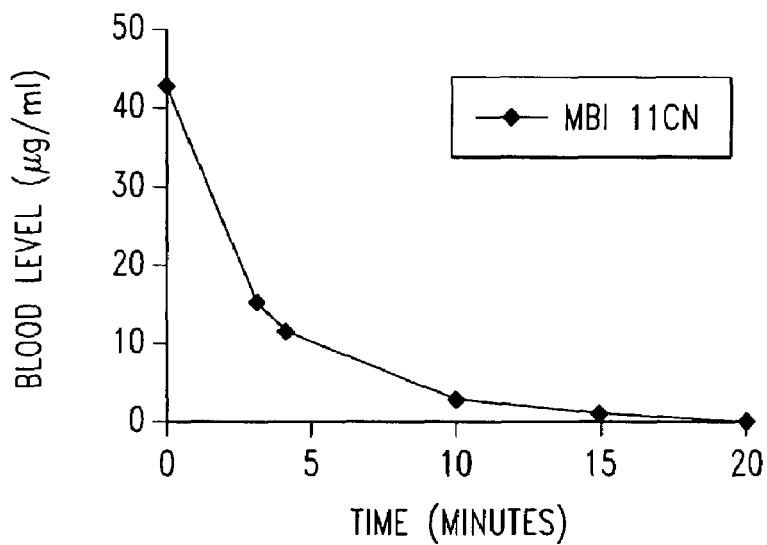
FIG. 15 is a graph presenting change in vivo MBI 11CN levels in blood at various times after intravenous injection.

Peptide levels in plasma in vivo are measured after iv or ip administration of 80-100% of the maximum tolerated dose of peptide analogue in either formulation C1 or D. MBI 11CN in formulation C1 is injected intravenously into the tail vein of CD1 ICRBR strain mice. At various times post-injection, mice are anesthetized and blood is drawn by cardiac puncture. Blood from individual mice is centrifuged to separate plasma from cells. Plasma is then analyzed by reversed phase HPLC column. The resulting elution profiles are analyzed for free peptide content by UV absorbance at 280 nm, and these data are converted to concentrations in blood based upon a calibrated standard. Each data point represents the average blood level from two mice. In this assay, the detection limit is approximately 1 µg/ml, less than 3% of the dose administered The earliest time point at which peptide can be measured is three minutes following injection, thus, the maximum observed concentration (in μg/ml) is extrapolated back to time zero (FIG. 15). The projected initial concentration corresponds well to the expected concentration of between 35 and 45 μg/ml. Decay is rapid, however, and when the curve is fitted to the equation for exponential decay, free circulating peptide is calculated to have a half life of 2.1 minutes. Free circulating peptide was not detectable in the blood of mice that were injected with MBI 11CN in formulation D, suggesting that peptide is not released as quickly from the complex as in vitro.

In addition, MBI 11CN is also administered to CD1 ICRBR strain mice by a single ip injection at an efficacious dose level of 40 mg/kg. Peptide is administered in both formulations C1 and D to determine if peptide complexation has any effect on blood levels. At various times post injection, mice are anesthetized and blood is drawn by cardiac puncture. Blood is collected and analyzed as for the iv injection.

Figure 16:
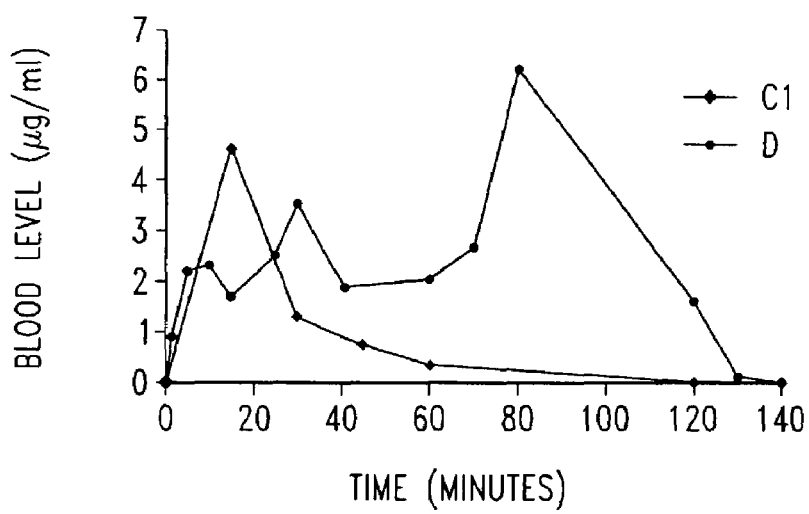
FIG. 16 is a graph presenting change in vivo MBI 11CN levels in plasma at various times after intraperitoneal injection.

MBI 11CN administered by this route demonstrated a quite different pharmacologic profile (FIG. 16). In formulation C1, peptide entered the blood stream quickly, with a peak concentration of nearly 5 μg/ml after 15 minutes, which declined to non-detectable levels after 60 minutes. In contrast, peptide in formulation D is present at a level above 2 μg/ml for approximately two hours. Therefore, formulation affects entry into, and maintenance of levels of peptide in the blood.

The in vivo lifetime of the cationic peptide and antibiotic agent combination is determined by administration, typically by intravenous or intraperitoneal injection, of 80-100% of the maximum tolerable dose of the combination in a suitable animal model, typically a mouse. At set times post-injection, each group of animals are anesthetized, blood is drawn, and plasma obtained by centrifugation. The amount of peptide or agent in the plasma supernatant is analyzed as for the in vitro determination.

Example 16

Toxicity of Cationic Peptides in vivo

The acute, single dose toxicity of various indolicidin analogues is tested in Swiss CD1 mice using various routes of administration. In order to determine the inherent toxicities of the peptide analogues in the absence of any formulation/delivery vehicle effects, the peptides are all administered in isotonic saline with the final pH between 6 and 7.

Intraperitoneal route. Groups of 6 mice are injected with peptide doses of between 80 and 5 mg/kg in 500 μl dose volumes. After peptide administration, the mice are observed for a period of 5 days, at which time the dose causing 50% mortality ($LD_{50}$), the dose causing 90-100% mortality ($LD_{90-100}$) and maximum tolerated dose (MTD) levels are determined. The $LD_{50}$ values are calculated using the method of Reed and Muench (*J. of Amer. Hyg.* 27: 493-497, 1938). The results presented in Table 31 show that the $LD_{50}$ values for MBI 11CN and analogues range from 21 to 52 mg/kg.

TABLE 31

| Peptide | $LD_{50}$ | $LD_{90-100}$ | MTD |
| --- | --- | --- | --- |
| MBI 11CN | 34 mg/kg | 40 mg/kg | 20 mg/kg |
| MBI 11B7CN | 52 mg/kg | >80 mg/kg | 30 mg/kg |

TABLE 31-continued

| Peptide | $LD_{50}$ | $LD_{90-100}$ | MTD |
| --- | --- | --- | --- |
| MBI 11E3CN | 21 mg/kg | 40 mg/kg | <20 mg/kg |
| MBI 11F3CN | 52 mg/kg | 80 mg/kg | 20 mg/kg |

The single dose toxicity of a cationic peptide and antibiotic agent combination is examined in outbred ICR mice. Intraperitoneal injection of the combination in isotonic saline is carried out at increasing dose levels. The survival of the animals is monitored for 7 days. The number of animals surviving at each dose level is used to determine the maximum tolerated dose (MTD). In addition, the MTD can be determined after administration of the peptide and agent by different routes, at different time points, and in different formulations.

TABLE 32

| Peptide # | MTD/mg/kg |
| --- | --- |
| Intraperitoneal injection | |
| MBI 10CN | >29 |
| MBI 11CN | >40 |
| MBI 26 | >37 |
| MBI 29 | 24 |
| Intravenous injection | |
| MBI 10CN | 5.6 |
| MBI 11CN | 6.1 |
| MBI 26 | >18 |

The single dose toxicity of MBI 10CN and MBI 11CN is examined in outbred ICR mice (Table 32). Intraperitoneal injection (groups of 2 mice) of MBI 10CN in formulation D showed no toxicity up to 29 mg/kg and under the same conditions MBI 11CN showed no toxicity up to 40 mg/kg.

Intravenous route. Groups of 6 mice are injected with peptide doses of 20, 16, 12, 8, 4 and 0 mg/kg in 100 μl volumes (4 ml/kg). After administration, the mice are observed for a period of 5 days, at which time the $LD_{50}$, $LD_{90-100}$ and MTD levels are determined. The results from the IV toxicity testing of MBI 11CN and three analogues are shown in Table 33. The $LD_{50}$, $LD_{90-100}$ and MTD values range from 5.8 to 15 mg/kg, 8 to 20 mg/kg and <4 to 12 mg/kg respectively.

TABLE 33

| Peptide | $LD_{50}$ | $LD_{90-100}$ | MTD |
| --- | --- | --- | --- |
| MBI 11CN | 5.8 mg/kg | 8.0 mg/kg | <4 mg/kg |
| MBI 11B7CN | 7.5 mg/kg | 16 mg/kg | 4 mg/kg |
| MBI 11F3CN | 10 mg/kg | 12 mg/kg | 8 mg/kg |
| MBI 11F4CN | 15 mg/kg | 20 mg/kg | 12 mg/kg |

Intravenous injection (groups of 10 mice) of MBI 10CN in formulation D showed an MTD of 5.6 mg/kg. Injection of 11 mg/kg gave 40% toxicity and 22 mg/kg gave 100% toxicity. Intravenous injection of MBI 11CN in formulation C (lyophilized) showed a MTD of 3.0 mg/kg. Injection at 6.1 mg/kg gave 10% toxicity and at 12 mg/kg 100% toxicity.

TABLE 34

| Peptide | Route | # Animals | Formulation | MTD (mg/kg) |
|---|---|---|---|---|
| MBI 10CN | ip | 2 | formulation D | 29 |
| MBI 11CN | ip | 2 | formulation D | 40 |
| MBI 10CN | iv | 10 | formulation D | 5.6 |
| MBI 11CN | iv | 10 | formulation C (lyophilized) | 3.0 |

These results are obtained using peptide/buffer solutions that were lyophilized after preparation and reconstituted with water. If the peptide solution is not lyophilized before injection, but used immediately after preparation, an increase in toxicity is seen, and the maximum tolerated dose can decrease by up to four-fold. For example, an intravenous injection of MBI 11CN as a non-lyophilized solution, formulation C1, at 1.5 mg/kg gives 20% toxicity and at 3.0 mg/kg gives 100% toxicity. HPLC analyses of the non-lyophilized and lyophilized formulations indicate that the MBI 11CN forms a complex with Tween 80, and this complexation of the peptide reduces its toxicity in mice.

In addition, mice are multiply injected by an intravenous route with MBI 11CN (Table 35). In one representative experiment, peptide administered in 10 injections of 0.84 mg/kg at 5 minute intervals is not toxic. However, two injections of peptide at 4.1 mg/kg administered with a 10 minute interval results in 60% toxicity.

TABLE 35

| Peptide | Route | Formulation | Dose Level (mg/kg) | # Injections | Time Interval | Result |
|---|---|---|---|---|---|---|
| MBI 11CN | iv | formulation D | 0.84 | 10 | 5 min | no toxicity |
| MBI 11CN | iv | formulation D | 4.1 | 2 | 10 min | 66% toxicity |

Subcutaneous route. The toxicity of MBI 11CN is also determined after subcutaneous (SC) administration. For SC toxicity testing, groups of 6 mice are injected with peptide doses of 128, 96, 64, 32 and 0 mg/kg in 300 μL dose volumes (12 mL/kg). After administration, the mice are observed for a period of 5 days. None of the animals died at any of the dose levels within the 5 day observation period. Therefore, the $LD_{50}$, $LD_{90-100}$ and MTD are all taken to be greater than 128 mg/kg. Mice receiving higher dose levels showed symptoms similar to those seen after IV injection suggesting that peptide entered the systemic circulation. These symptoms are reversible, disappearing in all mice by the second day of observations.

The single dose toxicity of MBI 10CN and MBI 11CN in different formulations is also examined in outbred ICR mice (Table 36). Intraperitoneal injection (groups of 2 mice) of MBI 10CN in formulation D show no toxicity up to 29 mg/kg and under the same conditions MBI 11CN show no toxicity up to 40 mg/kg.

Intravenous injection (groups of 10 mice) of MBI 10CN in formulation D show a maximum tolerated dose (MTD) of 5.6 mg/kg (Table 36). Injection of 11 mg/kg gave 40% toxicity and 22 mg/kg result in 100% toxicity. Intravenous injection of MBI 11CN in formulation C (lyophilized) show a MTD of 3.0 mg/kg. Injection at 6.1 mg/kg result in 10% toxicity and at 12 mg/kg 100% toxicity.

TABLE 36

| Peptide | Route | # Animals | Formulation | MTD (mg/kg) |
|---|---|---|---|---|
| MBI 10CN | ip | 2 | formulation D | >29 |
| MBI 11CN | ip | 2 | formulation D | >40 |
| MBI 10CN | iv | 10 | formulation D | 5.6 |
| MBI 11CN | iv | 10 | formulation C (lyophilized) | 3.0 |

These results are obtained using peptide/buffer solutions that are lyophilized after preparation and reconstituted with water. If the peptide solution is not lyophilized before injection, but used immediately after preparation, an increase in toxicity is seen, and the maximum tolerated dose can decrease by up to four-fold. For example, an intravenous injection of MBI 11CN as a non-lyophilized solution, formulation C1, at 1.5 mg/kg results in 20% toxicity and at 3.0 mg/kg gave 100% toxicity. HPLC analyses of the non-lyophilized and lyophilized formulations indicate that the MBI 11CN forms a complex with polysorbate, and this complexation of the peptide reduces its toxicity in mice.

In addition, mice are multiply injected by an intravenous route with MBI 11CN (Table 37). In one representative experiment, peptide administered in 10 injections of 0.84 mg/kg at 5 minute intervals is not lethal. However, two injections of peptide at 4.1 mg/kg administered with a 10 minute interval results in 60% mortality.

TABLE 37

| Peptide | Route | Formulation | Dose Level* | # Injections | Time Interval | Result |
|---|---|---|---|---|---|---|
| MBI 11CN | iv | formulation D | 0.84 | 10 | 5 min | no mortality |
| MBI 11CN | iv | formulation D | 4.1 | 2 | 10 min | 66% mortality |

*(mg/kg)

To assess the impact of dosing mice with peptide analogue, a series of histopathology investigations can be carried out. Groups of mice are administered analogue at dose levels that are either at, or below the MTD, or above the MTD, a lethal dose. Multiple injections may be used to mimic possible treatment regimes. Groups of control mice are not injected or injected with buffer only.

Following injection, mice are sacrificed at specified times and their organs immediately placed in a 10% balanced formalin solution. Mice that die as a result of the toxic effects of the analogue also have their organs preserved immediately. Tissue samples are taken and prepared as stained micro-sections on slides which are then examined microscopically. Damage to tissues is assessed and this information can be used to develop improved analogues, improved methods of administration or improved dosing regimes.

To assess the impact of dosing mice with peptide analogue, a series of histopathology investigations are carried out. Groups of two mice are administered MBI 11CN in formulation D by ip and iv injection. The dose levels are either at or below the MTD or a lethal dose above MTD. Groups of control mice are uninjected or injected with buffer only. At 0, 70 and 150 minutes after injection, the major organs of moribund or sacrificed mice are examined histologically for evidence of toxicity.

Mice given an iv injection of MBI 11CN are identified as follows:

| Control Mouse A: | No dose |
|---|---|
| Control Mouse B: | Buffer Dose Only (no peptide) |
| M70A,B: | MBI 11CN, 4 mg/kg, 70 minute observation |
| M150A,B: | MBI 11CN, 4 mg/kg, 150 minute observation |
| MXA,B: | MBI 11CN, 12 mg/kg (lethal dose) |

Mice given an ip injection of MBI 11CN are identified as follows:

| Control Mouse A: | No dose |
|---|---|
| Control Mouse B: | Buffer Dose Only (no peptide) |
| M70A,B: | MBI 11CN, 40 mg/kg, 70 minute observation |
| M150A,B: | MBI 11CN, 40 mg/kg, 150 minute observation |
| MXA,B: | MBI 11CN, 80 mg/kg (lethal dose) |

Following injection, the mice are sacrificed at the times indicated above and their organs immediately placed in a 10% balanced formalin solution. The tissue samples are prepared as stained micro-sections on slides and then examined microscopically.

Mice given a non-lethal dose were always lethargic, with raised fur and evidence of edema and hypertension, but recovered to normal within two hours. Tissues from these animals indicate that there was some damage to blood vessels, particularly within the liver and lung at both the observation times, but other initial abnormalities returned to normal within the 150 minute observation time. It is likely that blood vessel damage is a consequence of continuous exposure to high circulating peptide levels.

In contrast, mice given a lethal dose had completely normal tissues and organs, except for the liver and heart of the ip and iv dosed mice, respectively. In general, this damage is identified as disruption of the cells lining the blood vessels. It appears as though the rapid death of mice is due to this damage, and that the peptide did not penetrate beyond that point. Extensive damage to the hepatic portal veins in the liver and to the coronary arterioles in the heart was observed.

Further evidence points to a cumulative toxic effect, where the maximum dose iv is lethal when repeated after 10 minutes, but not when repeated after one hour.

Example 17

In vivo Efficacy of Cationic Peptides

Cationic peptides are tested for their ability to rescue mice from lethal bacterial infections. The animal model used is an intraperitoneal (ip) inoculation of mice with $10^6$-$10^8$ Gram-positive organisms with subsequent administration of peptide. The three pathogens investigated, methicillin-sensitive *S. aureus* (MSSA), methicillin-resistant *S. aureus* (MRSA), or *S. epidermidis* are injected ip into mice. For untreated mice, death occurs within 12-18 hours with MSSA and *S. epidermis* and within 6-10 hours with MRSA.

Peptide is administered by two routes, intraperitoneally, at one hour post-infection, or intravenously, with single or multiple doses given at various times pre- and post-infection.

MSSA infection. In a typical protocol, groups of 10 mice are infected intraperitoneally with a $LD_{90\text{-}100}$ dose ($5.2\times10^6$ CFU/mouse) of MSSA (Smith, ATCC # 19640) injected in brain-heart infusion containing 5% mucin. This strain of *S. aureus* is not resistant to any common antibiotics. At 60 minutes post-infection, MBI 10CN or MBI 11CN, in formulation D, is injected intraperitoneally at the stated dose levels. An injection of formulation alone serves as a negative control and administration of ampicillin serves as a positive control. The survival of the mice is monitored at 1, 2, 3 and 4 hrs post-infection and twice daily thereafter for a total of 8 days.

Figure 17:
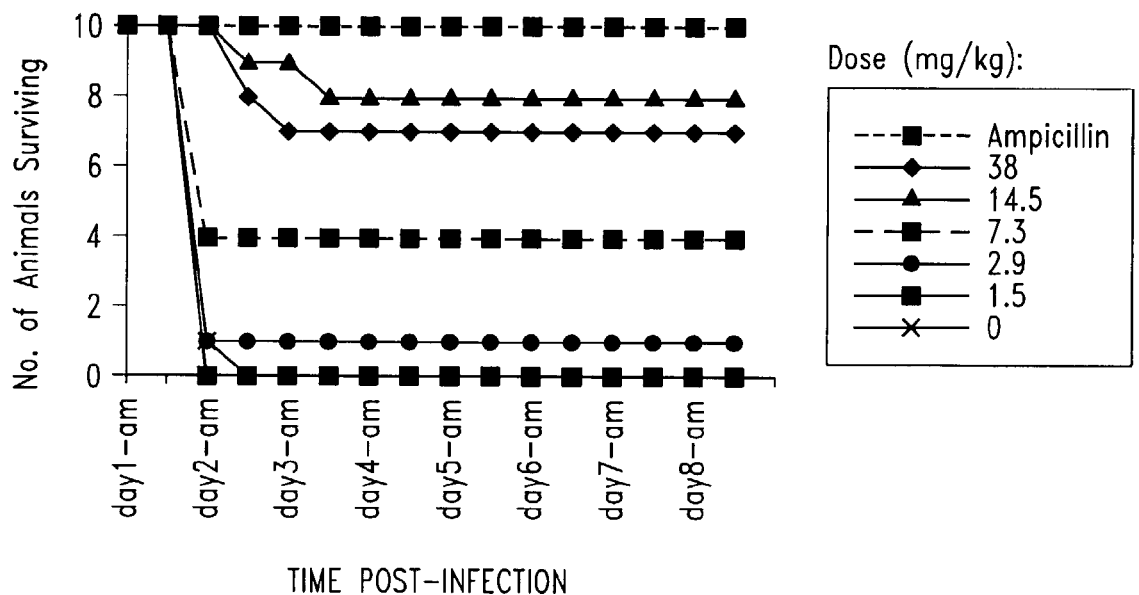
FIG. 17 is a graph showing the number of animals surviving an MSSA infection after intraperitoneal injection of MBI 10CN, ampicillin, or vehicle.
Figure 18:
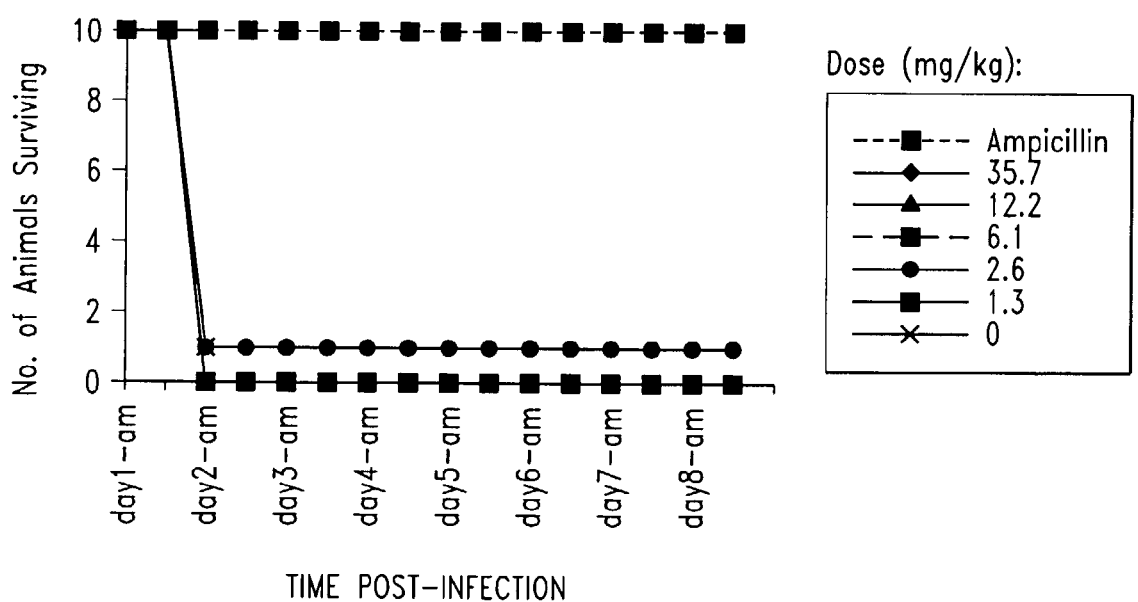
FIG. 18 is a graph showing the number of animals surviving an MSSA infection after intraperitoneal injection of MBI 11CN, ampicillin, or vehicle.
Figure 19:
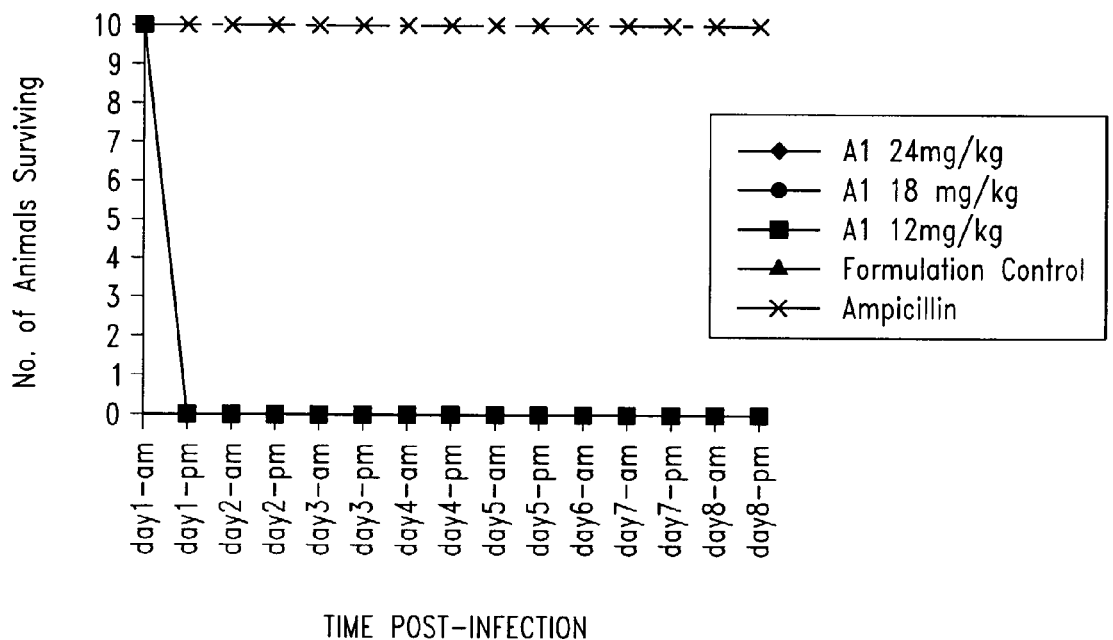
FIG. 19 is a graph showing the results of in vivo testing of MBI-11A1CN against S. aureus (Smith). Formulated peptide at various concentrations is administered by ip injection one hour after infection with S. aureus (Smith) by ip injection.
Figure 20:
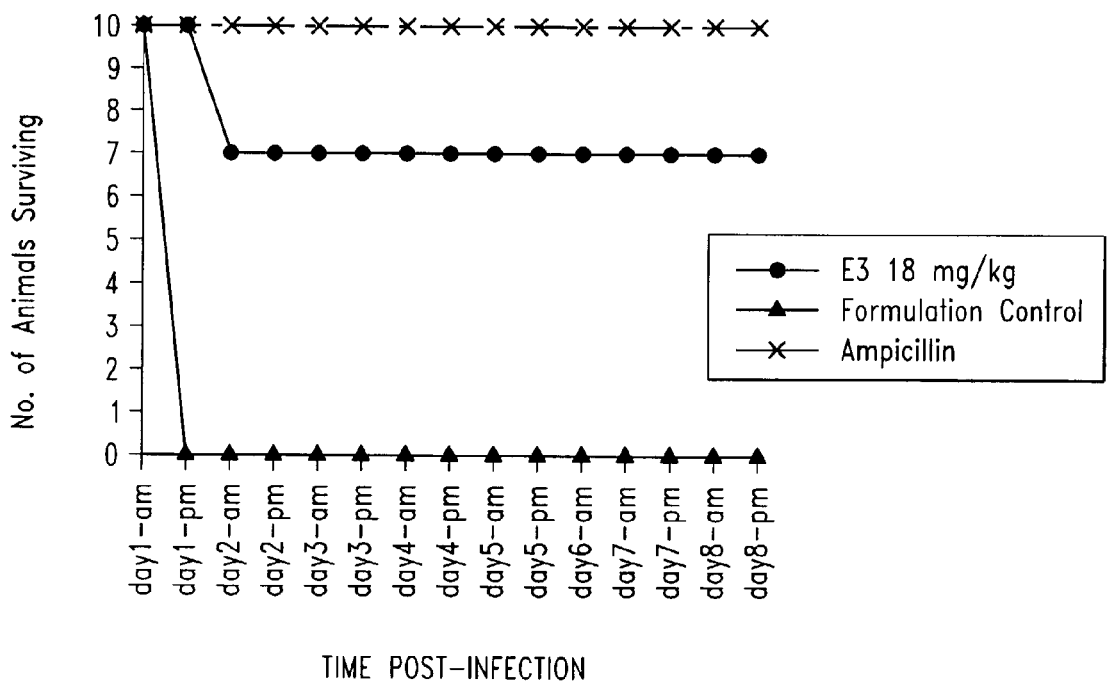
FIG. 20 is a graph showing the results of in vivo testing of MBI-11E3CN against S. aureus (Smith). Formulated peptide at various concentrations is administered by ip injection one hour after infection with S. aureus (Smith) by ip injection.
Figure 21:
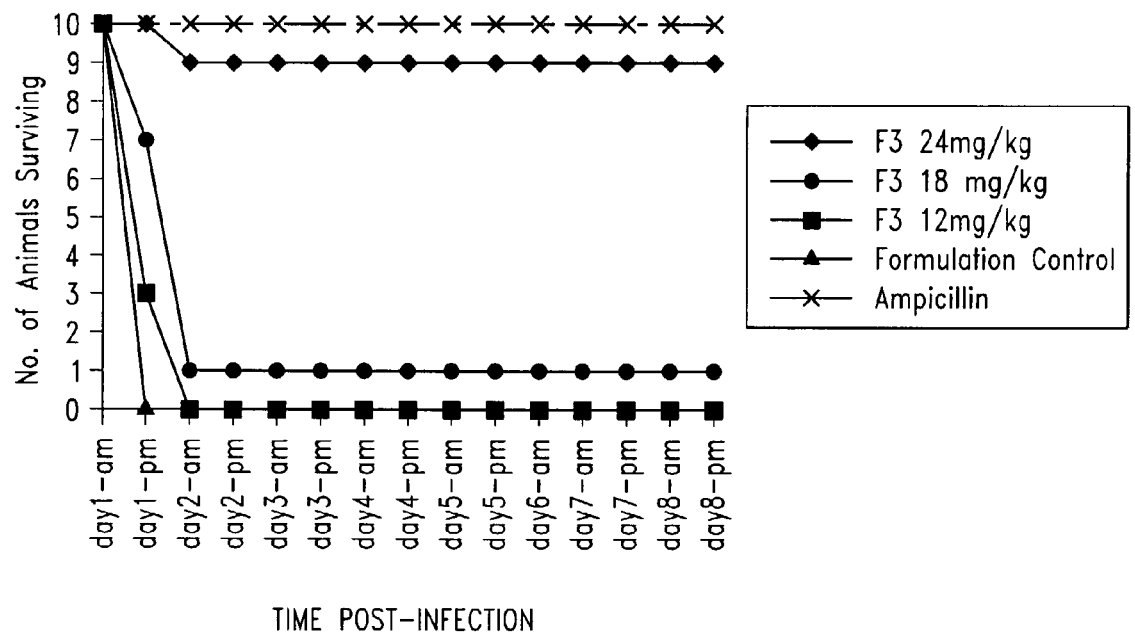
FIG. 21 is a graph showing the results of in vivo testing of: MBI-11F3CN against S. aureus (Smith). Formulated peptide at various concentrations is administered by ip injection one hour after infection with S. aureus (Smith) by ip injection.
Figure 22:
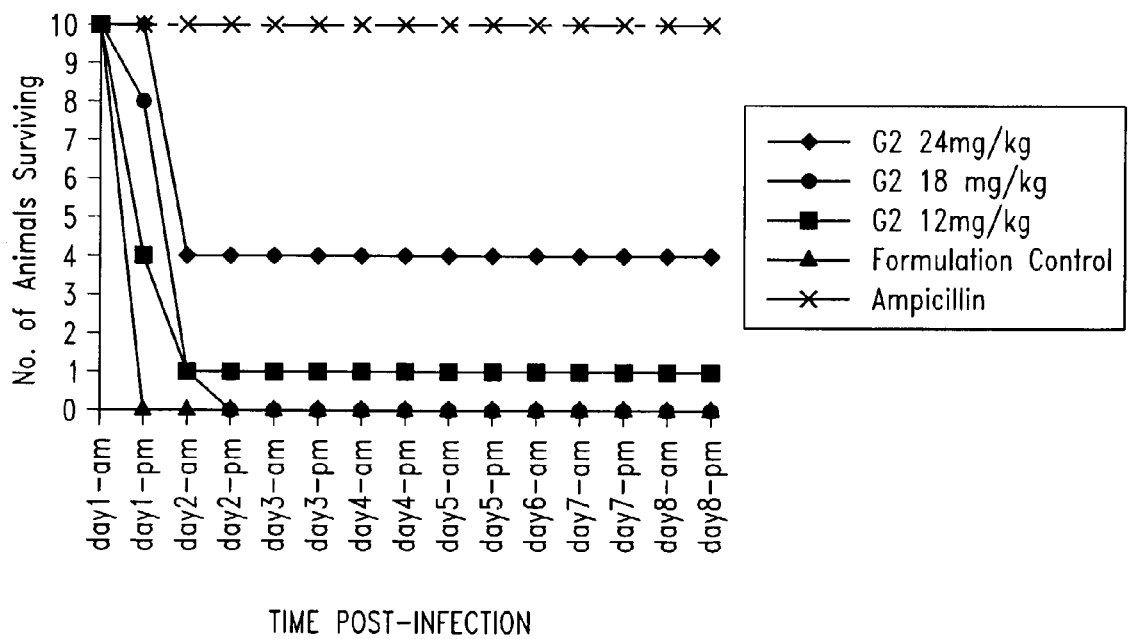
FIG. 22 is a graph showing the results of in vivo testing of MBI-11G2CN against S. aureus (Smith). Formulated peptide at various concentrations is administered by ip injection one hour after infection with S. aureus (Smith) by ip injection.
Figure 23:
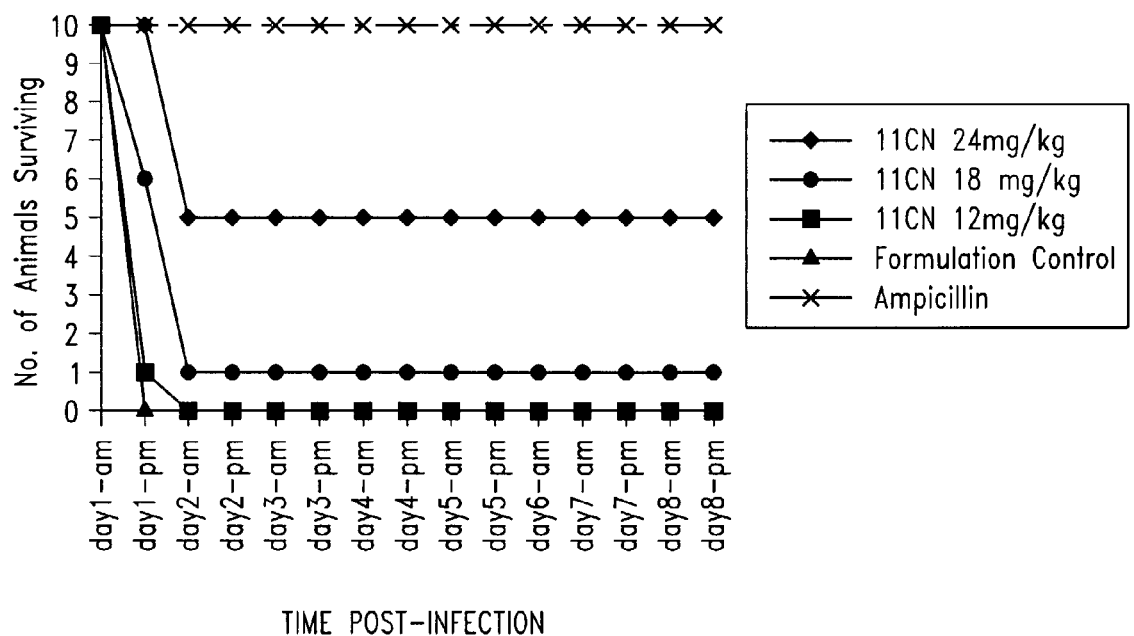
FIG. 23 is a graph showing the results of in vivo testing of MBI-11CN against S. aureus (Smith). Formulated peptide at various concentrations is administered by ip injection one hour after infection with S. aureus (Smith) by ip injection.
Figure 24:
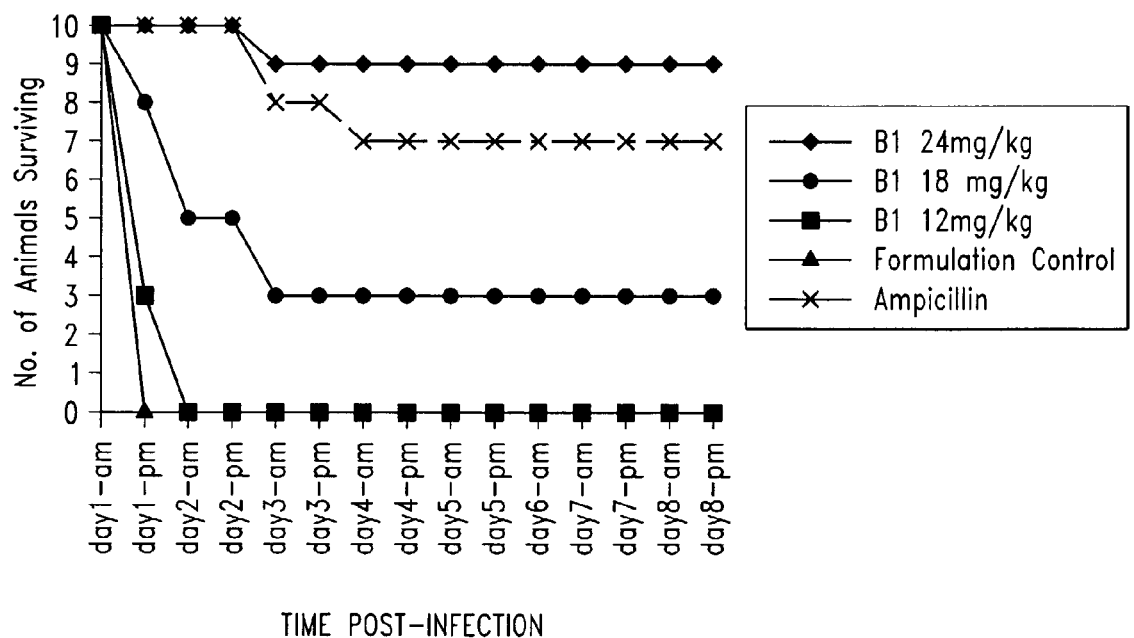
FIG. 24 is a graph showing the results of in vivo testing of MBI-11B1 CN against S. aureus (Smith). Formulated peptide at various concentrations is administered by ip injection one hour after infection with S. aureus (Smith) by ip injection.
Figure 25:
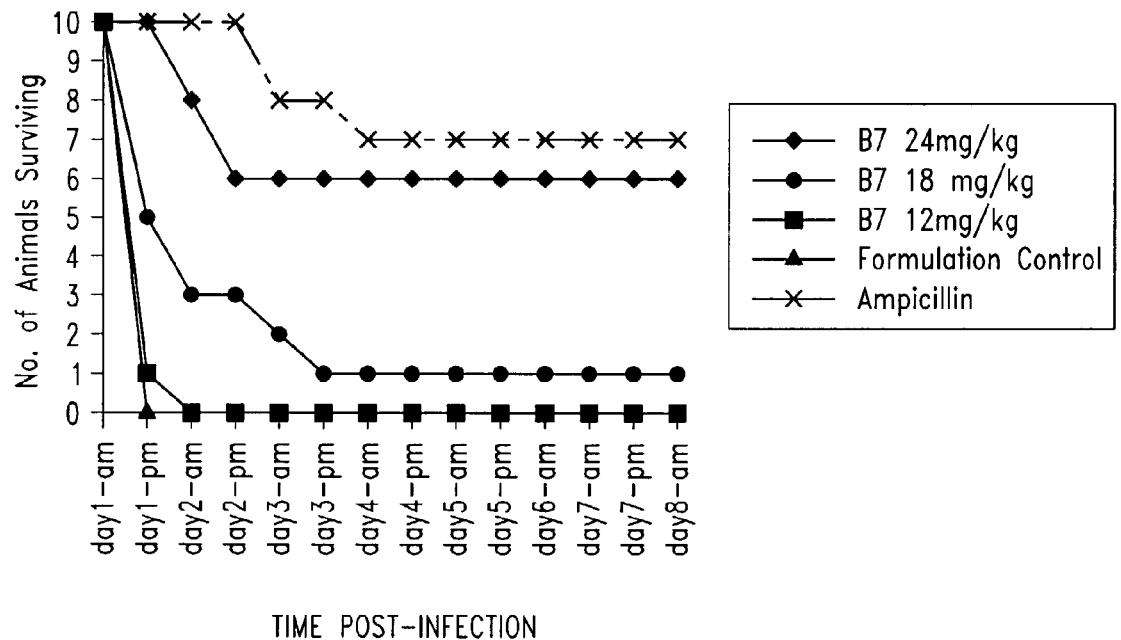
FIG. 25 is a graph showing the results of in vivo testing of MBI-11B7CN against S. aureus (Smith). Formulated peptide at various concentrations is administered by ip injection one hour after infection with S. aureus (Smith) by ip injection.
Figure 26:
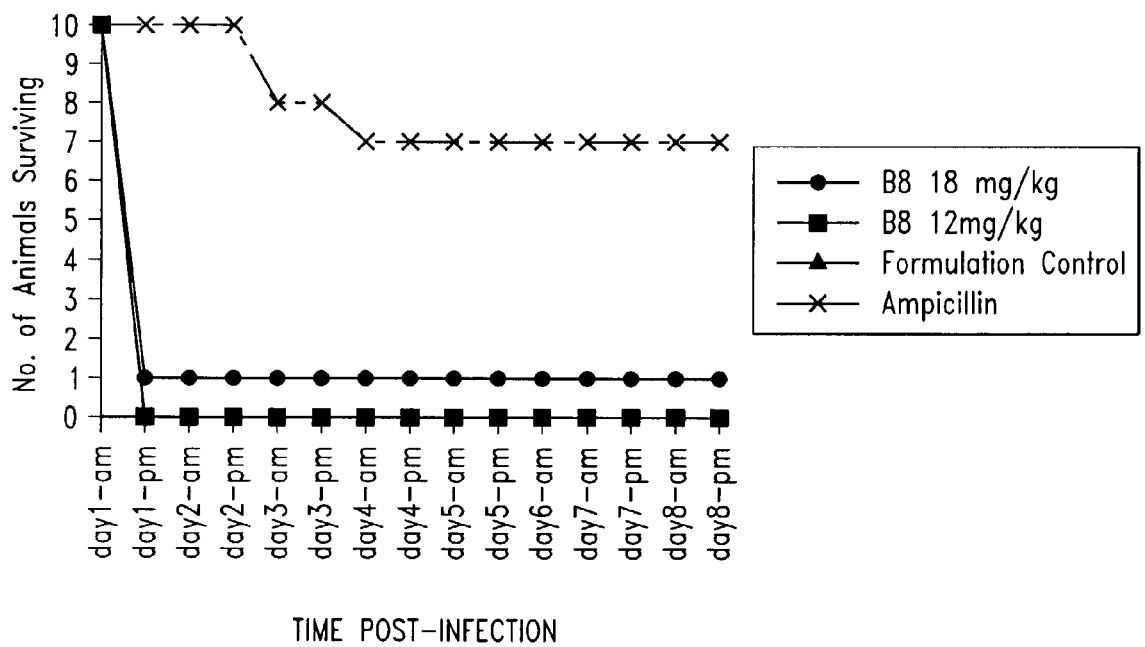
FIG. 26 is a graph showing the results of in vivo testing of MBI-11B8CN against S. aureus (Smith). Formulated peptide at various concentrations is administered by ip injection one hour after infection with S. aureus (Smith) by ip injection.
Figure 27:
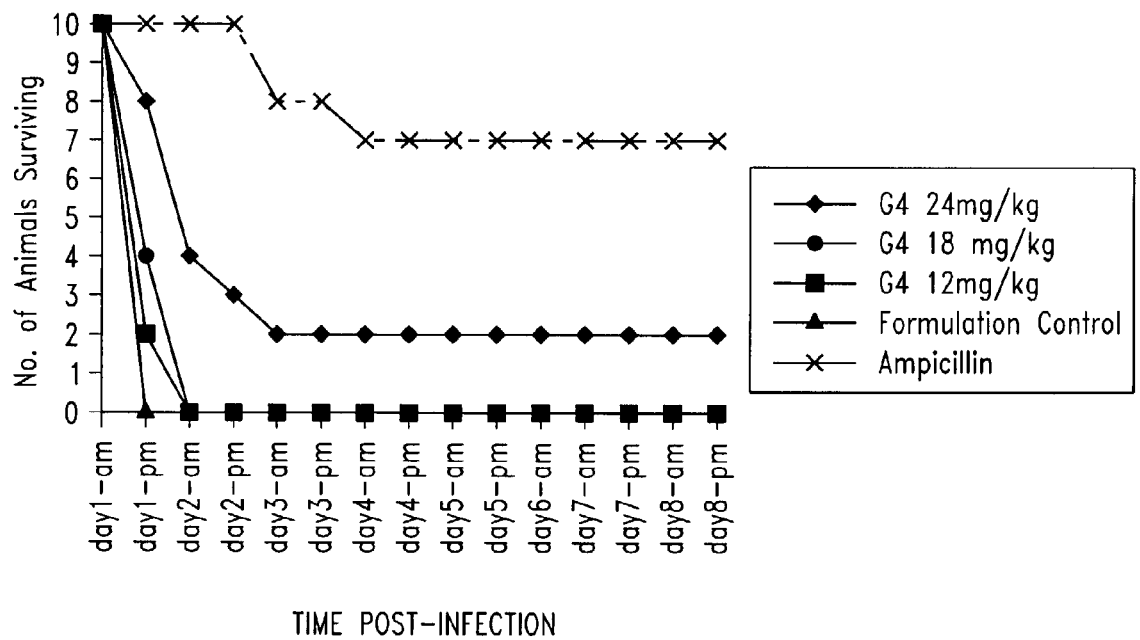
FIG. 27 is a graph showing the results of in vivo testing of MBI-11G4CN against S. aureus (Smith). Formulated peptide at various concentrations is administered by ip injection one hour after infection with S. aureus (Smith) by ip injection.

As shown in FIG. 17, MBI 10CN is maximally active against MSSA (70-80% survival) at doses of 14.5 to 38.0 mg/kg, although 100% survival is not achieved. Below 14.5 mg/kg, there is clear dose-dependent survival. At these lower dose levels, there appears to be an animal-dependent threshold, as the mice either die by day 2 or survive for the full eight day period. As seen in FIG. 18, MBI 11CN, on the other hand, rescued 100% of the mice from MSSA infection at a dose level of 35.7 mg/kg, and was therefore as effective as ampicillin. There was little or no activity at any of the lower dose levels, which indicates that a minimum bloodstream peptide level must be achieved during the time that bacteria are a danger to the host.

As shown above, blood levels of MBI 11CN can be sustained at a level of greater than 2 µg/ml for a two hour period inferring that this is higher than the minimum level.

Additionally, eight variants based on the sequence of MBI 11CN are tested against MSSA using the experimental system described above. Peptides prepared in formulation D are administered at dose levels ranging from 12 to 24 mg/kg and the survival of the infected mice is monitored for eight days (FIGS. 19-27). The percentage survival at the end of the observation period for each variant is summarized in Table 38. As shown in the table, several of the variants showed efficacy greater than or equal to MBI 11CN under these conditions.

TABLE 38

| % Survival | 24 mg/kg | 18 mg/kg | 12 mg/kg |
|---|---|---|---|
| 100 | | | |
| 90 | 11B1CN, 11F3CN | | |
| 80 | | | |
| 70 | | 11E3CN | |
| 60 | 11B7CN | | |
| 50 | 11CN | | |
| 40 | 11G2CN | | |
| 30 | | 11B1CN | |
| 20 | 11G4CN | | |
| 10 | | 11CN, 11B7CN, 11B8CN, 11F3CN | 11G2CN |
| 0 | 11A1CN | 11A1CN, 11G2CN, 11G4CN | 11CN, 11A1CN, 11B1CN, 11B7CN, 11B8CN, 11F3CN, 11G4CN |

*S. epidermidis* infection. Peptide analogues generally have lower MIC values against *S. epidermidis* in vitro, therefore, lower blood peptide levels might be more effective against infection.

In a typical protocol, groups of 10 mice are injected intraperitoneally with an $LD_{90\text{-}100}$ dose ($2.0\times10^8$ CFU/mouse) of *S. epidermidis* (ATCC #12228) in brain-heart infusion broth containing 5% mucin. This strain of *S. epidermidis* is 90% lethal after 5 days. At 15 mins and 60 mins post-infection, various doses of MBI 11CN in formulation D are injected intravenously via the tail vein. An injection of formulation only serves as the negative control and injection of gentamicin serves as the positive control; both are injected at 60 minutes post-infection. The survival of the mice is monitored at 1, 2, 3, 4, 6 and 8 hrs post-infection and twice daily thereafter for a total of 8 days.

Figure 28:
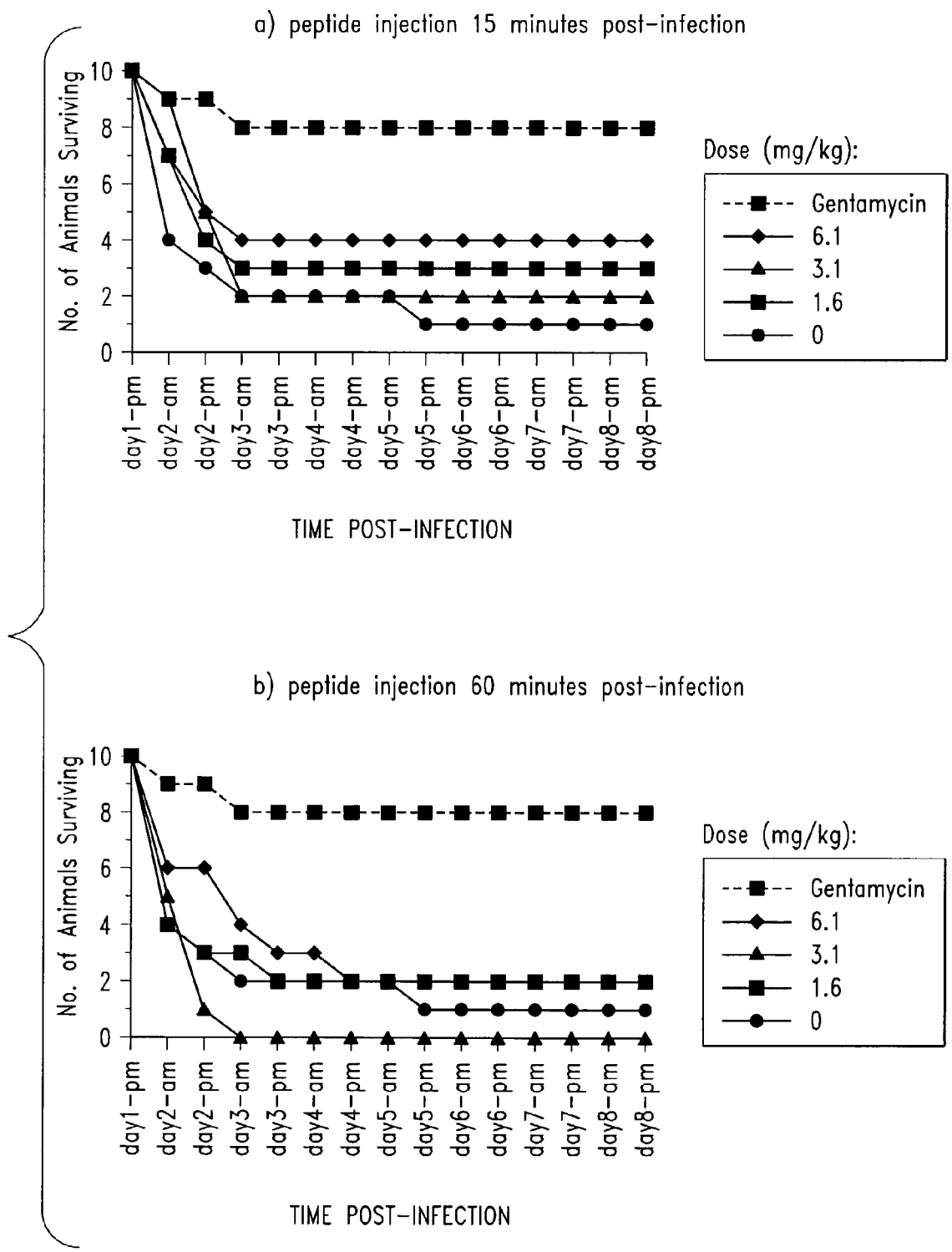
FIG. 28 displays graphs showing the number of animals surviving an S. epidermidis infection after intravenous injection of MBI 10CN, gentamicin, or vehicle. Panel a, i.v. injection 15 min post-infection; panel b, i.v. injection 60 min post-infection.

As shown in FIGS. 28A and 28B, MBI 11CN prolongs the survival of the mice. Efficacy is observed at all three dose levels with treatment 15 minutes post-infection, however, there is less activity at 30 minutes post-infection and no significant effect at 60 minutes post-infection. Time of administration appears to be important in this model system, with a single injection of 6.1 mg/kg 15 minutes post-infection giving the best survival rate.

MRSA infection. MRSA infection, while lethal in a short period of time, requires a much higher bacterial load than MSSA. In a typical protocol, groups of 10 mice are injected intraperitoneally with a $LD_{90-100}$ dose ($4.2 \times 10^7$ CFU/mouse) of MRSA (ATCC #33591) in brain-heart infusion containing 5% mucin. The treatment protocols are as follows, with the treatment times relative to the time of infection:

| | |
|---|---|
| 0 mg/kg | Formulation D alone (negative control), injected at 0 mins |
| 5 mg/kg | Three 5.5 mg/kg injections at −5, +55, and +115 mins |
| 1 mg/kg (2 hr) | Five 1.1 mg/kg injections at −5, +55, +115, +175 and +235 mins |
| 1 mg/kg (20 min) | Five 1.1 mg/kg injections at −10, −5, 0, +5, and +10 mins |
| Vancomycin | (positive control) injected at 0 mins |

Figure 29:
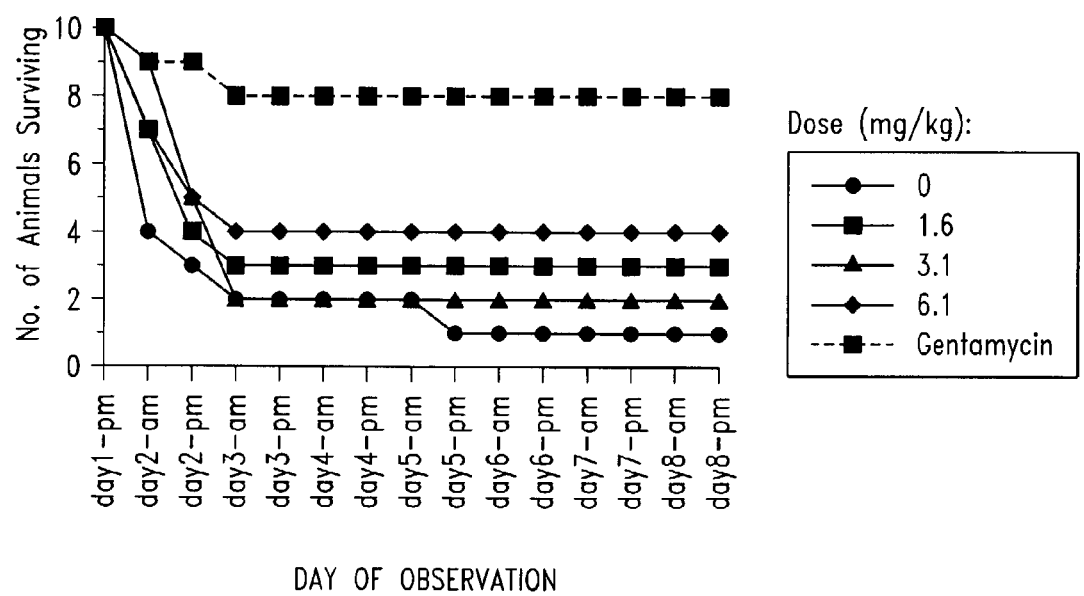
FIG. 29 is a graph showing the number of animals surviving an MRSA infection mice after intravenous injection of MBI 11CN, gentamicin, or vehicle.

MBI 11CN is injected intravenously in the tail vein in formulation D. Survival of mice is recorded at 1, 2, 3, 4, 6, 8, 10, 12, 20, 24 and 30 hrs post-infection and twice daily thereafter for a total of 8 days. There was no change in the number of surviving mice after 24 hrs (FIG. 29).

The 1 mg/kg (20 min) treatment protocol, with injections 5 minutes apart centered on the infection time, delayed the death of the mice to a significant extent with one survivor remaining at the end of the study. The results presented in Table 39 suggest that a sufficiently high level of MBI 11CN maintained over a longer time period would increase the number of mice surviving. The 5 mg/kg and 1 mg/kg (2 hr) results, where there is no improvement in survivability over the negative control, indicates that injections 1 hour apart, even at a higher level, are not effective against MRSA.

TABLE 39

| Time of Observation | Percentage of Animals Surviving | |
|---|---|---|
| (Hours post-infection) | No Treatment | Treatment |
| 6 | 50% | 70% |
| 8 | 0 | 40% |
| 10 | 0 | 30% |
| 12 | 0 | 20% |

Example 18

Activation of Polysorbate 80 by Ultraviolet Light

A solution of 2% (w/w) polysorbate 80 is prepared in water and 200 ml are placed in a 250 mL crystallizing dish or over suitable container. Containers must have a clear light path. Cover the vessel with a piece of UV transparent plastic wrap or other UV transparent material. In addition, the material should allow the exchange of air but minimize evaporation.

The solution is irradiated with ultraviolet light using a lamp emitting at 254 nm. Irradiation can also be performed using a lamp emitting at 302 nm. The solution should be stirred continuously to maximize the rate of activation. The activation is complete within 72 hours using a lamp with a output of 1800 μW/cm². The reaction is monitored by a reversed-phased HPLC assay, which measures the formation of APO-MBI 11CN-Tw80 when the light-activated polysorbate is reacted with MBI 11CN.

Figure 30A:
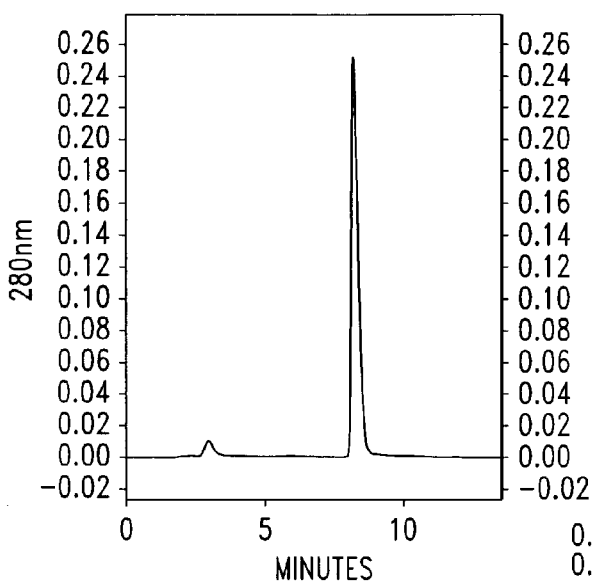
FIGS. 30A-30C present RP-HPLC traces analyzing samples for APS-peptide formation after treatment of activated polysorbate with a reducing agent. APS-MBI-11CN peptides are formed via lyophilization in 200 mM acetic acid-NaOH, pH 4.6, 1 mg/ml MBI 11CN, and 0.5% activated polysorbate 80. The stock solution of activated 2.0% polysorbate is treated with (a) no reducing agent, (b) 150 mM 2-mercaptoethanol, or (c) 150 mM sodium borohydride for 1 hour immediately before use.
Figure 30B:
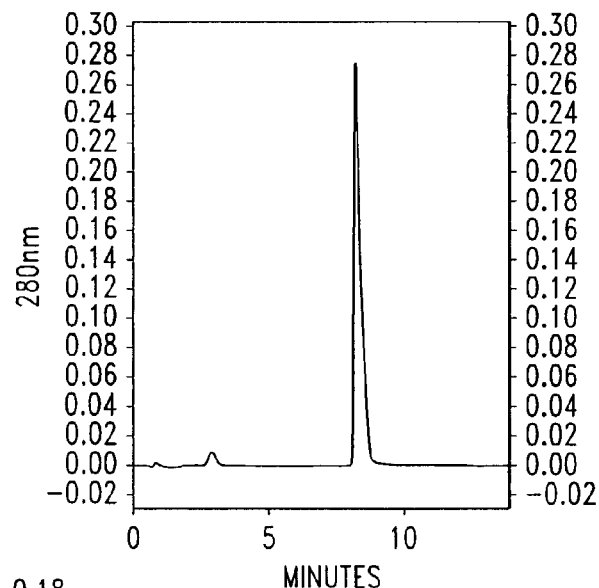
Figure 30C:
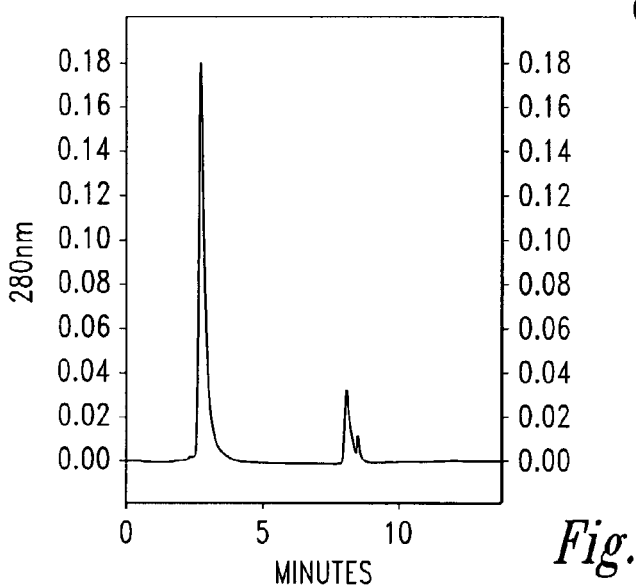

Some properties of activated polysorbate are determined. Because peroxides are a known by-product of exposing ethers to UV light, peroxide formation is examined through the effect of reducing agents on the activated polysorbate. As seen in FIG. 30A, activated polysorbate readily reacts with MBI 11CN. Pre-treatment with 2-mercaptoethanol (FIG. 30B), a mild reducing agent, eliminates detectable peroxides, but does not cause a loss of conjugate forming ability. Treatment with sodium borohydride (FIG. 30C), eliminates peroxides and eventually eliminates the ability of activated polysorbate to modify peptides. Hydrolysis of the borohydride in water raises the pH and produces borate as a hydrolysis product. However, neither a pH change nor borate are responsible.

These data indicate that peroxides are not involved in the modification of peptides by activated polysorbate. Sodium borohydride should not affect epoxides or esters in aqueous media, suggesting that the reactive group is an aldehyde or ketone. The presence of aldehydes in the activated polysorbate is confirmed by using a formaldehyde test, which is specific for aldehydes including aldehydes other than formaldehyde.

Furthermore, activated polysorbate is treated with 2,4-dinitrophenylhydrazine (DNPH) in an attempt to capture the reactive species. Three DNPH-tagged components are purified and analyzed by mass spectroscopy. These components are polysorbate-derived with molecular weights between 1000 and 1400. This indicates that low molecular weight aldehydes, such as formaldehyde or acetaldehyde, are involved.

Example 19

Activation of Polysorbate 80 by Ammonium Persulfate

A 200 mL solution of 2% (w/w) polysorbate 80 is prepared in water. To this solution, 200 mg of ammonium persulfate is added while stirring. The reaction is stirred for 1-2 hours with protection from ambient light. If a solution of less than 0.1% (w/w) ammonium persulfate is used, then exposure to ultraviolet light at 254 nm during this period is used to help complete the reaction. The peroxide level in the reaction is determined using a test kit. Peroxides are reduced by titration with 2-mercaptoethanol.

Example 20

Formation of APO-Modified Peptides

APO-modified peptides are prepared either in solid phase or liquid phase. For solid phase preparation, 0.25 ml of 4 mg/ml of MBI 11CN is added to 0.5 ml of 0.4 M Acetic acid-NaOH pH 4.6 followed by addition of 0.25 ml of UV-activated polysorbate. The reaction mix is frozen by placing it in a −80° C. freezer. After freezing, the reaction mix is lyophilized overnight.

Figure 31:
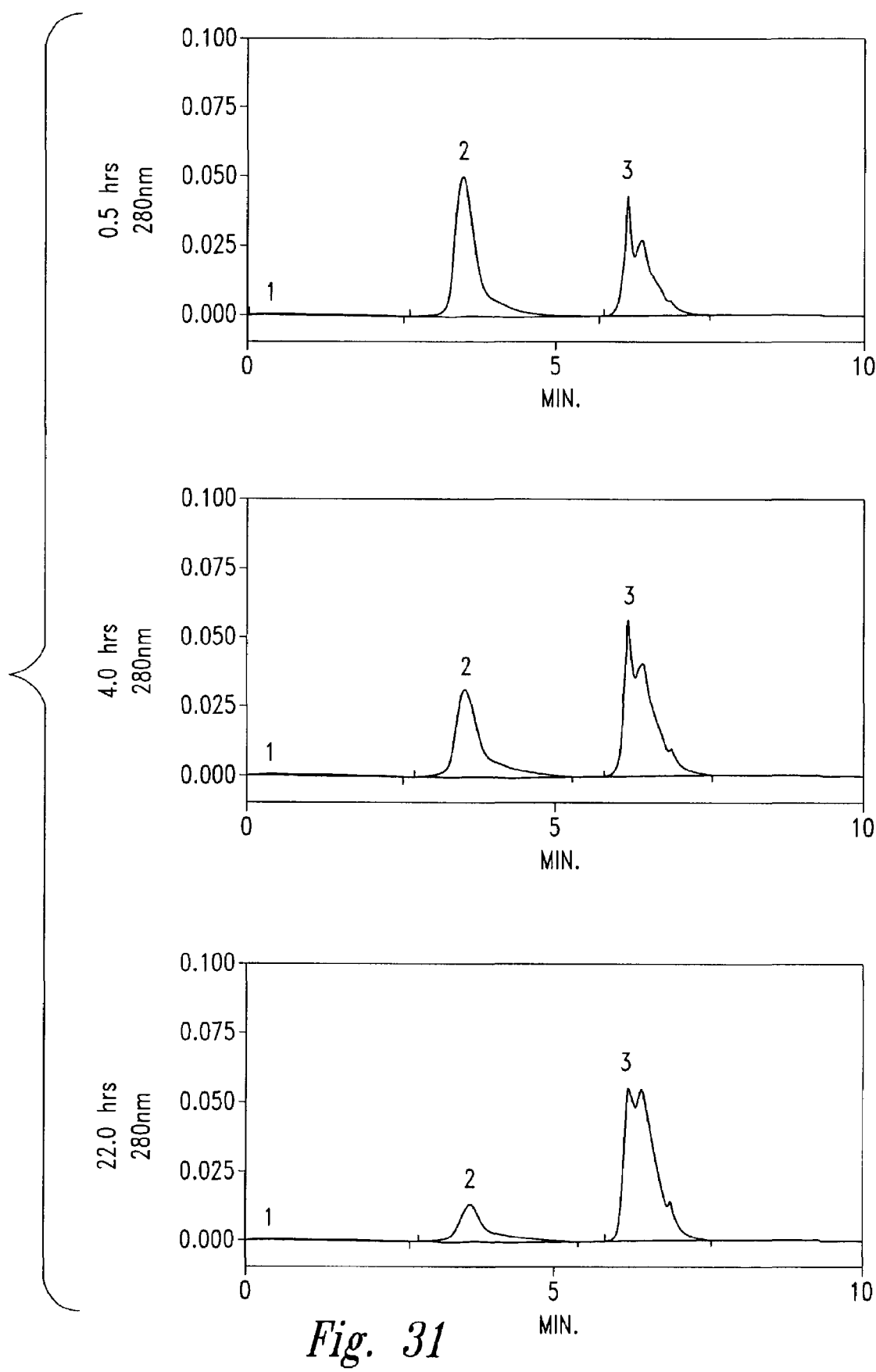
FIG. 31 presents RP-HPLC traces monitoring the formation of APS-MBI 11CN over time in aqueous solution. The reaction occurs in 200 mM sodium carbonate buffer pH 10.0, 1 mg/ml MBI 11CN, 0.5% activated polysorbate 80. Aliquots are removed from the reaction vessel at the indicated time points and immediately analyzed by RP-HPLC.

For preparing the conjugates in an aqueous phase, a sample of UV activated polysorbate 80 is first adjusted to a pH of 7.5 by the addition of 0.1M NaOH. This pH adjusted solution (0.5 ml) is added to 1.0 ml of 100 mM sodium carbonate, pH 10.0, followed immediately by the addition of 0.5 ml of 4 mg/ml of MBI 11CN. The reaction mixture is incubated at ambient temperature for 22 hours. The progress of the reaction is monitored by analysis at various time points using RP-HPLC (FIG. 31). In FIG. 31, peak 2 is unreacted peptide, peak 3 is APO-modified peptide. Type 1 is the left-most of peak 3 and Type 2 is the right-most of peak 3.

The table below summarizes data from several experiments. Unless otherwise noted in the table, the APO-modified peptides are prepared via the lyophilization method in 200 mM acetic acid-NaOH buffer, pH 4.6.

TABLE 40

| SEQUENCE | NAME | COMPLEX TYPE 1 | TYPE 2 |
|---|---|---|---|
| ILKKWPWWPWRRKamide | 11CN | Yes | Low |
| Solid phase, pH 2.0 | (SEQ ID NO: 99) | Yes | Yes |
| Solid phase, pH 4.6 | | Yes | Yes |
| Solid phase, pH 5.0 | | Yes | Yes |
| Solid phase, pH 6.0 | | Yes | Yes |
| Solid phase, pH 8.3 | | Trace | Trace |
| Solution, pH 2.0 | | Yes | Yes-Slow |
| Solution, pH 10.0 | | | |
| (Ac)$_4$-ILKKWPWWPWRRKamide | 11CN-Y1 (SEQ ID NO: 99) | No | No |
| ILRRWPWWPWRRKamide | 11B1CN (SEQ ID NO: 41) | Yes | Lowered |
| ILRWPWWPWRRKamide | 11B7CN (SEQ ID NO: 101) | Yes | Lowered |
| ILWPWWPWRRKamide | 11B8CN (SEQ ID NO: 66) | Yes | Lowered |
| ILRRWPWWPWRRRamide | 11B9CN (SEQ ID NO: 102) | Yes | Trace |
| ILKKWPWWPWKKKamide | 11B10CN (SEQ IDNO: 103) | Yes | Yes |
| iLKKWPWWPWRRKamide | 11E3CN (SEQ ID NO: 99) | Yes | Yes |
| ILKKWVWWPWRRKamide | 11F3CN (SEQ ID NO: 59) | Yes | Yes |
| ILKKWPWWPWKamide | 11G13CN (SEQ ID NO: 113) | Yes | Yes |
| ILKKWPWWPWRamide | 11G14CN (SEQ ID NO: 114) | Yes | Trace |

The modification of amino groups is further analyzed by determining the number of primary amino groups lost during attachment. The unmodified and modified peptides are treated with 2,4,6-trinitrobenzenesulfonic acid (TNBS) (R. L. Lundblad in *Techniques in Protein Modification and Analysis* pp. 151-154,1995).

Briefly, a stock solution of MBI 11CN at 4 mg/ml and an equimolar solution of APO-modified MBI 11CN are prepared. A 0.225 ml aliquot of MBI 11CN or APO-modified MBI 11CN is mixed with 0.225 ml of 200 mM sodium phosphate buffer, pH 8.8. A 0.450 ml aliquot of 1% TNBS is added to each sample, and the reaction is incubated at 37° C. for 30 minutes. The absorbance at 367 nm is measured, and the number of modified primary amino groups per molecule is calculated using an extinction coefficient of 10,500 $M^{-1}$ $cm^{-1}$ for the trinitrophenyl (TNP) derivatives.

The primary amino group content of the parent peptide is then compared to the corresponding APO-modified peptide. As shown below, the loss of a single primary amino group occurs during formation of modified peptide. Peptides possessing a 3,4 lysine pair consistently give results that are 1 residue lower than expected, which may reflect steric hindrance after titration of one member of the doublet.

TABLE 41

| PEPTIDE SEQUENCE | TNP/ PEPTIDE | TNP/APO-modified peptide | CHANGE |
|---|---|---|---|
| ILKKWPWWPWRRKamide (SEQ ID NO: 99) | 2.71 | 1.64 | 1.07 |
| ILRRWPWWPWRRKamide (SEQ ID NO: 41) | 1.82 | 0.72 | 1.10 |
| IIKKWPWWPWRRkamide (SEQ ID NO: 99) | 2.69 | 1.61 | 1.08 |
| ILKKWVWWPWRRKamide (SEQ ID NO: 59) | 2.62 | 1.56 | 1.06 |

Stability of APO-Modified Peptide Analogues

APO-modified peptides demonstrate a high degree of stability under conditions that promote the dissociation of ionic or hydrophobic complexes. APO-modified peptide in formulation D is prepared as 800 μg/ml solutions in water, 0.9% saline, 8M urea, 8M guanidine-HCl, 67% 1-propanol, 1M HCl and 1M NaOH and incubated for 1 hour at room temperature. Samples are analyzed for the presence of free peptide using reversed phase HPLC and the following chromatographic conditions:

Solvent A: 0.1% trifluoroacetic acid (TFA) in water
Solvent B: 0.1% TFA/95% acetonitrile in water
Media: POROS R2-20 (polystyrene divinylbenzene)
Elution: 0% B for 5 column volumes
    0-25% B in 3 column volumes
    25% B for 10 column volumes
    25-95% B in 3 column volumes
    95% B for 10 column volumes Under these conditions, free peptide elutes exclusively during the 25% B step and formulation-peptide complex during the 95% B step. None of the dissociating conditions mentioned above, with the exception of 1M NaOH in which some degradation is observed, are successful in liberating free peptide from APO-modified peptide. Additional studies are carried out with incubation at 55° C. or 85° C. for one hour. APO-modified peptide is equally stable at 55° C. and is only slightly less stable at 85° C. Some acid hydrolysis, indicated by the presence of novel peaks in the HPLC chromatogram, is observed with the 1M HCl sample incubated at 85° C. for one hour.

Example 21

Purification of APO-Modified MBI 11CN

A large scale preparation of APO-modified MBI 11CN is purified. Approximately 400 mg of MBI 11CN is APO-modified and dissolved in 20 ml of water. Unreacted MBI 11CN is removed by RP-HPLC. The solvent is then evaporated from the APO-modified MBI 11CN pool, and the residue is dissolved in 10 ml methylene chloride. The modified peptide is then precipitated with 10 ml diethyl ether. After 5 min at ambient temperature, the precipitate is collected by centrifugation at 5000xg for 10 minutes. The pellet is washed with 5 ml of diethyl ether and again collected by centrifugation at 5000xg for 10 minutes. The supernatants are pooled for analysis of unreacted polysorbate by-products. The precipitate is dissolved in 6 ml of water and then flushed with nitrogen by bubbling for 30 minutes to remove residual ether. The total yield from the starting MBI 11CN was 43%.

The crude APO-MBI29-Tw80 prepared from 200 mg of MBI 29 is suspended in 40 mL of methylene chloride and sonicated for 5 minutes to disperse large particles. The suspension is centrifuged in appropriate containers (Corning glass) at 3000-4000xg for 15 minutes at 10° C. to sediment insoluble material. The supernatant is decanted and saved.

The sediment is extracted twice more by adding 40 mL portions methylene chloride to the sediment and repeating the sonication/centrifugation step. The supernatants from the three extractions are pooled and concentrated 8-10 fold using a rotary evaporator. The solution is transferred to centrifuge tubes and 3 volumes of diethyl ether are added. The mixture is incubated for 15 minutes, then centrifuged at 3000-4000xg for 15 minutes at 10° C. to sediment the product. The supernatant is decanted and discarded. The residual ether may be removed with a stream of nitrogen.

Example 22

Biological Assays to Measure APO-Cationic Peptide Activity

All biological assays that compare APO-modified peptides with unmodified peptides are performed on an equimolar ratio. The concentration of APO-modified peptides can be determined by spectrophotometric measurement, which is used to normalize concentrations for biological assays. For example, a 1 mg/ml APO-modified MBI 11CN solution contains the same amount of peptide as a 1 mg/ml MBI 11CN solution, thus allowing direct comparison of toxicity and efficacy data.

APO-modified peptides are at least as potent as the parent peptides in vitro assays performed as described herein. MIC values against gram positive bacteria are presented for several APO-modified peptides and compared with the values obtained using the parent peptides (Table 5). The results indicate that the modified peptides are at least as potent in vitro as the parent peptides and may be more potent than the parent peptides against *E. faecalis* strains.

The agarose dilution assay measures antimicrobial activity of peptides and peptide analogues, which is expressed as the minimum inhibitory concentration (MIC) of the peptides. This assay is performed as described above. Representative MICs for various modified and unmodified cationic peptides are shown in the Table below.

TABLE 42

| | | | MIC (µg/mL) | |
| --- | --- | --- | --- | --- |
| Organism | Organism # | APO-Peptide | APO-Peptide | Peptide |
| *A. calcoaceticus* | AC002 | MBI11CN-Tw80 | 4 | 4 |
| *A. calcoaceticus* | AC002 | MBI11B1CN-Tw80 | 4 | 2 |
| *A. calcoaceticus* | AC002 | MBI11B7CN-Tw80 | 4 | 2 |
| *A. calcoaceticus* | AC002 | MBI11B7CN-Tx114r | 2 | 2 |
| *A. calcoaceticus* | AC002 | MBI11B7CN-F12-Tx114r | 1 | 1 |
| *A. calcoaceticus* | AC002 | MBI11E3CN-Tw80 | 2 | 1 |
| *A. calcoaceticus* | AC002 | MBI11F3CN-Tw80 | 8 | 2 |
| *A. calcoaceticus* | AC002 | MBI11F4CN-Tw80 | 4 | 4 |
| *A. calcoaceticus* | AC002 | MBI29-Tw80 | 4 | 1 |
| *E. cloacae* | ECL007 | MBI11CN-Tw80 | >128 | >128 |
| *E. cloacae* | ECL007 | MBI11B1CN-Tw80 | 128 | >128 |
| *E. cloacae* | ECL007 | MBI11B7CN-Tw80 | >128 | 128 |
| *E. cloacae* | ECL007 | MBI11B7CN-Tx114r | 128 | 128 |
| *E. cloacae* | ECL007 | MBI11B7CN-F12-Tx114r | >128 | >128 |
| *E. cloacae* | ECL007 | MBI11E3CN-Tw80 | 128 | >128 |
| *E. cloacae* | ECL007 | MBI11F3CN-Tw80 | 128 | >128 |
| *E. cloacae* | ECL007 | MBI11F4CN-Tw80 | 64 | 32 |
| *E. cloacae* | ECL007 | MBI29-Tw80 | 32 | >64 |
| *E. coli* | ECO005 | MBI11CN-Tw80 | 16 | 8 |
| *E. coli* | ECO005 | MBI11B1CN-Tw80 | 8 | 8 |
| *E. coli* | ECO005 | MBI11B7CN-Tw80 | 16 | 4 |
| *E. coli* | ECO005 | MBI11B7CN-Tx114r | 16 | 4 |
| *E. coli* | ECO005 | MBI11B7CN-F12-Tx114r | 32 | 16 |
| *E. coli* | ECO005 | MBI11E3CN-Tw80 | 8 | 4 |
| *E. coli* | ECO005 | MBI11F3CN-Tw80 | 128 | 16 |
| *E. coli* | ECO005 | MBI11F4CN-Tw80 | 8 | 8 |
| *E. coli* | ECO005 | MBI29-Tw80 | 16 | 4 |
| *E. faecalis* | EFS001 | MBI11CN-Tw80 | 8 | 32 |
| *E. faecalis* | EFS001 | MBI11B1CN-Tw80 | 4 | 32 |
| *E. faecalis* | EFS001 | MBI11B7CN-Tw80 | 8 | 8 |
| *E. faecalis* | EFS001 | MBI11B7CN-Tx114r | 0.5 | 0.5 |
| *E. faecalis* | EFS001 | MBI11B7CN-F12-Tx114r | 0.5 | 0.5 |
| *E. faecalis* | EFS001 | MBI11E3CN-Tw80 | 4 | 8 |
| *E. faecalis* | EFS001 | MBI11F3CN-Tw80 | 8 | 32 |
| *E. faecalis* | EFS001 | MBI29-Tw80 | 0.5 | 0.5 |
| *E. faecalis* | EFS004 | MBI11CN-Tw80 | 4 | 8 |
| *E. faecalis* | EFS004 | MBI11B1CN-Tw80 | 4 | 8 |
| *E. faecalis* | EFS004 | MBI11B7CN-Tw80 | 8 | 8 |
| *E. faecalis* | EFS004 | MBI11E3CN-Tw80 | 4 | 2 |
| *E. faecalis* | EFS004 | MBI11F3CN-Tw80 | 4 | 16 |
| *E. faecalis* | EFS008 | MBI11CN-Tw80 | 1 | 16 |
| *E. faecalis* | EFS008 | MBI11B1CN-Tw80 | 1 | 2 |
| *E. faecalis* | EFS008 | MBI11B7CN-Tw80 | 1 | 2 |
| *E. faecalis* | EFS008 | MBI11B7CN-Tx114r | 2 | 4 |

TABLE 42-continued

|  |  |  | MIC (µg/mL) | |
| --- | --- | --- | --- | --- |
| Organism | Organism # | APO-Peptide | APO-Peptide | Peptide |
| E. faecalis | EFS008 | MBI11B7CN-F12-Tx114r | 2 | 2 |
| E. faecalis | EFS008 | MBI11E3CN-Tw80 | 1 | 2 |
| E. faecalis | EFS008 | MBI11F3CN-Tw80 | 4 | 16 |
| E. faecalis | EFS008 | MBI11F4CN-Tw80 | 2 | 2 |
| E. faecalis | EFS008 | MBI29-Tw80 | 2 | 0.5 |
| K. pneumoniae | KP001 | MBI11CN-Tw80 | 8 | 16 |
| K. pneumoniae | KP001 | MBI11B1CN-Tw80 | 8 | 8 |
| K. pneumoniae | KP001 | MBI11B7CN-Tw80 | 8 | 4 |
| K. pneumoniae | KP001 | MBI11B7CN-Tx114r | 8 | 8 |
| K. pneumoniae | KP001 | MBI11B7CN-F12-Tx114r | 32 | 16 |
| K. pneumoniae | KP001 | MBI11E3CN-Tw80 | 4 | 8 |
| K. pneumoniae | KP001 | MBI11F3CN-Tw80 | 128 | 64 |
| K. pneumoniae | KP001 | MBI11F4CN-Tw80 | 8 | 4 |
| K. pneumoniae | KP001 | MBI29-Tw80 | 16 | 2 |
| P. aeruginosa | PA004 | MBI11CN-Tw80 | >128 | 128 |
| P. aeruginosa | PA004 | MBI11B1CN-Tw80 | 128 | 64 |
| P. aeruginosa | PA004 | MBI11B7CN-Tw80 | 128 | 128 |
| P. aeruginosa | PA004 | MBI11B7CN-Tx114r | 128 | 128 |
| P. aeruginosa | PA004 | MBI11B7CN-F12-Tx114r | >128 | >128 |
| P. aeruginosa | PA004 | MBI11E3CN-Tw80 | 64 | 32 |
| P. aeruginosa | PA004 | MBI11F3CN-Tw80 | 128 | 128 |
| P. aeruginosa | PA004 | MBI11F4CN-Tw80 | 128 | 32 |
| P. aeruginosa | PA004 | MBI29-Tw80 | >64 | 16 |
| S. aureus | SA010 | MBI11B1CN | 4 | 1 |
| S. aureus | SA010 | MBI11B7CN | 4 | 1 |
| S. aureus | SA010 | MBI11CN | 4 | 2 |
| S. aureus | SA010 | MBI11E3CN | 2 | 1 |
| S. aureus | SA010 | MBI11F3CN | 4 | 2 |
| S. aureus | SA011 | MBI11CN-Tw80 | 16 | 8 |
| S. aureus | SA011 | MBI11B1CN-Tw80 | 16 | 4 |
| S. aureus | SA011 | MBI11B7CN-Tw80 | 16 | 4 |
| S. aureus | SA011 | MBI11E3CN-Tw80 | 16 | 4 |
| S. aureus | SA011 | MBI11F3CN-Tw80 | 16 | 8 |
| S. aureus | SA014 | MBI11CN-Tw80 | 2 | 1 |
| S. aureus | SA014 | MBI11B1CN-Tw80 | 2 | 1 |
| S. aureus | SA014 | MBI11B7CN-Tw80 | 1 | 2 |
| S. aureus | SA014 | MBI11B7CN-Tx114r | 2 | 1 |
| S. aureus | SA014 | MBI11B7CN-F12-Tx114r | 2 | 2 |
| S. aureus | SA014 | MBI11E3CN-Tw80 | 1 | 1 |
| S. aureus | SA014 | MBI11F3CN-Tw80 | 8 | 8 |
| S. aureus | SA014 | MBI11F4CN-Tw80 | 2 | 2 |
| S. aureus | SA014 | MBI29-Tw80 | 2 | 1 |
| S. aureus | SA018 | MBI11CN-Tw80 | 64 | 64 |
| S. aureus | SA018 | MBI11B1CN-Tw80 | 32 | 16 |
| S. aureus | SA018 | MBI11B7CN-Tw80 | 32 | 16 |
| S. aureus | SA018 | MBI11E3CN-Tw80 | 32 | 16 |
| S. aureus | SA018 | MBI11F3CN-Tw80 | 64 | 16 |
| S. aureus | SA025 | MBI11CN-Tw80 | 2 | 4 |
| S. aureus | SA025 | MBI11B1CN-Tw80 | 4 | 1 |
| S. aureus | SA025 | MBI11B7CN-Tw80 | 2 | 1 |
| S. aureus | SA025 | MBI11E3CN-Tw80 | 2 | 1 |
| S. aureus | SA025 | MBI11F3CN-Tw80 | 4 | 2 |
| S. aureus | SA093 | MBI11CN-Tw80 | 2 | 2 |
| S. aureus | SA093 | MBI11B1CN-Tw80 | 2 | 1 |
| S. aureus | SA093 | MBI11B7CN-Tw80 | 2 | 1 |
| S. aureus | SA093 | MBI11B7CN-Tx114r | 1 | 1 |
| S. aureus | SA093 | MBI11B7CN-F12-Tx114r | 1 | 1 |
| S. aureus | SA093 | MBI11E3CN-Tw80 | 2 | 1 |
| S. aureus | SA093 | MBI11F3CN-Tw80 | 2 | 1 |
| S. aureus | SA093 | MBI29-Tw80 | 1 | 0.5 |
| S. epidermidis | SE010 | MBI11B7CN-Tx114r | 4 | 2 |
| S. epidermidis | SE010 | MBI11B7CN-F12-Tx114r | 4 | 8 |
| S. epidermidis | SE010 | MBI29-Tw80 | >64 | 4 |
| S. maltophilia | SMA002 | MBI11CN-Tw80 | 32 | >128 |
| S. maltophilia | SMA002 | MBI11B1CN-Tw80 | 32 | 32 |
| S. maltophilia | SMA002 | MBI11B7CN-Tw80 | 64 | 16 |
| S. maltophilia | SMA002 | MBI11B7CN-Tx114r | 32 | 16 |

TABLE 42-continued

|  |  |  | MIC (µg/mL) | |
| --- | --- | --- | --- | --- |
| Organism | Organism # | APO-Peptide | APO-Peptide | Peptide |
| S. maltophilia | SMA002 | MBI11B7CN-F12-Tx114r | 64 | 64 |
| S. maltophilia | SMA002 | MBI11E3CN-Tw80 | 128 | 64 |
| S. maltophilia | SMA002 | MBI11F3CN-Tw80 | 128 | 64 |
| S. maltophilia | SMA002 | MBI11F4CN-Tw80 | 32 | 16 |
| S. maltophilia | SMA002 | MBI29-Tw80 | 8 | 2 |
| S. marcescens | SMS003 | MBI11CN-Tw80 | >128 | >128 |
| S. marcescens | SMS003 | MBI11B1CN-Tw80 | >128 | >128 |
| S. marcescens | SMS003 | MBI11B7CN-Tw80 | >128 | >128 |
| S. marcescens | SMS003 | MBI11B7CN-Tx114r | >128 | >128 |
| S. marcescens | SMS003 | MBI11B7CN-F12-Tx114r | >128 | >128 |
| S. marcescens | SMS003 | MBI11E3CN-Tw80 | 128 | >128 |
| S. marcescens | SMS003 | MBI11F3CN-Tw80 | 128 | >128 |
| S. marcescens | SMS003 | MBI11F4CN-Tw80 | >128 | >128 |
| S. marcescens | SMS003 | MBI29-Tw80 | >64 | >128 |

Toxicities of APO-modified MBI 11CN and unmodified MBI 11CN are examined in Swiss CD-1 mice. Groups of 6 mice are injected iv with single doses of 0.1 ml peptide in 0.9% saline. The dose levels used are 0, 3, 5, 8, 10, and 13 mg/kg. Mice are monitored at 1, 3, and 6 hrs post-injection for the first day, then twice daily for 4 days. The survival data for MBI 11CN mice are presented in Table 43. For APO-modified MBI 11CN, 100% of the mice survived at all doses, including the maximal dose of 13 mg/kg.

TABLE 43

| Peptide administered (mg/kg) | No. Dead/ Total | Cumulative Dead | No. Surviving | Cumulative No. Dead/Total | % Dead |
| --- | --- | --- | --- | --- | --- |
| 13 | 6/6 | 18 | 0 | 18/18 | 100 |
| 10 | 6/6 | 12 | 0 | 12/12 | 100 |
| 8 | 6/6 | 6 | 0 | 6/6 | 100 |
| 5 | 0/6 | 0 | 6 | 0/6 | 0 |
| 3 | 0/6 | 0 | 12 | 0/12 | 0 |
| 0 | 0/6 | 0 | 18 | 0/18 | 0 |

As summarized below, the $LD_{50}$ for MBI 11CN is 7 mg/kg (Table 7), with all subjects dying at a dose of 8 mg/ml. The highest dose of MBI 11CN giving 100% survival was 5 mg/kg. The data show that APO-modified peptides are significantly less toxic than the parent peptides.

TABLE 44

| Test Peptide | $LD_{50}$ | $LD_{90-100}$ | MTD |
| --- | --- | --- | --- |
| MBI 11CN | 7 mg/kg | 8 mg/kg | 5 mg/kg |
| APO-MBI-11CN | >13 mg/kg* | >13 mg/kg* | >13 mg/kg* |

*could not be calculated with available data

In addition, APO-peptides and parent peptides are tested against a panel of cancer cell lines. Cell death is measured using the Cytotox (Promega) assay kit which measures the release of lactate dehydrogenase. As shown below the modified peptides had increased activity over the parent peptides.

TABLE 45

| | CELL LINE, $LC_{50}$, µg/mL ± S.E. | | | | | | | |
| --- | --- | --- | --- | --- | --- | --- | --- | --- |
| Peptide | PBL | HUVEC | H460 | K562 | DoHH-2 | P388 | P388AD R | MCF-7 | MCF-7ADR |
| 11CN | 57 | >190 | 200 | — | — | 30 | 25 | 11.8 ± 9 | 17 ± 1 |
| 11CN-Tw80 | 6 ± 6 | 16 ± 4 | 16 ± 4 | — | — | 1.9 ± 5 | 3.5 ± 2 | 11 | — |
| 11A3CN | >500 | >500 | >500 | >500 | >500 | >300 | >300 | — | — |
| 11A3CN-Tw80 | 12.7 ± 15 | 17 ± 9 | 15 ± 4 | 6 | 3.3 ± 0.05 | 5.6 ± 2 | 6.6 ± 3 | 28 | 13 |
| 11B7CN | 24 ± 10 | 90 ± 23 | 26 ± 25 | 34 ± 25 | 16.5 ± 3 | 13.8 | — | >700 | — |
| 11B7CN-Tw80 | 3.8 ± 1 | 12.8 ± 8 | >100 | 4.7 ± 3 | 3.3 ± 1 | 5.1 | — | 12 | — |
| 11E3CN | 22 ± 11 | 117 ± 7 | 18 | 9 | 3.6 | 13.9 ± 3 | 7.9 ± 3 | 5.6 ± 2 | 5.3 ± 1 |
| 11E3CN-Tw80 | 4.5 ± 2 | 12.8 ± 2 | 8.2 ± 4 | 4.9 ± 3 | 3.5 ± 0.7 | 5.9 ± 3 | 8.4 ± 1 | 8.1 ± 5 | 7.6 ± 2 |
| 21A11 | 30 ± 15 | 184 ± 100 | 48 | 56 ± 33 | 9.8 ± 0.3 | — | — | — | — |
| 21A11-Tw80 | 4.5 ± 4 | 17 ± 9.9 | 21 | 4.3 ± 2 | 4.7 ± 0.6 | 8.1 ± 3.4 | 9 | 18 | — |
| 29 | 12 ± 10 | 10 | 12.6 ± 10 | 1 | 2.1 ± 0.5 | 1.4 ± 0.5 | 2 ± 0.2 | 4 ± 2 | 3.2 ± 1 |
| 29-Tw80 | 8.7 ± 6 | 9.3 ± 2 | 1.7 | 2.1 ± 0.5 | 4 ± 0.5 | 7.6 ± 2.4 | 7.6 ± 2 | 15.5 ± 6 | 9.1 ± 5 |

PBL, peripheral blood lymphocytes; HUVEC, human umbilical vein endothelial cells; H460, non-small lung tumor; K562, chronic myelogenous leukemia; DoHH-2, B-cell cell lymphoma; P388, lymphocytic leukemia; P388ADR, lymphocytic leukemia, multidrug resistant; MCF-7, breast carcinoma; MCF-7ADR, breast carcinoma, multidrug resistant.

It will be appreciated that, although specific embodiments of the invention have been described herein for purposes of illustration, various modifications may be made without departing from the spirit and scope of the invention. Accordingly, the invention is not limited except as by the appended claims.

We claim:

1. An indolicidin analogue of up to 35 amino acids that comprise one of the following sequences:

11A4   Ile Leu Lys Lys Trp Pro Trp Pro Trp Arg Arg Lys (SEQ ID NO. 65),

11B8   Ile Leu Trp Pro Trp Trp Pro Trp Arg Arg Lys (SEQ ID NO. 66),

11D4   Ile Leu Lys Lys Trp Pro Trp Trp Pro Trp Arg Arg Lys Met Ile Leu Lys Lys Ala Gly Ser (SEQ ID NO. 69),

11D11   Ile Leu Lys Lys Trp Pro Trp Trp Pro Trp Arg Arg Lys Met (SEQ ID NO. 72),

11D19   Cys Leu Arg Trp Pro Trp Trp Pro Trp Arg Arg Lys (SEQ ID NO. 111),

11G2   Ile Lys Lys Trp Pro Trp Trp Pro Trp Arg Arg Lys (SEQ ID NO. 73),

11G3   Ile Leu Lys Lys Pro Trp Trp Pro Trp Arg Arg Lys (SEQ ID NO. 74),

11G4   Ile Leu Lys Lys Trp Trp Trp Pro Trp Arg Arg Lys (SEQ ID NO. 75),

11H01   Ala Leu Arg Trp Pro Trp Trp Pro Trp Arg Arg Lys (SEQ ID NO. 30),

11H05   Ile Leu Arg Trp Ala Trp Trp Pro Trp Arg Arg Lys (SEQ ID NO. 31).

2. An indolicidin analogue according to claim 1 and comprising the amino acid sequence Ile Leu Lys Lys Trp Trp Trp Pro Trp Arg Arg Lys (SEQ ID NO. 75).

3. An indolicidin analogue according to claim 1 and comprising the amino acid sequence Ala Leu Arg Trp Pro Trp Trp Pro Trp Arg Arg Lys (SEQ ID NO. 30).

4. The indolicidin analogue according to claim 1 and comprising the amino acid 11H05 Ile Leu Arg Trp Ala Trp Trp Pro Trp Arg Arg Lys (SEQ ID NO. 31).

5. The indolicidin analogue according to any one of claims 1-4 wherein the analogue has at least one amino acid altered to a corresponding D-amino acid.

6. The indolicidin analogue according to any one of claims 1-4 wherein the N-terminal and/or C-terminal amino acid is a D-amino acid.

7. The indolicidin analogue according to claim 4 wherein the N-terminal and C terminal amino acids are a D-amino acid.

8. The indolicidin analogue according to any one of claims 1-4 or 7 wherein the analogue is acetylated at the N-terminal amino acid.

9. The indolicidin analogue according to any one of claims 1-4 or 7 wherein the analogue is amidated at the C-terminal amino acid.

10. The indolicidin analogue according to any one of claims 1-4 or 7 wherein the analogue is esterified at the C-terminal amino acid.

11. The indolicidin analogue according to any one of claims 1-4 wherein the analogue is modified by incorporation of homoserine/homoserine lactone at the C-terminal amino acid.

12. A pharmaceutical composition comprising a physiologically acceptable buffer and at least one indolicidin analogue of up to 35 amino acids that comprise one of the following sequences:

```
11A9    Ile Leu Arg Trp Pro Trp Trp Pro Trp Trp Pro Trp Arg Arg Lys (SEQ ID NO. 39),

11A10   Trp Trp Arg Trp Pro Trp Trp Pro Trp Arg Arg Lys (SEQ ID NO. 40),

11B16   Ile Leu Arg Trp Pro Trp Trp Pro Trp Arg Arg Lys Ile Met Ile Leu Lys Lys Ala Gly
        Ser (SEQ ID NO. 47),

11B19   Ile Leu Arg Trp Pro Arg Arg Trp Pro Trp Arg Arg Lys (SEQ ID NO. 49),

11B20   Ile Leu Arg Trp Pro Trp Trp Pro Trp Arg Arg Lys Met Ile Leu Arg Trp Pro Trp Trp
        Pro Trp Arg Arg Lys Met Ala Ala (SEQ ID NO. 104),

11D19   Cys Leu Arg Trp Pro Trp Trp Pro Trp Arg Arg Lys (SEQ ID NO. 111),

11F3    Ile Leu Lys Lys Trp Val Trp Trp Pro Trp Arg Arg Lys (SEQ ID NO. 59),

11G28   Arg Trp Trp Trp Pro Trp Arg Arg Lys (SEQ ID NO. 63).
```

13. The pharmaceutical composition according to claim 12, further comprising an antibiotic agent.

14. The pharmaceutical composition according to claim 13, wherein the antibiotic is selected from the group consisting of penicillins, cephalosporins, carbacephems, cephamycins, carbapenems, monobactams, quinolones, tetracyclines, aminoglycosides, macrolides, glycopeptides, chloramphenicols, glycylcyclines, licosamides and fluoroquinolones.

15. The pharmaceutical composition according to claim 13, wherein the antibiotic is selected from the group consisting of Amikacin; Amoxicillin; Ampicillin; Azithromycin; Azlocillin; Aztreonam; Carbenicillin; Cefaclor; Cefamandole formate sodium; Cefazolin; Cefepime; Cefetamet; Cefixime; Cefmetazole; Cefonicid; Cefoperazone; Cefotaxime; Cefotetan; Cefoxitin; Cefpodoxime; Cefprozil; Cefsulodin; Ceftazidime; Ceftizoxime; Ceftriaxone; Cefuroxime; Cephalexin; Cephalothin; Chloramphenicol; Cinoxacin; Ciprofloxacin; Clarithromycin; Clindamycin; Cloxacillin; Coamoxiclavulanate; Dicloxacillin; Doxycycline; Enoxacin; Erythromycin; Erythromycin estolate; Erythromycin ethyl succinate; Erythromycin glucoheptonate; Erythromycin lactobionate; Erythromycin stearate; Ethambutol; Fleroxacin; Gentamicin; Imipenem; Isoniazid; Kanamycin; Lomefloxacin; Loracarbef; Meropenem Methicillin; Metronidazole; Mezlocillin; Minocycline hydrochloride; Mupirocin; Nafcillin; Nalidixic acid; Netilmicin; Nitrofurantoin; Norfloxacin; Ofloxacin; Oxacillin; Penicillin G; Piperacillin; Pyrazinamide; Rifabutin; Rifampicin; Roxithromycin; Streptomycin; Sulfamethoxazole; Synercid; Teicoplanin; Tetracycline; Ticarcillin; Tobramycin; Trimethoprim; Vancomycin; a combination of Piperacillin and Tazobactam; and derivatives thereof.

16. The pharmaceutical composition according to claim 13, wherein the antibiotic is selected from the group consisting of Amikacin; Amoxicillin; Ampicillin; Azithromycin; Cefoxitin; Ceftriaxone; Ciprofloxacin; Clarithromycin; Doxycycline; Erythromycin; Gentamicin; Mupirocin; Piperacillin; Teicoplanin; Tobramycin; Vancomycin; and a combination of Piperacillin and Tazobactam.

17. The pharmaceutical composition according to any one of claims 12 or 13, wherein the analogue has one or more amino acids altered to a corresponding D-amino acid.

18. The pharmaceutical composition according to any one of claims 12 or 13, wherein the N-terminal and/or C-terminal amino acid is a D-amino acid.

19. The pharmaceutical composition according to any one of claims 12 or 13, wherein the analogue is acetylated at the N-terminal amino acid.

20. The pharmaceutical composition according to any one of claims 12 or 13, wherein the analogue is amidated at the C-terminal amino acid.

21. The pharmaceutical composition according to any one of claims 12 or 13, wherein the analogue is esterified at the C-terminal amino acid.

22. The pharmaceutical composition according to any one of claims 12 or 13, wherein the analogue is modified by incorporation of homoserine/homoserine lactone at the C-terminal amino acid.

23. The pharmaceutical composition according to any one of claims 12 or 13, wherein the composition is incorporated in a liposome.

24. The pharmaceutical composition according to any one of claims 12 or 13, wherein the composition is incorporated in a slow-release vehicle.

25. A method of treating a microbial infection, comprising administering to a patient a therapeutically effective amount of a pharmaceutical composition according to any one of claims 12 or 13.

26. A method of treating a microbial infection, comprising administering to a patient a therapeutically effective amount of a pharmaceutical composition according to claim 23.

27. A method of treating a microbial infection, comprising administering to a patient a therapeutically effective amount of a pharmaceutical composition according to claim 24.

28. The method of claim 25, wherein the infection is due to a microorganism.

29. The method of claim 28, wherein the microorganism is selected from the group consisting of a bacterium, a fungus, and a parasite.

30. The method of claim 29, wherein the bacterium is a Gram-negative bacterium.

31. The method of claim 30, wherein the Gram-negative bacterium is selected from the group consisting of *Acinetobacter* spp.; *Enterobacter* spp.; *E. coli; H. influenzae;, K. pneumoniae; P. aeruginosa; S. marcescens*, and *S. maltophilia*.

32. The method of claim 30, wherein the Gram-negative bacterium is selected from the group consisting of *Bordetella pertussis; Brucella* spp.; *Campylobacter* spp.; *Haemophilus ducreyi; Helicobacter pylori; Legionella* spp.; *Moraxella catarrhalis; Neisseria* spp.; *Salmonella* spp.; *Shigella* spp., and *Yersinia* spp.

33. The method of claim 29, wherein the bacterium is a Gram-positive bacterium.

34. The method of claim 33, wherein the Gram-positive bacterium is selected from the group consisting of *E. faecalis, S. aureus, E. faecium, S. pyogenes, S. pneumoniae*, and coagulase-negative *Staphylococci*.

35. The method of claim 33, wherein the Gram-positive bacterium is selected from the group consisting of *Bacillus* spp., *Corynebacterium* spp., *Diphtheroids, Listeria* spp., and Viridans Streptococci.

36. The method of claim 29, wherein the bacterium is an anaerobe.

37. The method of claim 36, wherein the anaerobe is selected from the group consisting *Clostridium* spp., *Bacteroides* spp., and *Peptostreptococcus* spp.

38. The method of claim 29, wherein the bacterium is selected from the group consisting of *Borrelia* spp., *Chlamydia* spp., *Mycobacterium* spp., *Mycoplasma* spp., *Propionibacterium acne, Rickettsia* spp., *Treponema* spp., and *Ureaplasma* spp.

39. The method of claim 25, wherein the pharmaceutical composition is administered by intravenous injection, intraperitoneal injection or implantation, intramuscular injection or implantation, intrathecal injection, subcutaneous injection or implantation, intradermal injection, lavage, bladder washout, suppositories, pessaries, oral ingestion, topical application, enteric application, inhalation, aerosolization or nasal spray or drops.

40. The method of claim 26, wherein the pharmaceutical composition is administered by intravenous injection, intraperitoneal injection or implantation, intramuscular injection or implantation, intrathecal injection, subcutaneous injection or implantation, intradermal injection, lavage, bladder washout, suppositories, pessaries, oral ingestion, topical application, enteric application, inhalation, aerosolization or nasal spray or drops.

41. The method of claim 27, wherein the pharmaceutical composition is administered by intravenous injection, intraperitoneal injection or implantation, intramuscular injection or implantation, intrathecal injection, subcutaneous injection or implantation, intradermal injection, lavage, bladder washout, suppositories, pessaries, oral ingestion, topical application, enteric application, inhalation, aerosolization or nasal spray or drops.

* * * * *

```
                              SEQUENCE LISTING

<160> NUMBER OF SEQ ID NOS: 232

<210> SEQ ID NO 1
<211> LENGTH: 8
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(2)
<223> OTHER INFORMATION: Xaa = Hydrophobic Residue
<220> FEATURE:
<221> NAME/KEY: VARIANT
<222> LOCATION: (3)...(3)
<223> OTHER INFORMATION: Xaa = Proline or Valine
<220> FEATURE:
<221> NAME/KEY: VARIANT
<222> LOCATION: (4)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
<221> NAME/KEY: VARIANT
<222> LOCATION: (7)...(7)
<223> OTHER INFORMATION: Xaa = Hydrophobic Residue
<220> FEATURE:
<221> NAME/KEY: VARIANT
<222> LOCATION: (8)...(8)
<223> OTHER INFORMATION: Xaa = Basic Amino Acid

<400> SEQUENCE: 1

Arg Xaa Xaa Xaa Xaa Xaa Xaa Xaa
 1               5

<210> SEQ ID NO 2
<211> LENGTH: 8
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(1)
<223> OTHER INFORMATION: Xaa = Basic Amino Acid
<220> FEATURE:
<221> NAME/KEY: VARIANT
<222> LOCATION: (2)...(2)
<223> OTHER INFORMATION: Xaa = Hydrophobic Residue
<220> FEATURE:
<221> NAME/KEY: VARIANT
<222> LOCATION: (3)...(3)
<223> OTHER INFORMATION: Xaa = Proline or Valine
<220> FEATURE:
<221> NAME/KEY: VARIANT
<222> LOCATION: (4)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
```

```
<221> NAME/KEY: VARIANT
<222> LOCATION: (7)...(7)
<223> OTHER INFORMATION: Xaa = Hydrophobic Residue
<221> NAME/KEY: VARIANT
<222> LOCATION: (8)...(8)
<223> OTHER INFORMATION: Xaa = Basic Amino Acid
<220> FEATURE:
<223> OTHER INFORMATION: At least one residue at positions 3 and 6 is
      Valine

<400> SEQUENCE: 2

Xaa Xaa Xaa Xaa Xaa Xaa Xaa Xaa
 1               5

<210> SEQ ID NO 3
<211> LENGTH: 10
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(3)
<223> OTHER INFORMATION: Xaa = Basic Amino Acid
<220> FEATURE:
<221> NAME/KEY: VARIANT
<222> LOCATION: (4)...(4)
<223> OTHER INFORMATION: Xaa = Hydrophobic Residue
<220> FEATURE:
<221> NAME/KEY: VARIANT
<222> LOCATION: (5)...(5)
<223> OTHER INFORMATION: Xaa = Proline or Valine
<220> FEATURE:
<221> NAME/KEY: VARIANT
<222> LOCATION: (6)...(7)
<223> OTHER INFORMATION: Xaa = Hydrophobic Residue
<220> FEATURE:
<221> NAME/KEY: VARIANT
<222> LOCATION: (8)...(8)
<223> OTHER INFORMATION: Xaa = Proline or Valine
<220> FEATURE:
<221> NAME/KEY: VARIANT
<222> LOCATION: (9)...(9)
<223> OTHER INFORMATION: Xaa = Hydrophobic Residue
<220> FEATURE:
<221> NAME/KEY: VARIANT
<222> LOCATION: (10)...(10)
<223> OTHER INFORMATION: Xaa = Basic Amino Acid

<400> SEQUENCE: 3

Xaa Xaa Xaa Xaa Xaa Xaa Xaa Xaa Xaa Xaa
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(1)
<223> OTHER INFORMATION: Xaa= Basic Amino Acid
<220> FEATURE:
<221> NAME/KEY: VARIANT
<222> LOCATION: (2)...(3)
<223> OTHER INFORMATION: Xaa = Hydrophobic Residue
<220> FEATURE:
<221> NAME/KEY: VARIANT
<222> LOCATION: (4)...(4)
<223> OTHER INFORMATION: Xaa = Basic Amino Acid
<220> FEATURE:
<221> NAME/KEY: VARIANT
<222> LOCATION: (5)...(5)
<223> OTHER INFORMATION: Xaa = Proline or Valine
```

```
<220> FEATURE:
<221> NAME/KEY: VARIANT
<222> LOCATION: (6)...(6)
<223> OTHER INFORMATION: Xaa = Basic Amino Acid
<220> FEATURE:
<221> NAME/KEY: VARIANT
<222> LOCATION: (7)...(7)
<223> OTHER INFORMATION: Xaa = Hydrophobic Residue
<220> FEATURE:
<221> NAME/KEY: VARIANT
<222> LOCATION: (8)...(8)
<223> OTHER INFORMATION: Xaa = Basic Amino Acid
<220> FEATURE:
<221> NAME/KEY: VARIANT
<222> LOCATION: (9)...(9)
<223> OTHER INFORMATION: Xaa = Hydrophobic Residue
<220> FEATURE:
<221> NAME/KEY: VARIANT
<222> LOCATION: (10)...(10)
<223> OTHER INFORMATION: Xaa = Proline or Valine
<220> FEATURE:
<221> NAME/KEY: VARIANT
<222> LOCATION: (11)...(11)
<223> OTHER INFORMATION: Xaa = Basic Amino Acid

<400> SEQUENCE: 4

Xaa Xaa Xaa Xaa Xaa Xaa Xaa Xaa Xaa Xaa Xaa
 1               5                  10

<210> SEQ ID NO 5
<211> LENGTH: 17
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(1)
<223> OTHER INFORMATION: Xaa = Basic Amino Acid
<220> FEATURE:
<221> NAME/KEY: VARIANT
<222> LOCATION: (2)...(2)
<223> OTHER INFORMATION: Xaa = Hydrophobic Residue
<220> FEATURE:
<221> NAME/KEY: VARIANT
<222> LOCATION: (3)...(3)
<223> OTHER INFORMATION: Xaa = Proline or Valine
<220> FEATURE:
<221> NAME/KEY: VARIANT
<222> LOCATION: (4)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
<221> NAME/KEY: VARIANT
<222> LOCATION: (7)...(7)
<223> OTHER INFORMATION: Xaa = Hydrophobic Residue
<220> FEATURE:
<221> NAME/KEY: VARIANT
<222> LOCATION: (8)...(9)
<223> OTHER INFORMATION: Xaa = Basic Amino Acid
<220> FEATURE:
<221> NAME/KEY: VARIANT
<222> LOCATION: (13)...(14)
<223> OTHER INFORMATION: Xaa = Basic Amino Acid

<400> SEQUENCE: 5

Xaa Xaa Xaa Xaa Xaa Xaa Xaa Xaa Xaa Met Ile Leu Xaa Xaa Ala Gly
 1               5                  10                  15

Ser

<210> SEQ ID NO 6
```

```
<211> LENGTH: 18
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(1)
<223> OTHER INFORMATION: Xaa = Basic Amino Acid
<220> FEATURE:
<221> NAME/KEY: VARIANT
<222> LOCATION: (2)...(2)
<223> OTHER INFORMATION: Xaa = Hydrophobic Residue
<220> FEATURE:
<221> NAME/KEY: VARIANT
<222> LOCATION: (3)...(3)
<223> OTHER INFORMATION: Xaa = Proline or Valine
<220> FEATURE:
<221> NAME/KEY: VARIANT
<222> LOCATION: (4)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
<221> NAME/KEY: VARIANT
<222> LOCATION: (7)...(7)
<223> OTHER INFORMATION: Xaa = Hydrophobic Residue
<220> FEATURE:
<221> NAME/KEY: VARIANT
<222> LOCATION: (8)...(10)
<223> OTHER INFORMATION: Xaa = Basic Amino Acid
<220> FEATURE:
<221> NAME/KEY: VARIANT
<222> LOCATION: (14)...(15)
<223> OTHER INFORMATION: Xaa = Basic Amino Acid

<400> SEQUENCE: 6

Xaa Xaa Xaa Xaa Xaa Xaa Xaa Xaa Xaa Xaa Met Ile Leu Xaa Xaa Ala
 1               5                   10                  15

Gly Ser

<210> SEQ ID NO 7
<211> LENGTH: 18
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(1)
<223> OTHER INFORMATION: Xaa = Basic Amino Acid
<220> FEATURE:
<221> NAME/KEY: VARIANT
<222> LOCATION: (2)...(2)
<223> OTHER INFORMATION: Xaa = Hydrophobic Residue
<220> FEATURE:
<221> NAME/KEY: VARIANT
<222> LOCATION: (3)...(3)
<223> OTHER INFORMATION: Xaa = Proline or Valine
<220> FEATURE:
<221> NAME/KEY: VARIANT
<222> LOCATION: (4)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
<221> NAME/KEY: VARIANT
<222> LOCATION: (7)...(7)
<223> OTHER INFORMATION: Xaa = Hydrophobic Residue
<220> FEATURE:
<221> NAME/KEY: VARIANT
<222> LOCATION: (8)...(9)
```

```
<223> OTHER INFORMATION: Xaa = Basic Amino Acid
<220> FEATURE:
<221> NAME/KEY: VARIANT
<222> LOCATION: (10)...(10)
<223> OTHER INFORMATION: Xaa= Any Amino Acid
<220> FEATURE:
<221> NAME/KEY: VARIANT
<222> LOCATION: (14)...(15)
<223> OTHER INFORMATION: Xaa = Basic Amino Acid

<400> SEQUENCE: 7

Xaa Xaa Xaa Xaa Xaa Xaa Xaa Xaa Xaa Xaa Met Ile Leu Xaa Xaa Ala
 1               5                  10                  15

Gly Ser

<210> SEQ ID NO 8
<211> LENGTH: 19
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(1)
<223> OTHER INFORMATION: Xaa = Basic Amino Acid
<220> FEATURE:
<221> NAME/KEY: VARIANT
<222> LOCATION: (2)...(2)
<223> OTHER INFORMATION: Xaa = Hydrophobic Residue
<220> FEATURE:
<221> NAME/KEY: VARIANT
<222> LOCATION: (3)...(3)
<223> OTHER INFORMATION: Xaa = Proline or Valine
<220> FEATURE:
<221> NAME/KEY: VARIANT
<222> LOCATION: (4)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
<221> NAME/KEY: VARIANT
<222> LOCATION: (7)...(7)
<223> OTHER INFORMATION: Xaa = Hydrophobic Residue
<220> FEATURE:
<221> NAME/KEY: VARIANT
<222> LOCATION: (8)...(10)
<223> OTHER INFORMATION: Xaa = Basic Amino Acid
<220> FEATURE:
<221> NAME/KEY: VARIANT
<222> LOCATION: (11)...(11)
<223> OTHER INFORMATION: Xaa = Any Amino Acid
<220> FEATURE:
<221> NAME/KEY: VARIANT
<222> LOCATION: (15)...(16)
<223> OTHER INFORMATION: Xaa = Basic Amino Acid

<400> SEQUENCE: 8

Xaa Xaa Xaa Xaa Xaa Xaa Xaa Xaa Xaa Xaa Xaa Met Ile Leu Xaa Xaa
 1               5                  10                  15

Ala Gly Ser

<210> SEQ ID NO 9
<211> LENGTH: 10
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(1)
<223> OTHER INFORMATION: Xaa =  Basic Amino Acid
```

```
<220> FEATURE:
<221> NAME/KEY: VARIANT
<222> LOCATION: (2)...(2)
<223> OTHER INFORMATION: Xaa = Hydrophobic Residue
<220> FEATURE:
<221> NAME/KEY: VARIANT
<222> LOCATION: (3)...(3)
<223> OTHER INFORMATION: Xaa = Proline or Valine
<220> FEATURE:
<221> NAME/KEY: VARIANT
<222> LOCATION: (4)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
<221> NAME/KEY: VARIANT
<222> LOCATION: (7)...(7)
<223> OTHER INFORMATION: Xaa = Hydrophobic Residue
<220> FEATURE:
<221> NAME/KEY: VARIANT
<222> LOCATION: (8)...(9)
<223> OTHER INFORMATION: Xaa = Basic Amino Acid

<400> SEQUENCE: 9

Xaa Xaa Xaa Xaa Xaa Xaa Xaa Xaa Xaa Met
 1               5                   10

<210> SEQ ID NO 10
<211> LENGTH: 11
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(1)
<223> OTHER INFORMATION: Xaa = Basic Amino Acid
<220> FEATURE:
<221> NAME/KEY: VARIANT
<222> LOCATION: (2)...(2)
<223> OTHER INFORMATION: Xaa = Hydrophobic Residue
<220> FEATURE:
<221> NAME/KEY: VARIANT
<222> LOCATION: (3)...(3)
<223> OTHER INFORMATION: Xaa = Proline or Valine
<220> FEATURE:
<221> NAME/KEY: VARIANT
<222> LOCATION: (4)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
<221> NAME/KEY: VARIANT
<222> LOCATION: (7)...(7)
<223> OTHER INFORMATION: Xaa = Hydrophobic Residue
<220> FEATURE:
<221> NAME/KEY: VARIANT
<222> LOCATION: (8)...(9)
<223> OTHER INFORMATION: Xaa = Basic Amino Acid
<220> FEATURE:
<221> NAME/KEY: VARIANT
<222> LOCATION: (10)...(10)
<223> OTHER INFORMATION: Xaa = Any Amino Acid

<400> SEQUENCE: 10

Xaa Xaa Xaa Xaa Xaa Xaa Xaa Xaa Xaa Xaa Met
 1               5                   10

<210> SEQ ID NO 11
<211> LENGTH: 8
<212> TYPE: PRT
```

```
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(2)
<223> OTHER INFORMATION: Xaa = Basic Amino Acid
<220> FEATURE:
<221> NAME/KEY: VARIANT
<222> LOCATION: (3)...(6)
<223> OTHER INFORMATION: Xaa = Hydrophobic Residue

<400> SEQUENCE: 11

Leu Xaa Xaa Xaa Xaa Xaa Arg Lys
 1               5

<210> SEQ ID NO 12
<211> LENGTH: 9
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(3)
<223> OTHER INFORMATION: Xaa = Basic Amino Acid
<220> FEATURE:
<221> NAME/KEY: VARIANT
<222> LOCATION: (4)...(7)
<223> OTHER INFORMATION: Xaa = Hydrophobic Residue

<400> SEQUENCE: 12

Leu Xaa Xaa Xaa Xaa Xaa Xaa Arg Lys
 1               5

<210> SEQ ID NO 13
<211> LENGTH: 10
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(3)
<223> OTHER INFORMATION: Xaa = Basic Amino Acid
<220> FEATURE:
<221> NAME/KEY: VARIANT
<222> LOCATION: (4)...(4)
<223> OTHER INFORMATION: Xaa = Hydrophobic Residue
<220> FEATURE:
<221> NAME/KEY: VARIANT
<222> LOCATION: (5)...(5)
<223> OTHER INFORMATION: Xaa = Proline or Valine
<220> FEATURE:
<221> NAME/KEY: VARIANT
<222> LOCATION: (6)...(8)
<223> OTHER INFORMATION: Xaa = Hydrophobic Residue

<400> SEQUENCE: 13

Leu Xaa Xaa Xaa Xaa Xaa Xaa Xaa Arg Lys
 1               5                   10

<210> SEQ ID NO 14
<211> LENGTH: 11
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(3)        <223> Xaa = Basic Amino Acid
<220> FEATURE:
<221> NAME/KEY: VARIANT
```

```
<222> LOCATION: (4)...(4)
<223> OTHER INFORMATION: Xaa = Hydrophobic Residue
<220> FEATURE:
<221> NAME/KEY: VARIANT
<222> LOCATION: (5)...(5)
<223> OTHER INFORMATION: Xaa = Proline or Valine
<220> FEATURE:
<221> NAME/KEY: VARIANT
<222> LOCATION: (6)...(7)
<223> OTHER INFORMATION: Xaa = Hydrophobic Residue
<220> FEATURE:
<221> NAME/KEY: VARIANT
<222> LOCATION: (8)...(8)
<223> OTHER INFORMATION: Xaa = Proline or Valine
<220> FEATURE:
<221> NAME/KEY: VARIANT
<222> LOCATION: (9)...(9)
<223> OTHER INFORMATION: Xaa = Hydrophobic Residue

<400> SEQUENCE: 14

Leu Xaa Xaa Xaa Xaa Xaa Xaa Xaa Xaa Arg Lys
 1               5                  10

<210> SEQ ID NO 15
<211> LENGTH: 9
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(2)
<223> OTHER INFORMATION: Xaa = Basic Amino Acid
<220> FEATURE:
<221> NAME/KEY: VARIANT
<222> LOCATION: (3)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
<221> NAME/KEY: VARIANT
<222> LOCATION: (7)...(7)
<223> OTHER INFORMATION: Xaa = Hydrophobic Residue

<400> SEQUENCE: 15

Leu Xaa Xaa Xaa Xaa Xaa Xaa Arg Lys
 1               5

<210> SEQ ID NO 16
<211> LENGTH: 10
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(2)
<223> OTHER INFORMATION: Xaa = Basic Amino Acid
<220> FEATURE:
<221> NAME/KEY: VARIANT
<222> LOCATION: (3)...(3)
<223> OTHER INFORMATION: Xaa = Hydrophobic Residue
<220> FEATURE:
<221> NAME/KEY: VARIANT
<222> LOCATION: (4)...(4)
<223> OTHER INFORMATION: Xaa = Proline or Valine
<220> FEATURE:
<221> NAME/KEY: VARIANT
<222> LOCATION: (5)...(6)
<223> OTHER INFORMATION: Xaa = Hydrophobic Residue
<220> FEATURE:
<221> NAME/KEY: VARIANT
<222> LOCATION: (7)...(7)
```

```
<223> OTHER INFORMATION: Xaa = Proline or Valine
<220> FEATURE:
<221> NAME/KEY: VARIANT
<222> LOCATION: (8)...(8)
<223> OTHER INFORMATION: Xaa = Hydrophobic Residue

<400> SEQUENCE: 16

Leu Xaa Xaa Xaa Xaa Xaa Xaa Xaa Arg Lys
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(3)
<223> OTHER INFORMATION: Xaa = Basic Amino Acid
<220> FEATURE:
<221> NAME/KEY: VARIANT
<222> LOCATION: (4)...(6)
<223> OTHER INFORMATION: Xaa = Hydrophobic Residue
<220> FEATURE:
<221> NAME/KEY: VARIANT
<222> LOCATION: (7)...(7)
<223> OTHER INFORMATION: Xaa = Proline or Valine
<220> FEATURE:
<221> NAME/KEY: VARIANT
<222> LOCATION: (8)...(8)
<223> OTHER INFORMATION: Xaa = Hydrophobic Residue

<400> SEQUENCE: 17

Leu Xaa Xaa Xaa Xaa Xaa Xaa Xaa Arg Lys
 1               5                  10

<210> SEQ ID NO 18
<211> LENGTH: 9
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(2)
<223> OTHER INFORMATION: Xaa = Basic Amino Acid
<220> FEATURE:
<221> NAME/KEY: VARIANT
<222> LOCATION: (3)...(3)
<223> OTHER INFORMATION: Xaa = Hydrophobic Residue
<220> FEATURE:
<221> NAME/KEY: VARIANT
<222> LOCATION: (4)...(4)
<223> OTHER INFORMATION: Xaa = Proline or Valine
<220> FEATURE:
<221> NAME/KEY: VARIANT
<222> LOCATION: (5)...(7)
<223> OTHER INFORMATION: Xaa = Hydrophobic Residue

<400> SEQUENCE: 18

Leu Xaa Xaa Xaa Xaa Xaa Xaa Arg Lys
 1               5

<210> SEQ ID NO 19
<211> LENGTH: 10
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (2)...(2)
```

-continued

```
<223> OTHER INFORMATION: Xaa = Hydrophobic Residue
<220> FEATURE:
<221> NAME/KEY: VARIANT
<222> LOCATION: (3)...(3)
<223> OTHER INFORMATION: Xaa = Proline or Valine
<220> FEATURE:
<221> NAME/KEY: VARIANT
<222> LOCATION: (4)...(5)
<223> OTHER INFORMATION: Xaa = Hydrophobic Residue
<220> FEATURE:
<221> NAME/KEY: VARIANT
<222> LOCATION: (6)...(6)
<223> OTHER INFORMATION: Xaa = Proline or Valine
<220> FEATURE:
<221> NAME/KEY: VARIANT
<222> LOCATION: (7)...(7)
<223> OTHER INFORMATION: Xaa = Hydrophobic Residue

<400> SEQUENCE: 19

Leu Xaa Xaa Xaa Xaa Xaa Xaa Arg Arg Lys
 1               5                   10

<210> SEQ ID NO 20
<211> LENGTH: 11
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (3)...(3)
<223> OTHER INFORMATION: Xaa = Hydrophobic Residue
<220> FEATURE:
<221> NAME/KEY: VARIANT
<222> LOCATION: (4)...(4)
<223> OTHER INFORMATION: Xaa = Proline or Valine
<220> FEATURE:
<221> NAME/KEY: VARIANT
<222> LOCATION: (5)...(6)
<223> OTHER INFORMATION: Xaa = Hydrophobic Residue
<220> FEATURE:
<221> NAME/KEY: VARIANT
<222> LOCATION: (7)...(7)
<223> OTHER INFORMATION: Xaa = Proline or Valine
<220> FEATURE:
<221> NAME/KEY: VARIANT
<222> LOCATION: (8)...(8)
<223> OTHER INFORMATION: Xaa = Hydrophobic Residue

<400> SEQUENCE: 20

Leu Lys Xaa Xaa Xaa Xaa Xaa Xaa Arg Arg Lys
 1               5                   10

<210> SEQ ID NO 21
<211> LENGTH: 11
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(2)
<223> OTHER INFORMATION: Xaa = Basic Amino Acid
<220> FEATURE:
<221> NAME/KEY: VARIANT
<222> LOCATION: (3)...(3)
<223> OTHER INFORMATION: Xaa = Hydrophobic Residue
<220> FEATURE:
<221> NAME/KEY: VARIANT
<222> LOCATION: (4)...(4)
<223> OTHER INFORMATION: Xaa = Proline or Valine
<220> FEATURE:
<221> NAME/KEY: VARIANT
<222> LOCATION: (5)...(6)
<223> OTHER INFORMATION: Xaa = Hydrophobic Residue
```

```
<220> FEATURE:
<221> NAME/KEY: VARIANT
<222> LOCATION: (7)...(7)
<223> OTHER INFORMATION: Xaa = Proline or Valine
<220> FEATURE:
<221> NAME/KEY: VARIANT
<222> LOCATION: (8)...(8)
<223> OTHER INFORMATION: Xaa = Hydrophobic Residue
<221> NAME/KEY: VARIANT
<222> LOCATION: (9)...(11)
<223> OTHER INFORMATION: Xaa = Basic Amino Acid
<220> FEATURE:
<223> OTHER INFORMATION: At leat two residues at positions 3, 5, 6 and 8
      are Phenylalanine

<400> SEQUENCE: 21

Xaa Xaa Xaa Xaa Xaa Xaa Xaa Xaa Xaa Xaa Xaa
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: Indolicidin Analogue
<220> FEATURE:
<221> NAME/KEY: VARIANT
<222> LOCATION: (1)...(2)
<223> OTHER INFORMATION: Xaa = Basic Amino Acid
<220> FEATURE:
<221> NAME/KEY: VARIANT
<222> LOCATION: (3)...(3)
<223> OTHER INFORMATION: Xaa = Hydrophobic Residue
<220> FEATURE:
<221> NAME/KEY: VARIANT
<222> LOCATION: (4)...(4)
<223> OTHER INFORMATION: Xaa = Proline or Valine
<220> FEATURE:
<221> NAME/KEY: VARIANT
<222> LOCATION: (5)...(6)
<223> OTHER INFORMATION: Xaa = Hydrophobic Residue
<220> FEATURE:
<221> NAME/KEY: VARIANT
<222> LOCATION: (7)...(7)
<223> OTHER INFORMATION: Xaa = Proline or Valine
<220> FEATURE:
<221> NAME/KEY: VARIANT
<222> LOCATION: (8)...(8)
<223> OTHER INFORMATION: Xaa = Hydrophobic Residue
<221> NAME/KEY: VARIANT
<222> LOCATION: (9)...(11)
<223> OTHER INFORMATION: Xaa = Basic Amino Acid
<220> FEATURE:
<223> OTHER INFORMATION: At least two residues at positions 3, 5, 6 and
      8 are Tyrosine

<400> SEQUENCE: 22

Xaa Xaa Xaa Xaa Xaa Xaa Xaa Xaa Xaa Xaa Xaa
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 23

Ile Leu Arg Trp Pro Trp Trp Pro Trp Arg Arg Lys
 1               5                  10

<210> SEQ ID NO 24
<211> LENGTH: 20
```

```
<212> TYPE: PRT
<213> ORGANISM: Artificial Sequence
<220> FEATURE:
<223> OTHER INFORMATION: Indolicidin Analogue

<400> SEQUENCE: 24

Ile Leu Arg Trp Pro Trp Trp Pro Trp Arg Arg Lys Met Ile Leu Lys
 1               5                  10                  15
Lys Ala Gly Ser
            20

<210> SEQ ID NO 25
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 25

Lys Arg Arg Trp Pro Trp Trp Pro Trp Lys Lys Leu Ile
 1               5                  10

<210> SEQ ID NO 26
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 26

Trp Arg Ile Trp Lys Pro Lys Trp Arg Leu Pro Lys Trp
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 27

Ile Leu Arg Trp Val Trp Trp Val Trp Arg Arg Lys
 1               5                  10

<210> SEQ ID NO 28
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 28

Ile Leu Arg Arg Trp Val Trp Trp Val Trp Arg Arg Lys
 1               5                  10

<210> SEQ ID NO 29
<211> LENGTH: 10
<212> TYPE: PRT
<213> ORGANISM: Artificial Sequence
<220> FEATURE:
<223> OTHER INFORMATION: Indolicidin Analogue

<400> SEQUENCE: 29

Leu Arg Trp Trp Trp Pro Trp Arg Arg Lys
 1               5                  10
```

```
<210> SEQ ID NO 30
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 30

Ala Leu Arg Trp Pro Trp Trp Pro Trp Arg Arg Lys
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 31

Ile Leu Arg Trp Ala Trp Trp Pro Trp Arg Arg Lys
 1               5                  10

<210> SEQ ID NO 32
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 32

Trp Arg Trp Trp Lys Pro Lys Trp Arg Trp Pro Lys Trp
 1               5                  10

<210> SEQ ID NO 33
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 33

Ile Leu Lys Lys Ile Pro Ile Ile Pro Ile Arg Arg Lys
 1               5                  10

<210> SEQ ID NO 34
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 34

Ile Leu Lys Lys Tyr Pro Tyr Tyr Pro Tyr Arg Arg Lys
 1               5                  10

<210> SEQ ID NO 35
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 35

Ile Leu Lys Lys Tyr Pro Trp Tyr Pro Trp Arg Arg Lys
 1               5                  10

<210> SEQ ID NO 36
```

```
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 36

Ile Leu Lys Lys Phe Pro Trp Phe Pro Trp Arg Arg Lys
 1               5                  10

<210> SEQ ID NO 37
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 37

Ile Leu Lys Lys Phe Pro Phe Trp Pro Trp Arg Arg Lys
 1               5                  10

<210> SEQ ID NO 38
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 38

Ile Leu Arg Tyr Val Tyr Tyr Val Tyr Arg Arg Lys
 1               5                  10

<210> SEQ ID NO 39
<211> LENGTH: 15
<212> TYPE: PRT
<213> ORGANISM: Artificial Sequence
<220> FEATURE:
<223> OTHER INFORMATION: Indolicidin Analogue

<400> SEQUENCE: 39

Ile Leu Arg Trp Pro Trp Trp Pro Trp Trp Pro Trp Arg Arg Lys
 1               5                  10                  15

<210> SEQ ID NO 40
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 40

Trp Trp Arg Trp Pro Trp Trp Pro Trp Arg Arg Lys
 1               5                  10

<210> SEQ ID NO 41
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 41

Ile Leu Arg Arg Trp Pro Trp Trp Pro Trp Arg Arg Lys
 1               5                  10

<210> SEQ ID NO 42
<211> LENGTH: 12
```

```
<212> TYPE: PRT
<213> ORGANISM: Artificial Sequence
<220> FEATURE:
<223> OTHER INFORMATION: Indolicidin Analogue

<400> SEQUENCE: 42

Ile Leu Arg Arg Trp Pro Trp Trp Pro Trp Arg Lys
 1               5                  10

<210> SEQ ID NO 43
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 43

Ile Leu Lys Trp Pro Trp Trp Pro Trp Arg Arg Lys
 1               5                  10

<210> SEQ ID NO 44
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 44

Ile Leu Lys Lys Trp Pro Trp Trp Pro Trp Arg Lys
 1               5                  10

<210> SEQ ID NO 45
<211> LENGTH: 11
<212> TYPE: PRT
<213> ORGANISM: Artificial Sequence
<220> FEATURE:
<223> OTHER INFORMATION: Indolicidin Analogue

<400> SEQUENCE: 45

Ile Leu Lys Trp Pro Trp Trp Pro Trp Arg Lys
 1               5                  10

<210> SEQ ID NO 46
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 46

Lys Arg Arg Trp Pro Trp Trp Pro Trp Arg Leu Ile
 1               5                  10

<210> SEQ ID NO 47
<211> LENGTH: 21
<212> TYPE: PRT
<213> ORGANISM: Artificial Sequence
<220> FEATURE:
<223> OTHER INFORMATION: Indolicidin Analogue

<400> SEQUENCE: 47

Ile Leu Arg Trp Pro Trp Trp Pro Trp Arg Arg Lys Ile Met Ile Leu
 1               5                  10                  15

Lys Lys Ala Gly Ser
                20
```

```
<210> SEQ ID NO 48
<211> LENGTH: 21
<212> TYPE: PRT
<213> ORGANISM: Artificial Sequence
<220> FEATURE:
<223> OTHER INFORMATION: Indolicidin Analogue

<400> SEQUENCE: 48

Ile Leu Arg Trp Pro Trp Trp Pro Trp Arg Arg Lys Asp Met Ile Leu
 1               5                  10                  15

Lys Lys Ala Gly Ser
            20

<210> SEQ ID NO 49
<211> LENGTH: 14
<212> TYPE: PRT
<213> ORGANISM: Artificial Sequence
<220> FEATURE:
<223> OTHER INFORMATION: Indolicidin Analogue

<400> SEQUENCE: 49

Ile Leu Arg Trp Pro Trp Arg Arg Trp Pro Trp Arg Arg Lys
 1               5                  10

<210> SEQ ID NO 50
<211> LENGTH: 28
<212> TYPE: PRT
<213> ORGANISM: Artificial Sequence
<220> FEATURE:
<223> OTHER INFORMATION: Indolicidin Analogue

<400> SEQUENCE: 50

Ile Leu Arg Trp Pro Trp Trp Pro Trp Arg Arg Lys Met Ile Leu Arg
 1               5                  10                  15

Trp Pro Trp Trp Pro Trp Arg Arg Lys Met Ala Ala
            20                  25

<210> SEQ ID NO 51
<211> LENGTH: 20
<212> TYPE: PRT
<213> ORGANISM: Artificial Sequence
<220> FEATURE:
<223> OTHER INFORMATION: Indolicidin Analogue

<400> SEQUENCE: 51

Ile Leu Lys Lys Trp Pro Trp Pro Trp Arg Arg Met Ile Leu Lys
 1               5                  10                  15

Lys Ala Gly Ser
            20

<210> SEQ ID NO 52
<211> LENGTH: 21
<212> TYPE: PRT
<213> ORGANISM: Artificial Sequence
<220> FEATURE:
<223> OTHER INFORMATION: Indolicidin Analogue

<400> SEQUENCE: 52

Ile Leu Lys Lys Trp Pro Trp Trp Pro Trp Arg Arg Ile Met Ile Leu
 1               5                  10                  15

Lys Lys Ala Gly Ser
            20

<210> SEQ ID NO 53
<211> LENGTH: 13
```

```
<212> TYPE: PRT
<213> ORGANISM: Artificial Sequence
<220> FEATURE:
<223> OTHER INFORMATION: Indolicidin Analogue

<400> SEQUENCE: 53

Ile Leu Lys Lys Trp Pro Trp Trp Pro Trp Arg Arg Met
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Indolicidin Analogue

<400> SEQUENCE: 54

Ile Leu Lys Lys Trp Pro Trp Trp Pro Trp Arg Arg Ile Met
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Indolicidin Analogue

<400> SEQUENCE: 55

Ile Leu Lys Lys Trp Trp Trp Pro Trp Arg Lys
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Indolicidin Analogue

<400> SEQUENCE: 56

Ile Leu Lys Lys Trp Pro Trp Trp Trp Arg Lys
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 57

Ile Leu Lys Lys Trp Val Trp Trp Val Trp Arg Arg Lys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 58

Ile Leu Lys Lys Trp Pro Trp Trp Val Trp Arg Arg Lys
1               5                   10

<210> SEQ ID NO 59
<211> LENGTH: 13
<212> TYPE: PRT
```

```
<213> ORGANISM: Artificial Sequence
<220> FEATURE:
<223> OTHER INFORMATION: Indolicidin Analogue

<400> SEQUENCE: 59

Ile Leu Lys Lys Trp Val Trp Trp Pro Trp Arg Arg Lys
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 60

Lys Arg Arg Trp Val Trp Trp Val Trp Arg Leu Ile
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Indolicidin Analogue

<400> SEQUENCE: 61

Ile Leu Arg Trp Trp Val Trp Trp Val Trp Trp Arg Arg Lys
1               5                   10

<210> SEQ ID NO 62
<211> LENGTH: 8
<212> TYPE: PRT
<213> ORGANISM: Artificial Sequence
<220> FEATURE:
<223> OTHER INFORMATION: Indolicidin Analogue

<400> SEQUENCE: 62

Leu Arg Trp Pro Trp Trp Pro Trp
1               5

<210> SEQ ID NO 63
<211> LENGTH: 9
<212> TYPE: PRT
<213> ORGANISM: Artificial Sequence
<220> FEATURE:
<223> OTHER INFORMATION: Indolicidin Analogue

<400> SEQUENCE: 63

Arg Trp Trp Trp Pro Trp Arg Arg Lys
1               5

<210> SEQ ID NO 64
<211> LENGTH: 13
<212> TYPE: PRT
<213> ORGANISM: Artificial Sequence
<220> FEATURE:
<223> OTHER INFORMATION: Indolicidin Analogue

<400> SEQUENCE: 64

Arg Arg Ile Trp Lys Pro Lys Trp Arg Leu Pro Lys Arg
1               5                   10

<210> SEQ ID NO 65
<211> LENGTH: 12
<212> TYPE: PRT
<213> ORGANISM: Artificial Sequence
```

```
<220> FEATURE:
<223> OTHER INFORMATION: Indolicidin Analogue

<400> SEQUENCE: 65

Ile Leu Lys Lys Trp Pro Trp Pro Trp Arg Arg Lys
 1               5                  10

<210> SEQ ID NO 66
<211> LENGTH: 11
<212> TYPE: PRT
<213> ORGANISM: Artificial Sequence
<220> FEATURE:
<223> OTHER INFORMATION: Indolicidin Analogue

<400> SEQUENCE: 66

Ile Leu Trp Pro Trp Trp Pro Trp Arg Arg Lys
 1               5                  10

<210> SEQ ID NO 67
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 67

Leu Lys Lys Trp Pro Trp Trp Pro Trp Arg Arg Lys
 1               5                  10

<210> SEQ ID NO 68
<211> LENGTH: 8
<212> TYPE: PRT
<213> ORGANISM: Artificial Sequence
<220> FEATURE:
<223> OTHER INFORMATION: Indolicidin Analogue

<400> SEQUENCE: 68

Pro Trp Trp Pro Trp Arg Arg Lys
 1               5

<210> SEQ ID NO 69
<211> LENGTH: 21
<212> TYPE: PRT
<213> ORGANISM: Artificial Sequence
<220> FEATURE:
<223> OTHER INFORMATION: Indolicidin Analogue

<400> SEQUENCE: 69

Ile Leu Lys Lys Trp Pro Trp Trp Pro Trp Arg Arg Lys Met Ile Leu
 1               5                  10                  15

Lys Lys Ala Gly Ser
            20

<210> SEQ ID NO 70
<211> LENGTH: 7
<212> TYPE: PRT
<213> ORGANISM: Artificial Sequence
<220> FEATURE:
<223> OTHER INFORMATION: Indolicidin Analogue

<400> SEQUENCE: 70

Trp Trp Pro Trp Arg Arg Lys
 1               5

<210> SEQ ID NO 71
<211> LENGTH: 7
```

```
<212> TYPE: PRT
<213> ORGANISM: Artificial Sequence
<220> FEATURE:
<223> OTHER INFORMATION: Indolicidin Analogue

<400> SEQUENCE: 71

Ile Leu Lys Lys Trp Pro Trp
1               5

<210> SEQ ID NO 72
<211> LENGTH: 14
<212> TYPE: PRT
<213> ORGANISM: Artificial Sequence
<220> FEATURE:
<223> OTHER INFORMATION: Indolicidin Analogue

<400> SEQUENCE: 72

Ile Leu Lys Lys Trp Pro Trp Trp Pro Trp Arg Arg Lys Met
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 73

Ile Lys Lys Trp Pro Trp Trp Pro Trp Arg Arg Lys
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 74

Ile Leu Lys Lys Pro Trp Trp Pro Trp Arg Arg Lys
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 75

Ile Leu Lys Lys Trp Trp Trp Pro Trp Arg Arg Lys
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 76

Ile Leu Lys Lys Trp Pro Trp Trp Trp Arg Arg Lys
1               5                   10

<210> SEQ ID NO 77
<211> LENGTH: 12
<212> TYPE: PRT
```

```
<213> ORGANISM: Artificial Sequence
<220> FEATURE:
<223> OTHER INFORMATION: Indolicidin Analogue

<400> SEQUENCE: 77

Ile Leu Lys Lys Trp Pro Trp Trp Pro Arg Arg Lys
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Indolicidin Analogue

<400> SEQUENCE: 78

Ile Leu Lys Lys Trp Pro Trp Trp Pro Trp Lys
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Indolicidin Analogue

<400> SEQUENCE: 79

Ile Leu Lys Lys Trp Pro Trp Trp Pro Trp Arg
1               5                   10

<210> SEQ ID NO 80
<211> LENGTH: 9
<212> TYPE: PRT
<213> ORGANISM: Artificial Sequence
<220> FEATURE:
<223> OTHER INFORMATION: Indolicidin Analogue

<400> SEQUENCE: 80

Trp Pro Trp Trp Pro Trp Arg Arg Lys
1               5

<210> SEQ ID NO 81
<211> LENGTH: 10
<212> TYPE: PRT
<213> ORGANISM: Artificial Sequence
<220> FEATURE:
<223> OTHER INFORMATION: Indolicidin Analogue

<400> SEQUENCE: 81

Leu Trp Pro Trp Trp Pro Trp Arg Arg Lys
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 82

Ile Ala Arg Trp Pro Trp Trp Pro Trp Arg Arg Lys
1               5                   10

<210> SEQ ID NO 83
<211> LENGTH: 12
<212> TYPE: PRT
<213> ORGANISM: Artificial Sequence
```

```
<220> FEATURE:
<223> OTHER INFORMATION: Indolicidin Analogue

<400> SEQUENCE: 83

Ile Leu Ala Trp Pro Trp Trp Pro Trp Arg Arg Lys
 1               5                   10

<210> SEQ ID NO 84
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 84

Ile Leu Arg Ala Pro Trp Trp Pro Trp Arg Arg Lys
 1               5                   10

<210> SEQ ID NO 85
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 85

Ile Leu Arg Trp Pro Ala Trp Pro Trp Arg Arg Lys
 1               5                   10

<210> SEQ ID NO 86
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 86

Ile Leu Arg Trp Pro Trp Ala Pro Trp Arg Arg Lys
 1               5                   10

<210> SEQ ID NO 87
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 87

Ile Leu Arg Trp Pro Trp Trp Ala Trp Arg Arg Lys
 1               5                   10

<210> SEQ ID NO 88
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 88

Ile Leu Arg Trp Pro Trp Trp Pro Ala Arg Arg Lys
 1               5                   10

<210> SEQ ID NO 89
<211> LENGTH: 12
<212> TYPE: PRT
<213> ORGANISM: Artificial Sequence
<220> FEATURE:
```

<223> OTHER INFORMATION: Indolicidin Analogue

<400> SEQUENCE: 89

Ile Leu Arg Trp Pro Trp Trp Pro Trp Ala Arg Lys
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 90

Ile Leu Arg Trp Pro Trp Trp Pro Trp Arg Ala Lys
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Indolicidin Analogue

<400> SEQUENCE: 91

Ile Leu Arg Trp Pro Trp Trp Pro Trp Arg Arg Ala
1               5                   10

<210> SEQ ID NO 92
<211> LENGTH: 4
<212> TYPE: PRT
<213> ORGANISM: Artificial Sequence
<220> FEATURE:
<223> OTHER INFORMATION: Octomeric branched lysine core peptide

<400> SEQUENCE: 92

Lys Lys Lys Ala
1

<210> SEQ ID NO 93
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 93

Ile Leu Lys Lys Phe Pro Phe Phe Pro Phe Arg Arg Lys
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 94

Ile Leu Arg Arg Trp Pro Trp Trp Pro Trp Arg Arg Arg
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Cationic Peptide Analogue

```
<400> SEQUENCE: 95

Ile Leu Lys Lys Trp Pro Trp Trp Pro Trp Arg Arg Lys
1               5                   10

<210> SEQ ID NO 96
<211> LENGTH: 18
<212> TYPE: PRT
<213> ORGANISM: Artificial Sequence
<220> FEATURE:
<223> OTHER INFORMATION: Cationic Peptide Analogue

<400> SEQUENCE: 96

Gly Asn Asn Arg Pro Val Tyr Ile Pro Gln Pro Arg Pro Pro His Pro
1               5                   10                  15

Arg Ile

<210> SEQ ID NO 97
<211> LENGTH: 25
<212> TYPE: PRT
<213> ORGANISM: Artificial Sequence
<220> FEATURE:
<223> OTHER INFORMATION: Cationic Peptide Analogue

<400> SEQUENCE: 97

Lys Lys Ala Ala Ala Lys Ala Ala Ala Ala Lys Ala Ala Trp Ala
1               5                   10                  15

Ala Lys Ala Ala Ala Lys Lys Lys Lys
            20                  25

<210> SEQ ID NO 98
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 98

Ile Leu Pro Trp Lys Trp Pro Trp Trp Pro Trp Arg Arg
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 99

Ile Leu Lys Lys Trp Pro Trp Trp Pro Trp Arg Arg Lys
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 100

Ile Leu Lys Lys Phe Pro Phe Phe Pro Phe Arg Arg Lys
1               5                   10

<210> SEQ ID NO 101
<211> LENGTH: 11
```

```
<212> TYPE: PRT
<213> ORGANISM: Artificial Sequence
<220> FEATURE:
<223> OTHER INFORMATION: Cationic Peptide Analogue

<400> SEQUENCE: 101

Ile Leu Trp Pro Trp Trp Pro Trp Arg Arg Lys
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 102

Ile Leu Arg Arg Trp Pro Trp Trp Pro Trp Arg Arg Arg
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 103

Ile Leu Lys Lys Trp Pro Trp Trp Pro Trp Lys Lys Lys
1               5                   10

<210> SEQ ID NO 104
<211> LENGTH: 28
<212> TYPE: PRT
<213> ORGANISM: Artificial Sequence
<220> FEATURE:
<223> OTHER INFORMATION: Cationic Peptide Analogue

<400> SEQUENCE: 104

Ile Leu Arg Trp Pro Trp Trp Pro Trp Arg Arg Lys Ile Leu Met Arg
1               5                   10                  15

Trp Pro Trp Trp Pro Trp Arg Arg Lys Met Ala Ala
            20                  25

<210> SEQ ID NO 105
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 105

Ile Leu Lys Lys Trp Ala Trp Trp Pro Trp Arg Arg Lys
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 106

Ile Leu Lys Lys Trp Pro Trp Trp Ala Trp Arg Arg Lys
1               5                   10
```

```
<210> SEQ ID NO 107
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 107

Trp Trp Lys Lys Trp Pro Trp Trp Pro Trp Arg Arg Lys
 1               5                  10

<210> SEQ ID NO 108
<211> LENGTH: 14
<212> TYPE: PRT
<213> ORGANISM: Artificial Sequence
<220> FEATURE:
<223> OTHER INFORMATION: Cationic Peptide Analogue

<400> SEQUENCE: 108

Ile Leu Lys Lys Trp Pro Trp Trp Pro Trp Arg Arg Lys Met
 1               5                  10

<210> SEQ ID NO 109
<211> LENGTH: 13
<212> TYPE: PRT
<213> ORGANISM: Artificial Sequence
<220> FEATURE:
<223> OTHER INFORMATION: Cationic Peptide Analogue

<400> SEQUENCE: 109

Ile Leu Lys Lys Trp Pro Trp Trp Pro Trp Arg Arg Met
 1               5                  10

<210> SEQ ID NO 110
<211> LENGTH: 14
<212> TYPE: PRT
<213> ORGANISM: Artificial Sequence
<220> FEATURE:
<223> OTHER INFORMATION: Cationic Peptide Analogue

<400> SEQUENCE: 110

Ile Leu Lys Lys Trp Pro Trp Trp Pro Trp Arg Arg Ile Met
 1               5                  10

<210> SEQ ID NO 111
<211> LENGTH: 12
<212> TYPE: PRT
<213> ORGANISM: Artificial Sequence
<220> FEATURE:
<223> OTHER INFORMATION: Cationic Peptide Analogue

<400> SEQUENCE: 111

Cys Leu Arg Trp Pro Trp Trp Pro Trp Arg Arg Lys
 1               5                  10

<210> SEQ ID NO 112
<211> LENGTH: 12
<212> TYPE: PRT
<213> ORGANISM: Artificial Sequence
<220> FEATURE:
<223> OTHER INFORMATION: Cationic Peptide Analogue

<400> SEQUENCE: 112

Ile Leu Lys Lys Trp Pro Trp Trp Pro Trp Arg Arg
 1               5                  10

<210> SEQ ID NO 113
```

```
<211> LENGTH: 11
<212> TYPE: PRT
<213> ORGANISM: Artificial Sequence
<220> FEATURE:
<223> OTHER INFORMATION: Cationic Peptide Analogue

<400> SEQUENCE: 113

Ile Leu Lys Lys Trp Pro Trp Trp Pro Trp Lys
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Cationic Peptide Analogue

<400> SEQUENCE: 114

Ile Leu Lys Lys Trp Pro Trp Trp Pro Trp Arg
1               5                   10

<210> SEQ ID NO 115
<211> LENGTH: 24
<212> TYPE: PRT
<213> ORGANISM: Artificial Sequence
<220> FEATURE:
<223> OTHER INFORMATION: Cationic Peptide Analogue

<400> SEQUENCE: 115

Lys Lys Trp Trp Arg Arg Val Leu Ser Gly Leu Lys Thr Ala Gly Pro
1               5                   10                  15

Ala Ile Gln Ser Val Leu Asn Lys
            20

<210> SEQ ID NO 116
<211> LENGTH: 24
<212> TYPE: PRT
<213> ORGANISM: Artificial Sequence
<220> FEATURE:
<223> OTHER INFORMATION: Cationic Peptide Analogue

<400> SEQUENCE: 116

Lys Lys Trp Trp Arg Arg Ala Leu Gln Gly Leu Lys Thr Ala Gly Pro
1               5                   10                  15

Ala Ile Gln Ser Val Leu Asn Lys
            20

<210> SEQ ID NO 117
<211> LENGTH: 20
<212> TYPE: PRT
<213> ORGANISM: Artificial Sequence
<220> FEATURE:
<223> OTHER INFORMATION: Cationic Peptide Analogue

<400> SEQUENCE: 117

Lys Lys Trp Trp Arg Arg Val Leu Lys Gly Leu Ser Ser Gly Pro Ala
1               5                   10                  15

Leu Ser Asn Val
            20

<210> SEQ ID NO 118
<211> LENGTH: 20
<212> TYPE: PRT
<213> ORGANISM: Artificial Sequence
<220> FEATURE:
<223> OTHER INFORMATION: Cationic Peptide Analogue
```

```
<400> SEQUENCE: 118

Lys Lys Trp Trp Arg Arg Ala Leu Gln Ala Leu Lys Asn Gly Leu Pro
1               5                   10                  15

Ala Leu Ile Ser
            20

<210> SEQ ID NO 119
<211> LENGTH: 26
<212> TYPE: PRT
<213> ORGANISM: Artificial Sequence
<220> FEATURE:
<223> OTHER INFORMATION: Cationic Peptide Analogue

<400> SEQUENCE: 119

Lys Trp Lys Ser Phe Ile Lys Lys Leu Thr Ser Ala Ala Lys Lys Val
1               5                   10                  15

Val Thr Thr Ala Lys Pro Leu Ile Ser Ser
            20                  25

<210> SEQ ID NO 120
<211> LENGTH: 26
<212> TYPE: PRT
<213> ORGANISM: Artificial Sequence
<220> FEATURE:
<223> OTHER INFORMATION: Cationic Peptide Analogue

<400> SEQUENCE: 120

Lys Trp Lys Leu Phe Lys Lys Ile Gly Ile Gly Ala Val Leu Lys Val
1               5                   10                  15

Leu Thr Thr Gly Leu Pro Ala Leu Ile Ser
            20                  25

<210> SEQ ID NO 121
<211> LENGTH: 28
<212> TYPE: PRT
<213> ORGANISM: Artificial Sequence
<220> FEATURE:
<223> OTHER INFORMATION: Cationic Peptide Analogue

<400> SEQUENCE: 121

Lys Trp Lys Leu Phe Lys Lys Ile Gly Ile Gly Ala Val Leu Lys Val
1               5                   10                  15

Leu Thr Thr Gly Leu Pro Ala Leu Lys Leu Thr Lys
            20                  25

<210> SEQ ID NO 122
<211> LENGTH: 26
<212> TYPE: PRT
<213> ORGANISM: Artificial Sequence
<220> FEATURE:
<223> OTHER INFORMATION: Cationic Peptide Analogue

<400> SEQUENCE: 122

Lys Trp Lys Ser Phe Ile Lys Lys Leu Thr Thr Ala Val Lys Lys Val
1               5                   10                  15

Leu Thr Thr Gly Leu Pro Ala Leu Ile Ser
            20                  25

<210> SEQ ID NO 123
<211> LENGTH: 26
<212> TYPE: PRT
<213> ORGANISM: Artificial Sequence
<220> FEATURE:
```

```
<223> OTHER INFORMATION: Cationic Peptide Analogue

<400> SEQUENCE: 123

Lys Trp Lys Ser Phe Ile Lys Asn Leu Thr Lys Val Leu Lys Lys Val
1               5                   10                  15

Val Thr Thr Ala Leu Pro Ala Leu Ile Ser
            20                  25

<210> SEQ ID NO 124
<211> LENGTH: 26
<212> TYPE: PRT
<213> ORGANISM: Artificial Sequence
<220> FEATURE:
<223> OTHER INFORMATION: Cationic Peptide Analogue

<400> SEQUENCE: 124

Lys Trp Lys Ser Phe Ile Lys Lys Leu Thr Ser Ala Ala Lys Lys Val
1               5                   10                  15

Leu Thr Thr Gly Leu Pro Ala Leu Ile Ser
            20                  25

<210> SEQ ID NO 125
<211> LENGTH: 26
<212> TYPE: PRT
<213> ORGANISM: Artificial Sequence
<220> FEATURE:
<223> OTHER INFORMATION: Cationic Peptide Analogue

<400> SEQUENCE: 125

Lys Trp Lys Leu Phe Ile Lys Lys Leu Thr Pro Ala Val Lys Lys Val
1               5                   10                  15

Leu Leu Thr Gly Leu Pro Ala Leu Ile Ser
            20                  25

<210> SEQ ID NO 126
<211> LENGTH: 18
<212> TYPE: PRT
<213> ORGANISM: Artificial Sequence
<220> FEATURE:
<223> OTHER INFORMATION: Cationic Peptide Analogue

<400> SEQUENCE: 126

Gly Lys Pro Arg Pro Tyr Ser Pro Ile Pro Thr Ser Pro Arg Pro Ile
1               5                   10                  15

Arg Tyr

<210> SEQ ID NO 127
<211> LENGTH: 12
<212> TYPE: PRT
<213> ORGANISM: Artificial Sequence
<220> FEATURE:
<223> OTHER INFORMATION: Cationic Peptide Analogue

<400> SEQUENCE: 127

Arg Leu Ala Arg Ile Val Val Ile Arg Val Ala Arg
1               5                   10

<210> SEQ ID NO 128
<211> LENGTH: 26
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
```

```
<222> LOCATION: (4)...(4)
<223> OTHER INFORMATION: Xaa = Hydrophilic Residue
<220> FEATURE:
<221> NAME/KEY: VARIANT
<222> LOCATION: (5)...(6)
<223> OTHER INFORMATION: Xaa = Hydrophobic Residue
<220> FEATURE:
<221> NAME/KEY: VARIANT
<222> LOCATION: (7)...(8)
<223> OTHER INFORMATION: Xaa = Hydrophilic Residue
<220> FEATURE:
<221> NAME/KEY: VARIANT
<222> LOCATION: (9)...(9)
<223> OTHER INFORMATION: Xaa = Hydrophobic Residue
<220> FEATURE:
<221> NAME/KEY: VARIANT
<222> LOCATION: (10)...(11)
<223> OTHER INFORMATION: Xaa = Hydrophilic Residue
<220> FEATURE:
<221> NAME/KEY: VARIANT
<222> LOCATION: (12)...(13)
<223> OTHER INFORMATION: Xaa = Hydrophobic Residue
<220> FEATURE:
<221> NAME/KEY: VARIANT
<222> LOCATION: (14)...(15)
<223> OTHER INFORMATION: Xaa = Hydrophilic Residue

<400> SEQUENCE: 128

Lys Trp Lys Xaa Xaa Xaa Xaa Xaa Xaa Xaa Xaa Xaa Xaa Xaa Val
 1               5                  10                  15

Leu Thr Thr Gly Leu Pro Ala Leu Ile Ser
            20                  25

<210> SEQ ID NO 129
<211> LENGTH: 26
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (4)...(4)
<223> OTHER INFORMATION: Xaa = Hydrophilic Residue
<220> FEATURE:
<221> NAME/KEY: VARIANT
<222> LOCATION: (5)...(6)
<223> OTHER INFORMATION: Xaa = Hydrophobic Residue
<220> FEATURE:
<221> NAME/KEY: VARIANT
<222> LOCATION: (7)...(8)
<223> OTHER INFORMATION: Xaa = Hydrophilic Residue
<220> FEATURE:
<221> NAME/KEY: VARIANT
<222> LOCATION: (9)...(9)
<223> OTHER INFORMATION: Xaa = Hydrophobic Residue
<220> FEATURE:
<221> NAME/KEY: VARIANT
<222> LOCATION: (10)...(11)
<223> OTHER INFORMATION: Xaa = Hydrophilic Residue
<220> FEATURE:
<221> NAME/KEY: VARIANT
<222> LOCATION: (12)...(13)
<223> OTHER INFORMATION: Xaa = Hydrophobic Residue
<220> FEATURE:
<221> NAME/KEY: VARIANT
<222> LOCATION: (14)...(15)
<223> OTHER INFORMATION: Xaa = Hydrophilic Residue

<400> SEQUENCE: 129

Lys Trp Lys Xaa Xaa Xaa Xaa Xaa Xaa Xaa Xaa Xaa Xaa Xaa Val
 1               5                  10                  15

Val Thr Thr Ala Lys Pro Leu Ile Ser Ser
            20                  25
```

```
<210> SEQ ID NO 130
<211> LENGTH: 26
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (4)...(4)
<223> OTHER INFORMATION: Xaa = Hydrophilic Residue
<220> FEATURE:
<221> NAME/KEY: VARIANT
<222> LOCATION: (5)...(6)
<223> OTHER INFORMATION: Xaa = Hydrophobic Residue
<220> FEATURE:
<221> NAME/KEY: VARIANT
<222> LOCATION: (7)...(8)
<223> OTHER INFORMATION: Xaa = Hydrophilic Residue
<220> FEATURE:
<221> NAME/KEY: VARIANT
<222> LOCATION: (9)...(9)
<223> OTHER INFORMATION: Xaa = Hydrophobic Residue
<220> FEATURE:
<221> NAME/KEY: VARIANT
<222> LOCATION: (10)...(11)
<223> OTHER INFORMATION: Xaa = Hydrophilic Residue
<220> FEATURE:
<221> NAME/KEY: VARIANT
<222> LOCATION: (12)...(13)
<223> OTHER INFORMATION: Xaa = Hydrophobic Residue
<220> FEATURE:
<221> NAME/KEY: VARIANT
<222> LOCATION: (14)...(15)
<223> OTHER INFORMATION: Xaa = Hydrophilic Residue

<400> SEQUENCE: 130

Lys Trp Lys Xaa Xaa Xaa Xaa Xaa Xaa Xaa Xaa Xaa Xaa Xaa Xaa Ile
 1               5                   10                  15

Leu Thr Thr Gly Leu Pro Ala Leu Ile Ser
            20                  25

<210> SEQ ID NO 131
<211> LENGTH: 26
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (4)...(4)
<223> OTHER INFORMATION: Xaa = Hydrophilic Residue
<220> FEATURE:
<221> NAME/KEY: VARIANT
<222> LOCATION: (5)...(6)
<223> OTHER INFORMATION: Xaa = Hydrophobic Residue
<220> FEATURE:
<221> NAME/KEY: VARIANT
<222> LOCATION: (7)...(8)
<223> OTHER INFORMATION: Xaa = Hydrophilic Residue
<220> FEATURE:
<221> NAME/KEY: VARIANT
<222> LOCATION: (9)...(9)
<223> OTHER INFORMATION: Xaa = Hydrophobic Residue
<220> FEATURE:
<221> NAME/KEY: VARIANT
<222> LOCATION: (10)...(11)
<223> OTHER INFORMATION: Xaa = Hydrophilic Residue
<220> FEATURE:
<221> NAME/KEY: VARIANT
<222> LOCATION: (12)...(13)
<223> OTHER INFORMATION: Xaa = Hydrophobic Residue
<220> FEATURE:
<221> NAME/KEY: VARIANT
<222> LOCATION: (14)...(15)
<223> OTHER INFORMATION: Xaa = Hydrophilic Residue
```

```
<400> SEQUENCE: 131

Lys Trp Lys Xaa Xaa Xaa Xaa Xaa Xaa Xaa Xaa Xaa Xaa Xaa Gly
1               5                   10                  15

Gly Leu Leu Ser Asn Ile Val Thr Ser Leu
            20                  25

<210> SEQ ID NO 132
<211> LENGTH: 26
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (4)...(4)
<223> OTHER INFORMATION: Xaa = Hydrophilic Residue
<220> FEATURE:
<221> NAME/KEY: VARIANT
<222> LOCATION: (5)...(6)
<223> OTHER INFORMATION: Xaa = Hydrophobic Residue
<220> FEATURE:
<221> NAME/KEY: VARIANT
<222> LOCATION: (7)...(8)
<223> OTHER INFORMATION: Xaa = Hydrophilic Residue
<220> FEATURE:
<221> NAME/KEY: VARIANT
<222> LOCATION: (9)...(9)
<223> OTHER INFORMATION: Xaa = Hydrophobic Residue
<220> FEATURE:
<221> NAME/KEY: VARIANT
<222> LOCATION: (10)...(11)
<223> OTHER INFORMATION: Xaa = Hydrophilic Residue
<220> FEATURE:
<221> NAME/KEY: VARIANT
<222> LOCATION: (12)...(13)
<223> OTHER INFORMATION: Xaa = Hydrophobic Residue
<220> FEATURE:
<221> NAME/KEY: VARIANT
<222> LOCATION: (14)...(15)
<223> OTHER INFORMATION: Xaa = Hydrophilic Residue

<400> SEQUENCE: 132

Lys Trp Lys Xaa Xaa Xaa Xaa Xaa Xaa Xaa Xaa Xaa Xaa Xaa Gly
1               5                   10                  15

Pro Ile Leu Ala Asn Leu Val Ser Ile Val
            20                  25

<210> SEQ ID NO 133
<211> LENGTH: 20
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (7)...(8)
<223> OTHER INFORMATION: Xaa = Hydrophobic Residue
<220> FEATURE:
<221> NAME/KEY: VARIANT
<222> LOCATION: (9)...(9)
<223> OTHER INFORMATION: Xaa = Hydrophilic Residue
<220> FEATURE:
<221> NAME/KEY: VARIANT
<222> LOCATION: (10)...(11)
<223> OTHER INFORMATION: Xaa = Hydrophobic Residue
<220> FEATURE:
<221> NAME/KEY: VARIANT
<222> LOCATION: (12)...(13)
<223> OTHER INFORMATION: Xaa = Hydrophilic Residue

<400> SEQUENCE: 133
```

```
Lys Lys Trp Trp Arg Arg Xaa Xaa Xaa Xaa Xaa Xaa Gly Pro Ala
 1               5                  10                  15

Leu Ser Asn Val
            20

<210> SEQ ID NO 134
<211> LENGTH: 30
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(30)
<223> OTHER INFORMATION: Xaa = Any Amino Acid

<400> SEQUENCE: 134

Lys Lys Trp Trp Arg Arg Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa
            20                  25                  30

<210> SEQ ID NO 135
<211> LENGTH: 29
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(29)
<223> OTHER INFORMATION: Xaa = Any Amino Acid

<400> SEQUENCE: 135

Lys Lys Trp Trp Arg Arg Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa
            20                  25

<210> SEQ ID NO 136
<211> LENGTH: 28
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(28)
<223> OTHER INFORMATION: Xaa = Any Amino Acid

<400> SEQUENCE: 136

Lys Lys Trp Trp Arg Arg Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
            20                  25

<210> SEQ ID NO 137
<211> LENGTH: 27
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(27)
<223> OTHER INFORMATION: Xaa = Any Amino Acid

<400> SEQUENCE: 137
```

Lys Lys Trp Trp Arg Arg Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 138
<211> LENGTH: 26
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(26)
<223> OTHER INFORMATION: Xaa = Any Amino Acid

<400> SEQUENCE: 138

Lys Lys Trp Trp Arg Arg Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 139
<211> LENGTH: 25
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(25)
<223> OTHER INFORMATION: Xaa = Any Amino Acid

<400> SEQUENCE: 139

Lys Lys Trp Trp Arg Arg Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 140
<211> LENGTH: 24
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(24)
<223> OTHER INFORMATION: Xaa = Any Amino Acid

<400> SEQUENCE: 140

Lys Lys Trp Trp Arg Arg Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 141
<211> LENGTH: 23
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(23)
<223> OTHER INFORMATION: Xaa = Any Amino Acid

```
<400> SEQUENCE: 141

Lys Lys Trp Trp Arg Arg Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 142
<211> LENGTH: 22
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(22)
<223> OTHER INFORMATION: Xaa = Any Amino Acid

<400> SEQUENCE: 142

Lys Lys Trp Trp Arg Arg Xaa Xaa Xaa Xaa Xaa Xaa Xaa Xaa Xaa
1               5                   10                  15

Xaa Xaa Xaa Xaa Xaa Xaa
            20

<210> SEQ ID NO 143
<211> LENGTH: 21
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(21)
<223> OTHER INFORMATION: Xaa = Any Amino Acid

<400> SEQUENCE: 143

Lys Lys Trp Trp Arg Arg Xaa Xaa Xaa Xaa Xaa Xaa Xaa Xaa Xaa
1               5                   10                  15

Xaa Xaa Xaa Xaa Xaa
            20

<210> SEQ ID NO 144
<211> LENGTH: 20
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(20)
<223> OTHER INFORMATION: Xaa = Any Amino Acid

<400> SEQUENCE: 144

Lys Lys Trp Trp Arg Arg Xaa Xaa Xaa Xaa Xaa Xaa Xaa Xaa Xaa
1               5                   10                  15

Xaa Xaa Xaa Xaa
            20

<210> SEQ ID NO 145
<211> LENGTH: 29
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(29)
<223> OTHER INFORMATION: Xaa = Any Amino Acid
```

```
<400> SEQUENCE: 145

Lys Lys Trp Trp Lys Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa
                20                  25

<210> SEQ ID NO 146
<211> LENGTH: 28
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(28)
<223> OTHER INFORMATION: Xaa = Any Amino Acid

<400> SEQUENCE: 146

Lys Lys Trp Trp Lys Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
                20                  25

<210> SEQ ID NO 147
<211> LENGTH: 27
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(27)
<223> OTHER INFORMATION: Xaa = Any Amino Acid

<400> SEQUENCE: 147

Lys Lys Trp Trp Lys Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa
                20                  25

<210> SEQ ID NO 148
<211> LENGTH: 26
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(26)
<223> OTHER INFORMATION: Xaa = Any Amino Acid

<400> SEQUENCE: 148

Lys Lys Trp Trp Lys Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa
                20                  25

<210> SEQ ID NO 149
<211> LENGTH: 25
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(25)
```

<223> OTHER INFORMATION: Xaa = Any Amino Acid

<400> SEQUENCE: 149

Lys Lys Trp Trp Lys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 150
<211> LENGTH: 24
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(24)
<223> OTHER INFORMATION: Xaa = Any Amino Acid

<400> SEQUENCE: 150

Lys Lys Trp Trp Lys Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 151
<211> LENGTH: 23
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(23)
<223> OTHER INFORMATION: Xaa = Any Amino Acid

<400> SEQUENCE: 151

Lys Lys Trp Trp Lys Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 152
<211> LENGTH: 22
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(22)
<223> OTHER INFORMATION: Xaa = Any Amino Acid

<400> SEQUENCE: 152

Lys Lys Trp Trp Lys Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 153
<211> LENGTH: 21
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT

```
<222> LOCATION: (1)...(21)
<223> OTHER INFORMATION: Xaa = Any Amino Acid

<400> SEQUENCE: 153

Lys Lys Trp Trp Lys Xaa Xaa Xaa Xaa Xaa Xaa Xaa Xaa Xaa Xaa
 1               5                  10                  15

Xaa Xaa Xaa Xaa Xaa
            20

<210> SEQ ID NO 154
<211> LENGTH: 20
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(20)
<223> OTHER INFORMATION: Xaa = Any Amino Acid

<400> SEQUENCE: 154

Lys Lys Trp Trp Lys Xaa Xaa Xaa Xaa Xaa Xaa Xaa Xaa Xaa Xaa
 1               5                  10                  15

Xaa Xaa Xaa Xaa
            20

<210> SEQ ID NO 155
<211> LENGTH: 19
<212> TYPE: PRT
<213> ORGANISM: Artificial Sequence
<220> FEATURE:
<223> OTHER INFORMATION: Fusion Peptides
<220> FEATURE:
<221> NAME/KEY: VARIANT
<222> LOCATION: (1)...(19)
<223> OTHER INFORMATION: Xaa = Any Amino Acid

<400> SEQUENCE: 155

Lys Lys Trp Trp Lys Xaa Xaa Xaa Xaa Xaa Xaa Xaa Xaa Xaa Xaa
 1               5                  10                  15

Xaa Xaa Xaa

<210> SEQ ID NO 156
<211> LENGTH: 34
<212> TYPE: PRT
<213> ORGANISM: Apis mellifera

<400> SEQUENCE: 156

Tyr Val Pro Leu Pro Asn Val Pro Gln Pro Gly Arg Arg Pro Phe Pro
 1               5                  10                  15

Thr Phe Pro Gly Gln Gly Pro Phe Asn Pro Lys Ile Lys Trp Pro Gln
            20                  25                  30

Gly Tyr

<210> SEQ ID NO 157
<211> LENGTH: 34
<212> TYPE: PRT
<213> ORGANISM: Drosophila melanogaster

<400> SEQUENCE: 157

Val Phe Ile Asp Ile Leu Asp Lys Val Glu Asn Ala Ile His Asn Ala
 1               5                  10                  15

Ala Gln Val Gly Ile Gly Phe Ala Lys Pro Phe Glu Lys Leu Ile Asn
            20                  25                  30
```

Pro Lys

<210> SEQ ID NO 158
<211> LENGTH: 18
<212> TYPE: PRT
<213> ORGANISM: Apis mellifera

<400> SEQUENCE: 158

Gly Asn Asn Arg Pro Val Tyr Ile Pro Gln Pro Arg Pro Pro His Pro
1               5                   10                  15

Arg Ile

<210> SEQ ID NO 159
<211> LENGTH: 18
<212> TYPE: PRT
<213> ORGANISM: Apis mellifera

<400> SEQUENCE: 159

Gly Asn Asn Arg Pro Val Tyr Ile Pro Gln Pro Arg Pro Pro His Pro
1               5                   10                  15

Arg Leu

<210> SEQ ID NO 160
<211> LENGTH: 18
<212> TYPE: PRT
<213> ORGANISM: Apis mellifera

<400> SEQUENCE: 160

Gly Asn Asn Arg Pro Ile Tyr Ile Pro Gln Pro Arg Pro Pro His Pro
1               5                   10                  15

Arg Leu

<210> SEQ ID NO 161
<211> LENGTH: 12
<212> TYPE: PRT
<213> ORGANISM: Bos taurus

<400> SEQUENCE: 161

Arg Leu Cys Arg Ile Val Val Ile Arg Val Cys Arg
1               5                   10

<210> SEQ ID NO 162
<211> LENGTH: 42
<212> TYPE: PRT
<213> ORGANISM: Bos taurus

<400> SEQUENCE: 162

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
                20                  25                  30

Pro Pro Phe Arg Pro Pro Leu Arg Phe Pro
                35                  40

<210> SEQ ID NO 163
<211> LENGTH: 59
<212> TYPE: PRT
<213> ORGANISM: Bos taurus

<400> SEQUENCE: 163

Arg Arg Ile Arg Pro Arg Pro Pro Arg Leu Pro Arg Pro Arg Pro Arg

```
                1               5                  10                 15
Pro Leu Pro Phe Pro Arg Pro Gly Pro Arg Pro Ile Pro Arg Pro Leu
                        20                 25                 30

Pro Phe Pro Arg Pro Gly Pro Arg Pro Ile Pro Arg Pro Leu Pro Phe
                35                 40                 45

Pro Arg Pro Gly Pro Arg Pro Ile Pro Arg Pro
        50                 55
```

<210> SEQ ID NO 164
<211> LENGTH: 37
<212> TYPE: PRT
<213> ORGANISM: Manduca sexta

<400> SEQUENCE: 164

```
Trp Asn Pro Phe Lys Glu Leu Glu Arg Ala Gly Gln Arg Val Arg Asp
  1               5                  10                 15

Ala Val Ile Ser Ala Ala Pro Val Ala Thr Val Gly Gln Ala Ala
                20                 25                 30

Ala Ile Ala Arg Gly
             35
```

<210> SEQ ID NO 165
<211> LENGTH: 37
<212> TYPE: PRT
<213> ORGANISM: Manduca sexta

<400> SEQUENCE: 165

```
Trp Asn Pro Phe Lys Glu Leu Glu Arg Ala Gly Gln Arg Val Arg Asp
  1               5                  10                 15

Ala Ile Ile Ser Ala Gly Pro Val Ala Thr Val Gly Gln Ala Ala
                20                 25                 30

Ala Ile Ala Arg Gly
             35
```

<210> SEQ ID NO 166
<211> LENGTH: 37
<212> TYPE: PRT
<213> ORGANISM: Manduca sexta

<400> SEQUENCE: 166

```
Trp Asn Pro Phe Lys Glu Leu Glu Arg Ala Gly Gln Arg Val Arg Asp
  1               5                  10                 15

Ala Ile Ile Ser Ala Ala Pro Val Ala Thr Val Gly Gln Ala Ala
                20                 25                 30

Ala Ile Ala Arg Gly
             35
```

<210> SEQ ID NO 167
<211> LENGTH: 37
<212> TYPE: PRT
<213> ORGANISM: Manduca sexta

<400> SEQUENCE: 167

```
Trp Asn Pro Phe Lys Glu Leu Glu Arg Ala Gly Gln Arg Val Arg Asp
  1               5                  10                 15

Ala Val Ile Ser Ala Ala Ala Val Ala Thr Val Gly Gln Ala Ala Ala
                20                 25                 30

Ile Ala Arg Gly Gly
             35
```

```
<210> SEQ ID NO 168
<211> LENGTH: 24
<212> TYPE: PRT
<213> ORGANISM: Bombina variegata

<400> SEQUENCE: 168

Gly Ile Gly Ala Leu Ser Ala Lys Gly Ala Leu Lys Gly Leu Ala Lys
1               5                   10                  15

Gly Leu Ala Glx His Phe Ala Asn
            20

<210> SEQ ID NO 169
<211> LENGTH: 27
<212> TYPE: PRT
<213> ORGANISM: Bombina orientalis

<400> SEQUENCE: 169

Gly Ile Gly Ala Ser Ile Leu Ser Ala Gly Lys Ser Ala Leu Lys Gly
1               5                   10                  15

Leu Ala Lys Gly Leu Ala Glu His Phe Ala Asn
            20                  25

<210> SEQ ID NO 170
<211> LENGTH: 27
<212> TYPE: PRT
<213> ORGANISM: Bombina orientalis

<400> SEQUENCE: 170

Gly Ile Gly Ser Ala Ile Leu Ser Ala Gly Lys Ser Ala Leu Lys Gly
1               5                   10                  15

Leu Ala Lys Gly Leu Ala Glu His Phe Ala Asn
            20                  25

<210> SEQ ID NO 171
<211> LENGTH: 17
<212> TYPE: PRT
<213> ORGANISM: Megabombus pennsylvanicus

<400> SEQUENCE: 171

Ile Lys Ile Thr Thr Met Leu Ala Lys Leu Gly Lys Val Leu Ala His
1               5                   10                  15

Val

<210> SEQ ID NO 172
<211> LENGTH: 17
<212> TYPE: PRT
<213> ORGANISM: Megabombus pennsylvanicus

<400> SEQUENCE: 172

Ser Lys Ile Thr Asp Ile Leu Ala Lys Leu Gly Lys Val Leu Ala His
1               5                   10                  15

Val

<210> SEQ ID NO 173
<211> LENGTH: 58
<212> TYPE: PRT
<213> ORGANISM: Bos taurus

<400> SEQUENCE: 173

Arg Pro Asp Phe Cys Leu Glu Pro Pro Tyr Thr Gly Pro Cys Lys Ala
1               5                   10                  15
```

```
Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
         35                  40                  45

Glu Asp Cys Met Arg Thr Cys Gly Gly Ala
     50                  55

<210> SEQ ID NO 174
<211> LENGTH: 24
<212> TYPE: PRT
<213> ORGANISM: Rana esculenta

<400> SEQUENCE: 174

Phe Leu Pro Leu Leu Ala Gly Leu Ala Ala Asn Phe Leu Pro Lys Ile
1               5                   10                  15

Phe Cys Lys Ile Thr Arg Lys Cys
             20

<210> SEQ ID NO 175
<211> LENGTH: 33
<212> TYPE: PRT
<213> ORGANISM: Rana esculenta

<400> SEQUENCE: 175

Gly Ile Met Asp Thr Leu Lys Asn Leu Ala Lys Thr Ala Gly Lys Gly
1               5                   10                  15

Ala Leu Gln Ser Leu Leu Asn Lys Ala Ser Cys Lys Leu Ser Gly Gln
             20                  25                  30

Cys

<210> SEQ ID NO 176
<211> LENGTH: 37
<212> TYPE: PRT
<213> ORGANISM: Hyalophora cecropia

<400> SEQUENCE: 176

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
             20                  25                  30

Thr Gln Ile Ala Lys
         35

<210> SEQ ID NO 177
<211> LENGTH: 35
<212> TYPE: PRT
<213> ORGANISM: Hyalophora cecropia

<400> SEQUENCE: 177

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
             20                  25                  30

Lys Ala Leu
         35

<210> SEQ ID NO 178
<211> LENGTH: 40
<212> TYPE: PRT
<213> ORGANISM: Drosophila melanogaster
```

```
<400> SEQUENCE: 178

Gly Trp Leu Lys Lys Leu Gly Lys Arg Ile Glu Arg Ile Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg Gly
        35                  40

<210> SEQ ID NO 179
<211> LENGTH: 36
<212> TYPE: PRT
<213> ORGANISM: Hyalophora cecropia

<400> SEQUENCE: 179

Trp Asn Pro Phe Lys Glu Leu Glu Lys Val Gly Gln Arg Val Arg Asp
1               5                   10                  15

Ala Val Ile Ser Ala Gly Pro Ala Val Ala Thr Val Ala Gln Ala Thr
            20                  25                  30

Ala Leu Ala Lys
        35

<210> SEQ ID NO 180
<211> LENGTH: 31
<212> TYPE: PRT
<213> ORGANISM: Sus scrofa

<400> SEQUENCE: 180

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 181
<211> LENGTH: 37
<212> TYPE: PRT
<213> ORGANISM: Leiurus quin-questriatus hebraeus

<400> SEQUENCE: 181

Glx Phe Thr Asn Val Ser Cys Thr Thr Ser Lys Glu Cys Trp Ser Val
1               5                   10                  15

Cys Gln Arg Leu His Asn Thr Ser Arg Gly Lys Cys Met Asn Lys Lys
            20                  25                  30

Cys Arg Cys Tyr Ser
        35

<210> SEQ ID NO 182
<211> LENGTH: 13
<212> TYPE: PRT
<213> ORGANISM: Vespa crabo

<400> SEQUENCE: 182

Phe Leu Pro Leu Ile Leu Arg Lys Ile Val Thr Ala Leu
1               5                   10

<210> SEQ ID NO 183
<211> LENGTH: 35
<212> TYPE: PRT
<213> ORGANISM: Mus musculus

<400> SEQUENCE: 183

Leu Arg Asp Leu Val Cys Tyr Cys Arg Ser Arg Gly Cys Lys Gly Arg
```

```
                1               5                  10                  15
Glu Arg Met Asn Gly Thr Cys Arg Lys Gly His Leu Leu Tyr Thr Leu
                    20                  25                  30

Cys Cys Arg
        35

<210> SEQ ID NO 184
<211> LENGTH: 35
<212> TYPE: PRT
<213> ORGANISM: Mus musculus

<400> SEQUENCE: 184

Leu Arg Asp Leu Val Cys Tyr Cys Arg Thr Arg Gly Cys Lys Arg Arg
 1               5                  10                  15

Glu Arg Met Asn Gly Thr Cys Arg Lys Gly His Leu Met Tyr Thr Leu
                    20                  25                  30

Cys Cys Arg
        35

<210> SEQ ID NO 185
<211> LENGTH: 33
<212> TYPE: PRT
<213> ORGANISM: Oryctolagus cuniculus

<400> SEQUENCE: 185

Val Val Cys Ala Cys Arg Arg Ala Leu Cys Leu Pro Arg Glu Arg Arg
 1               5                  10                  15

Ala Gly Phe Cys Arg Ile Arg Gly Arg Ile His Pro Leu Cys Cys Arg
                    20                  25                  30

Arg

<210> SEQ ID NO 186
<211> LENGTH: 33
<212> TYPE: PRT
<213> ORGANISM: Oryctolagus cuniculus

<400> SEQUENCE: 186

Val Val Cys Ala Cys Arg Arg Ala Leu Cys Leu Pro Leu Glu Arg Arg
 1               5                  10                  15

Ala Gly Phe Cys Arg Ile Arg Gly Arg Ile His Pro Leu Cys Cys Arg
                    20                  25                  30

Arg

<210> SEQ ID NO 187
<211> LENGTH: 31
<212> TYPE: PRT
<213> ORGANISM: Cavia cutteri

<400> SEQUENCE: 187

Arg Arg Cys Ile Cys Thr Thr Arg Thr Cys Arg Phe Pro Tyr Arg Arg
 1               5                  10                  15

Leu Gly Thr Cys Ile Phe Gln Asn Arg Val Tyr Thr Phe Cys Cys
                    20                  25                  30

<210> SEQ ID NO 188
<211> LENGTH: 31
<212> TYPE: PRT
<213> ORGANISM: Cavia cutteri

<400> SEQUENCE: 188
```

-continued

```
Arg Arg Cys Ile Cys Thr Thr Arg Thr Cys Arg Phe Pro Tyr Arg Arg
 1               5                  10                  15

Leu Gly Thr Cys Leu Phe Gln Asn Arg Val Tyr Thr Phe Cys Cys
            20                  25                  30
```

<210> SEQ ID NO 189
<211> LENGTH: 30
<212> TYPE: PRT
<213> ORGANISM: Homo Sapien

<400> SEQUENCE: 189

```
Ala Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
            20                  25                  30
```

<210> SEQ ID NO 190
<211> LENGTH: 29
<212> TYPE: PRT
<213> ORGANISM: Homo Sapien

<400> SEQUENCE: 190

```
Cys Tyr Cys Arg Ile Pro Ala Cys Ile Ala Gly Glu Arg Arg Tyr Gly
 1               5                  10                  15

Thr Cys Ile Tyr Gln Gly Arg Leu Trp Ala Phe Cys Cys
            20                  25
```

<210> SEQ ID NO 191
<211> LENGTH: 33
<212> TYPE: PRT
<213> ORGANISM: Oryctolagus cuniculus

<400> SEQUENCE: 191

```
Val Val Cys Ala Cys Arg Arg Ala Leu Cys Leu Pro Arg Glu Arg Arg
 1               5                  10                  15

Ala Gly Phe Cys Arg Ile Arg Gly Arg Ile His Pro Leu Cys Cys Arg
            20                  25                  30

Arg
```

<210> SEQ ID NO 192
<211> LENGTH: 33
<212> TYPE: PRT
<213> ORGANISM: Oryctolagus cuniculus

<400> SEQUENCE: 192

```
Val Val Cys Ala Cys Arg Arg Ala Leu Cys Leu Pro Leu Glu Arg Arg
 1               5                  10                  15

Ala Gly Phe Cys Arg Ile Arg Gly Arg Ile His Pro Leu Cys Cys Arg
            20                  25                  30

Arg
```

<210> SEQ ID NO 193
<211> LENGTH: 32
<212> TYPE: PRT
<213> ORGANISM: Rattus norvegicus

<400> SEQUENCE: 193

```
Val Thr Cys Tyr Cys Arg Arg Thr Arg Cys Gly Phe Arg Glu Arg Leu
 1               5                  10                  15

Ser Gly Ala Cys Gly Tyr Arg Gly Arg Ile Tyr Arg Leu Cys Cys Arg
            20                  25                  30
```

<210> SEQ ID NO 194
<211> LENGTH: 32
<212> TYPE: PRT
<213> ORGANISM: Rattus norvegicus

<400> SEQUENCE: 194

Val Thr Cys Tyr Cys Arg Ser Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 195
<211> LENGTH: 38
<212> TYPE: PRT
<213> ORGANISM: Bos taurus

<400> SEQUENCE: 195

Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
            20                  25                  30

Lys Cys Cys Arg Ser Trp
        35

<210> SEQ ID NO 196
<211> LENGTH: 40
<212> TYPE: PRT
<213> ORGANISM: Bos taurus

<400> SEQUENCE: 196

Val Arg Asn His Val Thr Cys Arg Ile Asn Arg Gly Phe Cys Val Pro
1               5                   10                  15

Ile Arg Cys Pro Gly Arg Thr Arg Gln Ile Gly Thr Cys Phe Gly Pro
            20                  25                  30

Arg Ile Lys Cys Cys Arg Ser Trp
        35                  40

<210> SEQ ID NO 197
<211> LENGTH: 38
<212> TYPE: PRT
<213> ORGANISM: Bos taurus

<400> SEQUENCE: 197

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
        35

<210> SEQ ID NO 198
<211> LENGTH: 40
<212> TYPE: PRT
<213> ORGANISM: Sacrophaga peregrina

<400> SEQUENCE: 198

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

```
Lys Ala Val Cys Val Cys Arg Asn
        35                  40

<210> SEQ ID NO 199
<211> LENGTH: 38
<212> TYPE: PRT
<213> ORGANISM: Aeschna cyanea

<400> SEQUENCE: 199

Gly Phe Gly Cys Pro Leu Asp Gln Met Gln Cys His Arg His Cys Gln
 1               5                  10                  15

Thr Ile Thr Gly Arg Ser Gly Gly Tyr Cys Ser Gly Pro Leu Lys Leu
             20                  25                  30

Thr Cys Thr Cys Tyr Arg
             35

<210> SEQ ID NO 200
<211> LENGTH: 38
<212> TYPE: PRT
<213> ORGANISM: Leiurus quinquestriatus

<400> SEQUENCE: 200

Gly Phe Gly Cys Pro Leu Asn Gln Gly Ala Cys His Arg His Cys Arg
 1               5                  10                  15

Ser Ile Arg Arg Arg Gly Gly Tyr Cys Ala Gly Phe Phe Lys Gln Thr
             20                  25                  30

Cys Thr Cys Tyr Arg Asn
             35

<210> SEQ ID NO 201
<211> LENGTH: 32
<212> TYPE: PRT
<213> ORGANISM: Phyllomedusa sauvagii

<400> SEQUENCE: 201

Ala Leu Trp Lys Thr Met Leu Lys Lys Leu Gly Thr Met Ala Leu His
 1               5                  10                  15

Ala Gly Lys Ala Ala Leu Gly Ala Ala Asp Thr Ile Ser Gln Thr Gln
             20                  25                  30

EQ ID NO 202
<211> LENGTH: 19
<212> TYPE: PRT
<213> ORGANISM: Drosophila melanogaster

<400> SEQUENCE: 202

Gly Lys Pro Arg Pro Tyr Ser Pro Arg Pro Thr Ser His Pro Arg Pro
 1               5                  10                  15

Ile Arg Val

EQ ID NO 203
ENGTH: 46
<212> TYPE: PRT
<213> ORGANISM: Rana esculenta

<400> SEQUENCE: 203

Gly Ile Phe Ser Lys Leu Gly Arg Lys Lys Ile Lys Asn Leu Leu Ile
 1               5                  10                  15

Ser Gly Leu Lys Asn Val Gly Lys Glu Val Gly Met Asp Val Val Arg
```

```
                20                  25                  30
Thr Gly Ile Asp Ile Ala Gly Cys Lys Ile Lys Gly Glu Cys
        35                  40                  45
```

<210> SEQ ID NO 204
<211> LENGTH: 13
<212> TYPE: PRT
<213> ORGANISM: Bos taurus

<400> SEQUENCE: 204

```
Ile Leu Pro Trp Lys Trp Pro Trp Trp Pro Trp Arg Arg
1               5                   10
```

<210> SEQ ID NO 205
<211> LENGTH: 25
<212> TYPE: PRT
<213> ORGANISM: Bos taurus

<400> SEQUENCE: 205

```
Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25
```

<210> SEQ ID NO 206
<211> LENGTH: 34
<212> TYPE: PRT
<213> ORGANISM: Lactococcus lactis

<400> SEQUENCE: 206

```
Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys
```

<210> SEQ ID NO 207
<211> LENGTH: 34
<212> TYPE: PRT
<213> ORGANISM: Staphylococcus epidermidis

<400> SEQUENCE: 207

```
Thr Ala Gly Pro Ala Ile Arg Ala Ser Val Lys Gln Cys Gln Lys Thr
1               5                   10                  15

Leu Lys Ala Thr Arg Leu Phe Thr Val Ser Cys Lys Gly Lys Asn Gly
            20                  25                  30

Cys Lys
```

<210> SEQ ID NO 208
<211> LENGTH: 56
<212> TYPE: PRT
<213> ORGANISM: Bacillus subtilis

<400> SEQUENCE: 208

```
Met Ser Lys Phe Asp Asp Phe Asp Leu Asp Val Val Lys Val Ser Lys
1               5                   10                  15

Gln Asp Ser Lys Ile Thr Pro Gln Trp Lys Ser Glu Ser Leu Cys Thr
            20                  25                  30

Pro Gly Cys Val Thr Gly Ala Leu Gln Thr Cys Phe Leu Gln Thr Leu
        35                  40                  45
```

```
Thr Cys Asn Cys Lys Ile Ser Lys
     50                  55
```

<210> SEQ ID NO 209
<211> LENGTH: 37
<212> TYPE: PRT
<213> ORGANISM: Leuconostoc gelidum

<400> SEQUENCE: 209

```
Lys Tyr Tyr Gly Asn Gly Val His Cys Thr Lys Ser Gly Cys Ser Val
  1               5                  10                  15

Asn Trp Gly Glu Ala Phe Ser Ala Gly Val His Arg Leu Ala Asn Gly
             20                  25                  30

Gly Asn Gly Phe Trp
             35
```

<210> SEQ ID NO 210
<211> LENGTH: 23
<212> TYPE: PRT
<213> ORGANISM: Xenopus laevis

<400> SEQUENCE: 210

```
Gly Ile Gly Lys Phe Leu His Ser Ala Gly Lys Phe Gly Lys Ala Phe
  1               5                  10                  15

Val Gly Glu Ile Met Lys Ser
             20
```

<210> SEQ ID NO 211
<211> LENGTH: 23
<212> TYPE: PRT
<213> ORGANISM: Xenopus laevis

<400> SEQUENCE: 211

```
Gly Ile Gly Lys Phe Leu His Ser Ala Lys Lys Phe Gly Lys Ala Phe
  1               5                  10                  15

Val Gly Glu Ile Met Asn Ser
             20
```

<210> SEQ ID NO 212
<211> LENGTH: 21
<212> TYPE: PRT
<213> ORGANISM: Xenopus laevis

<400> SEQUENCE: 212

```
Gly Met Ala Ser Lys Ala Gly Ala Ile Ala Gly Lys Ile Ala Lys Val
  1               5                  10                  15

Ala Leu Lys Ala Leu
             20
```

<210> SEQ ID NO 213
<211> LENGTH: 24
<212> TYPE: PRT
<213> ORGANISM: Xenopus laevis

<400> SEQUENCE: 213

```
Gly Val Leu Ser Asn Val Ile Gly Tyr Leu Lys Lys Leu Gly Thr Gly
  1               5                  10                  15

Ala Leu Asn Ala Val Leu Lys Gln
             20
```

<210> SEQ ID NO 214
<211> LENGTH: 25

```
<212> TYPE: PRT
<213> ORGANISM: Xenopus laevis

<400> SEQUENCE: 214

Gly Trp Ala Ser Lys Ile Gly Gln Thr Leu Gly Lys Ile Ala Lys Val
1               5                   10                  15

Gly Leu Lys Glu Leu Ile Gln Pro Lys
            20                  25

<210> SEQ ID NO 215
<211> LENGTH: 14
<212> TYPE: PRT
<213> ORGANISM: Vespula lewisii

<400> SEQUENCE: 215

Ile Asn Leu Lys Ala Leu Ala Ala Leu Ala Lys Lys Ile Leu
1               5                   10

<210> SEQ ID NO 216
<211> LENGTH: 26
<212> TYPE: PRT
<213> ORGANISM: Apis mellifera

<400> SEQUENCE: 216

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 217
<211> LENGTH: 40
<212> TYPE: PRT
<213> ORGANISM: Phormia terronovae

<400> SEQUENCE: 217

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Gly Val Cys Val Cys Arg Asn
        35                  40

<210> SEQ ID NO 218
<211> LENGTH: 39
<212> TYPE: PRT
<213> ORGANISM: Phormia terronovae

<400> SEQUENCE: 218

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Arg
            20                  25                  30

Lys Gly Val Cys Val Arg Asn
        35

<210> SEQ ID NO 219
<211> LENGTH: 18
<212> TYPE: PRT
<213> ORGANISM: Limulus polyphemus

<400> SEQUENCE: 219

Arg Arg Trp Cys Phe Arg Val Cys Tyr Arg Gly Phe Cys Tyr Arg Lys
```

Cys Arg

<210> SEQ ID NO 220
<211> LENGTH: 18
<212> TYPE: PRT
<213> ORGANISM: Limulus polyphemus

<400> SEQUENCE: 220

Arg Arg Trp Cys Phe Arg Val Cys Tyr Lys Gly Phe Cys Tyr Arg Lys
1               5                   10                  15

Cys Arg

<210> SEQ ID NO 221
<211> LENGTH: 18
<212> TYPE: PRT
<213> ORGANISM: Sus scrofa

<400> SEQUENCE: 221

Arg Gly Gly Arg Leu Cys Tyr Cys Arg Arg Arg Phe Cys Val Cys Val
1               5                   10                  15

Gly Arg

<210> SEQ ID NO 222
<211> LENGTH: 16
<212> TYPE: PRT
<213> ORGANISM: Sus scrofa

<400> SEQUENCE: 222

Arg Gly Gly Arg Leu Cys Tyr Cys Arg Arg Arg Phe Cys Ile Cys Val
1               5                   10                  15

<210> SEQ ID NO 223
<211> LENGTH: 18
<212> TYPE: PRT
<213> ORGANISM: Sus scrofa

<400> SEQUENCE: 223

Arg Gly Gly Gly Leu Cys Tyr Cys Arg Arg Arg Phe Cys Val Cys Val
1               5                   10                  15

Gly Arg

<210> SEQ ID NO 224
<211> LENGTH: 51
<212> TYPE: PRT
<213> ORGANISM: Apis mellifera

<400> SEQUENCE: 224

Val Thr Cys Asp Leu Leu Ser Phe Lys Gly Gln Val Asn Asp Ser Ala
1               5                   10                  15

Cys Ala Ala Asn Cys Leu Ser Leu Gly Lys Ala Gly Gly His Cys Glu
                20                  25                  30

Lys Gly Val Cys Ile Cys Arg Lys Thr Ser Phe Lys Asp Leu Trp Asp
            35                  40                  45

Lys Tyr Phe
        50

<210> SEQ ID NO 225
<211> LENGTH: 39
<212> TYPE: PRT
<213> ORGANISM: Sacrophaga peregrina

```
<400> SEQUENCE: 225

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

<210> SEQ ID NO 226
<211> LENGTH: 39
<212> TYPE: PRT
<213> ORGANISM: Sacrophaga peregrina

<400> SEQUENCE: 226

Gly Trp Leu Lys Lys Ile Gly Lys Lys Ile Glu Arg Val Gly Gln His
1               5                   10                  15

Thr Arg Asp Ala Thr Ile Gln Val Ile Gly Val Ala Gln Gln Ala Ala
            20                  25                  30

Asn Val Ala Ala Thr Ala Arg
        35

<210> SEQ ID NO 227
<211> LENGTH: 47
<212> TYPE: PRT
<213> ORGANISM: Bos taurus

<400> SEQUENCE: 227

Ser Asp Glu Lys Ala Ser Pro Asp Lys His His Arg Phe Ser Leu Ser
1               5                   10                  15

Arg Tyr Ala Lys Leu Ala Asn Arg Leu Ala Asn Pro Lys Leu Leu Glu
            20                  25                  30

Thr Phe Leu Ser Lys Trp Ile Gly Asp Arg Gly Asn Arg Ser Val
        35                  40                  45

<210> SEQ ID NO 228
<211> LENGTH: 17
<212> TYPE: PRT
<213> ORGANISM: Tachypleus tridentatus

<400> SEQUENCE: 228

Lys Trp Cys Phe Arg Val Cys Tyr Arg Gly Ile Cys Tyr Arg Arg Cys
1               5                   10                  15

Arg

<210> SEQ ID NO 229
<211> LENGTH: 17
<212> TYPE: PRT
<213> ORGANISM: Tachypleus tridentatus

<400> SEQUENCE: 229

Arg Trp Cys Phe Arg Val Cys Tyr Arg Gly Ile Cys Tyr Arg Lys Cys
1               5                   10                  15

Arg

<210> SEQ ID NO 230
<211> LENGTH: 46
<212> TYPE: PRT
<213> ORGANISM: Hordeum vulgare

<400> SEQUENCE: 230
```

```
Lys Ser Cys Cys Lys Asp Thr Leu Ala Arg Asn Cys Tyr Asn Thr Cys
 1               5                  10                  15

Arg Phe Ala Gly Gly Ser Arg Pro Val Cys Ala Gly Ala Cys Arg Cys
                20                  25                  30

Lys Ile Ile Ser Gly Pro Lys Cys Pro Ser Asp Tyr Pro Lys
             35              40                  45

<210> SEQ ID NO 231
<211> LENGTH: 23
<212> TYPE: PRT
<213> ORGANISM: Trimeresurus wagleri

<400> SEQUENCE: 231

Gly Gly Lys Pro Asp Leu Arg Pro Cys Ile Ile Pro Pro Cys His Tyr
 1               5                  10                  15

Ile Pro Arg Pro Lys Pro Arg
                20

<210> SEQ ID NO 232
<211> LENGTH: 63
<212> TYPE: PRT
<213> ORGANISM: Androctonus australis hector

<400> SEQUENCE: 232

Val Lys Asp Gly Tyr Ile Val Asp Asp Val Asn Cys Thr Tyr Phe Cys
 1               5                  10                  15

Gly Arg Asn Ala Tyr Cys Asn Glu Glu Cys Thr Lys Leu Lys Gly Glu
                20                  25                  30

Ser Gly Tyr Cys Gln Trp Ala Ser Pro Tyr Gly Asn Ala Cys Tyr Cys
             35                  40                  45

Lys Leu Pro Asp His Val Arg Thr Lys Gly Pro Gly Arg Cys His
     50                  55                  60
```